US012570973B2

(12) United States Patent
Bunick et al.

(10) Patent No.: US 12,570,973 B2
(45) Date of Patent: Mar. 10, 2026

(54) COMPOSITIONS AND METHODS FOR INHIBITING INTERMEDIATE FILAMENT TETRAMERIZATION

(71) Applicant: YALE UNIVERSITY, New Haven, CT (US)

(72) Inventors: Christopher Bunick, Cheshire, CT (US); Sherif Eldirany, Glastonbury, CT (US); Minh Ho, New Haven, CT (US)

(73) Assignee: Yale University, New Haven, CT (US)

( * ) Notice: Subject to any disclaimer, the term of this patent is extended or adjusted under 35 U.S.C. 154(b) by 1171 days.

(21) Appl. No.: 17/283,405

(22) PCT Filed: Oct. 8, 2019

(86) PCT No.: PCT/US2019/055115
§ 371 (c)(1),
(2) Date: Apr. 7, 2021

(87) PCT Pub. No.: WO2020/076768
PCT Pub. Date: Apr. 16, 2020

(65) Prior Publication Data
US 2021/0340531 A1     Nov. 4, 2021

Related U.S. Application Data

(60) Provisional application No. 62/855,203, filed on May 31, 2019, provisional application No. 62/833,883, filed on Apr. 15, 2019, provisional application No. 62/742,484, filed on Oct. 8, 2018.

(51) Int. Cl.
| | |
|---|---|
| *C12N 15/11* | (2006.01) |
| *A61K 38/00* | (2006.01) |
| *A61P 35/00* | (2006.01) |
| *C07K 14/47* | (2006.01) |
| *C12N 9/22* | (2006.01) |
| *C12N 15/10* | (2006.01) |

(52) U.S. Cl.
CPC ............ *C12N 15/111* (2013.01); *A61P 35/00* (2018.01); *C07K 14/4702* (2013.01); *C07K 14/4741* (2013.01); *C12N 9/22* (2013.01); *C12N 15/1093* (2013.01); *A61K 38/00* (2013.01); *C12N 2310/20* (2017.05)

(58) Field of Classification Search
CPC .... C12N 15/111; C12N 9/22; C12N 15/1093; C12N 2310/20; A61P 35/00; A61P 27/00; C07K 14/4702; C07K 14/4741; C07K 14/47; A61K 38/00; A61K 38/1709; A61K 38/465; G01N 2500/02; G01N 2800/7047; G01N 33/574; G01N 2333/4742
See application file for complete search history.

(56) References Cited

PUBLICATIONS

Strelkov, Sergei V., et al. "Conserved segments 1A and 2B of the intermediate filament dimer: their atomic structures and role in filament assembly." EMBO J. Mar. 15, 2002 vol. 21 No. 6 pp. 1255-1266. (Year: 2002).*

Trogden, Kathryn P., et al. "An image-based small-molecule screen identifies vimentin as a pharmacologically relevant target of simvastatin in cancer cells." The FASEB Journal 32.5 (2018): 2841.(Year: 2018).*

Strelkov, Sergei V., et al. "Conserved segments 1A and 2B of the intermediate filament dimer: their atomic structures and role in filament assembly." The EMBO journal (2002). (Year: 2002).*

Mucke N, et al., "Molecular and biophysical characterization of assembly-starter units of human vimentin", J Mol Biol, (2004), 340:97-114.

Nagai K, et al., "Synthesis and sequence-specific proteolysis of hybrid proteins produced in Escherichia coli", Methods Enzymol, (1987), 153:461-81.

Omary B, "IF-pathies": a broad spectrum of intermediate filament-associated diseases, The Journal of Clinical Investigation, (2009), 119:1756-1762.

Otwinowski Z, et al., "Processing of X-ray Diffraction Data Collected in Oscillation Mode", In Methods in Enzymology, C.W. Carter JRMS, (ed), (1997), pp. 307-326. New York: Academic Press.

Paladini RD, et al., "Onset of re-epithelialization after skin injury correlates with a reorganization of keratin filaments in wound edge keratinocytes: defining a potential role for keratin 16", J Cell Biol, (1996), 132:381-97.

Pang AH, et al., "A crystal structure of coil 1B of vimentin in the filamentous form provides a model of a high-order assembly of a vimentin filament", FEBS J, (2018), 285:2888-2899.

Parry DA, et al., "Subfilamentous protofibril structures in fibrous proteins: cross-linking evidence for protofibrils in intermediate filaments", J Biol Chem, (2001), 276:39253-8.

Premchandar A, et al., "Structural Dynamics of the Vimentin Coiled-coil Contact Regions Involved in Filament Assembly as Revealed by Hydrogen-Deuterium Exchange", J Biol Chem, (2016), 291:24931-24950.

Ridge KM, et al., "Methods for Determining the Cellular Functions of Vimentin Intermediate Filaments", Methods Enzymol, (2016), 568:389-426.

Rodríguez MI, et al., "PARP-1 regulates metastatic melanoma through modulation of vimentin-induced malignant transformation", PLoS Genet, (2013), 9:e1003531.

(Continued)

Primary Examiner — John Charles Mckillop
(74) Attorney, Agent, or Firm — Riverside Law LLP

(57) ABSTRACT

The present invention provides compositions and methods for inhibiting intermediate filament tetramerization and formation.

2 Claims, 48 Drawing Sheets

Specification includes a Sequence Listing.

(56)        References Cited

PUBLICATIONS

Satelli A, et al., "Vimentin in cancer and its potential as a molecular target for cancer therapy", Cell Mol Life Sci, (2011), 68:3033-46.

Schoumacher M, et al., "Actin, microtubules, and vimentin intermediate filaments cooperate for elongation of invadopodia", J Cell Biol, (2010), 189:541-56.

Sharma P, et al., "Intermediate Filaments as Effectors of Cancer Development and Metastasis: A Focus on Keratins, Vimentin, and Nestin", Cells, (2019), 8.

Steinert PM, et al., "Conservation of the structure of keratin intermediate filaments: molecular mechanism by which different keratin molecules integrate into preexisting keratin intermediate filaments during differentiation", Biochemistry, (1993b), 32:10046-56.

Steinert PM, et al., "Diversity of intermediate filament structure. Evidence that the alignment of coiled-coil molecules in vimentin is different from that in keratin intermediate filaments", J Biol Chem, (1993d), 268:24916-25.

Steinert PM, et al., "Keratin intermediate filament structure. Crosslinking studies yield quantitative information on molecular dimensions and mechanism of assembly", J Mol Biol, (1993a), 230:436-52.

Steven AC, et al., "Structure of fibroblastic intermediate filaments: analysis of scanning transmission electron microscopy", Proc Natl Acad Sci U S A, (1982), 79:3101-5.

Steven AC, et al., "The distribution of mass in heteropolymer intermediate filaments assembled in vitro. Stem analysis of vimentin/desmin and bovine epidermal keratin", J Biol Chem, (1983), 258:8323-9.

Strelkov SV, et al., "Crystal structure of the human lamin A coil 2B dimer: implications for the head-to-tail association of nuclear lamins", J Mol Biol, (2004), 343:1067-80.

Strelkov SV, et al., "Divide-and-conquer crystallographic approach towards an atomic structure of intermediate filaments", J Mol Biol, (2001), 306:773-81.

Studier FW, "Protein production by auto-induction in high density shaking cultures", Protein Expr Purif, (2005), 41:207-34.

Sun J, et al., "High-Throughput Screening for Drugs that Modulate Intermediate Filament Proteins", Methods Enzymol, (2016), 568:163-85.

Sutoh Yoneyama M, et al. "Vimentin intermediate filament and plectin provide a scaffold for invadopodia, facilitating cancer cell invasion and extravasation for metastasis", Eur J Cell Biol , (2014), 93:157-69.

Tadokoro A, et al., "Vimentin Regulates Invasiveness and Is a Poor Prognostic Marker in Non-small Cell Lung Cancer", Anticancer Res, (2016), 36:1545-51.

Taouji S, et al., "Current Screens Based on the AlphaScreen Technology for Deciphering Cell Signalling Pathways", Curr Genomics, (2009), 10:93-101.

Terron-Kwiatkowski A, et al., "Mutation S233L in the 1B domain of keratin 1 causes epidermolytic palmoplantar keratoderma with "tonotubular "keratin", J Invest Dermatol, (2006), 126:607-613.

Vagin A, et al., "Molecular replacement with MOLREP", Acta Crystallogr D Biol Crystallogr, (2010), 66:22-5.

Vriend G "What If: a molecular modeling and drug design program", J Mol Graph, (1990), 8:52-6.

Wevers A, et al., "Palmoplantar keratoderma with tonotubular keratin", J Am Acad Dermatol, (1991), 24:638-42.

Z. Otwinowski, et al., "Processing of X-ray Diffraction Data Collected in Oscillation Mode", Methods in Enzymology, vol. 276: Macromolecular Crystallography, part A, (1997), 307-326, C.W. Carter, Jr. & R. M. Sweet, Eds., Academic Press (New York).

Zhao Y, et al., "Vimentin affects the mobility and invasiveness of prostate cancer cells", Cell Biochem Funct, (2008), 26:571-7.

Adams PD, et al., "PHENIX: a comprehensive Python-based system for macromolecular structure solution", Acta Crystallogr D Biol Crystallogr, (2010), 66:213-21.

Aebi U, et al., "The fibrillar substructure of keratin filaments unraveled", J Cell Biol, (1983), 97:1131-43.

Ali AM, et al., "Stapled Peptides Inhibitors: A New Window for Target Drug Discovery", Comput Struct Biotechnol J, (2019), 17:263-281.

Aziz A, et al., "The structure of vimentin linker 1 and rod 1B domains characterized by site-directed spin-labeling electron paramagnetic resonance, (SDSL-EPR), and X-ray crystallography", J Biol Chem, (2012), 287:28349-61.

Baker NA, et al., "Electrostatics of nanosystems: application to microtubules and the ribosome", Proc Natl Acad Sci USA (2001), 98:10037-41.

Battaglia RA, et al., "Vimentin on the move: new developments in cell migration", F1000Res, (2018), 7.

Bernot KM, et al., "A small surface hydrophobic stripe in the coiled-coil domain of type I keratins mediates tetramer stability," J Cell Biol, (2005), 168:965-74.

Bollong MJ, et al., "A vimentin binding small molecule leads to mitotic disruption in mesenchymal cancers", Proc Natl Acad Sci U S A, (2017), 114:E9903-E9912.

Bozza WP, et al., "Cytokeratin 8/18 protects breast cancer cell lines from Trail-induced apoptosis", Oncotarget, (2018), 9:23264-23273.

Bunick C, et al., "Evaporative microdialysis: an effective improvement in an established method of protein crystallization", Acta Crystallogr D Biol Crystallogr, (2000), 56:1430-1.

Bunick CG, et al., "Crystal structure of human profilaggrin s100 domain and identification of target proteins annexin ii, stratifin and hsp27", J Invest Dermatol (2015), 135:1801-9.

Bunick CG, et al., "The X-Ray Crystal Structure of the Keratin 1-Keratin 10 helix 2B heterodimer reveals molecular surface properties and biochemical insights into human skin disease", J Invest Dermatol, (2017), 137:142-150.

Bunick CG, et al., "Designing sequence to control protein function in an EF-hand protein", J Am Chem Soc, (2004), 126:5990-8.

Chaffer CL, et al., "A perspective on cancer cell metastasis", Science, (2011), 331:1559-64.

Chernyatina AA, et al., "Atomic structure of the vimentin central α-helical domain and its implications for intermediate filament assembly", Proc Natl Acad Sci U S A, (2012), 109:13620-5.

Chernyatina AA, et al., "How to Study Intermediate Filaments in Atomic Detail", Methods Enzymol, (2016), 568:3-33.

Chernyatina AA, et al., "Intermediate filament structure: the bottom-up approach", Curr Opin Cell Biol, (2015), 32:65-72.

Choi J, et al., "Genomic landscape of cutaneous T cell lymphoma", Nat Genet, (2015), 47:1011-9.

Chu YW, et al., "Experimental coexpression of vimentin and keratin intermediate filaments in human melanoma cells augments motility", Am J Pathol, (1996), 148:63-9.

Chu YW, et al., "Expression of complete keratin filaments in mouse L cells augments cell migration and invasion", Proc Natl Acad Sci U S A, (1993), 90:4261-5.

Chung BM, et al., "Networking galore: intermediate filaments and cell migration", Curr Opin Cell Biol , (2013), 25:600-12.

Costantini S, et al., "ESBRI: a web server for evaluating salt bridges in proteins", Bioinformation, (2008), 3:137-8.

Coulombe PA, et al., "Elucidating the early stages of keratin filament assembly", J Cell Biol, (1990), 111:153-69.

Danielsson, et al., "Vimentin Diversity in Health and Disease", Cells, (Sep. 21, 2018), 7(10) XP055703007.

Dolinsky TJ, et al., "PDB2PQR: an automate pipeline for the setup of Poisson Boltzmann electrostatics calculations", Nucleic Acids Res (2004), 32:665-7.

Ediriweera MK, et al., "In vitro assays and techniques utilized in anticancer drug discovery", J Appl Toxicol, (2019), 39:38-71.

Eldirany S, et al., "689 The x-ray crystal structure of human keratin 1 with S233L mutation demonstrates mechanism of pathogenic tonotubular keratin formation leading to epidermolytic palmoplantar keratoderma", Journal of Investigative Dermatology, (2018), 138.

Eldirany SA, et al., "Human keratin 1/10-1B tetramer structures reveal a knob-pocket mechanism in intermediate filament assembly", EMBO J, (2019).

Emsley P, et al., "Coot: model-building tools for molecular graphics", Acta Crystallogr D Biol Crystallogr (2004), 60:2126-32.

(56)     References Cited

PUBLICATIONS

Fernandez-Ortega C, et al., "Identification of Vimentin as a Potential Therapeutic Target against HIV Infection", Vir, (2016), 8(98):1-19.

Gandalovičová A, et al., "Migrastatics-Anti-metastatic and Anti-invasion Drugs: Promises and Challenges", Trends Cancer, (2017), 3:391-406.

Grimberg G, et al., "Novel and recurrent mutations in the 1B domain of keratin 1 in palmoplantar keratoderma with tonotubules", Br J Dermatol, (2009), 160:446-9.

Grin B, et al., "Withaferin a alters intermediate filament organization, cell shape and behavior", PLoS One, (2012), 7: e39065.

Guo, et al. , "Cytokeratin-8 in Anaplastic Thyroid Carcinoma: More than a simple structural cytoskeletal protein", Int. J. Mol. Sci, (2018), 19:577.

Hanson BL, et al., "Use of an open-flow helium cryostat for macromolecular cryocrystallography", Journal of Applied Crystallography, (1999), 32:814-820.

Herrmann H, et al., "Characterization of early assembly intermediates of recombinant human keratins", J Struct Biol, (2002), 137:82-96.

Herrmann H, et al., "Intermediate filament assembly: temperature sensitivity and polymorphism", Cell Mol Life Sci, (1999), 55:1416-31.

Herrmann H, et al., "Intermediate Filaments: Structure and Assembly", Cold Spring Harb Perspect Biol, (2016), 8.

Hulkower KI, et al., "Cell migration and invasion assays as tools for drug discovery", Pharmaceutics, (2011), 3:107-24.

Huo Y, et al., "Downregulation of vimentin expression increased drug resistance in ovarian cancer cells", Oncotarget, (2016), 7:45876-45888.

International Search Report and Written Opinion for App. No. PCT/US19/55115, dated Feb. 27, 2020, 13 pages.

Karantza V, "Keratins in health and cancer: more than mere epithelial markers", Oncogene, (2011), 30:127-138.

Kidd ME, et al., "The Role of Vimentin Intermediate Filaments in the Progression of Lung Cancer", Am J Resp Cell Mol Bio, (2014), 50(1):1-6.

Kim B, et al., "Crystal structure of the human glial fibrillary acidic protein 1B domain", Biochem Biophys Res Commun, (2018), 503:2899-2905.

Lee CH, et al., "Structural basis for heterodimeric assembly and perinuclear organization of keratin filaments", Nat Struct Mol Biol (2012), 19:707-15.

Leong HS, et al., "Invadopodia are required for cancer cell extravasation and are a therapeutic target for metastasis", Cell Rep, (2014), 8:1558-70.

Loschke F, et al., "Regulation of keratin network organization", Curr Opin Cell Biol, (2015), 32:56-64.

Mack JW, et al., "The mechanism of interaction of filaggrin with intermediate filaments. The ionic zipper hypothesis", J Mol Biol, (1993), 232:50-66.

Marqus S, et al., "Evaluation of the use of therapeutic peptides for cancer treatment", J Biomed Sci, (2017), 24:21.

Moll R, et al., "The human keratins: biology and pathology", Histochem Cell Biol, (2008), 129:705-33.

* cited by examiner

1A
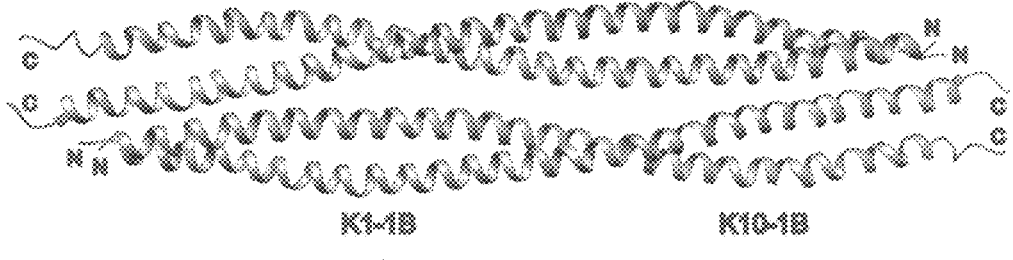
K1/K10-1B Heterotetramer
1B
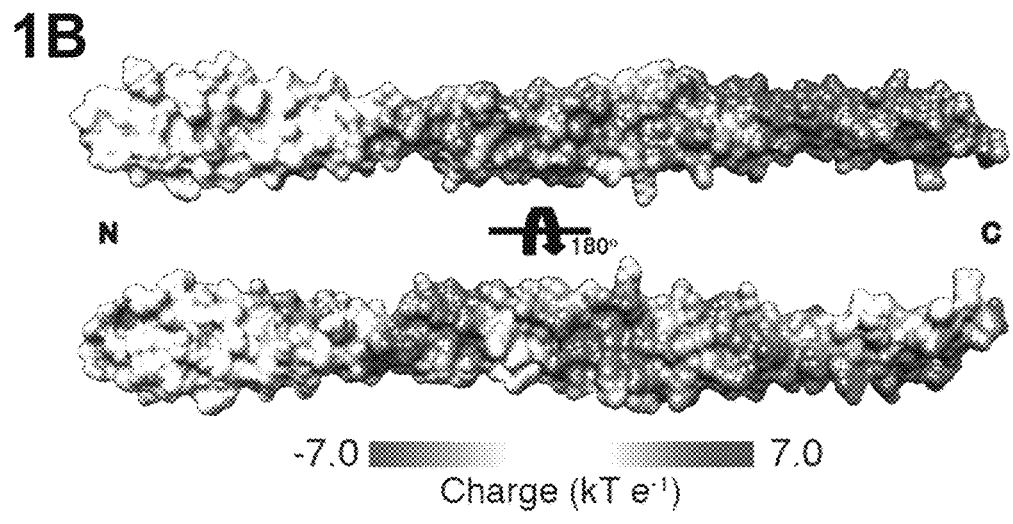
1C
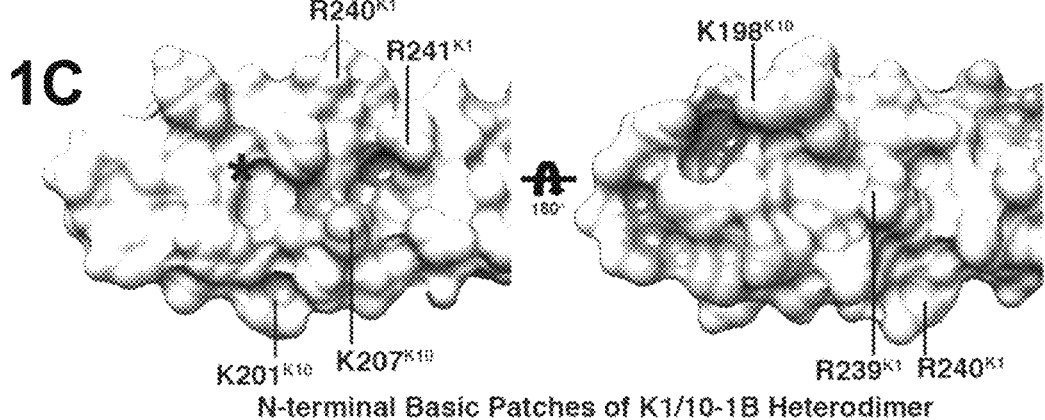
N-terminal Basic Patches of K1/10-1B Heterodimer
Figure 1

1E
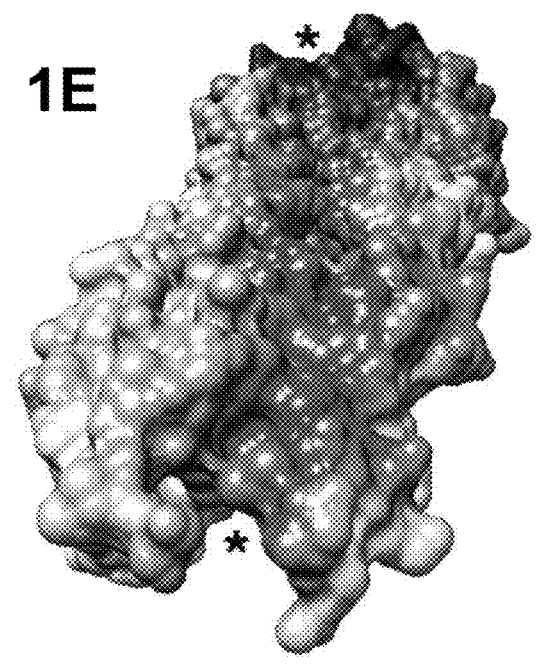
1F
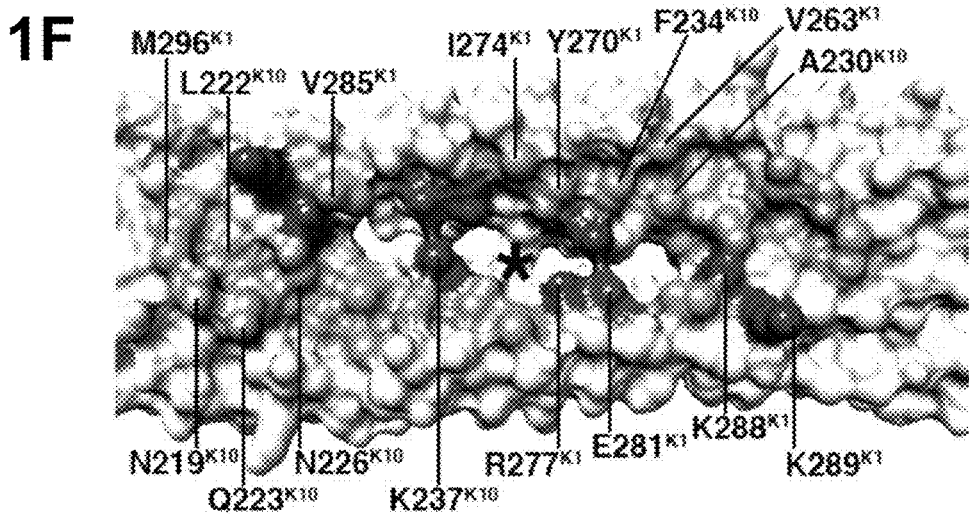
1G
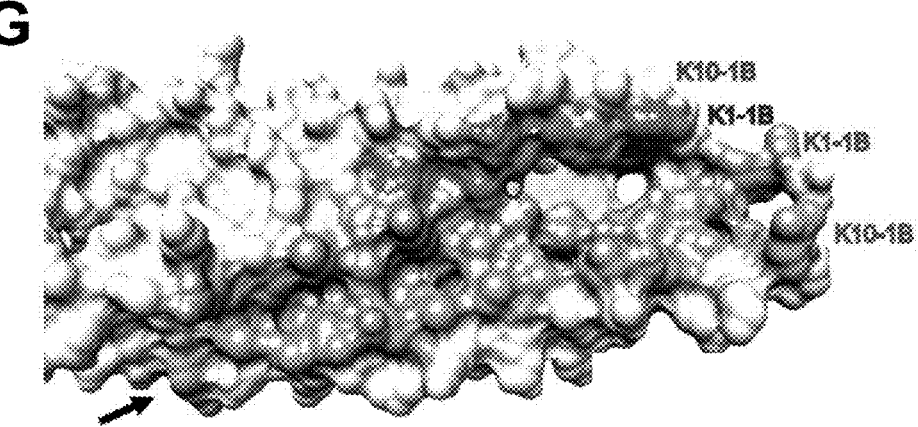
Figure 1 (cont'd)

2E
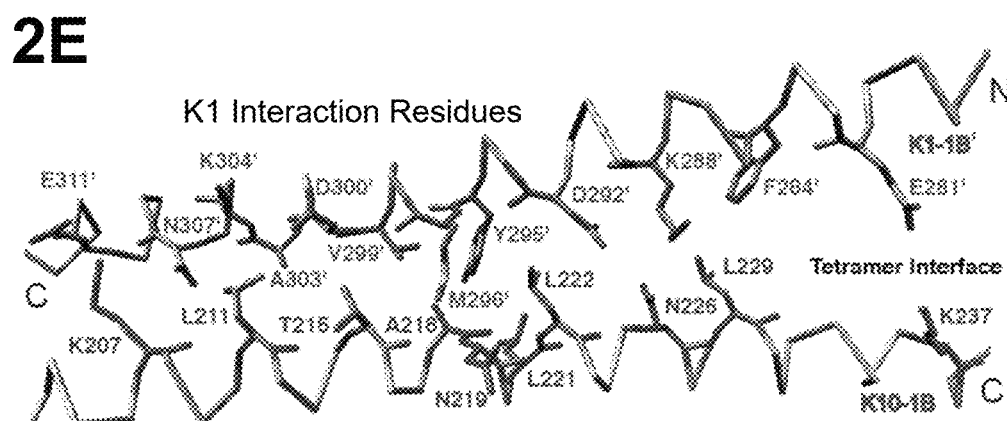
K1 Interaction Residues
K10 Hydrophobic Stripe
| K10 Stripe | K1 Interactions |
|---|---|
| K207 | E311 |
| L211 | D300, A303, K304, N307 |
| T215 | M296, D300 |
| A218 | Y295, M296, V299 |
| N219 | M296 |
| L221 | Y295 |
| L222 | D292, Y295, M296 |
| N226 | K288, D292 |
| L229 | F284, K288 |
| K237 | E281 |
2F
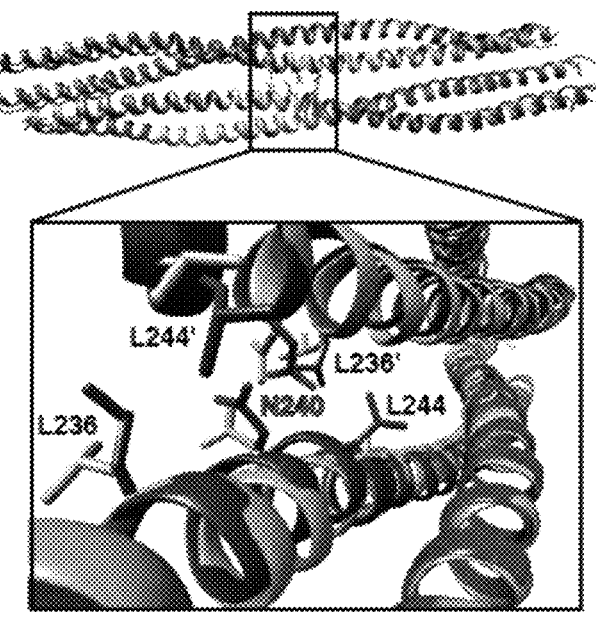
Figure 2 (con'td)

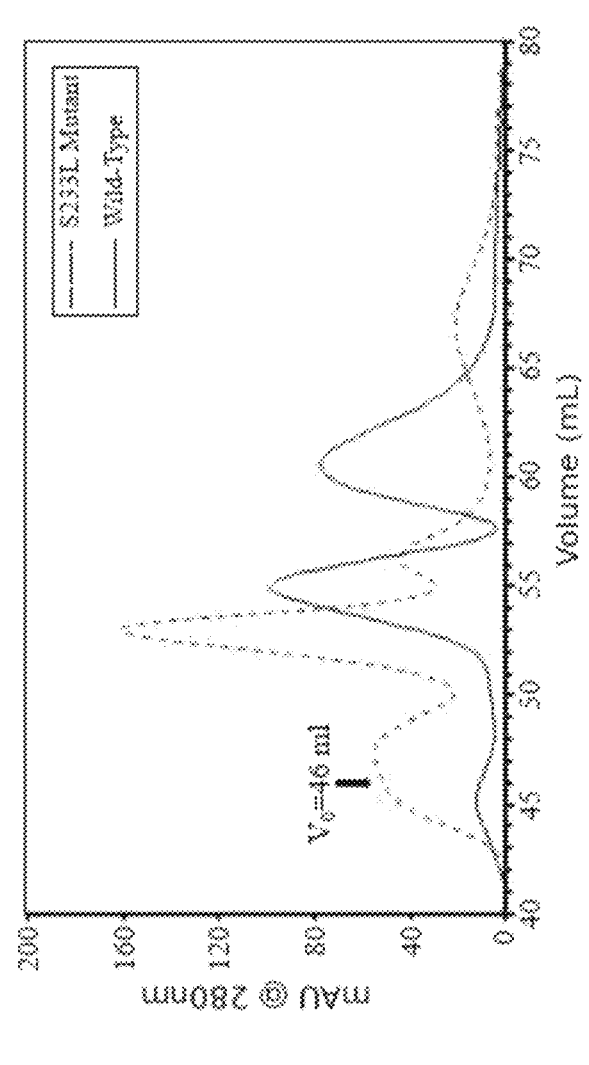
3B
Figure 3
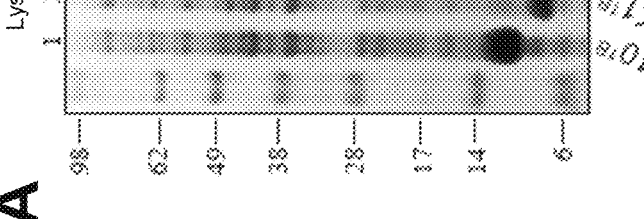
3A

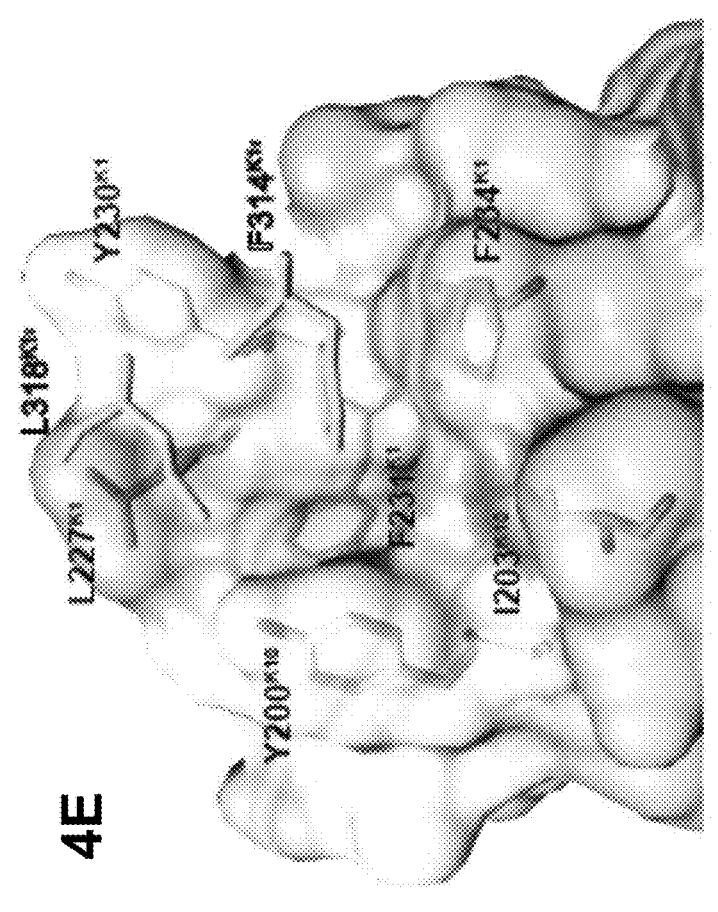
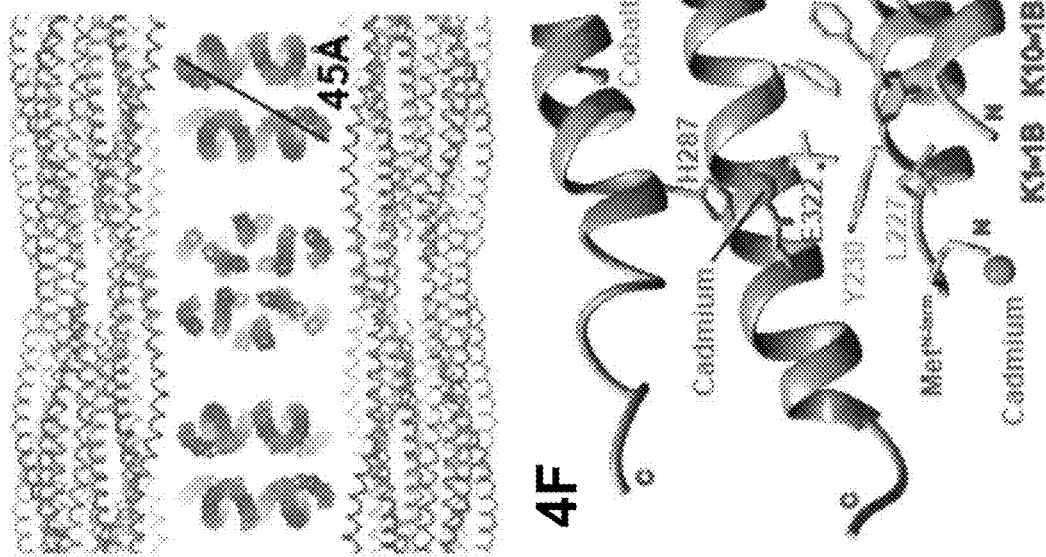
Figure 4 (cont'd)

6A    K10 Hydrophobic Stripe

K10-1B    207-KNQILNLTTDNANILLQIIMAPLAADDFRLK-237 (SEQ ID NO:68)

Vimentin-1B    158-RRQVQLTNDKARVEVERDNLAEDIMRLREK-188 (SEQ ID NO:69)

6B    K1 Interaction Residues

K1-1B    281-ENEFVTIKKDVDGAYMTKVDLQAKLDNLQQE-311 (SEQ ID NO:70)

Vimentin-1B    200-ENTLQSFRQDVDNASLARIDLERKVESLQEE-230 (SEQ ID NO:71)

6C    Anchoring Knob

K1-1B    314-WITAYQA-321 (SEQ ID NO:72)

Vimentin-1B    233-FLKKLHEE-240 (SEQ ID NO:73)

6D

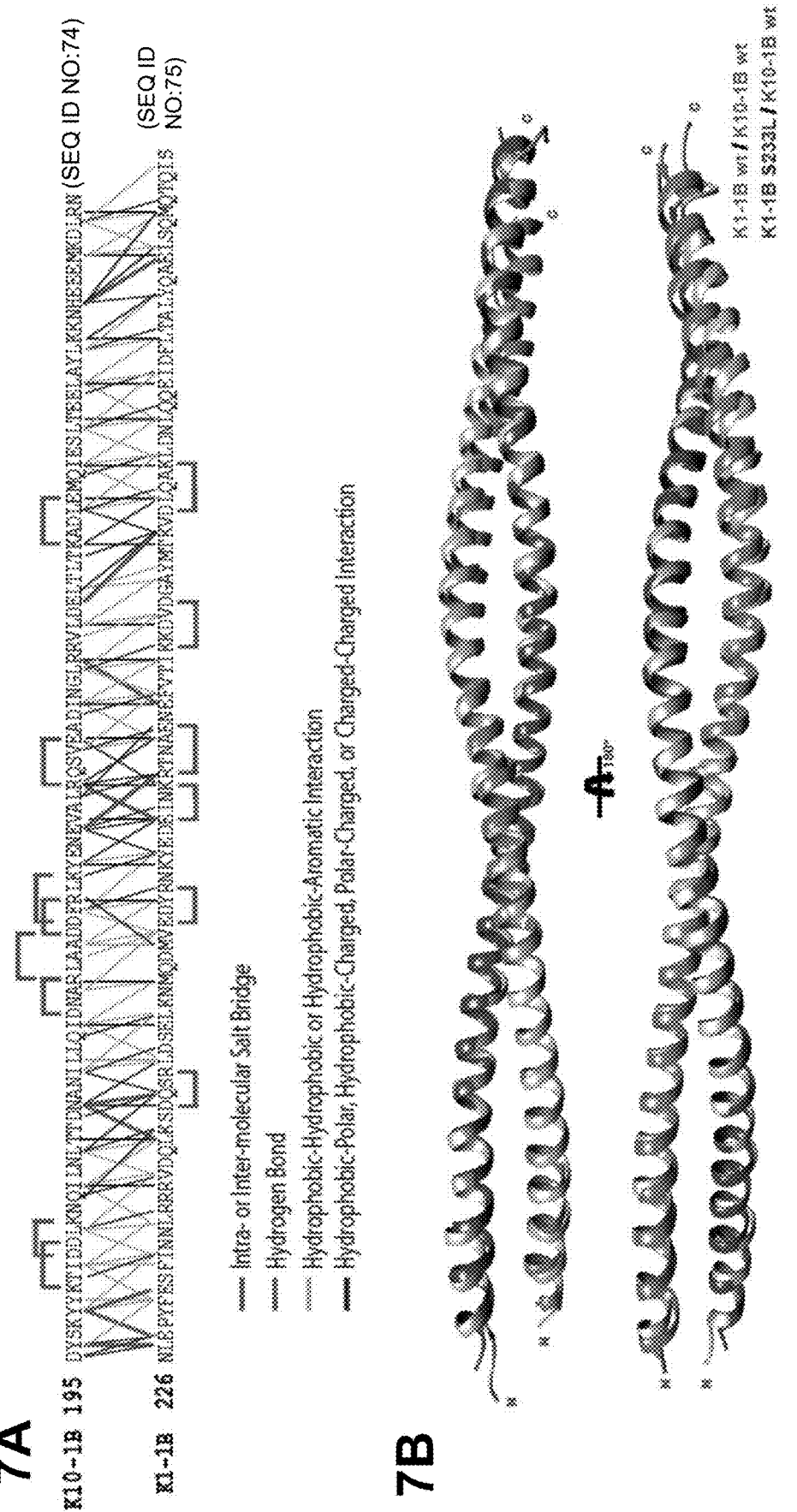

7A

K10-1B 195  GYSKYKTTEDKMQLEKTTDRMKVLLQQDMDMKLAADDFRLKYEDELTLRQSVEADINGLRRVLDELTLARADLEMQIESLKEEMILRLKKEEMDLRW (SEQ ID NO:74)

K1-1B 226  NLRRYTESFTNNTRRRVTDGLKSQRIDGELKNKQMDVEERNKYEDELMKTTVKTTVVDGAMFPYTRKEIVDGAVMPVRYD QAKLENLQEPLFALTQAKLSQNQTDTS  (SEQ ID NO:75)

Legend:
— Intra- or Inter-molecular Salt Bridge
= Hydrogen Bond
⋯ Hydrophobic-Hydrophobic or Hydrophobic-Aromatic Interaction
— Hydrophobic-Polar, Hydrophobic-Charged, Polar-Charged, or Charged-Charged Interaction

(SEQ ID NO:90)

mK10-1B     YYKTIEDLK mK10-1B     EMQIESLNEELAYLKK (SEQ ID NO:83)

mK1-1B      VDSLKSDQSR (SEQ ID NO:76)

mK1-1B      VELQAKR (SEQ ID NO:77)

mK1-1B      YEDEINKR (SEQ ID NO:86)

mK1-1B      YEDEINKR (SEQ ID NO:86)

mK1-1B      TNAENEFVTIKK (SEQ ID NO:78)

mK10-1B     LKYENEVTLR (SEQ ID NO:79)

mK1-1B      TKYEDEMNKR (SEQ ID NO:80)

mK10-1B     LKYENEVTLR (SEQ ID NO:81)

Crosslinked Mouse K1/K10-1B Tryptic Peptides (SEQ ID NO:82)

hK10-1B     199 YYKTIDDLK 207 hK10-1B     271 EMQIESLTEELAYLKK 285 (SEQ ID NO:83)

hK1-1B      242 VDQLKSDQSR 251 (SEQ ID NO:84)

hK1-1B      299 VDLQAKL 305 (SEQ ID NO:85)

hK1-1B      270 YEDEINKR 277 (SEQ ID NO:86)

hK1-1B      270 YEDEINKR 277 (SEQ ID NO:86)

hK1-1B      278 TNAENEFVTIKK 289 (SEQ ID NO:78)

hK10-1B     236 LKYENEVALR 245 (SEQ ID NO:87)

hK1-1B      269 NKYEDEINKR 277 (SEQ ID NO:88)

hK10-1B     236 LKYENEVALR 245 (SEQ ID NO:89)

Expected Corresponding Human K1/K10-1B Tryptic Peptides

| | Hydrophobic Pocket | SEQ ID NO | Anchoring Knob | SEQ ID NO |
|---|---|---|---|---|
| | 227 | | 314 | |
| K1 | LEPYFESFI | 91 | FLTALYQA | 117 |
| K2 | LEPIFQGYI | 92 | FLKVLYDA | 118 |
| K3 | LEPLFENHI | 93 | FLRTLYDA | 119 |
| K4 | LEPLFETYL | 94 | FLKVLYDA | 120 |
| K5 | LEPLFEQYI | 95 | FMKMFFDA | 121 |
| K6a | LEPLFEQYI | 96 | FLRALYDA | 122 |
| K6b | LEPLFEQYI | 97 | FLRALYDA | 123 |
| K6c | LEPLFEQYI | 98 | FLRALYDA | 124 |
| K7 | LPDIFEAQI | 99 | FLRTLNET | 125 |
| K8 | MDNMFESYI | 100 | FLRQLYEE | 126 |
| K71 | LEPILEGYI | 101 | FFRCLFEA | 127 |
| K72 | LEPIYEGYI | 102 | FFKCLYEG | 128 |
| K73 | LEPILEGYI | 103 | FFKCLYEG | 129 |
| K74 | LEPILEGYI | 104 | FLKCLYDA | 130 |
| K75 | LEPLFDSYT | 105 | FIHSVFDA | 131 |
| K76 | LEPCFESYI | 106 | FLRTLYEM | 132 |
| K77 | LEPLLENYI | 107 | FLKYLFLT | 133 |
| K78 | LEPVFEACL | 108 | FLKHLNEE | 134 |
| K79 | LEPLFEAYL | 109 | FLQQLYEM | 135 |
| K80 | LGHLYEEYQ | 110 | LMKTIYEQ | 136 |
| K81 | LEPLFEGYI | 111 | FLRRLYEE | 137 |
| K82 | IEPIFEGYI | 112 | FLKSLYEE | 138 |
| K83 | LEPLFAGYI | 113 | FLRRLYEE | 139 |
| K84 | LEPLFESYI | 114 | FLKTLYME | 140 |
| K85 | LEPLFSGYI | 115 | FLRRLYEE | 141 |
| K86 | LEPLFEGYI | 116 | FLRRLYEE | 142 |

Human Type II Keratins

| | Hydrophobic Pocket | SEQ ID NO | Anchoring Knob | SEQ ID NO |
|---|---|---|---|---|
| K1 | LEPYFESFI | 91 | FLTALYQA | 117 |
| K10 | DYSKYYKTI | 143 | YLKKNHEE | 171 |
| K9 | NYSPYYNTI | 144 | ALKKNHKE | 172 |
| K12 | DYSKYYPLI | 145 | YMKKNHED | 173 |
| K13 | DYSPYYKTI | 146 | YMKKNHEE | 174 |
| K14 | DYSPYFKTI | 147 | YLKKNHEE | 175 |
| K15 | DYSQYFKTI | 148 | YLKKNHEE | 176 |
| K16 | DYSPYFKTI | 149 | YLRKNHEE | 177 |
| K17 | DYSQYYRTI | 150 | YLKKNHEE | 178 |
| K18 | DWSHYFKII | 151 | FMKKNHEE | 179 |
| K19 | DYSHYYTTI | 152 | YLKKNHEE | 180 |
| K20 | DYSAYYRQI | 153 | LLKKEHQE | 181 |
| K23 | DYSQYEENI | 154 | LMKKHHEQ | 182 |
| K24 | DYSKYYSII | 155 | YLRKNHEE | 183 |
| K25 | DYSRYFPII | 156 | YLKKNHKE | 184 |
| K26 | DYSRYFSVI | 157 | YLKKSHEE | 185 |
| K27 | DYSRYFPII | 158 | YLKKNHEE | 186 |
| K28 | DYSRYHLTI | 159 | YLKKNHEE | 187 |
| K31 | SYQSYFKTI | 160 | CLKSNHEQ | 188 |
| K32 | DYQSHFRTI | 161 | CLKKNHEE | 189 |
| K33a | SYQSYFKTI | 162 | CLKQNHEQ | 190 |
| K33b | SYQSYFKTI | 163 | SLKQNHEQ | 191 |
| K34 | SYQSYFKTI | 164 | CLKKNHEE | 192 |
| K35 | DYQSYFRTI | 165 | CLKKNHEE | 193 |
| K36 | DYQSYFKTI | 166 | CLKKNHEE | 194 |
| K37 | DYQSYFRTI | 167 | SLKSNHEQ | 195 |
| K38 | DYQSYFHTI | 168 | SLKSNHEQ | 196 |
| K39 | DYLSYYTTI | 169 | CLKNNHKE | 197 |
| K40 | DYQRYFNTI | 170 | CLKKNHEE | 198 |

Human Type I Keratins
(plus K1 for comparison)

| | Hydrophobic Pocket | SEQ ID NO: | Anchoring Knob | SEQ ID NO: |
|---|---|---|---|---|
| K1 | LEPYFESFI | 91 | FLTALYQA | 117 |
| Vimentin | LGDLYEEEM | 199 | FLKKLHEE | 204 |
| Desmin | VAELYEEEL | 200 | FLKKVHEE | 205 |
| GFAP | LADVYQAEL | 201 | FLRKIHEE | 206 |
| Peripherin | ADQLCQEL | 202 | FLRKLHEE | 207 |
| Syncoilin | SLRAEQSPS | 203 | LVKQKLFK | 208 |

Human Type III Keratins
(plus K1 for comparison)

| | Hydrophobic Pocket | SEQ ID NO: | Anchoring Knob | SEQ ID NO: |
|---|---|---|---|---|
| K1 | LEPYFESFI | 91 | FLTALYQA | 91 |
| NF-L | FRALYEQEI | 209 | FLKKVHEE | 216 |
| NF-M | LGDAYDQEI | 210 | FLRSNHEE | 217 |
| NF-H | MGELYEREV | 211 | YLRRHHQE | 218 |
| Internexin | VGELFQREL | 212 | FVRQVHDE | 219 |
| Synemin a | TVQLYEDEV | 213 | LAMADWLR | 220 |
| Synemin b | TVQLYEDEV | 214 | LAMADWLR | 221 |
| Nestin | AVEALEQEK | 215 | FLQARTPT | 222 |

Human Type IV IFs
(plus K1 for comparison)

Figure 9:
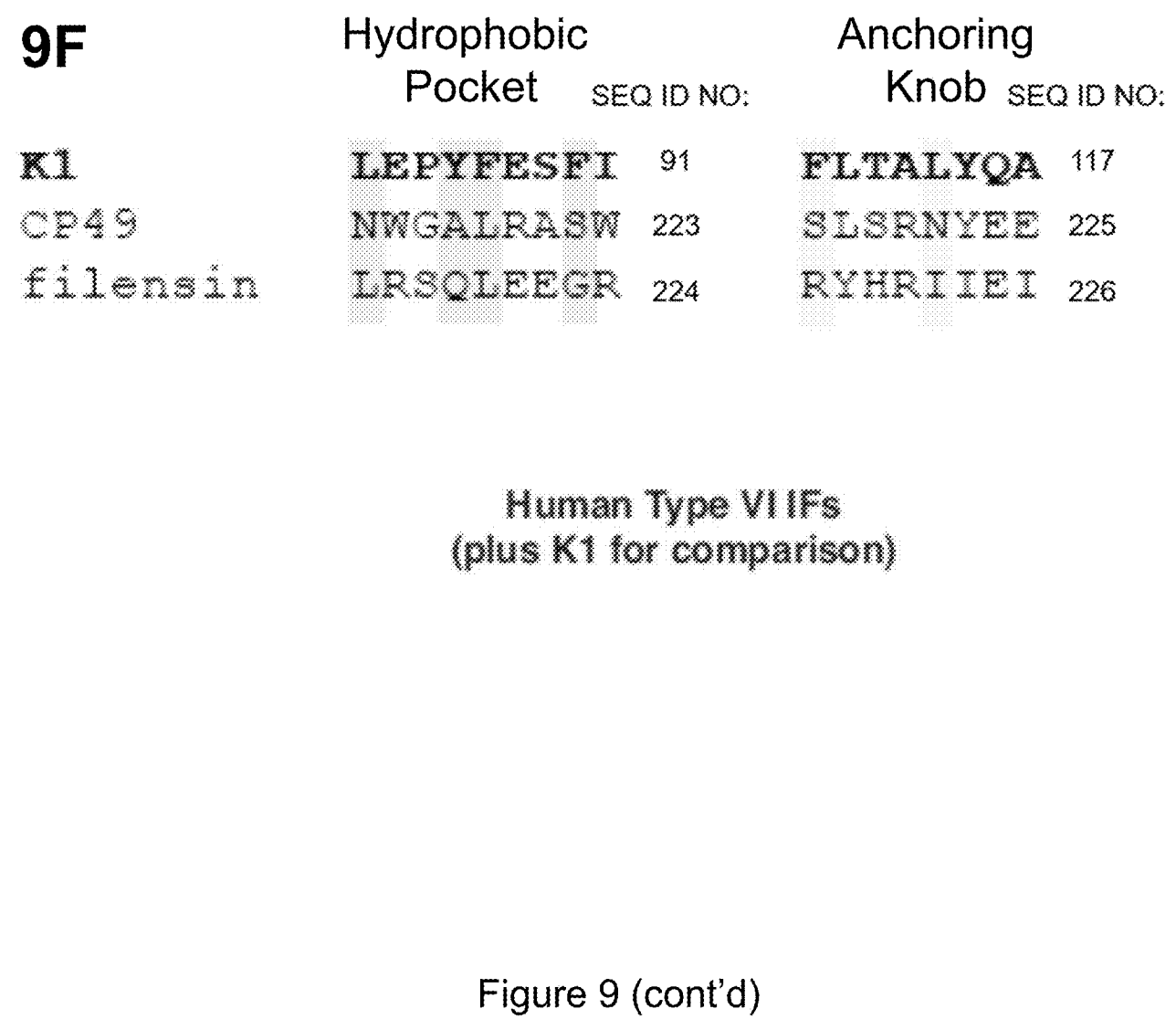

Hydrophobic
Pocket    SEQ ID NO:

Anchoring
Knob    SEQ ID NO:

K1    LEPYFESPI    91    FLTALYQA    117

CP49    NWGALRASW    223    SLSRNYEE    225 filensin    LRSQLEEGR    224    RYHRIIEI    226

Human Type VI IFs
(plus K1 for comparison)

| | Hydrophobic Pocket | SEQ ID NO: | Anchoring Knob | SEQ ID NO: |
|---|---|---|---|---|
| K1 | LEPYFESPI | 91 | FLTALYQA | 117 |
| Lamin B1 | ETRLYEVDS | 227 | ACLERIQE | 232 |
| Lamin B2 | ERRLYEVDS | 228 | AAEDRIRE | 233 |
| Lamin A | ETRLYEIDN | 229 | AKEAKLRD | 234 |
| Lamin C1 | ETRLYEIDN | 230 | AKEAKLRD | 235 |
| Lamin C2 | ETRLYEIDN | 231 | AKEAKLRD | 236 |

Human Type V IFs
(plus K1 for comparison)

Figure 9 (cont'd)

Keratin 1: Unique-34%, Conserved-66%

Keratin 10: Unique-20%, Conserved-80%

Amino Acid Conservation

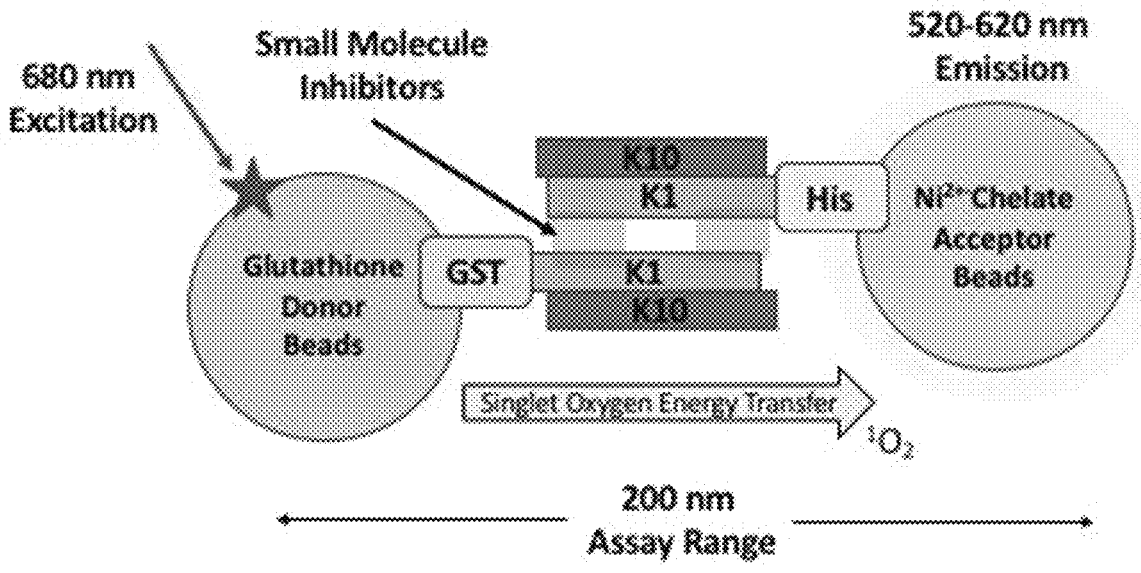
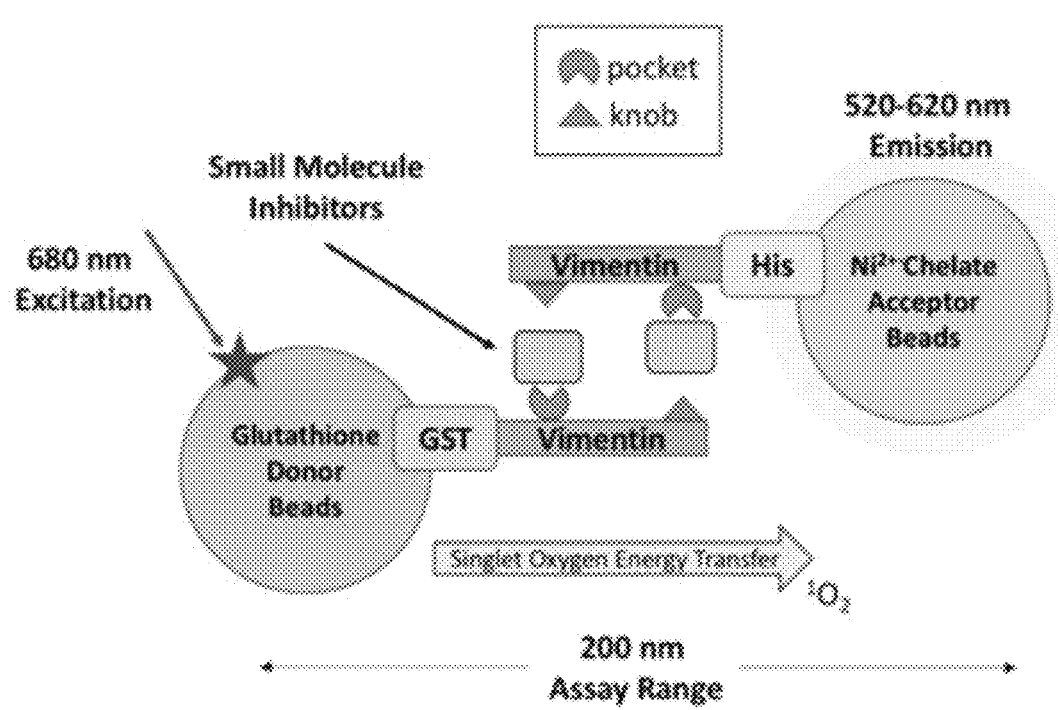
Figure 13

K8/K18 Knob/Pocket

K1/K10 Knob/Pocket

K5/K14 Knob/Pocket

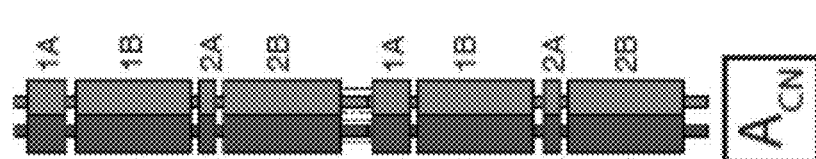
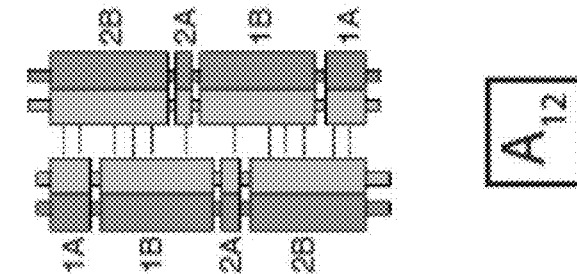
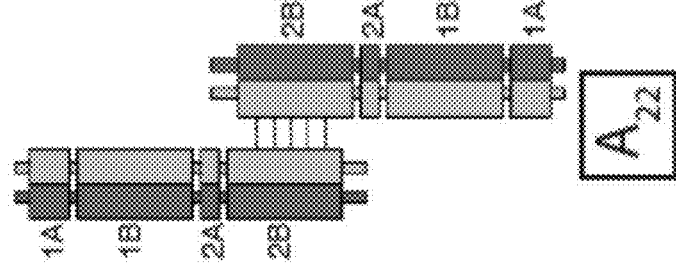
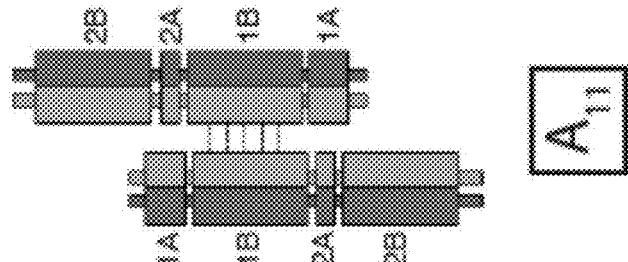
Figure 17

20B
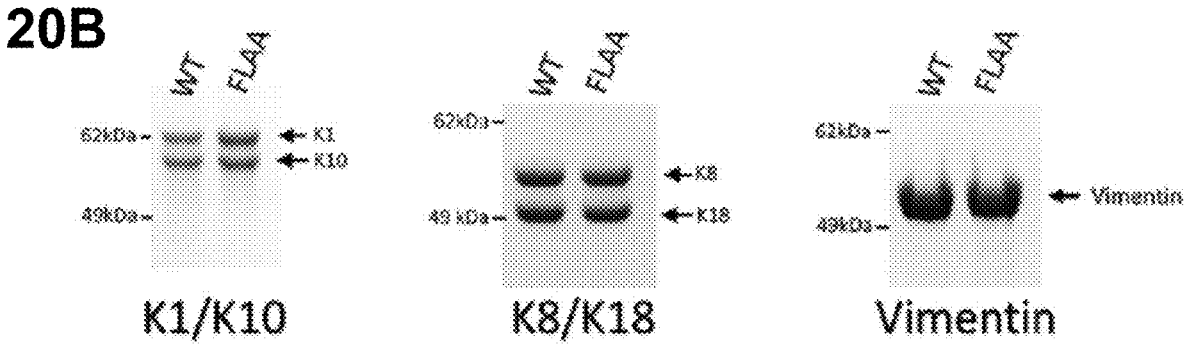
K1/K10  K8/K18  Vimentin
20C
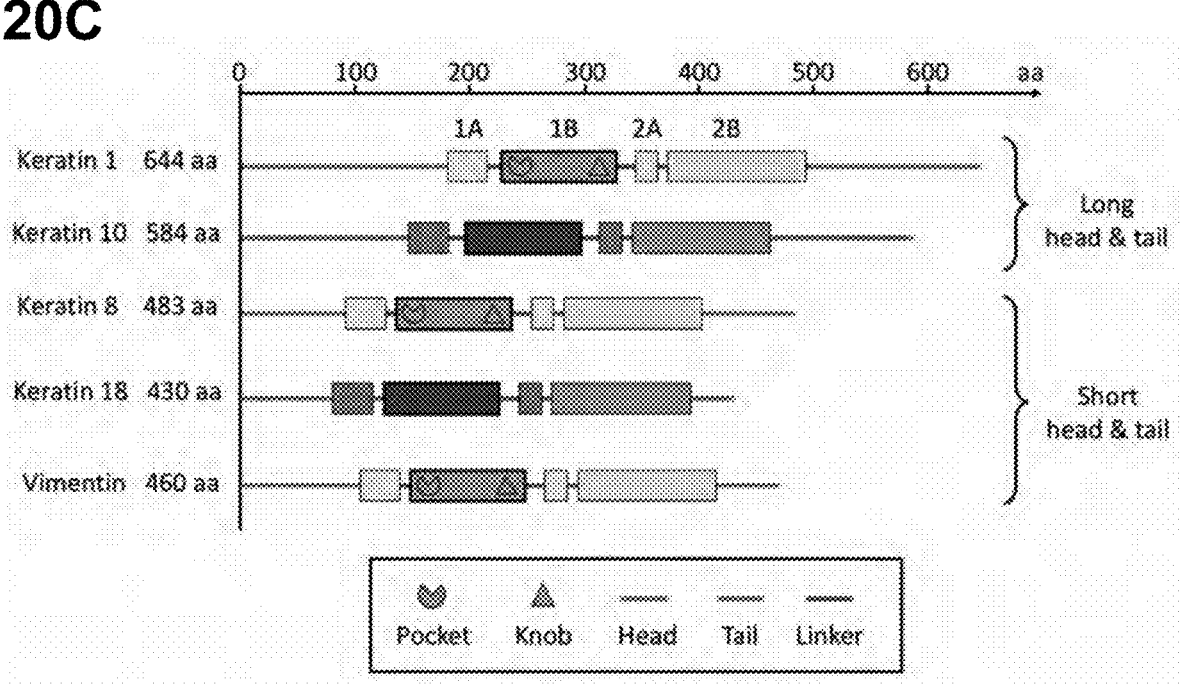
Figure 20 (cont'd)

21A K10 Hydrophobic Stripe

K10-1B     207-KNQILNLTTDNANILLQIDNARLAADDFRLK-237 (SEQ ID NO:68)

Vimentin-1B 158-PRQVDQLTNDKARVEVERDNLAEDIMRLREK-188 (SEQ ID NO:69)

21B K1 Interaction Residues

K1-1B     281-ENEFVTIKKDVDGAYMTKVDLQAKLDNLQQE-311 (SEQ ID NO:70)

Vimentin-1B 200-ENTLQSFRQDVDNASLARLDLERKVESLQEE-230

(SEQ ID NO:71)

21C Anchoring Knob

K1-1B     314-YLTAYQA-321 (SEQ ID NO:72)

Vimentin-1B 233-FLKKLHEE-240 (SEQ ID NO:73)

21D Vimentin-1B Homotetramer

21E
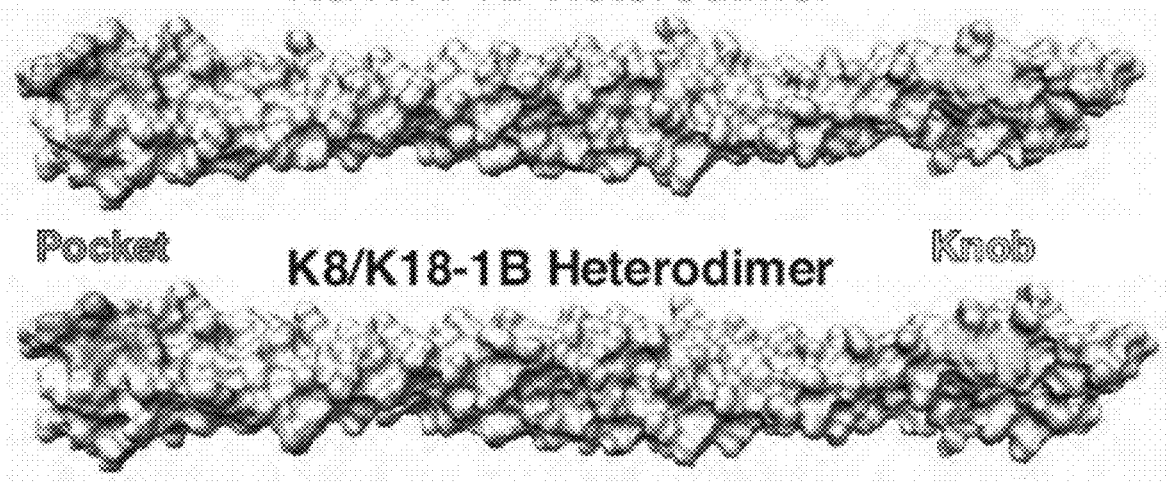
K5/K14-1B Heterodimer
K8/K18-1B Heterodimer
Pocket                                                                  Knob
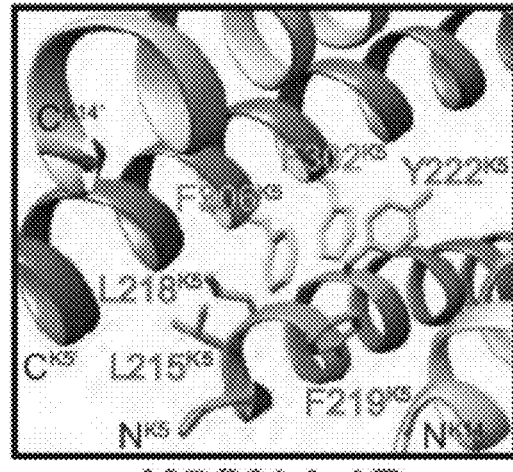
**K5/K14-1B
Heterotetramer**
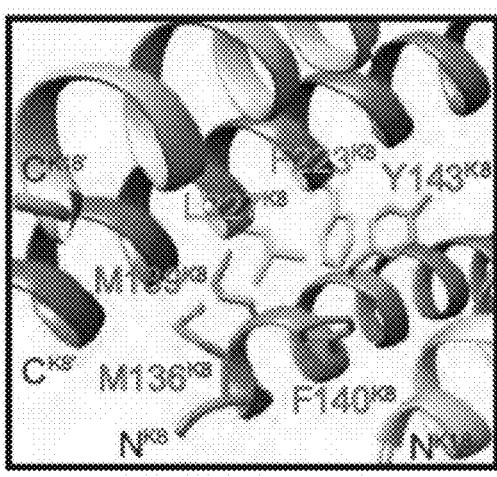
**K8/K18-1B
Heterotetramer**
Figure 21 (cont'd)

25A    Vim FL 25B abolished filaments    Vim FL + WT 1B (therapeutic candidate)

25C    Vim FL + Pocket Mutant 1B

25D    Vim FL + Knob Mutant 1B

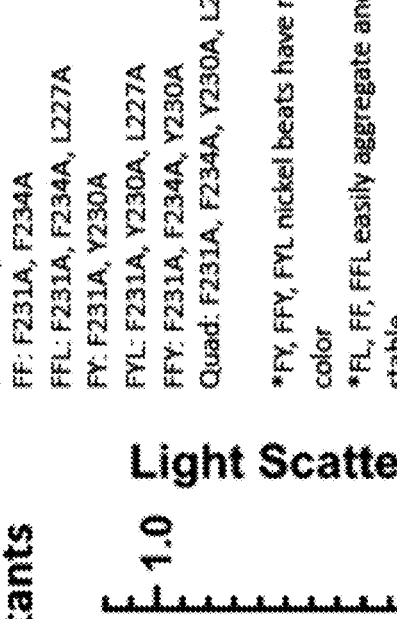
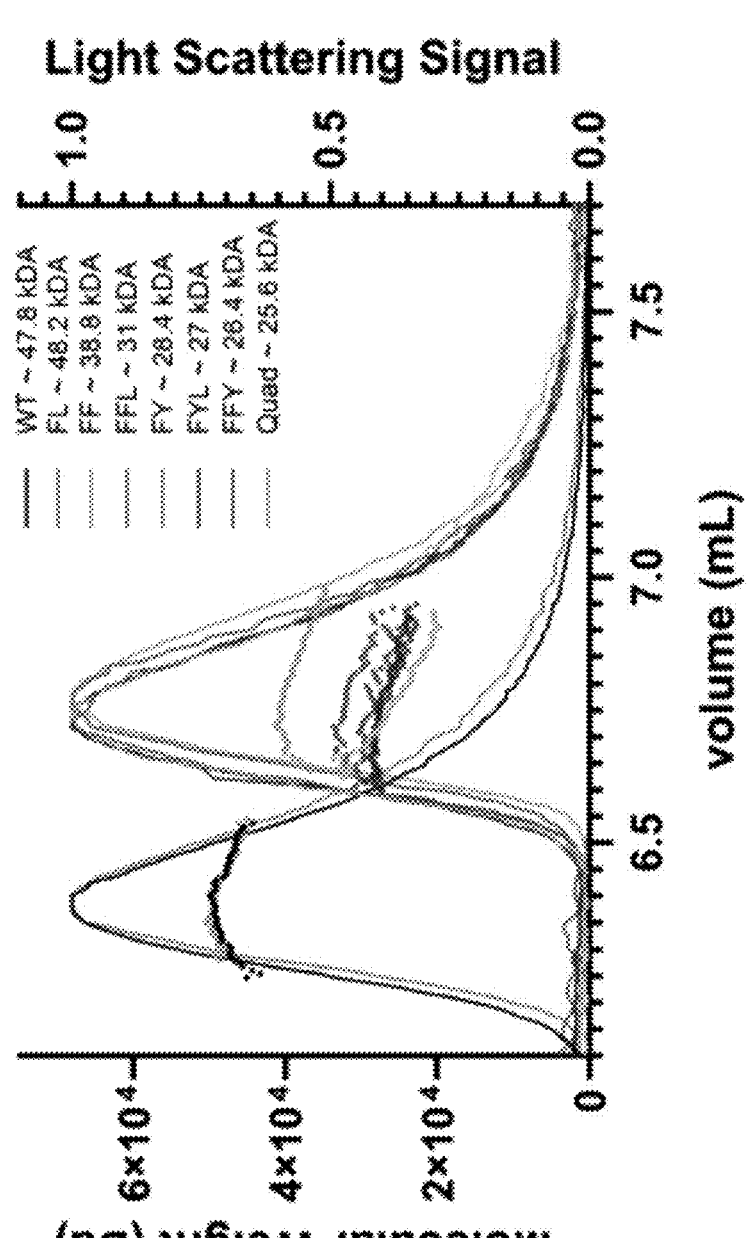
Figure 29

COMPOSITIONS AND METHODS FOR INHIBITING INTERMEDIATE FILAMENT TETRAMERIZATION

CROSS-REFERENCE TO RELATED APPLICATIONS

This application is the U.S. national phase application filed under 35 U.S.C. § 371 claiming benefit to International Patent Application No. PCT/US2019/055115, filed on Oct. 8, 2019, which is entitled to priority of U.S. Provisional Application Ser. No. 62/742,484, filed Oct. 8, 2018, U.S. Provisional Application Ser. No. 62/833,883, filed Apr. 15, 2019, and U.S. Provisional Application Ser. No. 62/855,203, filed on May 31, 2019, each of which is incorporated by reference herein in its entirety.

STATEMENT REGARDING FEDERALLY SPONSORED RESEARCH OR DEVELOPMENT

This invention was made with government support under AR070290 awarded by National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "047162-5265-00US-Sequence_Listing" in ASCII format. The text file containing the Sequence Listing of the present application was created on Apr. 7, 2021 and is 68,850 bytes in size.

BACKGROUND OF THE INVENTION

Keratin intermediate filaments (KIFs) are widespread in many tissues and are commonly over-expressed in many types of cancer. KIFs are formed by a process where two keratins (one type I and one type II) form a heterodimer, then heterodimers combine to form a tetramer, and tetramers then assemble into protofibrils, which ultimately assemble into the full, intact filament.

One of the most critical questions in keratin biology is how keratin heterodimers assemble into KIFs. A general understanding of the process is: one type I keratin and one type II keratin pair to form a parallel heterodimer; heterodimers then bind to form an anti-parallel tetramer; tetramers then merge to form a protofibril; and finally, protofibrils assemble into the complete KIF. A major knowledge gap exists in understanding the biochemical determinants of KIF assembly at atomic resolution. Recent x-ray crystal structures of the keratin 1/10 and keratin 5/14 helix 2B heterodimers provided key insights into heterodimer structure, such as the electrostatic and hydrophobic chemistry of the molecular surface. These structures did not, aside from a disulfide linkage related to inter-filament organization, capture information on how heterodimers assemble into KIFs.

The cytoskeleton within cells is composed of three major filamentous structures—actin microfilaments, intermediate filaments, and microtubules. Intermediate filaments (IFs) are named such because their diameter of 10-nm is between the diameter of microfilaments (~6-nm) and microtubules (~25-nm). IFs have numerous functions within cells, including cytoskeletal support, intracellular signaling, protein scaffolding, protein transport, and cellular stress management.

The importance of having IFs to perform these cellular functions is exemplified by the fact that over 80 human tissue-specific diseases have been linked to mutations in IF proteins. This broad group of IF-associated diseases are called "IF-pathies." One emphasis in personalized medicine is correlating a patient's genotype with phenotype; however, this concept is limited because it does not address the underlying macromolecular structure that bridges these two entities.

There is a major unmet need in clinical oncology for effective inhibitors of cancer metastasis. The following statement from an article on cancer cell metastasis highlights how significant the cancer metastasis problem is to society: "Metastasis is responsible for as much as 90% of cancer-associated mortality, yet it remains the most poorly understood component of cancer pathogenesis" (Chaffer & Weinberg, 2011, Science 331:1559-64).

IFs are a fundamental fibrous component of the cytoskeleton within cells and have an essential role in human health and disease: mutations in IF proteins cause or predispose humans to more than 80 diseases (Omary, 2009, J Clin Invest 119:1756-62). Relevant to this proposal, IFs also are increasingly being found to have an active role in cancer pathogenesis, including cancer cell invasion and metastasis (Chu et al., 1993, PNAS 90:4261-5; Chu et al., 1996, Am J Pathol 148:63-9). For example, keratins 1 and 10 were found to be over-expressed in squamous cell carcinoma (SCC), and keratins 6 and 16 upregulated in poorly differentiated SCC (Moll et al., 2008, Histochem Cell Biol 129:705-33). K8 was found to enhance growth of anaplastic thyroid cancer (Guo et al., 2018, Int J Mol Sci 19). Keratins 8 and 18 have been linked to cancer proliferation and negative regulation of apoptosis in breast cancer (Bozza et al., 2018, Oncotarget 9:23264-73). Another non-keratin IF protein, vimentin, causes increased invasion and metastasis of multiple cancer types (Chung et al., 2013, Curr Opin Cell Biol 25:600-12; Danielsson et al., 2018, cells, 7). For years IFs have served as diagnostic and prognostic markers in tumor pathology (Karanta et al., 2011, Oncogene 30:127-38). At least 17 types of cancer are associated with over-expressed keratins that serve as diagnostic tumor markers, including skin, breast, colon, liver, lung, pancreatic, and prostate cancers. Keratin expression patterns affect prognosis in at least 11 types of cancer. Together, this data supports the disruption of IFs as a valid treatment target.

Together, this data supports the disruption of IFs as a valid treatment target. The growing paradigm for IFs is that they are "effectors of cancer development and metastasis" (Sharma et al., 2019, Cells 8; Battaglia 2018, F1000Res 7). Vimentin's direct role in cancer metastasis, epithelial-mesenchymal transition, and facilitation of invadopodia (the microtentacles that help cancer cells migrate) make it an attractive therapeutic target (Satelli et al., 2011, Mol Life Sci 68: 3033-46; Sutoh et al., 2014, Euro J Cell Biol 93:157-69). Research has shown that both keratin and vimentin IFs are present in mature invadopodia, with intact vimentin IFs being required for the elongation phase of invadopodia (Schoumacher et al., 2010, J Cell Biol 189:541-56; Leong et al., 2014, Cell Rep 8:1558-70). This is consistent with the observation that vimentin was required for motility and invasion of prostate cancer (Zhao et al., 2008, Cel Biochem Funct 26:571-7). Despite these scientific advances, there are no current anti-cancer therapies in clinical use that target IFs.

There is a need in the art to identify how gene mutations alter IF protein structure and filament assembly in order to cause a specific clinical phenotype and for inhibitors of the assembly of KIFs. The present invention fills this need.

SUMMARY OF THE INVENTION

In one aspect, the invention provides a method for inhibiting intermediate filament formation. In one embodiment, the method comprises administering an inhibitor of the interaction between the anchoring knob domain of a first intermediate filament dimer and the hydrophobic pocket of a second intermediate filament dimer.

In one embodiment, the inhibitor is selected from a protein, a peptide, a peptidomemetic, an antibody, a small molecule chemical compound, CRISPR/Cas9, a nucleic acid, and a vector. In one embodiment, the inhibitor is a peptide.

In one embodiment, the method inhibits vimentin intermediate filament formation, wherein first intermediate filament dimer is a first vimentin homodimer, and the second intermediate filament dimer is a second vimentin homodimer. In one embodiment, the inhibitor prevents or reduces vimentin tetramerization.

In one embodiment, inhibitor is a peptide derived from the vimentin homodimer anchoring knob domain. In one embodiment, the peptide comprises a sequence at least 90% homologous to a sequence selected from the group consisting of SEQ ID NO:36-67.

In one embodiment, the inhibitor is CRISPR/Cas9 and the CRISPR/Cas9 comprises a guide RNA targeted to induce at least one mutation in the vimentin homodimer. In one embodiment, the least one mutation in the vimentin homodimer is at a vimentin residue selected from the group consisting of F233 and L237.

In one embodiment, the method inhibits keratin intermediate filament formation, wherein first intermediate filament dimer is a first K1/K10 heterodimer, and the second intermediate filament dimer is a second K1/K10 heterodimer. In one embodiment, the inhibitor prevents or reduces K1/K10 tetramerization.

In one embodiment, the inhibitor is a peptide derived from the K1/K10 anchoring knob domain. In one embodiment, the peptide comprises K1 residues F314 and L318. In one embodiment, the peptide comprises a sequence at least 90% homologous to a sequence selected from the group consisting of SEQ ID NO:3-34.

In one embodiment, the inhibitor is CRISPR/Cas9 and the CRISPR/Cas9 comprises a guide RNA targeted to induce at least one mutation in the K1/K10 heterodimer. In one embodiment, the least one mutation in the K1/K10 heterodimer is at a K1 residue selected from the group consisting of Y230, F231, F234, F314 and L318.

In one aspect, the invention provides a method of a disease or disorder associated with intermediate filament formation. In one embodiment, the method comprises administering an inhibitor of the interaction between the anchoring knob domain of a first intermediate filament dimer and the hydrophobic pocket of a second intermediate filament dimer.

In one embodiment, the method comprises administering an inhibitor of the interaction between the anchoring knob domain of a first K1/K10 heterodimer and the hydrophobic pocket of a second K1/K10 heterodimer. In one embodiment, the disease or disorder is selected from the group consisting of cancer, skin blistering and fragility disorders, disorders of keratinization, eye disease, scarring, and liver disease.

In one embodiment, the method comprises administering an inhibitor of the interaction between the anchoring knob domain of a first vimentin homodimer and the hydrophobic pocket of a second vimentin homodimer. In one embodiment, the disease or disorder is selected from the group consisting of lung injury, scarring, human immunodeficiency virus (HIV), cancer, and cataracts.

In one aspect, the invention provides a composition for inhibiting intermediate filament formation. In one embodiment, the composition comprises an inhibitor of the interaction between the anchoring knob domain of a first intermediate filament dimer and the hydrophobic pocket of a second intermediate filament dimer.

In one embodiment, the inhibitor inhibits the interaction between the anchoring knob domain of a first vimentin homodimer and the hydrophobic pocket of a second vimentin homodimer. In one embodiment, the inhibitor is a peptide comprising a sequence at least 90% homologous to one of SEQ ID NOs:36-67 or a nucleic acid molecule comprising a nucleic acid sequence encoding an amino acid sequence at least 90% homologous to one of SEQ ID NOs:36-67.

In one embodiment, the inhibitor inhibits the interaction between the anchoring knob domain of a first K1/K10 heterodimer and the hydrophobic pocket of a second K1/K10 heterodimer. In one embodiment, the inhibitor is a peptide comprising a sequence at least 90% homologous to one of SEQ ID NOs:3-34 or a nucleic acid molecule comprising a nucleic acid sequence encoding an amino acid sequence at least 90% homologous to one of SEQ ID NOs:3-34.

In one aspect, the invention provides a method of screening a library of compounds to provide an inhibitor of intermediate filament formation. In one embodiment, the method comprises (a) contacting a hydrophobic pocket domain of an intermediate filament dimer; (b) measuring a binding of the at least one compound to the hydrophobic pocket; (c) comparing the binding of the at least one compound to the hydrophobic pocket, with a binding of a comparator control to the hydrophobic pocket; and (d) selecting the at least one compound from the library when the binding of the at least one compound to the hydrophobic pocket, is increased at a statistically significant amount when compared with the binding of the comparator control to the hydrophobic pocket.

In one embodiment, the hydrophobic pocket domain of an intermediate filament dimer is the hydrophobic pocket domain of an K1/K10 heterodimer. In one embodiment, the hydrophobic pocket domain of an intermediate filament dimer is the hydrophobic pocket domain of a vimentin homodimer. In one embodiment, the invention provides a compound selected from a pool of modulators of inhibitor intermediate filament tetramer formation, wherein the pool is identified by the method of screening a library of compounds to provide an inhibitor of intermediate filament formation.

In one aspect, the invention provides a method of screening a library of compounds to provide an inhibitor of intermediate filament tetramer formation. In one embodiment, the method comprises (a) mixing a first intermediate filament dimer with at least one compound from the library to form a mixture; (b) adding a second intermediate filament dimer to the mixture; (c) measuring intermediate filament formation; (d) comparing the tetramer formation to a comparator control; and (e) selecting the at least one compound from the library when the tetramer formation is altered at a statistically significant amount when compared with the tetramer formation of the comparator control.

In one embodiment, the first intermediate filament dimer is a first K1/K10 heterodimer and the second intermediate filament dimer is a second K1/K10 heterodimer. In one embodiment, the first intermediate filament dimer is a first vimentin homodimer and the second intermediate filament dimer is a second vimentin homodimer.

In one embodiment, the invention provides a compound selected from a pool of modulators of inhibitor intermediate filament tetramer formation, wherein the pool is identified by the method of screening a library of compounds to provide an inhibitor of intermediate filament tetramer formation.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

FIG. 1A depicts a ribbon diagram of the wild-type K1/K10-1B crystal structure at 3.0 Å resolution. Helices within a heterodimer are oriented parallel, whereas the two heterodimers in the tetramer are anti-parallel.

FIG. 1B depicts the electrostatic surface potential mapped onto the K1/K10-1B heterodimer structure demonstrates a polarization of charge: the N-terminus has some basic charge (blue) while the majority of the distal 1B dimer is acidic (red). FIG. 1C depicts a close-up view of the N-terminal basic patches on the K1/K10-1B heterodimer. Three K1 (R239, R240, R241) and three K10 (K198, K201, K207) residues contribute positive charge. One basic patch (left) surrounds a hydrophobic pocket involved in tetramer formation (asterisk). FIGS. 1D and 1E depict the electrostatic surface potential mapped onto the K1/K10-1B tetramer structure which demonstrates it is overwhelmingly acidic: the anti-parallel orientation of the dimers within the tetramer eliminates the small basic potential at the dimer N-terminus. Unique molecular surface contours are present in the K1/K10-1B tetramer that do not exist in the dimer: one tetramer face has a long, linear, highly acidic surface groove (top of FIG. 1D, arrows; FIG. 1E, asterisks) whereas the other face contains a central concave pocket (bottom of FIG. 1D, asterisk) flanked by angled grooves (bottom of FIG. 1D, arrows). FIG. 1F depicts residues forming the central concave pocket on one face of the K1/K10-1B tetramer are shown and colored based on residue property (red, acidic; dark blue, basic; orange, hydrophobic; light blue, polar). The asterisk marks the 2-fold symmetry axis in the tetramer. FIG. 1G depicts a close-up of one "angled groove" (arrow) in the K1/K10-1B tetramer colored to demonstrate a portion of all four tetramer helices contributes to groove formation. Residues in the hydrophobic pocket/anchoring knob mechanism of tetramer assembly are yellow.

FIG. 2A through FIG. 2F, depicts experimental results demonstrating the biochemical basis for K1/K10-1B heterotetramer formation. FIG. 2A depicts results demonstrating that the molecular surface of the K1/K10-1B heterodimer can be divided into a predominantly hydrophobic face (top) and a predominantly polar face (bottom). The molecular surface is colored according to hydrophobic potential: hydrophobic residues are orange and polar residues are blue (color intensity indicates magnitude of potential). Select residues are labeled blue (K1) or pink (K10). FIG. 2B depicts results demonstrating that four key regions along the hydrophobic face of the K1/K10-1B heterodimer drive tetramer formation: an N-terminal hydrophobic pocket (gold), a K10 hydrophobic stripe (purple), K1 interaction residues (green), and a C-terminal anchoring knob (yellow). FIG. 2C depicts one end of the K1/K10-1B tetramer depicting the anchoring knob residues (yellow sticks) binding into the hydrophobic pocket (gold surface). FIG. 2D depicts a stick representation of the anchoring knob/hydrophobic pocket mechanism in tetramer formation. $F314^{K1'}$ and $L318^{K1'}$ wedge between $L227^{K1}$, $Y230^{K1}$, $F231^{K1}$ and $F234^{K1}$; the aromatic ring of $F314^{K1'}$ stacks against that of $F234^{K1}$. A salt bridge between $K207^{10}$ and $E311^{K1'}$ is shown. FIG. 2E depicts experimental results demonstrating that ten K10 residues (purple) in the hydrophobic stripe of one dimer (K10 helix backbone pink) interact with twelve K1' residues (green) from the partner dimer (K1' backbone light blue) to create an anti-parallel tetramer interface. FIG. 2F depicts a close-up view of the one region in the K1/K10-1B tetramer where K10 and K10' interact; this is facilitated by $L236^{K10}$ interacting with $L244^{K10'}$. $N240^{K10}$ is the center of the 2-fold symmetry in the tetramer, hence L236-L244' and the reciprocal L236'-L244 interactions are on either side of N240.

FIG. 3A through FIG. 3D, depicts the biophysical analysis of wild-type and $K1^{S233L}$ mutant keratin 1/10-1B in solution. FIG. 2A depicts recombinant bacterial expression lysates for $His_6$-tagged K10-1B (1), wild-type K1-1B (2), and $K1^{S233L}$-1B (3). Wild-type K1/K10-1B before (4) and after (5) nickel affinity purification. Wild-type K1/10-1B (6) and $K1^{S233L}$/K10-1B (7) after thrombin removal of $His_6$-tag on K10 and subsequent gel filtration (untagged K10 overlaps with K1 after tag removal). FIG. 2B depicts gel filtration of wild-type K1/K10-1B (solid line) produced two peaks from 52 to 67 mL whereas the $K1^{S233L}$/K10-1B mutant (dotted line) produced one major peak from 50 to 55 ml that eluted earlier than wild-type. V0=Void Volume. FIG. 3C depicts multi-angle light scattering results demonstrating wild-type K1/K10-1B (solid line) exists mostly as a tetramer (observed MW 49100; calculated tetramer MW 49700), with a small amount of dimer (observed MW 26160; calculated MW 24840), in 100 mM NaCl solution. This does not change in 200 mM NaCl. K1S233L/K10-1B forms higher MW aggregates than wild-type in both 100 mM NaCl (observed MW 62640) and 200 mM NaCl (observed MW 86870) solutions. FIG. 3D depicts circular dichroism showing identical helical secondary structure for wild type K1/K10-1B and mutant $K1^{S233L}$/K10-1B.

FIG. 4A through FIG. 4F, depicts structural features of mutant $K1^{S233L}$/K10-1B. FIG. 4A depicts the N-terminus of the wild-type K1/K10-1B (left) and mutant $K1^{S233L}$/K10-1B (right) heterodimer structures depicted as a ribbon (top) and molecular surface (bottom). Both $S233^{K1}$ and $S233L^{K1}$ are surface-exposed, but $S233L^{K1}$ generates a new hydrophobic surface patch compared to wild-type S233K1. FIG. 4B depicts the crystal structure of $K1^{S233L}$/K10-1B octamer presented as a ribbon diagram. FIG. 4C depicts a close up view of the biochemical interactions between two K1/K10 tetramers (T1, T2) caused by the $L233^{K1}$ mutation (red). $L233^{K1}$ mediates hydrophobic assembly of the octamer by interacting with five residues from the opposing tetramer: $Y230^{K1'}$, $L233^{K1'}$, $F234^{K1'}$, $F314^{K1'}$, $Ala317^{K1'}$. FIG. 4D depicts a section of the $K1^{S233L}$/K10-1B crystal lattice demonstrating "pseudo-tonotubular" structures (corresponding to the octamer) with diameter of 45 Å. FIG. 4E depicts one end of the K1$^{S233L}$/K10-1B tetramer structure depicting L227$^{K1}$ interacting with L318$^{K1'}$ to form the N-terminal boundary of the hydrophobic pocket. The hydrophobic pocket from one dimer is depicted as a transparent molecular surface and colored according to hydrophobic potential (orange, hydrophobic; white to blue, polar); only the anchoring knob residues from the partner dimer are shown (yellow sticks). FIG. 4F depicts cadmium ions (green spheres) bound to the N-terminal methionine of K1-1B and to C-terminal residues E322$^{K1}$ and H287$^{K10}$ caused small structural changes at the termini (e.g. position of L227$^{K1}$) compared to the S233L$^{K1}$ mutant structure.

FIG. 5A and FIG. 5B, depicts R267Y$^{K1}$ and F231L$^{K1}$ mutations modeled onto the K1/K10-1B tetramer structure. FIG. 5A depicts experimental results demonstrating that R267$^{K1}$ occupies a solvent-exposed position in the center of the K1-1B coil (blue); mutation to tyrosine (red) is not predicted to interfere with K1/K10 dimer or tetramer assembly. FIG. 5B depicts experimental results demonstrating that F231$^{K1}$ (dark blue) lies at the tetramer interface and forms part of the hydrophobic pocket that binds the anchoring knob (yellow) in K1/K10-1B tetramer assembly. Mutation of F231$^{K1}$ to leucine (red) alters this position's interactions with F314$^{K1'}$ and L318$^{K1'}$ of the anchoring knob; the structural model suggests a weakening of interactions which could cause disruption of the hydrophobic pocket/anchoring knob tetramer assembly mechanism.

FIG. 6A through FIG. 6D, depicts a comparison between the K1/K10-1B A$_{11}$-heterotetramer and the vimentin-1B A$_{11}$-homotetramer. FIG. 6A the sequence alignment between the K10-1B hydrophobic stripe (ten residues colored purple) and the corresponding vimentin-1B region demonstrates that only two of five K10 hydrophobic residues (orange background) are identical (A169$^{vim}$) or similar (V173$^{vim}$) in vimentin. Four out of five non-hydrophobic residues in the K10 stripe are identical or similar in vimentin. FIG. 6B depicts results demonstrating that of twelve K1 interaction residues (green), ten are identical or similar in vimentin (bold); Y295$^{K1}$ and A303$^{K1}$ are the exceptions. FIG. 6C depicts results demonstrating that the K1-1B anchoring knob is identical to that in vimentin-1B: F233$^{vim}$ and L237$^{vim}$ (bold) are homologous to F314 and L318 in K1 (yellow). FIG. 6D depicts a structural representation of vimentin-1B A$_{11}$-homotetramer (PDB Code 3UF1). (Top) One homodimer is shown as a white molecular surface with the N-terminal hydrophobic pocket colored orange and the C-terminal anchoring knob colored yellow. The partner homodimer is shown as a maroon chain trace with the relevant anchoring knob and hydrophobic pocket residues shown as yellow and blue sticks, respectively. (Bottom) Zoomed-in image of the hydrophobic pocket/anchoring knob mechanism of vimentin homotetramerization. L149, Y150, and E153 from one helix and M154 from the homodimer partner helix form the pocket (orange) bound by F233 and L237 (yellow).

FIG. 7, comprising FIG. 7A and FIG. 7B, depicts the structural analysis wild-type K1/K10-1B and mutant K1$^{S233L}$/K10-1B heterodimer structures. FIG. 7A depicts the amino acid contacts at the heterodimer interface for both wild-type K1/K10-1B and mutant K1$^{S233L}$/K10-1B x-ray crystal structures were analyzed and plotted onto a single residue contact map. Intramolecular (within K1 or K10 only) and intermolecular (between K1 and K10) salt bridges are plotted red. Hydrogen bonds are plotted green. Interactions between hydrophobic residues are plotted orange (hydrophobic residues are defined as A, I, L, F, V, P, M, W), including hydrophobic interaction with the aromatic residue tyrosine. Other types of molecular contacts are plotted black. Analyses were performed using WHAT IF (defines atoms as 'in contact' when the distance between their Van der Waals surfaces is <1.0 Å), ESBRI, and PDBePISA. Since S233$^{K1}$ is a surface-exposed residue, its mutation to L233 does not impact the heterodimer interface. Hence, the analysis of both heterodimer interfaces was used to obtain the contact map. FIG. 7B depicts the wild-type K1/K10-1B and mutant K1$^{S233L}$/K10-1B heterodimer structures superimposed demonstrating they have a root-mean-square-deviation (RMSD) of 0.736 Å. The superposition shows slight variation in the positioning of the K10 C-terminus.

FIG. 8A and FIG. 8B, depicts mapping of cross-linked mouse K1/K10-1B tryptic peptide data onto the human K1/K10-1B tetramer structure. FIG. 8A depicts a comparison of five cross-linked mouse K1/K10-1B tryptic peptides previously described (*J. Mol. Biol.* (1993) 230, 436-452.) with the expected corresponding cross-links in human K1/K10-1B. Cross-linked lysines are color-coded for easier identification in panel b. Lysine 237 from K10 appears in two distinct cross-linked species (magenta and blue). FIG. 8B depicts the crystal structure of human K1/K10-1B with backbone presented in ribbon diagram and pertinent lysine side chains as sticks. Previously DST (disulfosuccinimidyl tartrate) was used as cross-linking reagent [cross-link arm of 0.6 nm]; this means lysines within ~15 Å can cross-link. In the structure, K288$^{K1}$ and K237$^{K10}$ are 13.4 Å apart. K201$^{K10}$ and K284$^{K10}$ are 16.8 Å apart, and K246$^{K1}$ and K304$^{K1}$ are 21.6 Å apart: both of these lysine pairings are structurally adjacent and can be expected to form the observed lysine cross-links when factoring in protein dynamics in solution (i.e., the crystal structure is a static picture of a protein moment in time, but in solution, the lysine side chains, based on proximity in the tetramer structure, should be able to move into a conformation amenable to cross-link formation with DST). It is also important to note previous reports had peptide cross-links of various oligomer sizes; thus, the presence of an octamer species (two tetramers) will influence the cross-links observed. Both K269$^{K1}$ and K276$^{K1}$ are surface-exposed residues that structurally appear to require the higher order oligomer to explain the observed cross-links. The key point is the positions of the lysines in the wild-type K1/K10-1B tetramer structure are consistent with the biochemical cross-linking data.

FIG. 9, comprising FIG. 9A through FIG. 9F, depicts amino acid sequence analysis of the hydrophobic pocket-anchoring knob mechanism of keratin tetramer assembly. Multiple sequence alignments of the hydrophobic pocket and anchoring knob regions of helix 1B are shown for all six types of intermediate filaments. Orange (pocket) and yellow (knob) background highlights mark positions critical for K1-mediated K1/K10-1B tetramer assembly. FIG. 9A depicts an alignment demonstrating that the hydrophobic pocket and anchoring knob sequences are highly conserved in type II keratins; these structural motifs utilize bulky hydrophobic and aromatic residues. FIG. 9B depicts an alignment demonstrating that consistent with structural analysis of K1/K10-1B showing K1-1B contributes both the hydrophobic pocket and anchoring knob residues involved in tetramer formation, type I keratins do not conserve either the pocket or knob. FIG. 9C depicts an alignment demonstrating that type III IFs, except for syncoilin, mostly conserve the anchoring knob sequence; desmin and glial fibrillary acidic protein (GFAP) substitute leucine in the distal position with other hydrophobic residues (valine and isoleucine, respectively). As for the hydrophobic pocket, type III IFs do not conserve the K1 sequence, particularly at the distal phenylalanine position. However, structural analysis of a vimentin homotetramer demonstrated a hydrophobic pocket exists and binds an anchoring knob (FIG. 6). The critical point is that the sequence, residue positions, and manner of pocket formation differs between type III IFs and type II keratins. The residues involved in pocket formation for vimentin are underlined. FIG. 9D depicts an alignment demonstrating that type IV IFs have a vimentin-like hydrophobic pocket, but lack a bulky hydrophobic residue at the knob position equivalent to L318K1. A unique type IV IF pocket-knob mechanism cannot be excluded; perhaps the proximal phenylalanine is sufficient. FIG. 9E depicts an alignment demonstrating that lamins (type V IFs) do not conserve the K1 pocket-knob sequences. FIG. 9F depicts an alignment demonstrating that eye lens IFs (type VI) do not conserve the K1 pocket-knob sequences.

FIG. 10B depicts mapping of amino acid sequence differences between K1/K5 and K10/K14 onto the molecular surface of the wild-type K1/K10-1B structure. FIG. 10A depicts residues in K1 (blue) and K10 (pink) that are unique (non-identical) compared with basal keratins K5 and K14, respectively, are mapped onto the K1/K10-1B heterodimer structure (represented as a molecular surface). Residues that are conserved/identical are tan. K1 residues that are non-identical to K5 are colored blue, while K10 residues that are non-identical to K14 are colored pink. The majority of unique residues for K1 and K10 align along the outer aspect of the helices. The majority of the conserved residues lie along the dimer interface. This distribution of unique residues enables keratins to maximize the diversity of surface properties, such as surface charge and shape, while maintaining a common structural coiled-coil fold. FIG. 10B depicts the same mapping and coloring of unique residues applied to the K1/K10-1B tetramer structure.

FIG. 11A and FIG. 11B, depicts the Observed electron density throughout the K1$^{S233L}$/K10-1B crystal structure. FIG. 11A depicts experimental results demonstrating that the two K1$^{S233L}$-1B and two K10-1B molecules composing the K1$^{S233L}$/K10-1B tetrameric crystal structure are depicted as yellow sticks in electron density (blue, contoured at 0.8σ). A red box highlights one anchoring knob-hydrophobic pocket site in the symmetric, anti-parallel tetramer. FIG. 11B depicts a close-up view of one anchoring knob-hydrophobic pocket site in the K1$^{S233L}$/K10-1B crystal structure (K10 residues have been omitted for clarity). The K1-1B containing the hydrophobic pocket is depicted as blue sticks in electron density (cyan, contoured at 0.8σ). The K1-1B' from the partner heterodimer contains the anchoring knob and is depicted as yellow sticks in electron density (green, contoured at 0.8σ).

FIG. 13 is a schematic depicting a screening assay for keratin tetramer formation. K1, which harbors both the hydrophobic pocket and anchoring knob residues, is treated uniquely for dimer 1 (GST tag on K1) compared to dimer 2 (His tag on K1).

FIG. 17 depicts the four proposed modes of keratin tetramer alignment in filament formation.

FIG. 20A depicts a sequence alignment between the K10-1B hydrophobic stripe (ten residues colored purple) and the corresponding vimentin-1B region demonstrates that only two of five K10 hydrophobic residues (orange background) are identical (A169$^{vim}$) or similar (V173$^{vim}$) in vimentin. Four out of five non-hydrophobic residues in the K10 stripe are identical or similar in vimentin. FIG. 21B depicts experimental results demonstrating that of twelve K1 interaction residues (green), ten are identical or similar in vimentin (bold); Y295$^{K1}$ and A303$^{K1}$ are the exceptions. FIG. 21C depicts experimental results demonstrating that the K1-1B anchoring knob is identical to that in vimentin-1B: F233$^{vim}$ and L237$^{vim}$ (bold) are homologous to F314 and L318 in K1 (yellow). FIG. 21D depicts a structural representation of vimentin-1B A$_{11}$-homotetramer (PDB Code 3UF1). (Top) One homodimer is shown as a white molecular surface with the N-terminal hydrophobic pocket colored orange and the C-terminal anchoring knob colored yellow. The partner homodimer is shown as a maroon chain trace with the relevant anchoring knob and hydrophobic pocket residues shown as yellow and blue sticks, respectively. (Bottom) Zoomed-in image of the hydrophobic pocket/anchoring knob mechanism of vimentin homotetramerization. L149, Y150, and E153 from one helix and M154 from the homodimer partner helix form the pocket (orange) bound by F233 and L237 (yellow). M154$^{vim}$ is positioned closest to F233vim (3.32 Å), followed by E153 (3.58 Å), Y150 (4.28 Å), and L149 (5.0 Å), suggesting that F233$^{vim}$ interactions with M154$^{vim}$ and E153$^{vim}$ are important for vimentin-1B tetramerization. (E) The K1/K10-1B tetramer structure was used as a template to model the K5/K14-1B and K8/K18-1B structures to demonstrate that the conservation of the anchoring knob/hydrophobic pocket mechanism exists among type II keratins as well as type III IFs like vimentin.

FIG. 23A through FIG. 23D, depicts a comparison of K1/K10-1B and vimentin-1B tetramer structures. FIG. 23A depicts sequence alignments of K1-1B and K10-1B each with vimentin 1B. There is 36% sequence identity between K1-1B and vimentin 1B (yellow), and 33% sequence identity between K10-1B and vimentin 1B (green).

FIG. 23B depicts the wild-type K1/K10-1B and vimentin-1B (PDB Code 3UF1) tetramer structures were superimposed and have a RMSD of 1.3 Å. FIG. 23C depicts the keratin residues that are identical to vimentin-1B were mapped onto a molecular surface representation of the K1/K10-1B tetramer structure and colored yellow (K1-1B) or green (K10-1B). All K1/K10-1B residues not identical to vimentin-1B were mapped onto the molecular surface of the K1/K10-1B tetramer structure and colored red, demonstrating a significant proportion of the K1/K10-1B molecular surface will have differences in chemistry compared to vimentin-1B. FIG. 23D depicts results to further illustrate how the molecular surface of the K1/K10-1B tetramer differs from vimentin-1B. Both identical residues (lighter colors) and residues unique to K1 or K10 (darker colors) were divided into hydrophobic, positively charged, and negatively charged groups and mapped onto the K1/K10-1B tetramer molecular surface. The majority of the unique hydrophobic residues are located in the central region of the 1B domain, whereas the unique charged residues appear evenly distributed. Definitions of residues were acidic (D, E), basic (K, R), and hydrophobic (A, F, I, L, M, P, V, W)

FIG. 25A depicts electron microscopy of wild-type full length vimentin filaments. FIG. 25B depicts electron microscopy demonstrating that wild-type vimentin-1B peptide abolishes vimentin filament assembly. FIG. 25C depicts electron microscopy demonstrating that vimentin-1B peptide with pocket mutation no longer prevents vimentin filament assembly. FIG. 25D depicts electron microscopy demonstrating that vimentin-1B peptide with knob mutation no longer prevents vimentin filament assembly.

FIG. 29 depicts mutagenesis studies of K1/K10-1B pocket double and triple mutants compared to WT.

DETAILED DESCRIPTION

Figure 1:
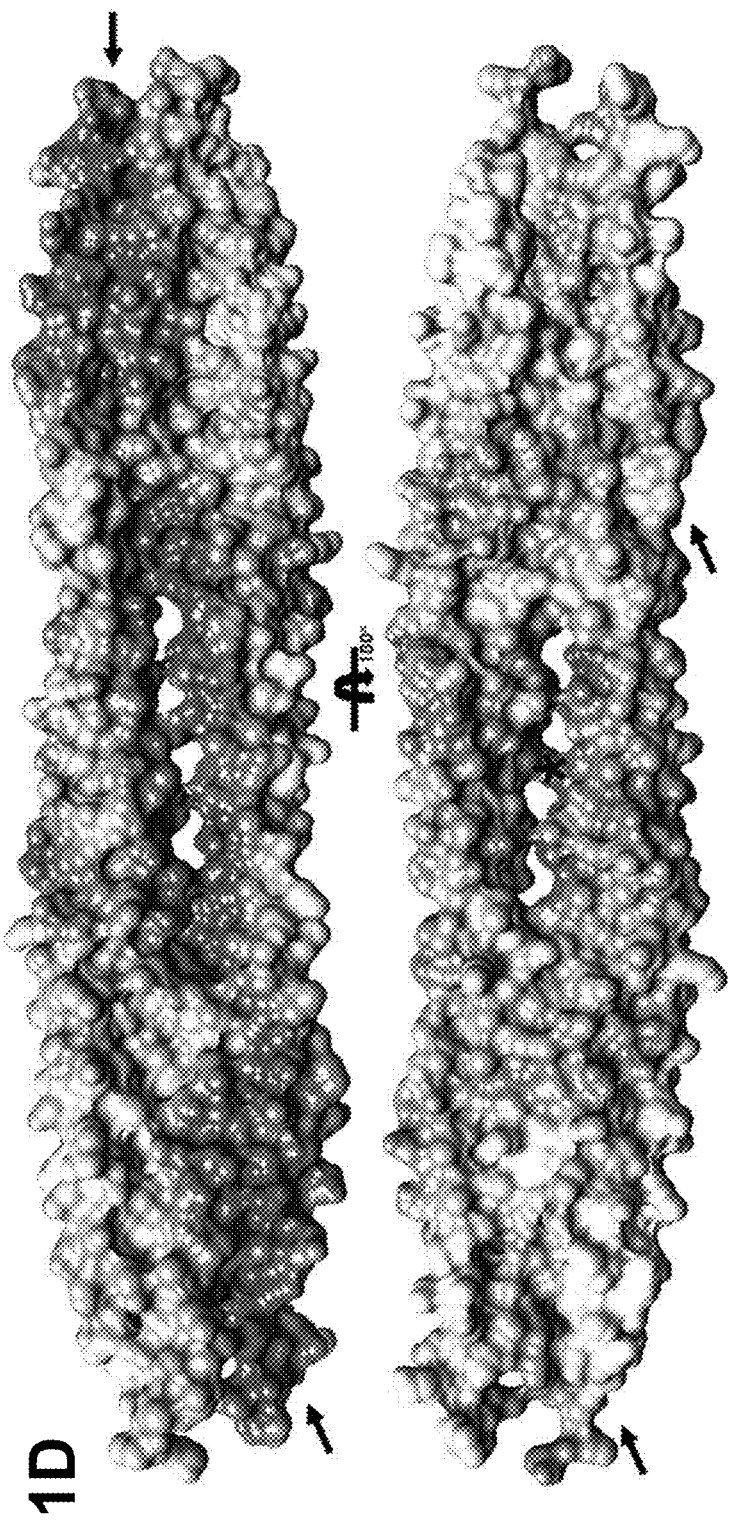
FIG. 1, comprising FIG. 1A through FIG. 1G depicts experimental results demonstrating the molecular surface properties of the wild-type K1/K10-1B dimer and tetramer.

In one aspect, the present invention provides compositions and methods for inhibiting the tetramerization of the keratin 1/keratin 10 (K1/K10) heterodimer. In one embodiment, the present invention provides compositions and methods for inhibiting the formation of keratin intermediate filaments (KIFs). For example, in one embodiment, the compositions and methods inhibit the interaction between the anchoring knob of a first keratin 1/keratin 10 heterodimer and the hydrophobic pocket of a second keratin 1/keratin 10 heterodimer. In one embodiment, the hydrophobic pocket comprises the keratin 1 residues Y230, F231 and F234 of the keratin 1/keratin 10 heterodimer. In one embodiment, the anchoring knob comprises keratin 1 residues F314 and L318 of keratin 1/keratin 10 heterodimer In one aspect, the invention provides a keratin 1, keratin 10, or keratin 1/keratin 10 heterodimer-derived peptide. In one embodiment, the keratin 1, keratin 10, or keratin 1/keratin 10 heterodimer-derived peptide is a linear peptide. In one embodiment, the linear peptide comprises a sequence selected from SEQ ID NOs: 3-34, or a fragment thereof, or a sequence at least 90% homologous to a sequence selected from SEQ ID NOs: 3-34, or a fragment thereof.

In another aspect, the invention provides a method of treating or preventing a disease or disorder associated with over expression of KIFs. In one embodiment, the invention provides a method of treating or preventing cancer. In one embodiment, the invention provides a method of treating or preventing skin blistering and fragility disorders (epidermolysis bullosa simplex), disorders of keratinization (epidermolytic ichthyosis, palmoplantar keratoderma, pachyonychia congenita), eye disease (Meesmann corneal dystrophy), and liver disease (cirrhosis), cataracts (vimentin), amyotrophic lateral sclerosis/Lou Gehrig's disease (peripherin), and brain cancer (neurofilaments). For example, in one embodiment, the invention provides method of treating or preventing a disease or disorder in a subject in need thereof by administering to the subject an effective amount of a composition of the invention.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "effective amount" or "therapeutically effective amount" of a compound is that amount of compound which is sufficient to provide a beneficial effect to the subject to which the compound is administered.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human. As used herein, a subject is preferably a mammal such as a non-primate (e.g., cows, pigs, horses, cats, dogs, rats, etc.) and a primate (e.g., monkey and human), most preferably a human.

"Parenteral" administration of a composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

A "therapeutic" treatment is a treatment administered to a subject who exhibits signs of pathology, for the purpose of diminishing or eliminating those signs.

As used herein, "treating a disease or disorder" means reducing the frequency or severity with which at least one sign or symptom of the disease or disorder is experienced by a patient.

The phrase "therapeutically effective amount," as used herein, refers to an amount that is sufficient or effective to reduce, prevent or treat (delay or prevent the onset of, prevent the progression of, inhibit, decrease or reverse) the frequency or severity of at least one sign or symptom of a disease or disorder, including alleviating symptoms of such diseases.

To "treat" a disease or disorder as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates, in part, to the unexpected finding that the keratin 1/keratin 10 (K1/K10) heterodimer has a hydrophobic pocket formed at the N-terminus providing a receptor site for the C-terminal anchoring knob on a neighboring K1/K10 heterodimer which facilitates tetramer formation. In one embodiment, the invention provides compositions for inhibiting the tetramerization of the K1/K10 heterodimer. Structural analysis of the K1/K10 tetramer complex described herein revealed that a hydrophobic pocket comprising the K1 residues Y230, F231 and F234 on one K1/K10 heterodimer interacts with an anchoring knob domain comprising K1 residues F314 and L318 on the second K1/K10 heterodimer and is essential to tetramer formation. Accordingly, in one aspect, the invention provides an inhibitor of the interaction between the K1/K10 hydrophobic pocket and the K1/K10 anchoring knob. In one embodiment, the inhibitor is a K1/K10 anchoring knob domain-derived peptide.

The present invention, in part, relates to the unexpected finding that that loss of knob structure has a damaging impact on IF assembly (the rate of and/or the length of) across IF types including keratins with long heads and tails (K1/K10), keratins with short heads and tails (K8/18), and heterodimeric and homodimeric (vimentin) IF proteins. In one embodiment, the invention provides compositions for inhibiting the tetramerization of IFs. In one embodiment, the invention provides compositions for inhibiting the tetramerization of the vimentin homodimer.

Further, it is contemplated herein that the novel inhibitors disclosed herein have various applications, including the treatment and prevention of diseases and disorders associated with high levels or over-expression of IFs including KIFs and vimentin. In one embodiment, the inhibitors of the invention may treat or prevent diseases or disorders, including but not limited to cancer. In one embodiment, the inhibitors of the invention may treat or prevent cancer metastasis. Accordingly, the invention provides methods for treating or preventing a disease or disorder associated with high levels or overexpression of KIFs in a subject in need thereof. In one embodiment, the method comprises administering to the subject an effective amount of a composition comprising a K1/K10 heterodimer-derived peptide. In another embodiment, the method comprises administering to the subject an effective amount of a nucleic acid encodes a K1/K10 heterodimer-derived peptide The invention also provides methods for treating or preventing a disease or disorder associated with high levels or overexpression of vimentin in a subject in need thereof. In one embodiment, the method comprises administering to the subject an effective amount of a composition comprising a vimentin-derived peptide. In another embodiment, the method comprises administering to the subject an effective amount of a nucleic acid encodes a vimentin-derived peptide Compositions In one embodiment, the present invention provides a composition for inhibiting the tetramerization of intermediate filaments (IFs). In one embodiment, the present invention provides a composition for inhibiting the tetramerization of keratin intermediate filaments (KIFs). In one embodiment, the present invention provides a composition for inhibiting the tetramerization of the keratin 1/keratin 10 (K1/K10) heterodimer. In one embodiment, the present invention provides a composition for inhibiting the tetramerization of the keratin 5/keratin 14 (K5/K14) heterodimer. In one embodiment, the present invention provides a composition for inhibiting the tetramerization of the keratin 1/keratin 10 (K1/K10) heterodimer. In one embodiment, the present invention provides a composition for inhibiting the tetramerization of the keratin 8/keratin 18 (K8/K18) heterodimer.

In one embodiment, the present invention provides a composition for inhibiting the tetramerization of vimentin. In one embodiment, the present invention provides a composition for inhibiting the tetramerization of GFAP, desmin, neurofilament, lamin, or nestin.

In one embodiment, the present invention provides a composition for inhibiting the tetramerization of the keratin 1/keratin 10 (K1/K10) heterodimer. Tetramerization of the K1/K10 heterodimer is essential to formation of keratin intermediate filaments (KIFs). Thus, in one embodiment, the invention provides a composition for inhibiting KIF formation. In various embodiments, the composition inhibits the interaction between the anchoring knob of a first K1/K10 heterodimer and the hydrophobic pocket of a second K1/K10 heterodimer.

In one embodiment, the composition of the invention comprises an inhibitor of K1/K10 heterodimer tetramerization. An inhibitor of K1/K10 heterodimer tetramerization is any compound, molecule, or agent that reduces, inhibits, or prevents the binding of a first K1/K10 heterodimer to a second K1/K10 heterodimer. For example, an inhibitor of K1/K10 heterodimer tetramerization is any compound, molecule, or agent that reduces the interaction between the anchoring knob of a first K1/K10 heterodimer and the hydrophobic pocket of a second K1/K10 heterodimer. In various embodiments, an inhibitor of the interaction between the anchoring knob of a first K1/K10 heterodimer and the hydrophobic pocket of a second K1/K10 heterodimer comprises a nucleic acid, a peptide, a small molecule chemical compound, an antagonist, an aptamer, an antibody, a peptidomimetic, or any combination thereof.

In one embodiment, K1 has a sequence of:

```
                                       (SEQ ID NO: 1)
MSRQFSSRSGYRSGGGFSSGSAGIINYQRRTTSSSTRRSGGGGGRFSSCG

GGGGSFGAGGGFGSRSLVNLGGSKSISISVARGGGRGSGFGGGYGGGGFG

GGGFGGGGFGGGGIGGGGFGGFGSGGGGFGGGGFGGGGYGGGYGPVCPPG

GIQEVTINQSLLQPLNVEIDPEIQKVKSREREQIKSLNNQFASFIDKVRF

LEQQNQVLQTKWELLQQVDTSTRTHNLEPYFESFINNLRRRVDQLKSDQS

RLDSELKNMQDMVEDYRNKYEDEINKRTNAENEFVTIKKDVDGAYMTKVD

LQAKLDNLQQEIDFLTALYQAELSQMQTQISETNVILSMDNNRSLDLDSI

IAEVKAQNEDIAQKSKAEAESLYQSKYEELQITAGRHGDSVRNSKIEISE

LNRVIQRLRSEIDNVKKQISNLQQSISDAEQRGENALKDAKNKLNDLEDA

LQQAKEDLARLLRDYQELMNTKLALDLEIATYRTLLEGEESRMSGECAPN

VSVSVSTSHTTISGGGSRGGGGGYGSGGSSYGSGGGSYGSGGGGGGRG

SYGSGGSSYGSGGGSYGSGGGGGHGSYGSGSSSGGYRGGSGGGGGSSG

GRGSGGGSSGGSIGGRGSSSGGVKSSGGSSSVRFVSTTYSGVTR.
```

In one embodiment, K10 has a sequence of:

```
                                       (SEQ ID NO: 2)
MSVRYSSSKHYSSSRSGGGGGGGCGGGGVSSLRISSSKGSLGGGFSSG

GFSGGSFSRGSSGGGCFGGSSGGYGGLGGFGGGSFRGSYGSSSFGGSYGG
```

-continued

```
IFGGGSFGGGSFGGGSFGGGGFGGGGFGGGFGGGFGGDGGLLSGNEKVTM

QNLNDRLASYLDKVRALEESNYELEGKIKEWYEKHGNSHQGEPRDYSKYY

KTIDDLKNQILNLTTTDNANILLQIDNARLAADDFRLKYENEVALRQSVEA

DINGLRRVLDELTLTKADLEMQIESLTEELAYLKKNHEEEMKDLRNVSTG

DVNVEMNAAPGVDLTQLLNNMRSQYEQLAEQNRKDAEAWFNEKSKELTTE

IDNNIEQISSYKSEITELRRNVQALEIELQSQLALKQSLEASLAETEGRY

CVQLSQIQAQISALEEQLQQIRAETECQNTEYQQLLDIKIRLENEIQTYR

SLLEGEGSSGGGGRGGGSFGGGYGGGSSGGGSSGGGHGGGHGGSSGGGYG

GGSSGGGSSGGGYGGGSSSGGHGGSSSGGYGGGSSGGGGGGYGGGSSGGG

SSSGGGYGGGSSSGGHKSSSSGSVGESSSKGPRY.
```

In one embodiment, the present invention provides a composition for inhibiting the tetramerization of the vimentin homodimer. Tetramerization of the vimentin homodimer is essential to formation of intermediate filaments (IFs). Thus, in one embodiment, the invention provides a composition for inhibiting IF formation. In various embodiments, the composition inhibits the interaction between the anchoring knob of a first vimentin homodimer and the hydrophobic pocket of a second vimentin homodimer.

In one embodiment, the composition of the invention comprises an inhibitor of vimentin homodimer tetramerization. An inhibitor of vimentin homodimer tetramerization is any compound, molecule, or agent that reduces, inhibits, or prevents the binding of a first vimentin homodimer to a second vimentin homodimer. For example, an inhibitor of vimentin homodimer tetramerization is any compound, molecule, or agent that reduces the interaction between the anchoring knob of a first vimentin homodimer and the hydrophobic pocket of a second vimentin homodimer. In various embodiments, an inhibitor of the interaction between the anchoring knob of a first vimentin homodimer and the hydrophobic pocket of a second vimentin homodimer comprises a nucleic acid, a peptide, a small molecule chemical compound, an antagonist, an aptamer, an antibody, a peptidomimetic, or any combination thereof.

In one embodiment, the present invention provides a composition for inhibiting the tetramerization of vimentin. Tetramerization of the vimentin is essential to formation of vimentin intermediate filaments. An inhibitor of vimentin tetramerization is any compound, molecule, or agent that reduces, inhibits, or prevents the binding of a first vimentin homodimer to a second vimentin homodimer. For example, an inhibitor of vimentin homodimer tetramerization is any compound, molecule, or agent that reduces the interaction between the anchoring knob of a first vimentin homodimer and the hydrophobic pocket of a second vimentin homodimer. In various embodiments, an inhibitor of the interaction between the anchoring knob of a first vimentin homodimer and the hydrophobic pocket of a second vimentin homodimer comprises a nucleic acid, a peptide, a small molecule chemical compound, an antagonist, an aptamer, an antibody, a peptidomimetic, or any combination thereof.

In one embodiment, vimentin has the sequence of (SEQ ID NO: 35)
```
MSTRSVSSSSYRRMFGGPGTASRPSSSRSYVTTSTRTYSLGSALRPSTSR

SLYASSPGGVYATRSSAVRLRSSVPGVRLLQDSVDFSLADAINTEFKNTR
```

-continued
```
TNEKVELQELNDRFANYIDKVRFLEQQNKILLAELEQLKGQGKSRLGDLY

EEEMRELRRQVDQLTNDKARVEVERDNLAEDIMRLREKLQEEMLQREEAE

NTLQSFRQDVDNASLARLDLERKVESLQEEIAFLKKLHEEEIQELQAQIQ

EQHVQIDVDVSKPDLTAALRDVRQQYESVAAKNLQEAEEWYKSKFADLSE

AANRNNDALRQAKQESTEYRRQVQSLTCEVDALKGTNESLERQMREMEEN

FAVEAANYQDTIGRLQDEIQNMKEEMARHLREYQDLLNVKMALDIEIATY

RKLLEGEESRISLPLPNFSSLNLRETNLDSLPLVDTHSKRTLLIKTVETR

DGQVINETSQHHDDLE
```

Small Molecule Inhibitors

In various embodiments, the inhibitor is a small molecule. When the inhibitor is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule inhibitor of the invention comprises an organic molecule, inorganic molecule, biomolecule, synthetic molecule, and the like.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

The small molecule and small molecule compounds described herein may be present as salts even if salts are not depicted and it is understood that the invention embraces all salts and solvates of the inhibitors depicted here, as well as the non-salt and non-solvate form of the inhibitors, as is well understood by the skilled artisan. In some embodiments, the salts of the inhibitors of the invention are pharmaceutically acceptable salts.

Where tautomeric forms may be present for any of the inhibitors described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the inhibitors described. The recitation of the structure or name herein is intended to embrace all possible stereoisomers of inhibitors depicted. All forms of the inhibitors are also embraced by the invention, such as crystalline or non-crystalline forms of the inhibitors. Compositions comprising an inhibitor of the invention are also intended, such as a composition of substantially pure inhibitor, including a specific stereochemical form thereof, or a composition comprising mixtures of inhibitors of the invention in any ratio, including two or more stereochemical forms, such as in a racemic or non-racemic mixture.

In one embodiment, the small molecule inhibitor of the invention comprises an analog or derivative of an inhibitor described herein.

In one embodiment, the small molecules described herein are candidates for derivatization. As such, in certain instances, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule inhibitors described herein are derivatized/analogued as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog," "analogue," or "derivative" is meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically. An analog or derivative of any of a small molecule inhibitor in accordance with the present invention can be used to inhibit intermediate filament tetramerization and/or treat a disease or disorder associated with intermediate filament overexpression, or intermediate filament formation. In one embodiment, An analog or derivative of any of a small molecule inhibitor in accordance with the present invention can be used to inhibit K1/K10 tetramerization, and/or treat a disease or disorder associated with KIF overexpression, or KIF formation. In one embodiment, An analog or derivative of any of a small molecule inhibitor in accordance with the present invention can be used to inhibit vimentin tetramerization, and/or treat a disease or disorder associated with vimentin overexpression, or vimentin formation.

In one embodiment, the small molecule inhibitors described herein can independently be derivatized/analogued by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

Polypeptide Inhibitors

In one aspect, the invention provides isolated peptides and compositions comprising isolated peptides. In one embodiment, the peptide inhibits the interaction between a first KIF heterodimer and a second KIF heterodimer. In one embodiment, the peptide inhibits the interaction between a first KIF homodimer and a second KIF homodimer. In one embodiment, the peptide inhibits the interaction between a KIF homodimer and a KIF heterodimer.

In one embodiment, the peptide inhibits the interaction between a first K1/K10 heterodimer and a second K1/K10 heterodimer. In one embodiment, the peptide inhibitor that inhibits K1/K10 tetramerization. In one embodiment, the peptide inhibitor of the invention inhibits K1/K10 tetramerization directly by binding to the K1/K10 hydrophobic pocket thereby preventing the binding of the anchoring knob of a second K1/K10 heterodimer. In another embodiment, the peptide inhibitor of the invention inhibits K1/K10 tetramerization by competing with endogenous K1/K10. In yet another embodiment, the peptide inhibitor of the invention inhibits K1/K10 tetramerization by acting as a trans dominant negative mutant.

In one embodiment, the peptide binds to the K1/K10 hydrophobic pocket. The isolated peptides may be used to inhibit the interaction between a first K1/K10 heterodimer and a second K1/K10 heterodimer.

In one embodiment, the peptide is a K1, K10, or K1/K10 heterodimer-derived peptide. In one embodiment, the K1, K10, or K1/K10 heterodimer-derived peptide is derived from the K1/K10 anchoring knob. In one embodiment, the K1, K10, or K1/K10 heterodimer-derived peptide is derived from the K1/K10 anchoring knob. In one embodiment, the K1/K10 anchoring knob-derived peptide mimics the K1/K10 anchoring knob binding in the K1/K10 hydrophobic pocket. In one embodiment, the K1, K10, or K1/K10 heterodimer is derived from K1 amino acids 314-318. In one embodiment, the peptide comprises a sequence selected from SEQ ID NO:3-34. In one embodiment, the peptide comprises a sequence at least about 90%, 91%, 92%, 93%, 94%, 95%, 96%, 97%, 98%, or 99% identical to a sequence selected from SEQ ID NO:3-34.

| Peptide Inhibitor | SEQ ID NO |
|---|---|
| VDLQAKLDNLQQEIDFLTALYQAELSQMQTQIS | 3 |
| FLTAL | 4 |
| FLTALY | 5 |
| DFLTAL | 6 |
| DFLTALY | 7 |
| IDFLTAL | 8 |
| IDFLTALY | 9 |
| EIDFLTAL | 10 |

-continued

| Peptide Inhibitor | SEQ ID NO |
|---|---|
| EIDFLTALY | 11 |
| EIDFLTALYQ | 12 |
| EIDFLTALYQA | 13 |
| EIDFLTALYQAE | 14 |
| EIDFLTALYQAEL | 15 |
| EIDFLTALYQAELS | 16 |
| EIDFLTALYQAELSQ | 17 |
| EIDFLTALYQAELSQM | 18 |
| EIDFLTALYQAELSQMQ | 19 |
| EIDFLTALYQAELSQMQT | 20 |
| EIDFLTALYQAELSQMQTQ | 21 |
| EIDFLTALYQAELSQMQTQI | 22 |
| EIDFLTALYQAELSQMQTQIS | 23 |
| QEIDFLTALYQAELSQMQTQIS | 24 |
| QQEIDFLTALYQAELSQMQTQIS | 25 |
| LQQEIDFLTALYQAELSQMQTQIS | 26 |
| NLQQEIDFLTALYQAELSQMQTQIS | 27 |
| DNLQQEIDFLTALYQAELSQMQTQIS | 28 |
| LDNLQQEIDFLTALYQAELSQMQTQIS | 29 |
| KLDNLQQEIDFLTALYQAELSQMQTQIS | 30 |
| AKLDNLQQEIDFLTALYQAELSQMQTQIS | 31 |
| QAKLDNLQQEIDFLTALYQAELSQMQTQIS | 32 |
| LQAKLDNLQQEIDFLTALYQAELSQMQTQIS | 33 |
| DLQAKLDNLQQEIDFLTALYQAELSQMQTQIS | 34 |

In one embodiment, the peptide inhibitor that inhibits K5/K14 tetramerization. In one embodiment, the peptide inhibitor of the invention inhibits K5/K14 tetramerization directly by binding to the K5/K14 hydrophobic pocket thereby preventing the binding of the anchoring knob of a second K5/K14 heterodimer. In another embodiment, the peptide inhibitor of the invention inhibits K5/K14 tetramerization by competing with endogenous K5/K14. In yet another embodiment, the peptide inhibitor of the invention inhibits K5/K14 tetramerization by acting as a trans dominant negative mutant.

In one embodiment, the peptide binds to the K5/K14 hydrophobic pocket. The isolated peptides may be used to inhibit the interaction between a first K5/K14 heterodimer and a second K5/K14 heterodimer.

In one embodiment, the peptide is a K5, K14, or K5/K14 heterodimer-derived peptide. In one embodiment, the K5, K14, or K5/K14 heterodimer-derived peptide is derived from the K5/K14 anchoring knob. In one embodiment, the K5, K14, or K5/K14 heterodimer-derived peptide is derived from the K1/K10 anchoring knob. In one embodiment, the K5/K14 anchoring knob-derived peptide mimics the K5/K14 anchoring knob binding in the K5/K14 hydrophobic pocket.

In one embodiment, the peptide inhibitor that inhibits K8/K18 tetramerization. In one embodiment, the peptide inhibitor of the invention inhibits K8/K18 tetramerization directly by binding to the K8/K18 hydrophobic pocket thereby preventing the binding of the anchoring knob of a second K8/K18 heterodimer. In another embodiment, the peptide inhibitor of the invention inhibits K8/K18 tetramerization by competing with endogenous K8/K18. In yet another embodiment, the peptide inhibitor of the invention inhibits K8/K18 tetramerization by acting as a trans dominant negative mutant.

In one embodiment, the peptide binds to the K8/K18 hydrophobic pocket. The isolated peptides may be used to inhibit the interaction between a first K8/K18 heterodimer and a second K8/K18 heterodimer.

In one embodiment, the peptide is a K8, K18, or K8/K18 heterodimer-derived peptide. In one embodiment, the K8, K18, or K8/K18 heterodimer-derived peptide is derived from the K8/K18 anchoring knob. In one embodiment, the K8, K18, or K8/K18 heterodimer-derived peptide is derived from the K1/K10 anchoring knob. In one embodiment, the K8/K18 anchoring knob-derived peptide mimics the K8/K18 anchoring knob binding in the K8/K18 hydrophobic pocket.

In one aspect, the invention provides isolated peptides and compositions comprising isolated peptides. In one embodiment, the peptide inhibits the interaction between a first KIF heterodimer and a second KIF heterodimer. In one embodiment, the peptide inhibits the interaction between a first KIF homodimer and a second KIF homodimer. In one embodiment, the peptide inhibits the interaction between a KIF homodimer and a KIF heterodimer.

In one embodiment, the peptide inhibits the interaction between a first vimentin homodimer and a second vimentin homodimer. In one embodiment, the peptide inhibitor that inhibits vimentin tetramerization. In one embodiment, the peptide inhibitor of the invention inhibits vimentin tetramerization directly by binding to the vimentin homodimer hydrophobic pocket thereby preventing the binding of the anchoring knob of a second vimentin homodimer. In another embodiment, the peptide inhibitor of the invention inhibits vimentin tetramerization by competing with endogenous vimentin. In yet another embodiment, the peptide inhibitor of the invention inhibits vimentin tetramerization by acting as a trans dominant negative mutant.

In one embodiment, the peptide binds to the vimentin homodimer hydrophobic pocket. The isolated peptides may be used to inhibit the interaction between a first vimentin homodimer and a second vimentin homodimer.

In one embodiment, the peptide is a vimentin or vimentin homodimer-derived peptide. In one embodiment, the vimentin or vimentin homodimer-derived peptide is derived from the vimentin homodimer anchoring knob. In one embodiment, the vimentin or vimentin homodimer-derived peptide is derived from the vimentin homodimer anchoring knob. In one embodiment, the vimentin homodimer anchoring knob-derived peptide mimics the vimentin homodimer anchoring knob binding in the vimentin homodimer hydrophobic pocket.

In one embodiment, the vimentin or vimentin homodimer is derived from vimentin amino acids 233-237. In one embodiment, the peptide comprises a sequence selected from SEQ ID NO:36-67. In one embodiment, the peptide comprises a sequence at least about 90%, 91%, 92%, 93%, 94%, 95%, 96%, 97%, 98%, or 99% identical to a sequence selected from SEQ ID NO: 36-67.

25

| Peptide Inhibitor | SEQ ID NO |
|---|---|
| LDLERKVESLQEEIAFLKKLHEEEIQELQAQIQ | 36 |
| FLKKL | 37 |
| FLKKLH | 38 |
| AFLKKL | 39 |
| AFLKKLH | 40 |
| IAFLKKL | 41 |
| IAFLKKLH | 42 |
| EIAFLKKL | 43 |
| EIAFLKKLH | 44 |
| EIAFLKKLHE | 45 |
| EIAFLKKLHEE | 46 |
| EIAFLKKLHEEE | 47 |
| EIAFLKKLHEEEI | 48 |
| EIAFLKKLHEEEIQ | 49 |
| EIAFLKKLHEEEIQE | 50 |
| EIAFLKKLHEEEIQEL | 51 |
| EIAFLKKLHEEEIQELQ | 52 |
| EIAFLKKLHEEEIQELQA | 53 |
| EIAFLKKLHEEEIQELQAQ | 54 |
| EIAFLKKLHEEEIQELQAQI | 55 |
| EIAFLKKLHEEEIQELQAQIQ | 56 |
| EEIAFLKKLHEEEIQELQAQIQ | 57 |
| QEEIAFLKKLHEEEIQELQAQIQ | 58 |
| LQEEIAFLKKLHEEEIQELQAQIQ | 59 |
| SLQEEIAFLKKLHEEEIQELQAQIQ | 60 |
| ESLQEEIAFLKKLHEEEIQELQAQIQ | 61 |
| VESLQEEIAFLKKLHEEEIQELQAQIQ | 62 |
| KVESLQEEIAFLKKLHEEEIQELQAQIQ | 63 |
| RKVESLQEEIAFLKKLHEEEIQELQAQIQ | 64 |
| ERKVESLQEEIAFLKKLHEEEIQELQAQIQ | 65 |
| LERKVESLQEEIAFLKKLHEEEIQELQAQIQ | 66 |
| DLERKVESLQEEIAFLKKLHEEEIQELQAQIQ | 67 |

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

Nucleic Acid Inhibitors

In one aspect, the invention provides isolated nucleic acids and compositions comprising isolated nucleic acids encoding peptides inhibitors of inhibits the interaction between a first IF dimer and a second IF dimer. In one embodiment, the nucleic acid encodes a peptide inhibitor of the interaction between a first IF homodimer and a second IF homodimer. In one embodiment, the nucleic acid encodes a peptide inhibitor of the interaction between a first IF homodimer and a second IF homodimer. In one embodiment, the nucleic acid encodes a peptide inhibitor of the interaction between a IF homodimer and a IF heterodimer.

In one aspect, the invention provides isolated nucleic acids and compositions comprising isolated nucleic acids encoding peptides inhibitors of inhibits the interaction between a first KIF heterodimer and a second KIF heterodimer. In one embodiment, the nucleic acid encodes a peptide inhibitor of the interaction between a first KIF homodimer and a second KIF homodimer. In one embodiment, the nucleic acid encodes a peptide inhibitor of the interaction between a KIF homodimer and a KIF heterodimer.

In one embodiment, the present invention provides isolated nucleic acids and compositions comprising isolated nucleic acids encoding a peptide inhibitor of K8/K18 tetramerization. In one embodiment, the present invention provides isolated nucleic acids and compositions comprising isolated nucleic acids encoding a peptide inhibitor of K5/K14 tetramerization. In one embodiment, the present invention provides isolated nucleic acids and compositions comprising isolated nucleic acids encoding a peptide inhibitor of vimentin tetramerization.

In one embodiment, the present invention provides isolated nucleic acids and compositions comprising isolated nucleic acids encoding a peptide inhibitor of K1/K10 tetramerization.

In one embodiment, the present invention provides isolated nucleic acids and compositions comprising isolated nucleic acids encoding a peptide inhibitor of K1/K10 tetramerization. In one embodiment, the isolated nucleic acids encode a K1, K10, or K1/K10 heterodimer-derived peptide of the invention. In one embodiment, the isolated nucleic acid encodes a peptide having a sequence of one of SEQ ID NO:3-34. In one embodiment, the isolated nucleic acid encodes a peptide having a sequence at least about 90%, 91%, 92%, 93%, 94%, 95%, 96%, 97%, 98%, or 99% identical to one of SEQ ID NO:3-34.

Further, the invention encompasses an isolated nucleic acid encoding a peptide having substantial homology to a peptide disclosed herein. In certain embodiments, the isolated nucleic acid sequence encodes a peptide having at least about 75%, 80%, 85%, 90%, 91%, 92%, 93%, 94%, 95%, 96%, 97%, 98%, or 99% sequence identity with an amino acid sequence selected from SEQ NOs: 3-34.

In one embodiment, the present invention provides isolated nucleic acids and compositions comprising isolated nucleic acids encoding a peptide inhibitor of vimentin tetramerization.

In one embodiment, the present invention provides isolated nucleic acids and compositions comprising isolated nucleic acids encoding a peptide inhibitor of vimentin tetramerization. In one embodiment, the isolated nucleic acids encode a vimentin monomer or vimentin homodimer-derived peptide of the invention. In one embodiment, the isolated nucleic acid encodes a peptide having a sequence of one of SEQ ID NO:36-67. In one embodiment, the isolated nucleic acid encodes a peptide having a sequence at least about 90%, 91%, 92%, 93%, 94%, 95%, 96%, 97%, 98%, or 99% identical to one of SEQ ID NO:36-37.

Further, the invention encompasses an isolated nucleic acid encoding a peptide having substantial homology to a peptide disclosed herein. In certain embodiments, the isolated nucleic acid sequence encodes a peptide having at least about 75%, 80%, 85%, 90%, 91%, 92%, 93%, 94%, 95%, 96%, 97%, 98%, or 99% sequence identity with an amino acid sequence selected from SEQ NOs: 36-37.

The isolated nucleic acid sequence encoding the peptide can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The isolated nucleic acid may comprise any type of nucleic acid, including, but not limited to DNA and RNA. For example, in one embodiment, the composition comprises an isolated DNA molecule, including for example, an isolated cDNA molecule, encoding an inhibitor of K1/K10 tetramerization. In one embodiment, the composition comprises an isolated RNA molecule encoding an inhibitor of K1/K10 tetramerization. For example, in one embodiment, the composition comprises an isolated DNA molecule, including for example, an isolated cDNA molecule, encoding an inhibitor of vimentin tetramerization. In one embodiment, the composition comprises an isolated RNA molecule encoding an inhibitor of vimentin tetramerization.

The nucleic acid molecules of the present invention can be modified to improve stability in serum or in growth medium for cell cultures. Modifications can be added to enhance stability, functionality, and/or specificity and to minimize immunostimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In some instances, the nucleic acid molecule comprises at least one of the following chemical modifications: 2'-H, 2'-O-methyl, or 2'-OH modification of one or more nucleotides. In certain embodiments, a nucleic acid molecule of the invention can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the invention can include 2'-O-methyl, 2'-fluorine, 2'-O-methoxyethyl, 2'-O-amino-propyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-amino-propyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. (Nucleic Acids Res., 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribo-phosphate backbone, e.g., non-charged mimics of the ribo-phosphate backbone.

Modifications of the nucleic acid of the invention may be present at one or more of, a phosphate group, a sugar group, backbone, N-terminus, C-terminus, or nucleobase.

The present invention also includes a vector in which the isolated nucleic acid of the present invention is inserted. The art is replete with suitable vectors that are useful in the present invention.

In brief summary, the expression of natural or synthetic nucleic acids encoding an inhibitor of IF tetramerization is typically achieved by operably linking a nucleic acid encoding the inhibitor of IF tetramerization or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adeno-viruses, adeno-associated viruses, herpes viruses, and lenti-viruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepato-cytes. They also have the added advantage of low immuno-genicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of patho-genicity, minimal immunogenicity, and the ability to trans-duce postmitotic cells in a stable and efficient manner. Expression of a particular gene contained within an AAV vector can be specifically targeted to one or more types of cells by choosing the appropriate combination of AAV serotype, promoter, and delivery method In certain embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any poly-nucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metal-lothionine promoter, a glucocorticoid promoter, a progester-one promoter, and a tetracycline promoter.

Enhancer sequences found on a vector also regulates expression of the gene contained therein. Typically, enhanc-ers are bound with protein factors to enhance the transcrip-tion of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost tran-scription of the gene present within the vector.

In order to assess the expression of an inhibitor of IF tetramerization, such as the expression of an inhibitor of KIF or the expression of an inhibitor of a vimentin homodimer tetramerization, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially trans-fected cells and for evaluating the functionality of regulatory sequences. In general, a reporter gene is a gene that is not present in or expressed by the recipient organism or tissue and that encodes a polypeptide whose expression is mani-fested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be trans-ferred into a host cell by physical, chemical, or biological means.

Physical methods for introducing a polynucleotide into a host cell include calcium phosphate precipitation, lipofec-tion, particle bombardment, microinjection, electroporation, and the like. Methods for producing cells comprising vectors and/or exogenous nucleic acids are well-known in the art. See, for example, Sambrook et al. (2012, Molecular Clon-ing: A Laboratory Manual, Cold Spring Harbor Laboratory, New York). A preferred method for the introduction of a polynucleotide into a host cell is calcium phosphate trans-fection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as mac-romolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, inter-spersed within the lipid bilayer of a liposome, attached to a liposome via a linking molecule that is associated with both the liposome and the oligonucleotide, entrapped in a lipo-some, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated composi-tions are not limited to any particular structure in solution. For example, they may be present in a bilayer structure, as micelles, or with a "collapsed" structure. They may also simply be interspersed in a solution, possibly forming aggre-gates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocar-bons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Chol") can be obtained from Calbiochem-Behring; dimyristyl phosphati-dylglycerol ("DMPG") and other lipids may be obtained from Avanti Polar Lipids, Inc. (Birmingham, AL). Stock solutions of lipids in chloroform or chloroform/methanol can be stored at about −20□C. Chloroform is used as the only solvent since it is more readily evaporated than metha-nol. "Liposome" is a generic term encompassing a variety of single and multilamellar lipid vehicles formed by the gen-eration of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contem-plated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, the inhibitor of IF tetramerization may comprise one or more components of a CRISPR-Cas system. In one embodiment, the inhibitor of KIF tetramerization may comprise one or more components of a CRISPR-Cas system. In one embodiment, the inhibitor of vimentin tetramerization may comprise one or more components of a CRISPR-Cas system. CRISPR methodologies employ a nuclease, CRISPR-associated (Cas), that complexes with small RNAs as guides (gRNAs) to cleave DNA in a sequence-specific manner upstream of the protospacer adjacent motif (PAM) in any genomic location. CRISPR may use separate guide RNAs known as the crRNA and tracrRNA. These two separate RNAs have been combined into a single RNA to enable site-specific mammalian genome cutting through the design of a short guide RNA. Cas and guide RNA (gRNA) may be synthesized by known methods. Cas/guide-RNA (gRNA) uses a non-specific DNA cleavage protein Cas, and an RNA oligo to hybridize to target and recruit the Cas/gRNA complex. In one embodiment, a guide RNA (gRNA) targeted K1 or K10 and a CRISPR-associated (Cas) peptide form a complex to induce mutations within the targeted gene. In one embodiment, the inhibitor comprises a gRNA or a nucleic acid molecule encoding a gRNA. In one embodiment, the inhibitor comprises a Cas peptide or a nucleic acid molecule encoding a Cas peptide.

In one embodiment the gRNA targets K1 to introduce a mutation into K1, wherein the mutation abolishes K1/K10 tetramerization. For example, in one embodiment the gRNA targets K1 to introduces a mutation at a residue selected from Y230, F231, F234, E281, F284, K288, D292, M296, Y295, V299, D300, A303 K304, N307, E311, F314, and L318. In one embodiment the gRNA targets K1 to introduce a mutation to disrupt the anchoring knob-hydrophobic pocket. In one embodiment, the anchoring knob-hydrophobic pocket disrupting mutation is a mutation at a residue selected from selected from Y230, F231, F234, F314, and L318.

In one embodiment the gRNA targets K10 to introduce a mutation into K10, wherein the mutation abolishes K1/K10 tetramerization. For example, in one embodiment the gRNA targets K10 to introduce a mutation at a residue selected from K207, L211, T215, A218, N219, L221, L222, N226, L229, and L236.

In one embodiment the gRNA targets vimentin to introduce a mutation into vimentin, wherein the mutation abolishes vimentin tetramerization. For example, in one embodiment the gRNA targets vimentin to introduces a mutation at a residue selected from L149, Y150, E153, M154, E200, L203, R207, D211, S214, L215, L218, D219, R222, K223, S226, E230, F233, and L237. In one embodiment the gRNA targets vimentin to introduce a mutation to disrupt the anchoring knob-hydrophobic pocket. In one embodiment, the anchoring knob-hydrophobic pocket disrupting mutation is a mutation at a residue selected from selected from L149, Y150, E153, M154, F233, and L237.

In one embodiment the gRNA targets vimentin to introduce a mutation into vimentin, wherein the mutation abolishes vimentin tetramerization. For example, in one embodiment the gRNA targets vimentin to introduce a mutation at a residue selected from R158, D162, N166, A169, R170, E172, V173, N177, E180, and E187.

In one embodiment, the gRNA targets vimentin to introduce a mutation in vimentin, wherein the mutation abolishes vimentin tetramerization. For example, embodiment the gRNA targets vimentin to introduce a mutation at a residue selected from F233 and L237.

The guide RNA sequence can be a sense or anti-sense sequence. In the CRISPR-Cas system derived from *S. pyogenes* (spCas9), the target DNA typically immediately precedes a 5'-NGG or NAG proto-spacer adjacent motif (PAM). Other Cas9 orthologs may have different PAM specificities. For example, Cas9 from *S. thermophilus* (stCas9) requires 5'-NNAGAA for CRISPR 1 and 5'-NGGNG for CRISPR3 and *Neiseria menigiditis* (nmCas9) requires 5'-NNNN-GATT. Cas9 from *Staphylococcus aureus* subsp. *aureus* (saCas9) requires 5'-NNGRRT (R=A or G). The specific sequence of the guide RNA may vary, but, regardless of the sequence, useful guide RNA sequences will be those that minimize off-target effects while achieving high efficiency mutation of the K1/K10 heterodimer.

In certain embodiments, the composition comprises multiple different gRNA molecules, each targeted to a different target sequence. In certain embodiments, this multiplexed strategy provides for increased efficacy. These multiplex gRNAs can be expressed separately in different vectors or expressed in one single vector.

The isolated nucleic acid molecules of the invention, including the RNA molecules (e.g., crRNA, tracrRNA, gRNA) or nucleic acids encoding the RNA molecules, may be produced by standard techniques. For example, polymerase chain reaction (PCR) techniques can be used to obtain an isolated nucleic acid containing a nucleotide sequence described herein, including nucleotide sequences encoding a polypeptide described herein. PCR can be used to amplify specific sequences from DNA as well as RNA, including sequences from total genomic DNA or total cellular RNA. Various PCR methods are described in, for example, *PCR Primer: A Laboratory Manual, 2$^{nd}$ edition*, Dieffenbach and Dveksler, eds., Cold Spring Harbor Laboratory Press, 2003. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

The isolated nucleic acids also can be chemically synthesized, either as a single nucleic acid molecule (e.g., using automated DNA synthesis in the 3' to 5' direction using phosphoramidite technology) or as a series of oligonucleotides. Isolated nucleic acids of the invention also can be obtained by mutagenesis of, e.g., a naturally occurring portion crRNA, tracrRNA, RNA-encoding DNA, or of a Cas9-encoding DNA In certain embodiments, the isolated RNA molecules are synthesized from an expression vector encoding the RNA molecule, as described in detail elsewhere herein.

In one embodiment, the Cas9 protein comprises an amino acid sequence identical to the wild type *Streptococcus pyogenes* Cas9 amino acid sequence. In some embodiments, the Cas protein may comprise the amino acid sequence of a Cas protein from other species, for example other *Streptococcus* species, such as *thermophilus; Pseudomona aeruginosa, Escherichia coli*, or other sequenced bacteria genomes and archaea, or other prokaryotic microorganisms. Other Cas proteins, useful for the present invention, known or can be identified, using methods known in the art (see e.g., Esvelt et al., 2013, Nature Methods, 10: 1116-1121). In certain embodiments, the Cas protein may comprise a modified amino acid sequence, as compared to its natural source. For example, in one embodiment, the wild type *Streptococcus pyrogenes* Cas9 sequence can be modified. For example, in certain embodiments, the Cas9 protein comprises dCas9 having point mutations D10A and H840A, thereby rendering the protein as catalytically deficient. In certain embodiments, the amino acid sequence can be codon optimized for efficient expression in human cells (i.e., "humanized) or in a species of interest.

Antibody Inhibitors

The invention also contemplates an inhibitor of IF tetramerization comprising an antibody, or antibody fragment, specific for an IF heterodimer or homodimer.

In one embodiment, inhibitor of KIF tetramerization comprises an antibody, or antibody fragment, specific for a KIF heterodimer. For example, the antibody inhibitor of K1/K10 tetramerization is an antibody, or antibody fragment, specific for K1, K10 or a K1/K10 heterodimer. For example, in one embodiment, the antibody or antibody fragment can inhibit the binding of one K1/K10 heterodimer to a second K1/K10 heterodimer to inhibit or reduce K1/K10 tetramerization. In one embodiment, the antibody specifically binds to K1/K10. In one embodiment the antibody specifically binds to the K1/K10 hydrophobic pocket. In one embodiment, the antibody specifically binds to one or more of the K1/K10 hydrophobic pocket residues K1 Y230, K1 F231 and/or K1 F234. In one embodiment, the antibody specifically binds to the K1/K10 anchoring knob. In one embodiment, the antibody specifically binds to one or more of the K1/K10 anchoring knob residues K1 F314, and/or K1 L318. In one embodiment, the anti-K1/K10 heterodimer antibody is a polyclonal antibody. In another embodiment, the anti-K1/K10 heterodimer antibody is a monoclonal antibody. In some embodiments, the anti-K1/K10 heterodimer antibody is a chimeric antibody. In further embodiments, the anti-K1/K10 heterodimer antibody is a humanized antibody. In some embodiments, the antibody is an antibody fragment.

The invention also contemplates an inhibitor of K8/K18 tetramerization comprising an antibody, or antibody fragment, specific for K8, K18 or a K8/K18 heterodimer. For example, in one embodiment, the antibody or antibody fragment can inhibit the binding of one K8/K18 heterodimer to a second K8/K18 heterodimer to inhibit or reduce K8/K18 tetramerization. In one embodiment, the antibody specifically binds to K8/K18. In one embodiment the antibody specifically binds to the K8/K18 hydrophobic pocket. In one embodiment, the antibody specifically binds to the K8/K18 anchoring knob. In one embodiment, the anti-K8/K18 heterodimer antibody is a polyclonal antibody. In another embodiment, the anti-K8/K18 heterodimer antibody is a monoclonal antibody. In some embodiments, the anti-K8/K18 heterodimer antibody is a chimeric antibody. In further embodiments, the anti-K8/K18 heterodimer antibody is a humanized antibody. In some embodiments, the antibody is an antibody fragment.

The invention also contemplates an inhibitor of K5/K14 tetramerization comprising an antibody, or antibody fragment, specific for K5, K14 or a K5/K14 heterodimer. For example, in one embodiment, the antibody or antibody fragment can inhibit the binding of one K5/K14 heterodimer to a second K5/K14 heterodimer to inhibit or reduce K5/K14 tetramerization. In one embodiment, the antibody specifically binds to K5/K14. In one embodiment the antibody specifically binds to the K5/K14 hydrophobic pocket. In one embodiment, the antibody specifically binds to the K5/K14 anchoring knob. In one embodiment, the anti-K5/K14 heterodimer antibody is a polyclonal antibody. In another embodiment, the anti-K5/K14 heterodimer antibody is a monoclonal antibody. In some embodiments, the anti-K5/K14 heterodimer antibody is a chimeric antibody. In further embodiments, the anti-K5/K14 heterodimer antibody is a humanized antibody. In some embodiments, the antibody is an antibody fragment.

The invention also contemplates an inhibitor of vimentin tetramerization comprising an antibody, or antibody fragment, specific for vimentin or a vimentin homodimer. For example, in one embodiment, the antibody or antibody fragment can inhibit the binding of one vimentin homodimer to a second vimentin homodimer to inhibit or reduce vimentin tetramerization. In one embodiment, the antibody specifically binds to vimentin. In one embodiment the antibody specifically binds to the vimentin homodimer hydrophobic pocket. In one embodiment, the antibody specifically binds to the vimentin homodimer anchoring knob. In one embodiment, the anti-vimentin homodimer antibody is a polyclonal antibody. In another embodiment, the anti-vimentin homodimer antibody is a monoclonal antibody. In some embodiments, the anti-vimentin homodimer antibody is a chimeric antibody. In further embodiments, the anti-vimentin homodimer antibody is a humanized antibody. In some embodiments, the antibody is an antibody fragment.

In some embodiments, the antibody is an intact monoclonal or polyclonal antibody, or immunologically portion or active fragment thereof. Thus, in various embodiments, the antibody of invention is a polyclonal antibody, monoclonal antibody, intracellular antibody ("intrabody"), Fv, Fab, Fab', F(ab)2 and F(ab')2, single chain antibody (scFv), heavy chain antibody (e.g., such as a camelid antibody), synthetic antibody, chimeric antibody, or humanized antibodies (see, for example, Harlow et al., 1999, Using Antibodies: A Laboratory Manual, Cold Spring Harbor Laboratory Press, NY; Harlow et al., 1989, Antibodies: A Laboratory Manual, Cold Spring Harbor, NY; Houston et al., 1988, Proc. Natl. Acad. Sci. USA 85:5879-5883; Bird et al., 1988, Science 242:423-426). Antibodies can be prepared using intact polypeptides or fragments containing an immunizing antigen of interest. The polypeptide or oligopeptide used to immunize an animal may be obtained from the translation of RNA or synthesized chemically and can be conjugated to a carrier protein, if desired. Suitable carriers that may be chemically coupled to peptides include bovine serum albumin and thyroglobulin, keyhole limpet hemocyanin. The coupled polypeptide may then be used to immunize the animal (e.g., a mouse, a rat, or a rabbit).

CAR-T

In one embodiment, a Chimeric Antigen Receptor bearing T cell (CAR T-cell) incorporates the antigen binding domain of a KIF or IF antibody with one or more intracellular signaling domain(s) of T cells to produce a localized, tumor specific immune response. CAR T-cells have several advantages over monoclonal antibodies: they actively migrate into the tumor, proliferate in response to antigen bearing tumor cells, secrete factors that recruit other arms of the immune response and can survive long term to provide ongoing protection from relapse. Another benefit of a CAR-T cell over an antibody therapeutic targeting the same antigen is that the CAR T-cell may also be further modified to enhance safety and function. For example, a T cell can be modified to include expression of a homing receptor which enhances T cell specificity and the ability of the T cell(s) to infiltrate cancer cells or tumors or they may include an "off switch" that can function to eliminate cells when toxicity occurs. Furthermore, and importantly for the treatment of multiple myeloma and its related disorders, the T cell may be modified to express additional biologically active or pharmaceutically active molecules that may enhance the anti-tumor response, such as, for example, tumor suppressive cytokines. CAR T-cells encompass all classes and subclasses of T-lymphocytes including CD4$^+$ and CD8$^+$ T cells as well as effector T cells, memory T cells, regulatory T cells, and the like. The T lymphocytes that are genetically modified may be "derived" or "obtained" from the subject who will receive the treatment using the generically modified T cells or they may "derived" or "obtained" from a different subject.

In one embodiment, the CAR T-cells are further genetically modified to produce or express a IF tetramerization inhibitor which allow for focused delivery to the tumor microenvironment/cancer cells, while avoiding systemic toxicity. In one embodiment, the CAR-T cells express an inhibitor of KIF tetramerization. In one embodiment, the CAR-T cells express an inhibitor of K1/K10 tetramerization. In one embodiment, CAR-T cells express a peptide binding to the K1/K10 hydrophobic pocket. In one embodiment, CAR-T cells express a K1, K10, or K1/K10 heterodimer-derived peptide. In one embodiment, CAR-T cells express a peptide derived from the K1/K10 anchoring knob. In one embodiment, CAR-T cells express a peptide derived from K1 amino acids 314-318. In one embodiment, CAR-T cells express a peptide comprising a sequence selected from SEQ ID NO:3-34 In one embodiment, CAR-T cells express a peptide comprising a sequence at least 90% homologous to a sequence selected from SEQ ID NO:3-34.

In one embodiment, the CAR-T cells express an inhibitor of vimentin tetramerization. In one embodiment, CAR-T cells express a peptide binding to the vimentin homodimer hydrophobic pocket. In one embodiment, CAR-T cells express a vimentin monomer or vimentin homodimer-derived peptide. In one embodiment, CAR-T cells express a peptide derived from the vimentin homodimer anchoring knob. In one embodiment, CAR-T cells express a peptide derived from vimentin amino acids 233-237. In one embodiment, CAR-T cells express a peptide comprising a sequence selected from SEQ ID NO:36-67. In one embodiment, CAR-T cells express a peptide comprising a sequence at least 90% homologous to a sequence selected from SEQ ID NO:36-67.

In one embodiment, the CAR T-cells are further genetically modified to produce or express a vimentin tetramerization inhibitor which allow for focused delivery to the tumor microenvironment/cancer cells, while avoiding systemic toxicity. In one embodiment, the CAR-T cells express an inhibitor of vimentin tetramerization. In one embodiment, CAR-T cells express a peptide binding to the vimentin homodimer hydrophobic pocket. In one embodiment, CAR-T cells express a vimentin or vimentin homodimer-derived peptide. In one embodiment, CAR-T cells express a peptide derived from the vimentin homodimer anchoring knob.

Delivery System

In one embodiment, the present invention provides a delivery vehicle comprising an inhibitor of KIF or IF tetramerization. For example, in one embodiment, the present invention provides a delivery vehicle comprising an inhibitor of K1/K10 tetramerization, K5/K14 tetramerization, K8/K18 tetramerization or vimentin. Exemplary delivery vehicles include, but are not limited to, microspheres, microparticles, nanoparticles, polymerosomes, liposomes, and micelles. For example, in certain embodiments, the delivery vehicle is loaded with an inhibitor of K1/K10 tetramerization, K5/K14 tetramerization, K8/K18 tetramerization, or vimentin tetramerization. In certain embodiments, the delivery vehicle provides for controlled release, delayed release, or continual release of its loaded cargo. In certain embodiments, the delivery vehicle comprises a targeting moiety that targets the delivery vehicle to a treatment site.

In one embodiment, the present invention provides a scaffold or substrate composition comprising an inhibitor of IF tetramerization. In one embodiment, the present invention provides a scaffold or substrate composition comprising an inhibitor of KIF tetramerization. The present invention provides a scaffold or substrate composition comprising an inhibitor of comprising an inhibitor of K1/K10 tetramerization, K5/K14 tetramerization, or K8/K18 tetramerization. For example, in one embodiment the scaffold or substrate composition comprises a K1/K10 heterodimer-derived peptide, a nucleic acid molecule encoding a K1/K10 heterodimer-derived peptide, a cell producing a K1/K10 heterodimer-derived peptide, a CRISPR/Cas system targeting the K1/K10 heterodimer, or a combination thereof. For example, in one embodiment, a K1/K10 heterodimer-derived peptide, a nucleic acid molecule encoding a K1/K10 heterodimer-derived peptide, a cell producing a K1/K10 heterodimer-derived peptide, a CRISPR/Cas system targeting the K1/K10 heterodimer, or a combination thereof within a scaffold. In another embodiment K1/K10 heterodimer-derived peptide, a nucleic acid molecule encoding a K1/K10 heterodimer-derived peptide, a cell producing a K1/K10 heterodimer-derived peptide, a CRISPR/Cas system targeting the K1/K10 heterodimer, or a combination thereof is applied to the surface of a scaffold.

In one embodiment the scaffold or substrate composition comprises a vimentin homodimer-derived peptide, a nucleic acid molecule encoding a vimentin homodimer-derived peptide, a cell producing a vimentin homodimer-derived peptide, a CRISPR/Cas system targeting the vimentin homodimer, or a combination thereof. For example, in one embodiment, a vimentin homodimer-derived peptide, a nucleic acid molecule encoding a vimentin homodimer-derived peptide, a cell producing a vimentin homodimer-derived peptide, a CRISPR/Cas system targeting the vimentin homodimer, or a combination thereof within a scaffold. In another embodiment vimentin homodimer-derived peptide, a nucleic acid molecule encoding a vimentin homodimer-derived peptide, a cell producing a vimentin homodimer-derived peptide, a CRISPR/Cas system targeting the vimentin homodimer, or a combination thereof is applied to the surface of a scaffold.

The scaffold of the invention may be of any type known in the art. Non-limiting examples of such a scaffold includes a, hydrogel, electrospun scaffold, foam, mesh, sheet, patch, and sponge.

The present invention also provides pharmaceutical compositions comprising one or more of the compositions described herein. Formulations may be employed in admixtures with conventional excipients, i.e., pharmaceutically acceptable organic or inorganic carrier substances suitable for administration to the wound or treatment site. The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., other analgesic agents.

Administration of the compositions of this invention may be carried out, for example, by parenteral, by intravenous, intratumoral, subcutaneous, intramuscular, or intraperitoneal injection, or by infusion or by any other acceptable systemic method.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, PA), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

In an embodiment, the composition includes an antioxidant and a chelating agent that inhibits the degradation of one or more components of the composition. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the composition of the invention in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid.

Methods

In one aspect, the invention provides methods to inhibit the interaction between a first IF dimer and a second IF dimer. For example, in one embodiment, the invention provides methods to inhibit the interaction between a first KIF heterodimer and a second KIF heterodimer. In one embodiment, the invention provides methods to inhibit the interaction between a first K1/K10 heterodimer and a second K1/K10 heterodimer. In one embodiment, the invention provides methods to inhibit K1/K10 tetramerization. In one embodiment, the invention provides methods to inhibit KIF formation. In one embodiment, the method comprises administering an effective amount of a K1/K10 tetramerization to a subject in need thereof.

In one embodiment, the invention provides methods to inhibit the interaction between a first K5/K14 heterodimer and a second K5/K14 heterodimer. In one embodiment, the invention provides methods to inhibit K5/K14 tetramerization. In one embodiment, the invention provides methods to inhibit KIF formation. In one embodiment, the method comprises administering an effective amount of a K5/K14 tetramerization to a subject in need thereof.

In one embodiment, the invention provides methods to inhibit the interaction between a first K8/K18 heterodimer and a second K8/K18 heterodimer. In one embodiment, the invention provides methods to inhibit K8/K18 tetramerization. In one embodiment, the invention provides methods to inhibit KIF formation. In one embodiment, the method comprises administering an effective amount of a K8/K18 tetramerization to a subject in need thereof.

In one aspect, the invention provides methods to inhibit the interaction between a first K1/K10 heterodimer and a second K1/K10 heterodimer. In one embodiment, the invention provides methods to inhibit K1/K10 tetramerization. In one embodiment, the invention provides methods to inhibit KIF formation. In one embodiment, the method comprises administering an effective amount of a K1/K10 tetramerization to a subject in need thereof.

In one aspect, the invention provides methods to inhibit the interaction between a first K5/K14 heterodimer and a second K5/K14 heterodimer. In one embodiment, the invention provides methods to inhibit K5/K14 tetramerization. In one embodiment, the invention provides methods to inhibit KIF formation. In one embodiment, the method comprises administering an effective amount of a K5/K14 tetramerization to a subject in need thereof.

In one aspect, the invention provides methods to inhibit the interaction between a first K8/K18 heterodimer and a second K8/K18 heterodimer. In one embodiment, the invention provides methods to inhibit K8/K18 tetramerization. In one embodiment, the invention provides methods to inhibit KIF formation. In one embodiment, the method comprises administering an effective amount of a K8/K18 tetramerization to a subject in need thereof.

In one aspect, the invention provides methods to inhibit the interaction between a first vimentin homodimer and a second vimentin homodimer. In one embodiment, the invention provides methods to inhibit vimentin tetramerization. In one embodiment, the invention provides methods to inhibit IF formation. In one embodiment, the method comprises administering an effective amount of a vimentin tetramerization to a subject in need thereof.

In one embodiment, the method comprises administering an effective amount of an inhibitor that inhibits the interaction between the hydrophobic pocket of a first K1/K10 heterodimer and the anchoring knob of a second K1/K10 heterodimer. In one embodiment, the method comprises administering an effective amount of an inhibitor that binds to the K1/K10 hydrophobic pocket.

In one embodiment, the method comprises administering an effective amount of an inhibitor that inhibits the interaction between the hydrophobic pocket of a first K5/K14 heterodimer and the anchoring knob of a second K5/K14 heterodimer. In one embodiment, the method comprises administering an effective amount of an inhibitor that binds to the K5/K14 hydrophobic pocket.

In one embodiment, the method comprises administering an effective amount of an inhibitor that inhibits the interaction between the hydrophobic pocket of a first K8/K18 heterodimer and the anchoring knob of a second K8/K18 heterodimer. In one embodiment, the method comprises administering an effective amount of an inhibitor that binds to the K8/K18 hydrophobic pocket.

In one embodiment, the method comprises administering an effective amount of an inhibitor that inhibits the interaction between the hydrophobic pocket of a first vimentin homodimer and the anchoring knob of a second vimentin homodimer. In one embodiment, the method comprises administering an effective amount of an inhibitor that binds to the vimentin homodimer hydrophobic pocket.

In one embodiment, the inhibitor is at least one selected from the group consisting of a protein, a peptide, a peptidomemetic, an antibody, a ribozyme, a small molecule chemical compound, a nucleic acid, and a vector.

In one embodiment, the inhibitor is a K1, K10, or K1/K10 heterodimer-derived peptide. In one embodiment, the inhibitor is a peptide derived from the K1/K10 anchoring knob. In one embodiment, the inhibitor is a peptide derived from K1 amino acids 314-318. In one embodiment, the inhibitor is a peptide comprising a fragment of a protein having a sequence of one of SEQ ID NO:1-2. In one embodiment, the inhibitor is a peptide comprising a fragment of a protein having a sequence at least 90% homologous to one of SEQ ID NO:1-2. In one embodiment, the inhibitor is a peptide comprising a sequence of one of SEQ ID NO:3-34. In one embodiment, the inhibitor is a peptide comprising a sequence at least about 90%, 91%, 92%, 93%, 94%, 95%, 96%, 97%, 98%, or 99% identical to one of SEQ ID NO:3-34.

In one embodiment, the method comprises administering an effective amount of a composition that mutates at least one K1/K10 residue critical for K1/K10 tetramerization. In one embodiment, the at least one K1/K10 residue is selected from the group consisting of K1 Y230, K1 F231, K1 F234, K1 F314, and K1 L318.

In one embodiment, the inhibitor is a K5, K14, or K5/K14 heterodimer-derived peptide. In one embodiment, the inhibitor is a peptide derived from the K5/K14 anchoring knob. In one embodiment, the inhibitor is a K8, K18, or K1/K18 heterodimer-derived peptide. In one embodiment, the inhibitor is a peptide derived from the K1/K18 anchoring knob.

In one embodiment, the inhibitor is a vimentin monomer, or vimentin homodimer-derived peptide. In one embodiment, the inhibitor is a peptide derived from the vimentin homodimer anchoring knob. In one embodiment, the inhibitor is a peptide derived from vimentin amino acids 233-237. In one embodiment, the inhibitor is a peptide comprising a fragment of a protein having a sequence of SEQ ID NO:35. In one embodiment, the inhibitor is a peptide comprising a fragment of a protein having a sequence at least 90% homologous to SEQ ID NO:35. In one embodiment, the inhibitor is a peptide comprising a sequence of one of SEQ ID NO:36-67. In one embodiment, the inhibitor is a peptide comprising a sequence at least about 90%, 91%, 92%, 93%, 94%, 95%, 96%, 97%, 98%, or 99% identical to one of SEQ ID NO:36-67.

The invention also provides methods for the treatment or prevention of a disease or disorder in a subject in need thereof. In one embodiment, the disease or disorder is associated with IF overexpression or IF formation. In one embodiment, the disease or disorder is associated with KIF overexpression or KIF formation. Exemplary diseases and disorders treated or prevented by way of the present invention, include, but are not limited, to cancer, skin blistering and fragility disorders (epidermolysis bullosa simplex), disorders of keratinization (epidermolytic ichthyosis, palmoplantar keratoderma, pachyonychia congenita), eye disease (Meesmann corneal dystrophy), and liver disease (cirrhosis).

The invention also provides methods for the treatment or prevention of a disease or disorder in a subject in need thereof. In one embodiment, the disease or disorder is associated with IF overexpression or IF formation. Exemplary diseases and disorders treated or prevented by way of the present invention, include, but are not limited, to cancer (e.g. Sharma et al., 2019, Cells 8:497, which is incorporated by reference herein), cancer metastasis, scarring, skin blistering and fragility disorders (epidermolysis bullosa simplex), disorders of keratinization (epidermolytic ichthyosis, palmoplantar keratoderma, pachyonychia congenita), eye disease (Meesmann corneal dystrophy), and liver disease (cirrhosis).

In one embodiment, the disease or disorder is associated with vimentin overexpression or vimentin formation. Exemplary diseases and disorders treated or prevented by way of the present invention, include, but are not limited to, lung injury (e.g. Surolia et al., 2019, JCI Insight. 4:e123253, which is incorporated by reference herein), HIV (e.g., Fernandez-Orega et al., 2016, Viruses 8:98, which is incorporated by reference herein); cancer (e.g. Kidd et al., 2013, Am J Resp Cell Mol Biol 50:1-6, which is incorporated by reference herein), and cataracts.

In one embodiment, the disease or disorder is associated with non-keratin intermediate filaments (Types III through VI), overexpression or non-keratin intermediate filaments (Types III through VI) formation. Exemplary diseases and disorders treated or prevented by way of the present invention, include, cataracts (vimentin), amyotrophic lateral sclerosis/Lou Gehrig's disease (peripherin), and brain cancer (neurofilaments).

One of skill in the art will appreciate that the inhibitors of the invention can be administered singly or in any combination. Further, the inhibitors of the invention can be administered singly or in any combination in a temporal sense, in that they may be administered concurrently, or before, and/or after each other. One of ordinary skill in the art will appreciate, based on the disclosure provided herein, that the inhibitor compositions of the invention can be used to prevent or a disease or disorder associated with IF overexpression or IF formation to treat or a disease or disorder associated with KIF overexpression or KIF formation, and that an inhibitor composition can be used alone or in any combination with another modulator to effect a therapeutic result.

In one embodiment, the invention includes a method comprising administering a combination of inhibitors described herein. In certain embodiments, the method has an additive effect, wherein the overall effect of the administering a combination of inhibitors is approximately equal to the sum of the effects of administering each individual inhibitor. In other embodiments, the method has a synergistic effect, wherein the overall effect of administering a combination of inhibitors is greater than the sum of the effects of administering each individual inhibitor.

The method comprises administering a combination of inhibitors in any suitable ratio. For example, in one embodiment, the method comprises administering two individual inhibitors at a 1:1 ratio. However, the method is not limited to any particular ratio. Rather any ratio that is shown to be effective is encompassed.

The composition of the invention may be administered to a patient or subject in need in a wide variety of ways. Modes of administration include intraoperatively intravenous, intravascular, intramuscular, subcutaneous, intracerebral, intraperitoneal, soft tissue injection, surgical placement, arthroscopic placement, and percutaneous insertion, e.g., direct injection, cannulation or catheterization. Any administration may be a single application of a composition of invention or multiple applications. Administrations may be to single site or to more than one site in the individual to be treated. Multiple administrations may occur essentially at the same time or separated in time.

Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions of the present invention may be administered in a manner appropriate to the disease to be treated (or prevented). The quantity and frequency of administration will be determined by such factors as the condition of the subject, and the type and severity of the subject's disease, although appropriate dosages may be determined by clinical trials.

When "therapeutic amount" is indicated, the precise amount of the compositions of the present invention to be administered can be determined by a physician with consideration of individual differences in age, weight, disease type, extent of disease, and condition of the patient (subject).

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the compositions of the present invention are administered to a patient by intradermal or subcutaneous injection. In another embodiment, the compositions of the present invention are preferably administered by i.v. injection.

In one embodiment, the invention provides a method of treating or preventing cancer in a subject in need thereof, the method comprising administering to the subject an effective amount of a composition comprising an inhibitor of K1/K10 tetramerization.

In one embodiment, the invention provides a method of treating or preventing cancer in a subject in need thereof, the method comprising administering to the subject an effective amount of a composition comprising an inhibitor of K5/K14 tetramerization.

In one embodiment, the invention provides a method of treating or preventing cancer in a subject in need thereof, the method comprising administering to the subject an effective amount of a composition comprising an inhibitor of K8/K18 tetramerization.

In one embodiment, the invention provides a method of treating or preventing cancer in a subject in need thereof, the method comprising administering to the subject an effective amount of a composition comprising an inhibitor of vimentin tetramerization.

In some embodiments of the methods for treating or preventing cancer in a subject in need thereof, a second agent is administered to the subject, such as an antineoplastic agent or a chemotherapeutic agent.

In another embodiment, the invention provides a method to treat cancer comprising treating the subject prior to, concurrently with, or subsequently to the treatment with a composition of the invention, with a complementary therapy for the cancer, such as surgery, chemotherapy, chemotherapeutic agent, radiation therapy, or hormonal therapy or a combination thereof.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cisplatinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazolo-acridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

The compositions of the invention can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (*vinca* alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the compositions of the invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine;

crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine;

carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil;

pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

The following are non-limiting examples of cancers that can be treated by the disclosed methods and compositions: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytotna/Malignant Glioma; Craniopharyngioma; Ependymoblastoma; Ependymoma; Medulloblastoma; Medulloepithelioma; Pineal Parenchymal Tumors of intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocytoma of Bone and Osteosarcoma; Medulloblastoma; Melanoma; Melanoma, intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis; Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Celt Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; and Wilms Tumor.

Pharmaceutical Compositions

The present invention envisions treating a disease, for example, cancer, in a subject by the administration of a composition comprising an inhibitor of K1/K10 tetramerization.

Administration of the therapeutic agent in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the subject, and whether prevention or treatment is to be achieved. Such factors can be readily determined by the clinician employing animal models or other test systems which are well known to the art.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent or modified cell may be directly injected into the tumor. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The agents of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the pharmaceutical composition of the present invention may be delivered via various routes and to various sites in a mammal body to achieve a particular effect (see, e.g., Rosenfeld et al., 1991; Rosenfeld et al., 1991a; Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

Screening

The present invention relates to the discovery that keratin 1/keratin 10 (K1/K10) heterodimer has a hydrophobic pocket formed at the N-terminus providing a receptor site for the C-terminal anchoring knob on a neighboring K1/K10 heterodimer which facilitates tetramer formation. K1/K10 tetramerization of the K1/K10 heterodimer is essential to formation of keratin intermediate filaments (KIFs). KIF formation is an important therapeutic target for many diseases and disorders including, but not limited to cancer. Thus, in one embodiment, the invention provides a method of screening a library of compounds to provide a pool of KIF formation inhibitors.

In one embodiment, the method of screening compounds comprises contacting a first K1/K10 heterodimer with at least one compound from the library, measuring K1/K10 tetramer formation, comparing the tetramer formation to a comparator control; and selecting the at least one compound from the library when the tetramer formation is altered at a statistically significant amount when compared with the tetramer formation of the comparator control.

In one embodiment, a compound is selected when the tetramer formation is increased compared to the tetramer formation of the comparator control. In one embodiment, a compound is selected when the tetramer formation is decreased compared to the tetramer formation of the comparator control.

In one embodiment, the method comprises contacting a hydrophobic pocket domain of a K1/K10 heterodimer, with at least one compound from the library; measuring a binding of the at least one compound to the hydrophobic pocket; comparing the binding of the at least one compound to the hydrophobic pocket, with a binding of a comparator control to the hydrophobic pocket; and selecting the at least one compound from the library when the binding of the at least one compound to the hydrophobic pocket, is increased at a statistically significant amount when compared with the binding of the comparator control to the hydrophobic pocket. In one embodiment, the hydrophobic pocket domain comprises at least K1 residues Y230, F231, and F234.

The present invention relates to the unexpected finding that that loss of knob structure has a damaging impact on IF assembly (the rate of and/or the length of) across IF types including keratins with long heads and tails (K1/K10), keratins with short heads and tails (K8/18), and heterodimeric and homodimeric (vimentin) IF proteins. K1/K10 tetramerization of the K1/K10 heterodimer is essential to formation of keratin intermediate filaments (KIFs). IF formation is an important therapeutic target for many diseases and disorders including, but not limited to cancer and scarring. Thus, in one embodiment, the invention provides a method of screening a library of compounds to provide a pool of IF formation inhibitors.

In one embodiment, the method of screening compounds comprises contacting a first vimentin homodimer with at least one compound from the library, measuring vimentin tetramer formation, comparing the tetramer formation to a comparator control; and selecting the at least one compound from the library when the tetramer formation is altered at a statistically significant amount when compared with the tetramer formation of the comparator control.

In one embodiment, a compound is selected when the tetramer formation is increased compared to the tetramer formation of the comparator control. In one embodiment, a compound is selected when the tetramer formation is decreased compared to the tetramer formation of the comparator control.

In one embodiment, the method comprises contacting a hydrophobic pocket domain of a vimentin homodimer, with at least one compound from the library; measuring a binding of the at least one compound to the hydrophobic pocket; comparing the binding of the at least one compound to the hydrophobic pocket, with a binding of a comparator control to the hydrophobic pocket; and selecting the at least one compound from the library when the binding of the at least one compound to the hydrophobic pocket, is increased at a statistically significant amount when compared with the binding of the comparator control to the hydrophobic pocket.

Methods of measuring binding between a ligand and its target are well known to those of ordinary skill in the art. Examples of methodologies to measure compound binding to the hydrophobic pocket domain of a K1/K10 heterodimer, vimentin homodimer, K1/K10 tetramer formation, or vimentin tetramer formation include, but are not limited to saturation binding, scatchard plot, competition binding, fluorescence polarization, fluorescence resonance energy transfer, surface plasmon resonance, immunoprecipitation, BioLayer Interferometry (BLI), Western blot, dot blot, surface plasmon resonance (SPR), enzyme-linked immunosorbent assay (ELISA), homogeneous time resolved fluorescence, AlphaScreen, or AlphaLISA assays, and mass spectrometry based methods.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, are not to be construed as limiting in any way the remainder of the disclosure.

Example 1: Molecular Basis for Keratin Filament Assembly from Keratin 1-Keratin 10 Helix 1B Tetramer Keratin intermediate filament assembly mechanisms are poorly understood at atomic resolution. That data presented herein describes a 3.0 Å resolution structure of the wild-type human keratin 1/keratin 10 helix 1B heterotetramer, elucidating biochemical determinants for the $A_{11}$ mode of axial alignment in keratin filaments. Four regions on a hydrophobic face of the K1/K10-1B heterodimer dictate tetramer assembly: the N-terminal hydrophobic pocket (defined by $Y230^{K1}$, $F231^{K1}$, and $F234^{K1}$), a K10 hydrophobic stripe, K1 interaction residues, and a C-terminal anchoring knob (formed by $F314^{K1}$ and $L318^{K1}$). To demonstrate how pathogenic mutations cause skin disease by altering filament assembly, a 2.2 Å resolution structure of K1/10-1B containing a $S233L^{K1}$ mutation linked to epidermolytic palmoplantar keratoderma was determined. Circular dichroism and light scattering demonstrated enhanced aggregation of $K1^{S233L}/K10$-1B in solution without affecting secondary structure. The $K1^{S233L}/K10$-1B octamer structure revealed $S233L^{K1}$ caused aberrant hydrophobic interactions between 1B tetramers.

The data presented herein demonstrates advances in keratin filament biology: atomic resolution insight into the $A_{11}$ mode of axial alignment in keratin filaments and insight into the pathogenic mechanisms of tonotubular keratin formation associated with EPPK. This research addresses knowledge gaps in keratin filament assembly and how pathogenic mutations can lead to human skin disease by altering that assembly.

The materials and methods are now described.

Protein Production and Purification. Plasmids of K1-1B, K10-1B, and K1$^{S233L}$-1B were purchased from GenScript. Each protein was expressed in *Escherichia coli* strain BL21 (DE3) at 37° C. in Luria Broth Miller. Protein expression was induced with 1 mM isopropyl-D-thiogalactopyranoside and proceeded for 3-4 hours. After pelleting cells by centrifugation at 2500×g, 10 minutes, at 4° C., they were suspended in 50 mM Tris-HCl buffer (pH 7.8) containing 0.5M NaCl, 20 mM imidazole, 1% Nonidet P-40, 6 mM MgCl2, 1 mM CaCl2 and 1× EDTA-free protease inhibitor cocktail. For the wild-type heterodimer preparation, K1-1B cell suspension was mixed with K10-1B cell suspension. For the S233L mutant preparation, K1-1B S233L cell suspension was mixed with K10-1B cell suspension. Both wild-type and mutant heterodimers were purified following the same procedure. Cells were lysed by sonication on ice, followed by incubation of lysate with ~30 units/mL DNase I at 37° C. for 15 minutes. The solution was centrifuged at 15000×g, 15 minutes, at 4° C. The supernatant was subjected to batch nickel affinity purification using previously described methods (Bunick et al., 2015). The clarified solution containing the untagged heterocomplex was applied to a Superdex75 (26/60) gel filtration column in 100 mM Tris-HCl buffer (pH 7.4) containing 0.2M NaCl. Collected fractions were analyzed by sodium dodecyl sulfate polyacrylamide gel electrophoresis (SDS-PAGE), and selected pooled fractions were concentrated in a 10000 Da molecular weight cutoff centrifugal filter unit.

Multi-angle light scattering. K1-K10-1B (2.4 mg/ml) in 20 mM Tris-HCl buffer (pH 7.4) containing 100 mM was applied at 0.5 ml per minute to Superdex 75 gel filtration column in-line with DAWN HELEOS II light scattering instrument (laser wavelength 658 nm). Data collection and analysis was performed using Astra software version 5.3.4.20. This procedure was repeated using K1$^{S233L}$-K10-1B (2.3 mg/ml). The same procedures were then repeated with buffer containing 200 mM NaCl using a Superdex 200 gel filtration column.

Circular Dichroism. Circular dichroism (CD) measurements were made on solutions containing wild-type K1/K10-1B or mutant K1$^{S233L}$/K10-1B at 0.5 mg/mL in 100 mM Tris-HCl buffer (pH 7.4) containing 0.2M NaCl. A Chirascan spectrometer was used to scan the samples in a 0.1 cm pathlength cuvette from wavelength 260 nm to 190 nm (2 nm/s) at 22° C.

Crystallization and x-ray data collection. Sitting-drop vapor diffusion crystallization was performed at 25° C. by mixing 3 μl of protein with 3 μl of reservoir solution. X-ray data was collected on crystals maintained at ~100K using the 24-ID-C beamline at the Advanced Photon Source at Argonne National Laboratory. Diffraction data was processed using HKL-2000.

Wild-type K1/K10-1B (23.7 mg/ml) in 100 mM Tris-HCl buffer (pH 7.4) containing 0.2M NaCl was crystallized using 0.1M HEPES buffer (pH 7.5) containing 5 mM cobalt(II) chloride, 5 mM cadmium dichloride, 5 mM magnesium chloride, 5 mM nickel(II) chloride, and 11% polyethylene glycol 3350. Crystals were soaked 1-3 min in a cryoprotectant solution containing 25% propylene glycol in mother liquor prior to flash-freezing in liquid nitrogen. A native data set on a single crystal was collected (λ=0.9795 Å). The crystal belonged to the trigonal space group P3₁21 (cell dimensions: a=106.69 Å, b=106.69 Å, c=70.32 Å, α=β=90°, γ=120°).

Mutant K1$^{S233L}$/K10-1B (22.8 mg/ml) in 100 mM Tris-HCl buffer (pH 7.4) containing 0.2M NaCl was crystallized using 0.1M Tris buffer (pH 8.5) containing 1.5M ammonium sulfate and 12% glycerol. Crystals were soaked 1-3 min in a cryoprotectant solution containing 27% glycerol in mother liquor prior to flash-freezing in liquid nitrogen. One native data set on a single crystal was collected (λ=0.9795 Å). The native crystal belonged to the hexagonal space group P6422 (cell dimensions: a=93.29 Å, b=93.29 Å, c=124.74 Å, α=β=90°, γ=120°). A second data set was collected, using a different crystal from the same growth condition soaked in mercury solution, at the mercury edge (λ=1.00841 Å) and had strong anomalous signal. The heavy atom soak was performed as follows: a K1$^{S233L}$/K10-1B crystal was transferred to a 10 μL drop of mother liquor solution containing 1 mM potassium tetraiodomercurate(II) and soaked for 1 hour at room temperature. It was then transferred and soaked for 1 minute in a cryoprotectant solution containing 27% glycerol in mother liquor prior to flash-freezing in liquid nitrogen. The heavy atom crystal belonged to the hexagonal space group P6₄22 (cell dimensions: a=93.62 Å, b=93.62 Å, c=122.74 Å, α=β=90°, γ=120°).

Structure determination, refinement, and analysis. The K1/K10-1B and K1$^{S233L}$/K10-1B structures were determined by heavy atom phasing with MOLREP. The structures underwent iterative rounds of model building (Coot) and refinement (Refmac5, PHENIX) using standard geometric (bond length, bond angle) and secondary structure restraints (Table S1). The final model of the wild-type K1/K10-1B crystal asymmetric unit contained one K1-1B and one K10-1B molecule in complex. The final Ramachandran statistics were: residues in favorable regions, 98.1%; in allowed regions, 1.43%; in outlier regions, 0.48%. The final model of the K1$^{S233L}$/K10-1B mutant crystal asymmetric unit contained one K1-1B S233L and one K10-1B molecules. The final Ramachandran statistics were: residues in favorable regions, 99%; in allowed regions, 1%; in outlier regions, 0%. Electrostatics were calculated using PDB2PQR and Adaptive Poisson-Boltzmann Software (APBS). Structural analyses were performed using Coot, UCSF Chimera (Resource for Biocomputing, Visualization, and Informatics, University of California, San Francisco), WHAT IF, ESBRI, and PDBePISA (The European Bioinformatics Institute, European Molecular Biology Laboratory, UK). Figures were prepared using UCSF Chimera and Adobe Illustrator. Atomic coordinates and structure factors have been deposited in the Protein Data Bank under the accession code TBD.

The results are now described.

Wild-type K1/K10-1B structure. The x-ray crystal structure of the human K1/K10 helix 1B heterotetrameric complex was determined to 3.0 Å resolution (FIG. 1A). The tetramer is composed of two K1/K10-1B heterodimers arranged anti-parallel. The K1 and K10 molecules within the heterodimer structure form a parallel coiled-coil, spanning K1 residues (226-331) and K10 residues (195-296). Key molecular interactions along the K1/K10-1B heterodimer interface are detailed (FIG. 7). The K1/K10-1B tetramer did not exhibit supercoiling of the coiled-coil heterodimers. Throughout this example the protein-protein interactions occurring between the two antiparallel dimers of the tetramer are denoted by associating a prime symbol with the residue(s) from the second dimer (e.g. K1-K1').

The electrostatic surface potential of the K1/K10-1B heterodimer is similar to that observed in the K1/K10-2B heterodimer: there is polarization of charge with the distal three-fourths of the complex being acidic, whereas the proximal one-fourth is more basic (FIG. 1B). The basic patch at the N-terminus of K1/K10-1B contains residues from both K1 (R239, R240, R241) and K10 (K198, K201, K207) (FIG. 1C); this is in contrast to the 2B heterodimer, where a linear N-terminal basic patch was solely formed by nine K1 residues.

Acidic Groove on Molecular Surface of 1B Tetramer

Due to K1/K10-1B heterodimers aligning anti-parallel in the tetramer, the basic electrostatic surface potential at the N-terminus of the heterodimer is diminished by the strength of the adjacent acidic C-terminus in the tetramer (FIG. 1D). The electrostatic surface potential of the K1/K10-1B tetramer is mainly acidic.

There are unique surface contours present in the K1/K10-1B tetramer that are not present in the heterodimer structure (FIGS. 1D-1G). One face of the tetramer contains a linear groove that extends from one end all the way to the other; this groove has the highest acidic electrostatic surface potential in the K1/K10-1B tetramer structure (FIGS. 1D and 1E). In contrast, the tetramer face 180° opposite the acidic linear groove contains a central concave pocket ~66.7 Å long by 17.7 Å wide (FIG. 1F), flanked by two symmetric angled grooves ~54.9 Å long at either end of the molecule (FIG. 1G).

Hydrophobic Interactions Drive 1B Tetramer Formation

Figure 2:
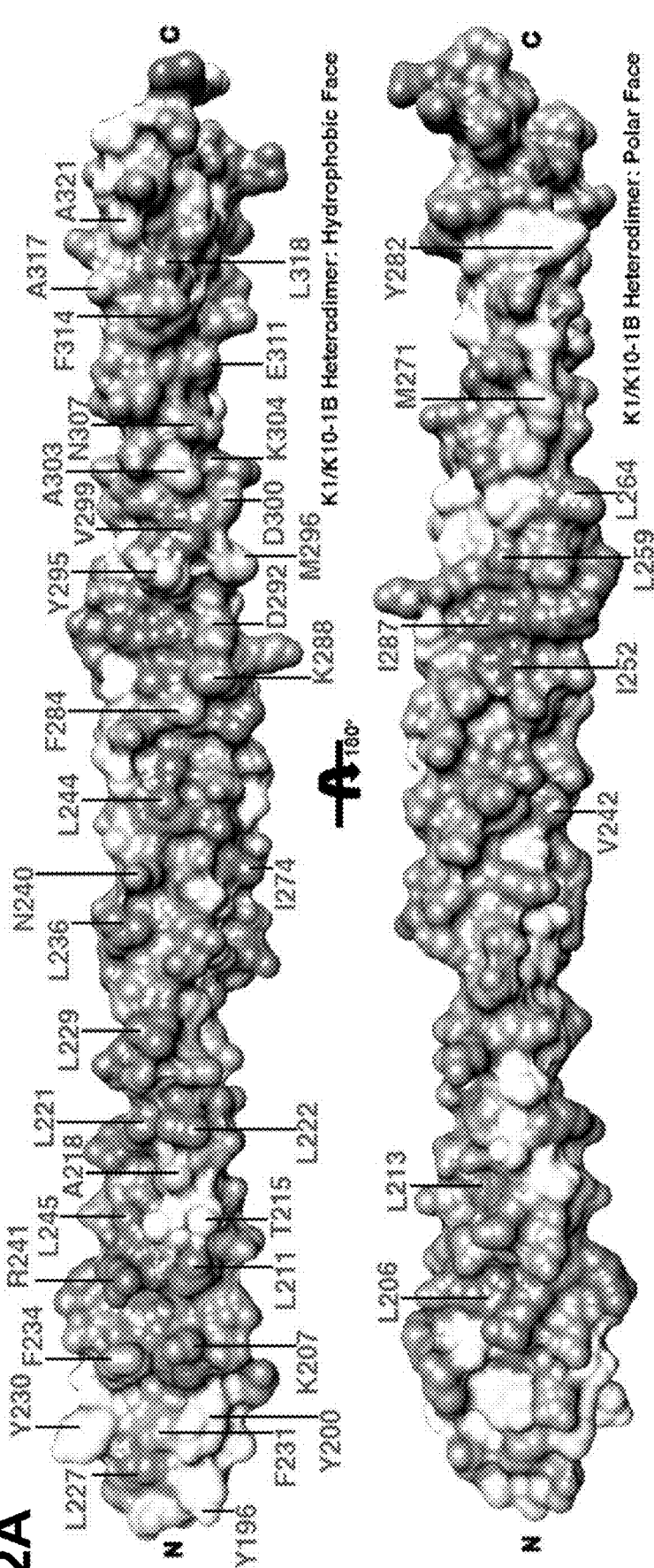
FIG. 2, comprising
Figure 2:
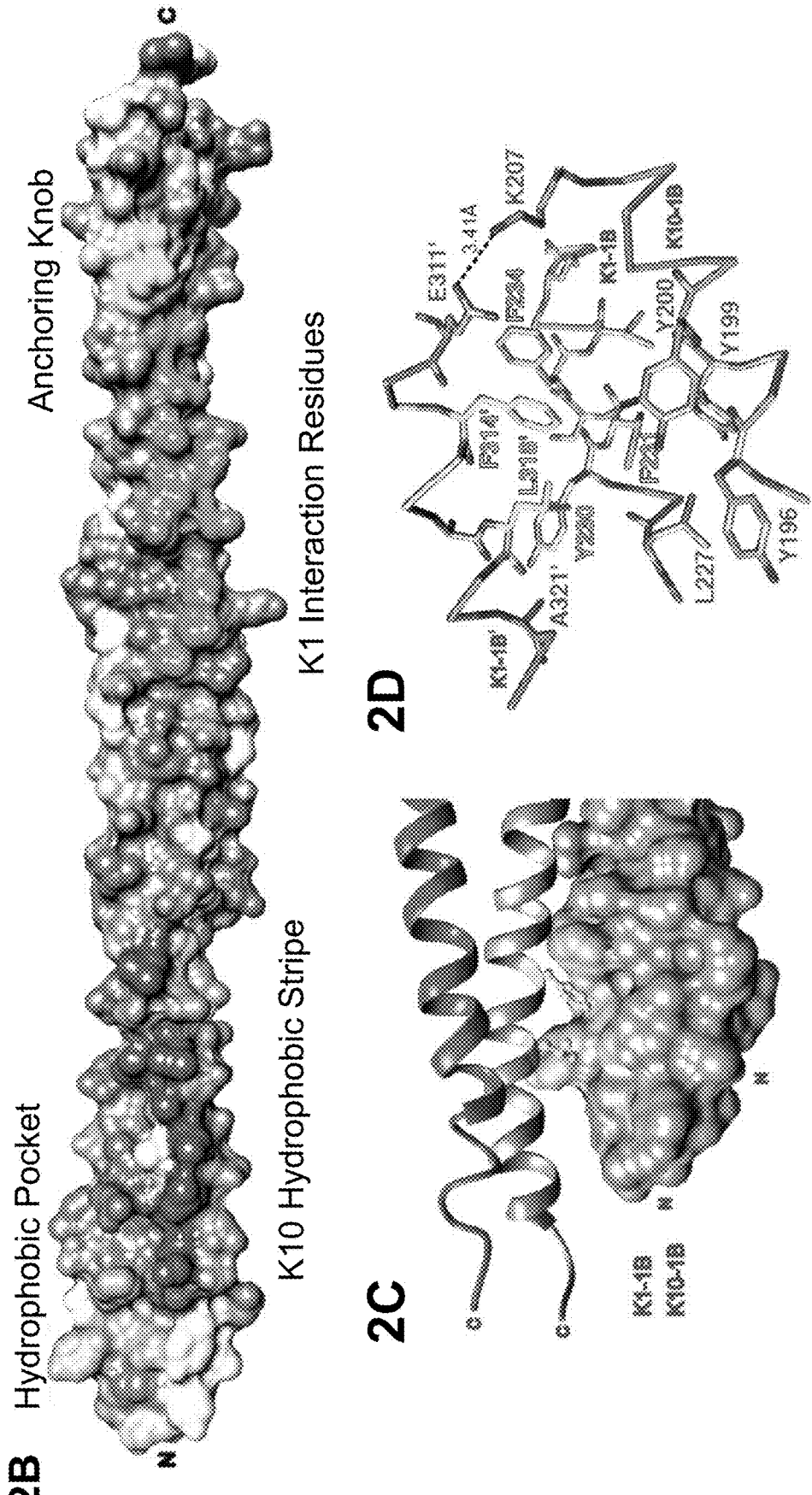

Mapping of hydrophobic surface potential onto the K1/K10-1B heterodimer structure demonstrated that one heterodimer face contains multiple surface-exposed hydrophobic residues, whereas the face 180° opposite is largely polar with only a few exposed hydrophobic residues (FIG. 2A). The hydrophobic face of the K1/K10-1B heterodimer contains the molecular determinants of tetramer assembly. It can be divided into four key segments from N- to C-terminus: a hydrophobic pocket, a K10 hydrophobic stripe, K1 interaction residues, and an anchoring knob (FIG. 2B).

At the N-terminus of the K1/K10-1B heterodimer there is a hydrophobic pocket formed by three K1 residues (Y230, F231, and F234). The concavity between these aromatic residues is the receptor site for the C-terminal anchoring knob on a neighboring K1/K10-1B heterodimer, facilitating tetramer formation (FIG. 2C). The C-terminal anchoring knob is composed of two K1 residues (F314 and L318). $F314^{K1'}$ binds by wedging between $F231^{K1}$ and $F234^{K1}$, creating a ring-stacking interaction with $F234^{K1}$ (FIG. 2d). $L318^{K1'}$ interacts with $F231^{K1}$ and $Y230^{K1}$ (~3.8 and 4.2 Å respectively), and knob-pocket docking brings $A321^{K1'}$ near $Y230^{K1}$ (~3.6 Å) and $L318^{K1'}$ near $L227^{K1}$ (~4.6 Å).

Adjacent to the hydrophobic pocket, and aligned along the outer aspect of the α-helical ridge, are several K10 residues constituting a predominantly hydrophobic stripe (FIGS. 2A and 2B). "Hydrophobic stripe" was termed from modelling analysis of K6/K16/K17 dimers; however, in the K1/K10-1B tetramer structure the function of this protein region proves more complex. The K10 helical ridge on the N-terminal half of the K1/K10-1B heterodimer is defined by eleven K10 residues: K207, T215, A218, N219, L221, L222, N226, L229, K237, and L236. Several of these residues are not hydrophobic (K207, T215, N219, N226, K237) but make meaningful interactions to stabilize tetramer assembly and thus are considered part of the stripe (FIG. 2E). $K207^{K10}$ forms a salt bridge with $E311^{K1'}$, while $T215^{K10}$ interacts with $M296^{K1'}$ and $D300^{K1'}$ (FIGS. 2D and 2E). K10 hydrophobic residues L211, A218, L221, L222 and L229 all have interactions with K1' residues less than 5 Å apart (FIG. 2F).

The hydrophobic face of the K1/10-1B heterodimer contains a segment consisting of "K1 interaction residues" between the K10 hydrophobic stripe and the C-terminal anchoring knob. K1 interaction residues exist on the K1 α-helix whose helical ridge forms most of the distal hydrophobic face. In the K1/10-1B tetramer twelve K1 residues from this segment have hydrophobic or electrostatic interactions with ten K10 hydrophobic stripe residues from the binding heterodimer (FIG. 2E).

$S233L^{K1}$ Mutation Drives Aggregation of K1/K10-1B in Solution

Figure 3:
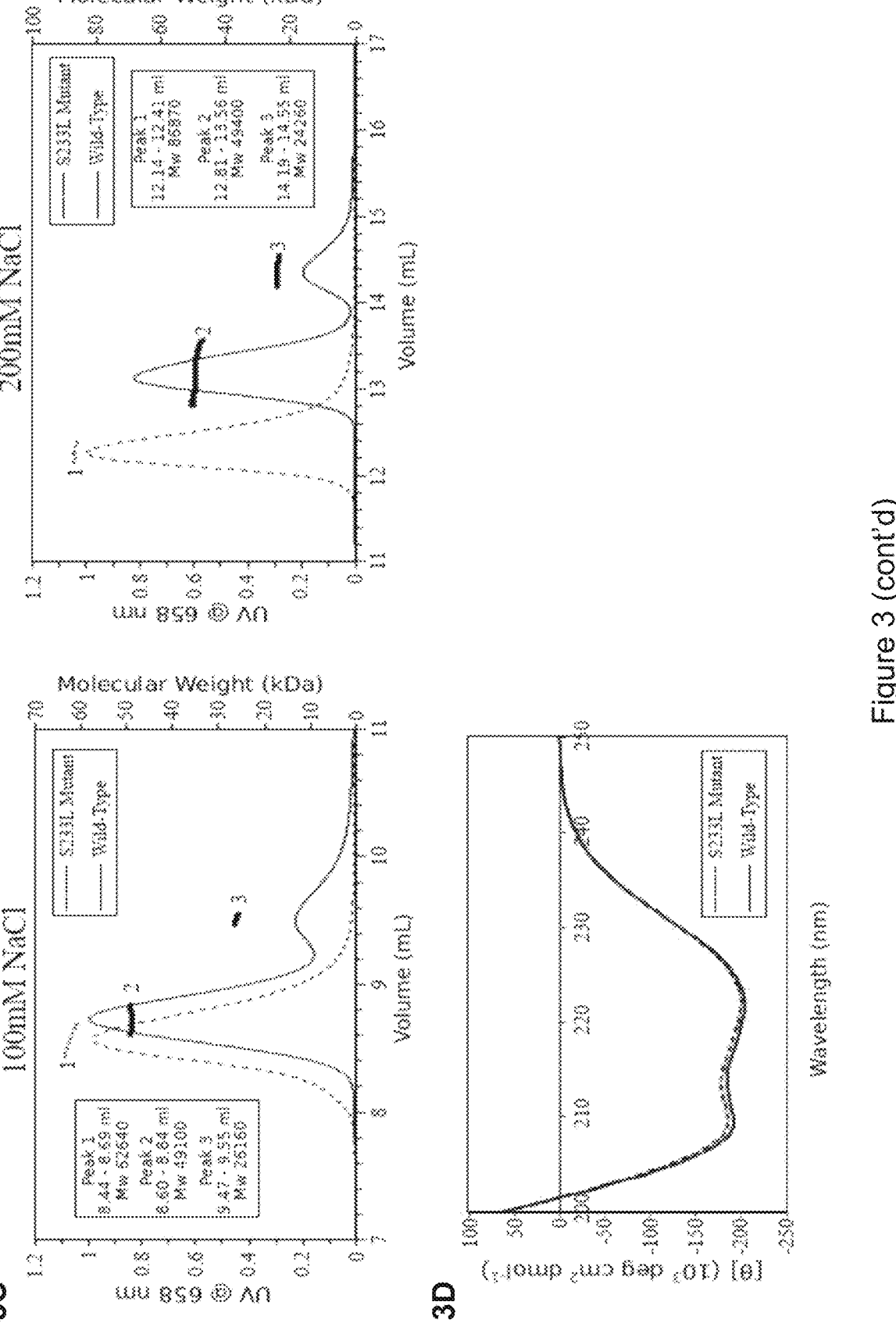
FIG. 3, comprising

Keratin 1 containing the missense mutation S233L, which is pathogenic for epidermolytic palmoplantar keratoderma, was produced and purified to investigate how the mutation affects K1/K10-1B heterodimer structure and function (FIG. 3A). After His-tag removal from K10, K1/K10-1B wild-type and $K1^{S233L}$ complexes were analyzed by gel filtration. Wild-type K1/K10-1B separated into two main peaks (FIG. 3B, solid line), whereas $K1^{233L}$/K10-1B formed one major peak (FIG. 3B, dotted line) that eluted earlier than the wild-type complex. This suggested $K1^{233L}$/K10-1B formed a higher molecular weight complex in solution than wild-type K1/K10-1B.

To characterize the molecular weight (MW) of these complexes, K1/K10-1B and $K1^{233L}$/K10-1B were analyzed by multi-angle light scattering in either 100 mM NaCl or 200 mM NaCl solutions (FIG. 3C). Wild-type K1/K10-1B (solid line) formed a tetramer species (peak 2, ~49 kDa) and a dimer species (peak 3, ~24-26 kDa) in both 100 mM and 200 mM NaCl conditions (wild-type heterodimer calculated MW is 24,840). In contrast, $K1^{233L}$/K10-1B (dotted line) formed a single species of ~62 kDa in 100 mM NaCl solution and ~86 kDa in 200 mM NaCl solution. This demonstrated $K1^{233L}$/K10-1B formed higher MW aggregates than wild-type K1/K10-1B in solution. The increased MW for the mutant complex under higher ionic strength is consistent with enhanced hydrophobic interaction.

Circular dichroism demonstrated that $S233L^{K1}$ does not alter the secondary structure of K1/K10-1B (FIG. 3D). Both wild-type K1/K10-1B (solid line) and K1233L/K10-1B (dotted line) complexes had identical α-helical secondary structure in solution.

Pseudo-Tonotubular Keratin in Mutant $K1s^{233L}$/K10-1B Octamer Structure

Figure 4:
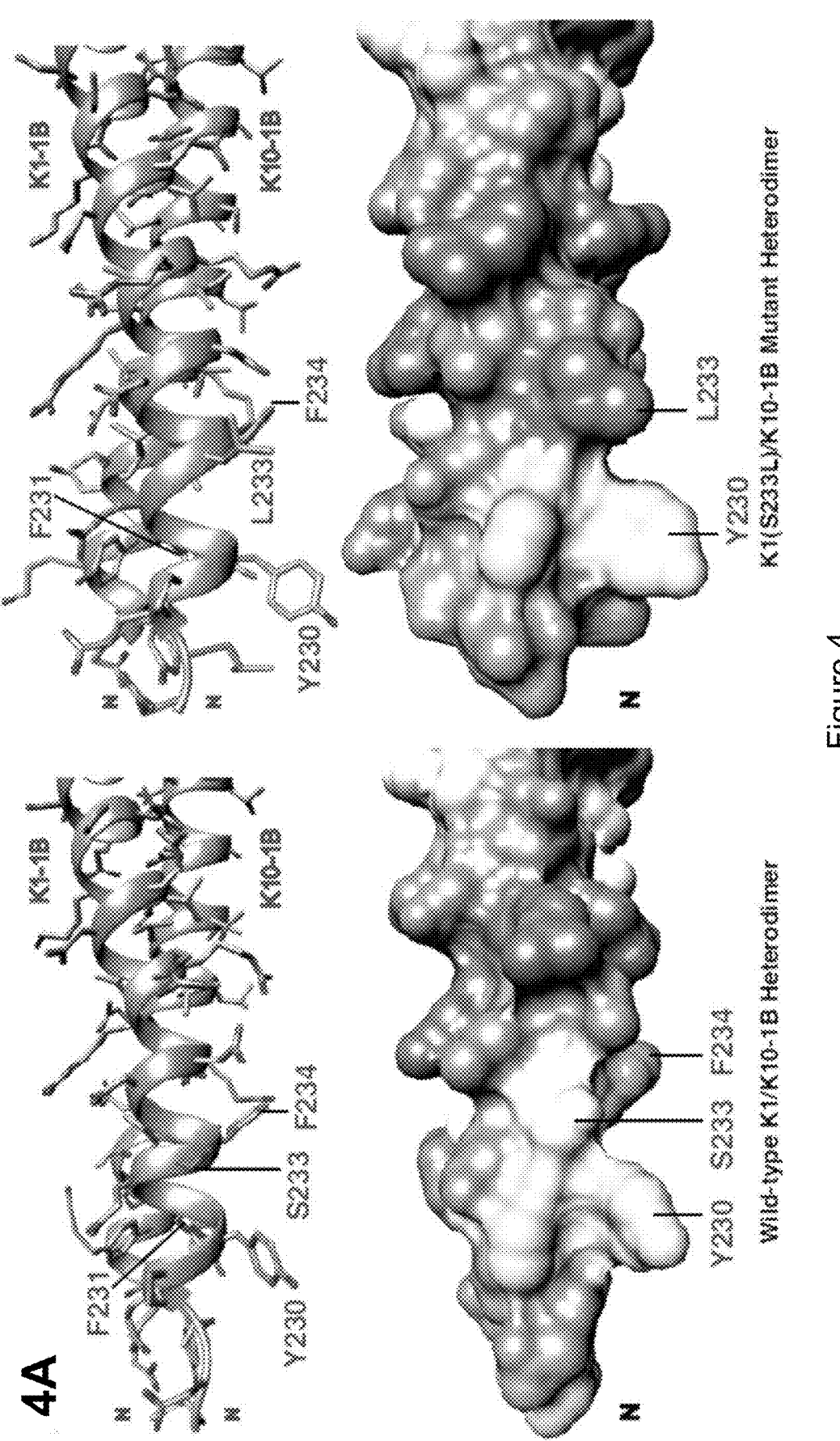
FIG. 4, comprising
Figure 4:
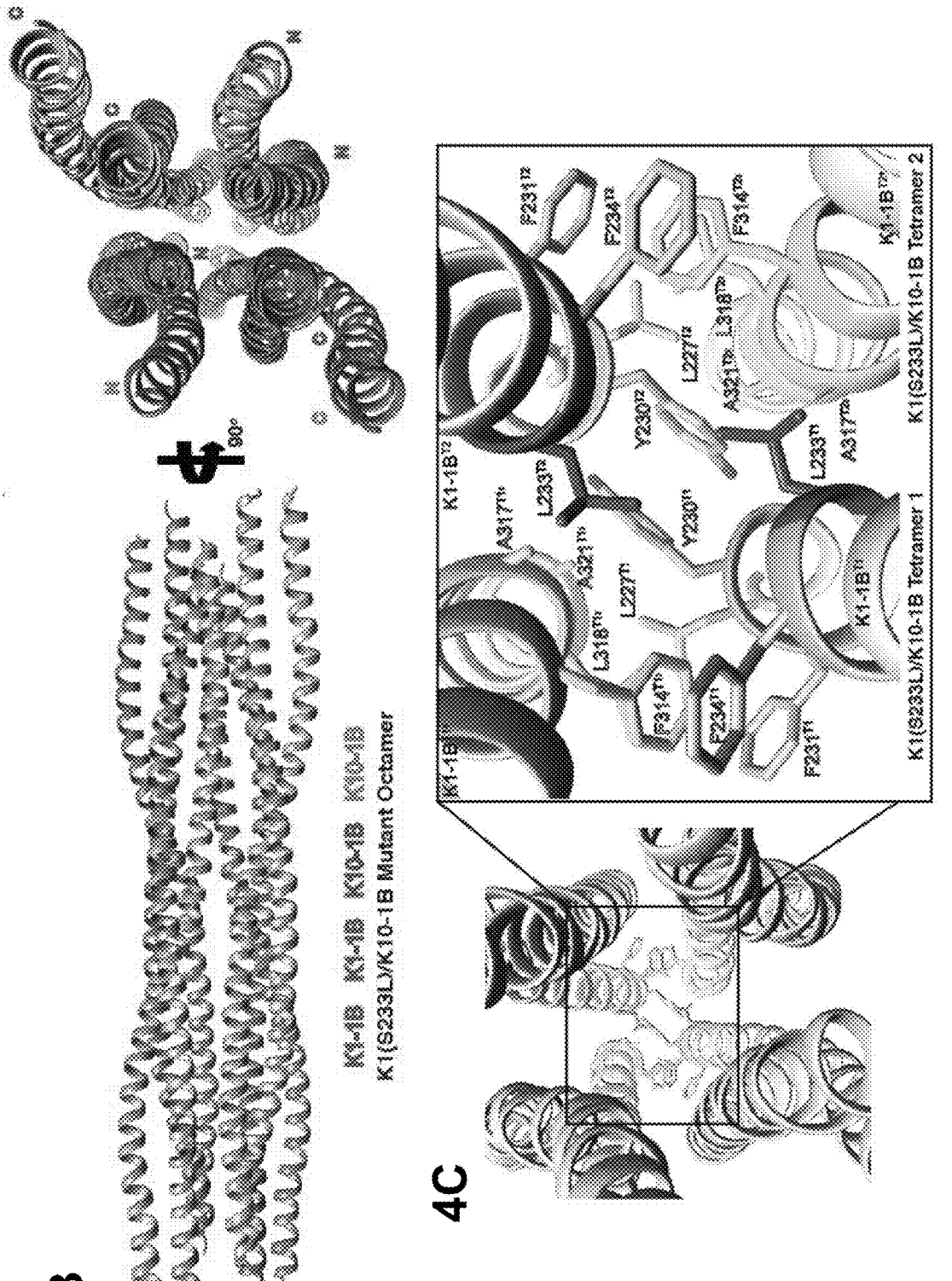

To further investigate how $S233L^{K1}$ mutation impacts K1/K10-1B structure, the $K1^{S233L}$/K10-1B crystal structure was determined to 2.2 Å resolution (Table 1). Both S233 from the wild-type K1/K10-1B structure and L233 from the mutant $K1^{S233L}$/K10-1B structure occupy solvent exposed positions at the N-terminus of the 1B heterodimer. The $S233L^{K1}$ mutation changes the surface potential at this site from polar (wild-type) to hydrophobic (mutant) (FIG. 4A). Near position 233, along the inter-molecular interface of the 1B heterodimer, are two critical K1 phenylalanines (F231 and F234) involved in heterodimer stabilization and in forming the hydrophobic pocket.

The increased hydrophobic surface potential created by $S233L^{K1}$ mutation did not alter heterodimer or tetramer formation, but rather altered how tetramers interacted with each other (FIG. 4B). This explains why the $K1^{S233L}$/K10-1B structure was determined as an octamer. Specifically, $L233^{K1}$ from one tetramer bound to five residues from a different tetramer (the aromatic portion of $Y230^{K1'}$, $L233^{K1'}$, $F234^{K1'}$, $F314^{K1'}$ and $Ala317^{K1'}$) to drive hydrophobic assembly of an octamer (FIG. 4C). Due to the anti-parallel symmetry of the tetramer, the same interactions by $L233^{K1}$ occur at both ends of the octamer. $L233^{K1}$ closely interacts with itself, $L233^{K1'}$ (~3.8 Å), and Ala317K1' (~3.9 Å). $L233^{K1}$ additionally interacts with three aromatic residues over slightly longer distances: 4.3 Å ($F314^{K1'}$), 4.8 Å ($Y230^{K1'}$) and 5.5 Å ($F234^{K1'}$). All three of these aromatic residues are involved in the hydrophobic pocket/anchoring knob mechanism of tetramer assembly. As two tetramers bind in the K1$^{S233L}$/K10-1B octamer, Y230 from one hydrophobic pocket binds with Y230 from the adjacent pocket (FIG. 4C).

Examination of K1$^{S233L}$/K10-1B crystal lattice packing revealed a repetitive arrangement of a circular structure (the K1$^{S233L}$/K10-1B octamer) (FIG. 4D). At first glance it appears the octamer mimics the tonotubular keratin observed under electron microscopy from EPPK skin. The diameter of the octamer, however, is only ~45 Å (4.5 nm), which is about one-tenth the diameter of the observed in vitro tonotubular keratin (430 Å or 43 nm). Hence, the octamer is referred to as pseudo-tonotubular keratin.

Comparing wild-type and mutant K1/K10-1B tetramer structures, the major interactions between the hydrophobic pocket and anchoring knob, as described above for the wild-type structure, are preserved in the mutant. However, there are additional findings in the mutant structure that further characterize the hydrophobic pocket/anchoring knob mechanism for tetramer assembly. First, the L227$^{K1}$ sidechain occupies a position much closer to L318$^{K1'}$, forming the N-terminal wall of the hydrophobic pocket and stabilizing the anchoring knob via interactions with L318$^{K1'}$ (L318' Cδ1 to L227 Cβ distance decreases from 4.7 to 3.8 Å; L318' Cδ1 to L227 Cδ2 distance decreases from 6.4 to 4.1 Å) (FIG. 4E). The conformation of L227$^{K1}$ appears to be altered by cadmium binding of the N-terminal methionine in the wild-type K1/K10-1B structure (FIG. 4F); this does not occur in the K1$^{S233L}$/K10-1B mutant structure because its crystallization condition did not contain cadmium. Second, there are two K10 residues, Y200$^{K10}$ and I203$^{K10}$ that in the mutant structure are less than 4.3 Å away from F314$^{K1'}$ and L318$^{K1'}$ (FIG. 4F); they are ~5 Å away in the wild-type structure. These conformational differences are not a direct consequence of the K1$^{S233L}$ mutation itself, but rather local structure perturbations from cadmium binding at the N-terminus of K1 (N-terminal methionine) and C-terminus of K1/K10 (E322$^{K1}$ and H287$^{K10}$) in the wild-type K1/K10-1B tetramer crystals (FIG. 4F).

One K10 helical ridge hydrophobic residue (L236) is not considered part of the hydrophobic stripe because it functions differently than the stripe residues. All ten K10 residues, defined above as "hydrophobic strip,e" contribute to tetramer formation by binding K1 residues from the partner heterodimer. L236$^{K10}$ exists at the interface between K10 helices in the center of the 1B tetramer structure, and thus is involved in K10-K10' interactions. In the wild-type K1/K10-1B structure L236$^{10}$ is ~4.9 Å away from its closest hydrophobic neighbor (L244 K10'); however, in the mutant K1$^{S233L}$/K10-1B structure L236$^{K10}$ and L244$^{K10'}$ are ~4.0 Å apart signifying this interaction could have a role in K10-K10' stabilization in the tetramer (FIG. 2F).

TABLE 1

| | Wild-type K1/K10-1B Crystal Diffraction Data | K1$^{S233L}$/K10-1B |
|---|---|---|
| Space Group | P 31 2 1 | P 64 2 2 |
| Unit Cell Dimensions a, b, c (Å) α, β, γ (°) | 106.38, 106.68, 70.32 90, 90, 120 | 93.30, 93.30, 124.74 90, 90, 120 |
| Resolution range (outer shell), Å | 46.20-2.98 (3.05-2.98) † | 46.65-2.39 (2.43-2.39) |
| I/σI | 11.72 (0.64) | 20.2 (1.92) |
| Resolution (Å) where I/σI~1.9 | 3.46 | 2.39 |
| CC(1/2) in outer shell, % | 64.0 | 78.7 |

TABLE 1-continued

| | Wild-type K1/K10-1B Crystal Diffraction Data | K1$^{S233L}$/K10-1B |
|---|---|---|
| Space Group | P 31 2 1 | P 64 2 2 |
| Completeness, % | 89.5 (69.9) | 99.9 (99.5) |
| R$_{merge}$ | 0.132 (1.185) | 0.139 (0.969) |
| No. crystals used | 1 | 1 |
| No. unique refelctions | 8414 | 13342 |
| Redundancy | 8.0 (5.0) | 13.3 (10.0) |
| Wilson B-factor, Å$^2$ | 86.2 | 67.3 |
| | Refinement | |
| R$_{work}$, % | 0.279 (0.417) | 0.271 (0.349) |
| R$_{free}$, % | 0.298 (0.478) | 0.294 (0.371) |
| | No. of Non-Hydrogen Atoms | |
| Protein | 1731 | 1751 |
| Ligands/Ions | 9 | 4 |
| Waters | 35 | 60 |
| | R.m.s. Deviations | |
| Bond lengths, (Å) | 0.006 | 0.004 |
| Angles, (°) | 0.876 | 0.587 |
| Chirality | 0.036 | 0.029 |
| Planarity | 0.004 | 0.005 |
| Dihedral, (°) | 18.415 | 17.408 |
| Average B-factor (overall), Å$^2$ | 146.0 | 106.3 |

† Values in parentheses are for highest-resolution (outer) shell

Structural Modeling of F231L$^{K1}$ and R267Y$^{K1}$ Mutations

Figure 5:
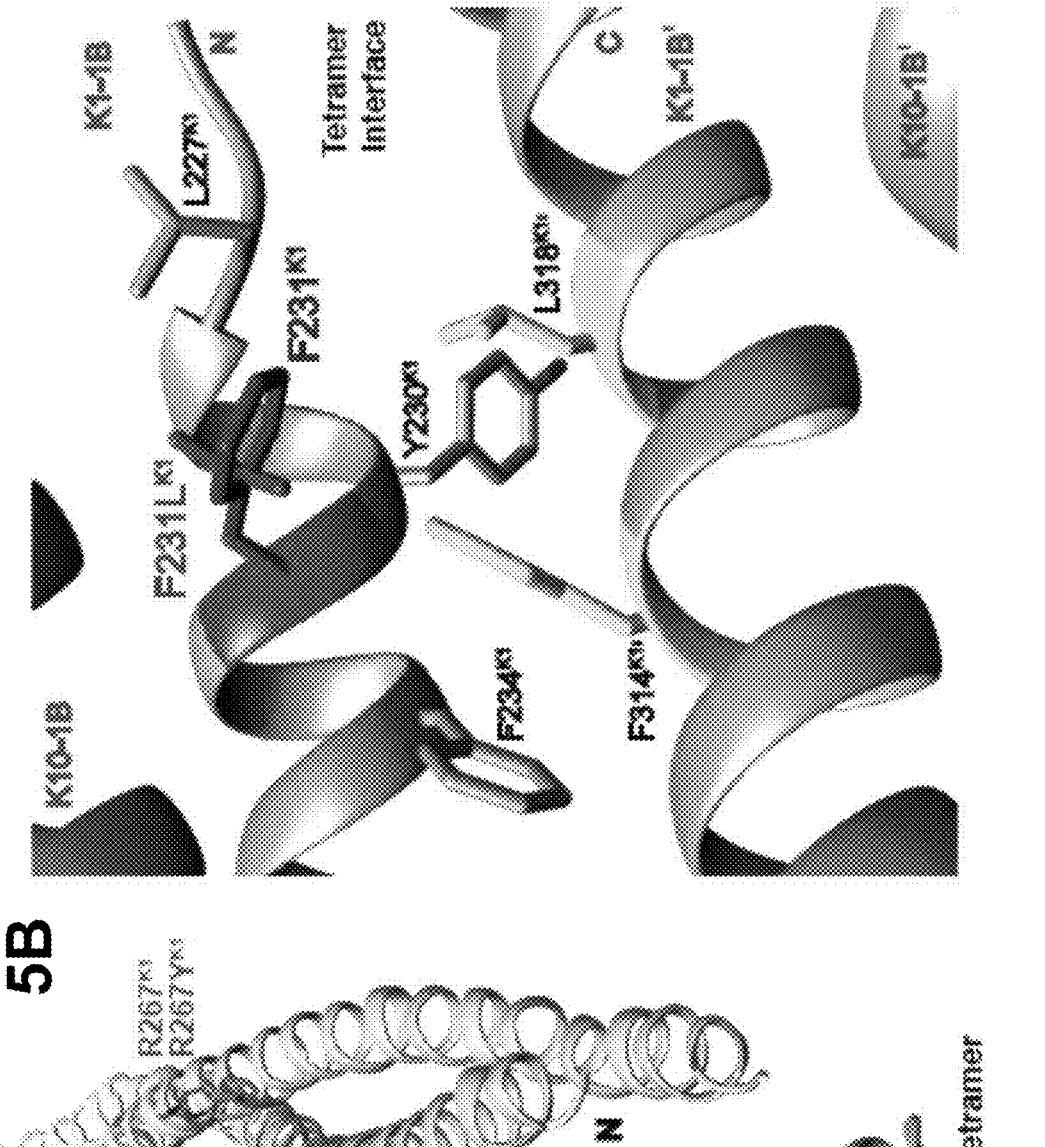
FIG. 5, comprising

Literature on EPPK patients with tonotubular keratin references two additional mutations: a pathogenic F231L$^{K1}$ mutation causing EPPK and tonotubular keratin, and a non-pathogenic R267Y$^{K1}$ mutation in a British control subject with no skin disease. To explain the discrepancy in pathogenicity between these mutations at a structural level, the wild-type K1/K10-1B crystal structure was used to model F231L$^{K1}$ and R267Y$^{K1}$ mutations. The lack of pathogenicity for R267Y$^{K1}$ is the most straightforward of the two; R267 occupies a solvent-exposed position in the central aspect of the K1-1B coil that is not involved in heterodimer, tetramer, or octamer formation (FIG. 5A). R267Y$^{K1}$ can be accommodated without major structural consequence, thus it is more appropriate to consider it a normal variant.

F231L$^{K1}$ alters the structure of the hydrophobic pocket that binds the anchoring knob in K1/K10-1B tetramer assembly. F231L$^{K1}$ changes the parameters of interaction between position 231 and the key anchoring knob residues, F314$^{K1'}$ and L318$^{K1'}$ (FIGS. 2B-2D). Specifically, the interaction distance between L318$^{K1'}$ and mutant L231$^{K1}$ is ~1.2 Å longer (4.98 Å) compared to wild-type F231$^{K1}$ (3.8 Å) (FIG. 5B). The closest interaction distance between F314$^{K1'}$ and mutant L231$^{K1}$ is unchanged compared to wild-type F231$^{K1}$ (3.4 Å), but F231$^{K1}$ loses its interactions with the F231 aromatic ring. Together, the modeling data suggests mutant L231$^{K1}$ has weakened interactions with F314$^{K1'}$ and L318$^{K1'}$, potentially leading to pathogenic disruption of the hydrophobic pocket/anchoring knob tetramer assembly mechanism.

There is a lack of atomic resolution structural data delineating the biochemical mechanisms of keratin intermediate filament (KIF) assembly. KIFs are more than ever implicated in cellular processes and functions well beyond structural and mechanical integrity. Thus, it is critical to meticulously answer using experimentally determined high-resolution structures the unsettled question of how human keratin heterodimers assemble into higher order filaments. Furthermore, many human diseases caused by keratin mutation do not affect heterodimer structure, but rather alter or disrupt KIF assembly. To fully understand the correlation between genotype, three-dimensional keratin structure, and human phenotype, the mechanisms of filament assembly need to be established in atomic resolution detail. The wild-type K1/K10-1B tetramer and mutant K1$^{S233L}$/K10-1B octamer crystal structures are important advances in KIF structure determination; they provide an atomic resolution mechanism for tetramer formation in the $A_{11}$ mode of axial alignment and illustrate how a pathogenic mutation associated with EPPK can disrupt normal tetramer interactions.

Figure 8:
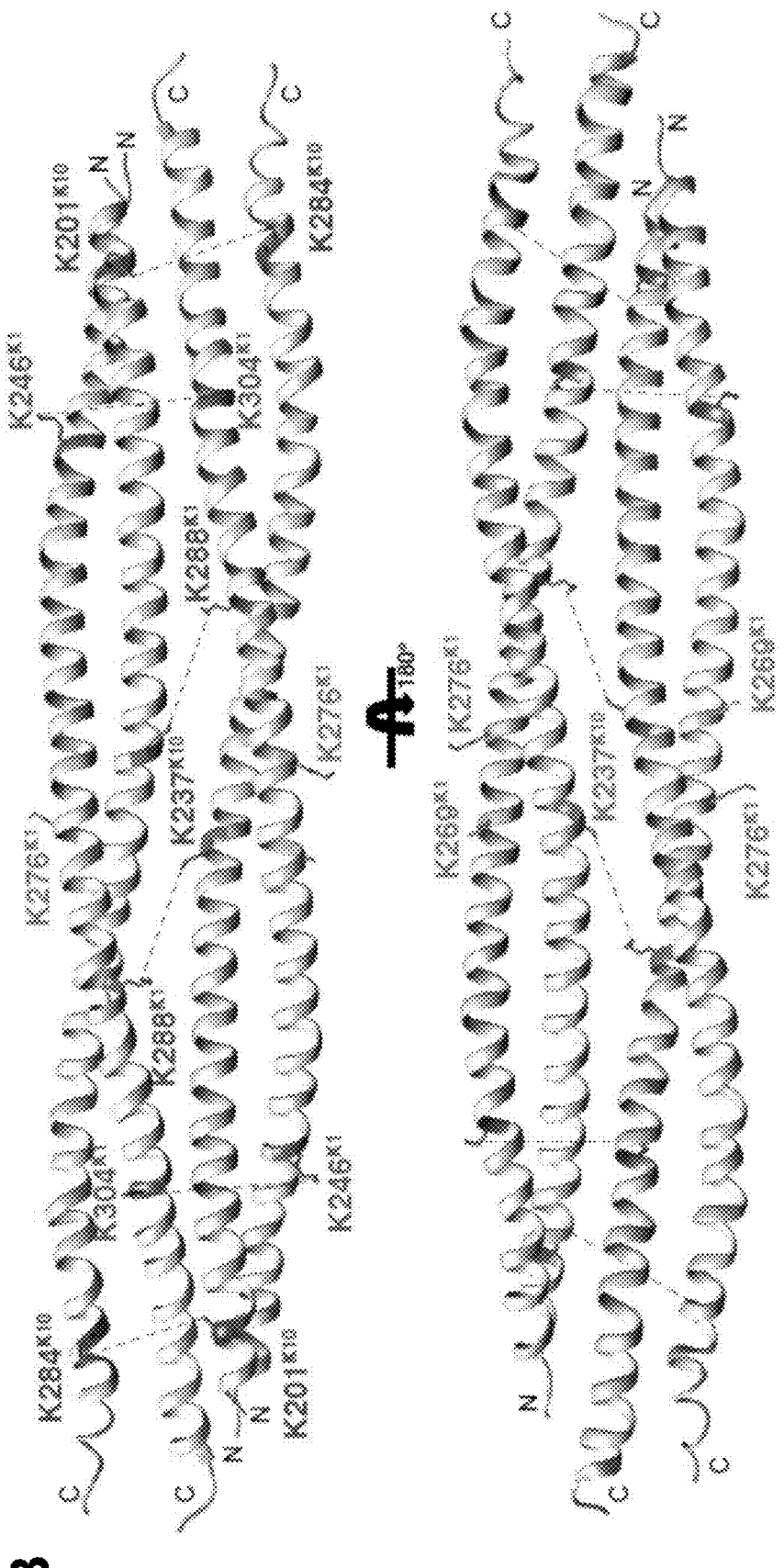
FIG. 8, comprising

Several factors support the wild-type K1/K10-1B structure as the biologically relevant Au-aligned tetramer. First, gel filtration and light scattering studies demonstrated K1/K10-1B existed as a tetramer in solution prior to crystallization. Second, the K1/K10-1B tetramer is consistent with cross-linking studies predicting $A_{11}$ alignment. Steinert and colleagues identified five cross-linked tryptic peptides from mouse K1/K10 filaments mapped to helix 1B; all five lysine pairings can be explained by structural proximity in the human K1/K10-1B tetramer structure (FIG. 8). Third, Coulombe and colleagues identified a hydrophobic stripe on type I keratins during K6/K16/K17 modeling; as hypothesized, the K10 hydrophobic stripe is a major factor in K1/K10-1B tetramer formation. However, the stripe's role in $A_{11}$ tetramer formation proved more complex than anticipated: it was one of four key regions defining tetramer assembly, it did not self-associate, and its main interactions occurred with K1 residues. Fourth, S233L$^{K1}$ mutation was hypothesized to alter heterodimer and/or filament interactions through the creation of aberrant surface hydrophobicity, ultimately leading to tonotubular keratin. The K1$^{S233L}$/K10-1B structure validated this by showing S233L$^{K1}$ caused tetramer aggregation through specific hydrophobic interactions with residues involved in the tetramer assembly mechanism. Lastly, structural comparison of the K1/K10-1B heterotetramer with the vimentin 1B $A_{11}$-homotetramer (a type III IF) revealed that the hydrophobic pocket/anchoring knob mechanism of tetramer assembly is generally conserved; however, there are major differences between the determinants of keratin and vimentin tetramer formation.

The wild-type K1/K10-1B tetramer and mutant K1$^{S233L}$/K10-1B octamer crystal structures provide new information about human keratin tetramer formation in the $A_{11}$ mode of axial alignment and illustrate how a pathogenic mutation associated with EPPK can disrupt normal tetramer interactions. This work helps address the lack of atomic resolution structural data for the keratin intermediate filament (KIF) assembly mechanism. KIFs are more than ever implicated in cellular processes and functions well beyond structural and mechanical integrity. Many human diseases caused by keratin mutation do not affect heterodimer structure, but rather alter or disrupt KIF assembly; this creates a need for experimentally determined high-resolution structures focused on understanding KIF assembly.

The structural data, and gel filtration and light scattering studies presented herein which demonstrate that K1/K10-1B exists as a tetramer in solution prior to crystallization, give strong support to the previously proposed $A_{11}$ alignment of the K1/K10-1B tetramer. First, the K1/K10-1B tetramer is consistent with cross-linking studies predicting $A_{11}$ alignment. Five cross-linked tryptic peptides from mouse K1/K10 filaments were previously mapped to helix 1B6; all five lysine pairings can be explained by structural proximity in the human K1/K10-1B tetramer structure (FIG. 8). Second, a hydrophobic stripe on type I keratins was previously identified during K6/K16/K17 modeling; as hypothesized, the K10 hydrophobic stripe is a major factor in K1/K10-1B tetramer formation. However, the stripe's role in $A_{11}$ tetramer formation proved more complex than anticipated: it was one of four key regions defining tetramer assembly, it did not self-associate, and its main interactions occurred with K1 residues. Third, the Au alignment validates the hypothesis that the S233L$^{K1}$ mutation alters heterodimer and/or filament interactions through the creation of aberrant surface hydrophobicity, ultimately leading to tonotubular keratin. The K1$^{S233L}$/K10-1B structure validated this by showing S233L$^{K1}$ caused tetramer aggregation through specific hydrophobic interactions with residues involved in the tetramer assembly mechanism.

Structural comparison of the K1/K10-1B heterotetramer with the vimentin 1B $A_{11}$-homotetramer (a type III IF) revealed major differences between the determinants of keratin and vimentin tetramer formation while confirming that the hydrophobic pocket/anchoring knob mechanism of tetramer assembly is generally conserved. Besides the obvious difference that vimentin forms homodimers rather than heterodimers like the keratins, vimentin does not contain a hydrophobic stripe aiding tetramer formation The K10 hydrophobic stripe contains five key hydrophobic residues with interactions (to K1') that stabilize the 1B tetramer; only one hydrophobic residue is conserved (A218') and one similar (L222$^{K10}$ to valine) in vimentin (FIG. 6A). Vimentin conserves none of the four critical leucines in the K10 hydrophobic stripe. Of the twelve K1 interaction residues, five are completely conserved and another five are similar in vimentin (FIG. 6B).

In contrast to the K10 hydrophobic stripe and K1 interaction residues, the C-terminal anchoring knob is entirely conserved in vimentin helix 1B (FIG. 6C). Vimentin's F233 and L237 form the anchoring knob and are homologous to F314 and L318 in K1. Like K1/K10, the vimentin anchoring knob binds into a hydrophobic pocket at the N-terminus of a neighboring vimentin 1B homodimer. Vimentin's hydrophobic pocket, however, is formed differently than K1. There are four key vimentin residues that form the hydrophobic pocket: L149, Y150, E153 (the aliphatic portion), and M154. Unlike K1/K10-1B, where all of the hydrophobic pocket is formed by K1 residues (and not K10), vimentin's hydrophobic pocket is formed by residues from both homodimer helices. L149, Y150, and E153 are on one helix and M154 comes from the homodimer partner helix (FIG. 6D). The identification of the hydrophobic pocket/anchoring knob mechanism in vimentin 1B tetramer formation explains why several prior vimentin crystal structures failed to show tetramerization: the vimentin construct either didn't contain the N-terminal sequence needed to form a complete hydrophobic pocket (PDB Codes 3SWR and 4YPC) or lacked the C-terminal sequence containing the anchoring knob (PDB Codes 3SSU and 3S4R).

The importance of the hydrophobic pocket/anchoring knob mechanism to higher order KIF formation is validated by multiple sequence alignment. For all type II keratins, including the hair and nail keratins, the anchoring knob positions are highly conserved: position 314$^{K1}$ is conserved as phenylalanine in 25/26 type II keratins (K80 has leucine); position 318$^{K1}$ is conserved as leucine in 23/26 type II keratins (K5 has phenylalanine, K75 valine, and K80 isoleucine) (FIG. 9). Similarly, the hydrophobic pocket is highly conserved: positions 227$^{K1}$ and 230$^{K1}$ are conserved as a large hydrophobic residue in 26/26 and 25/26 type II keratins (K76 has cysteine at 230); position 231$^{K1}$ is conserved as an aromatic residue in 22/26 type II keratins (K71, K73, K74, and K77 have leucine); position $234^{K1}$ is conserved as an aromatic residue in 23/26 type II keratins (K3 has histidine, K7 glutamine, and K78 cysteine).

The 28 type I keratins do not have a hydrophobic pocket or anchoring knob. There are no large hydrophobic residues at the analogous $Y230^{K1}$ position, 20/28 residues at the analogous $F234^{K1}$ position are threonine, and 25/28 residues at the analogous L318K1 position are asparagine. Type V IFs (lamins) and the type VI IFs (eye lens) do not have sequence resemblance to either the K1 pocket or knob. Except for syncoilin (no similarity), the primary sequences of type III IFs suggest they contain a vimentin-like hydrophobic pocket and a K1- and vimentin-like anchoring knob. Type IV IFs appear to have a vimentin-like hydrophobic pocket, but they lack a bulky hydrophobic residue at the knob position equivalent to $L318^{K1}$. These findings suggest that the biochemical mechanisms of higher order intermediate filament assembly are not identical across all IF types.

Figure 10:
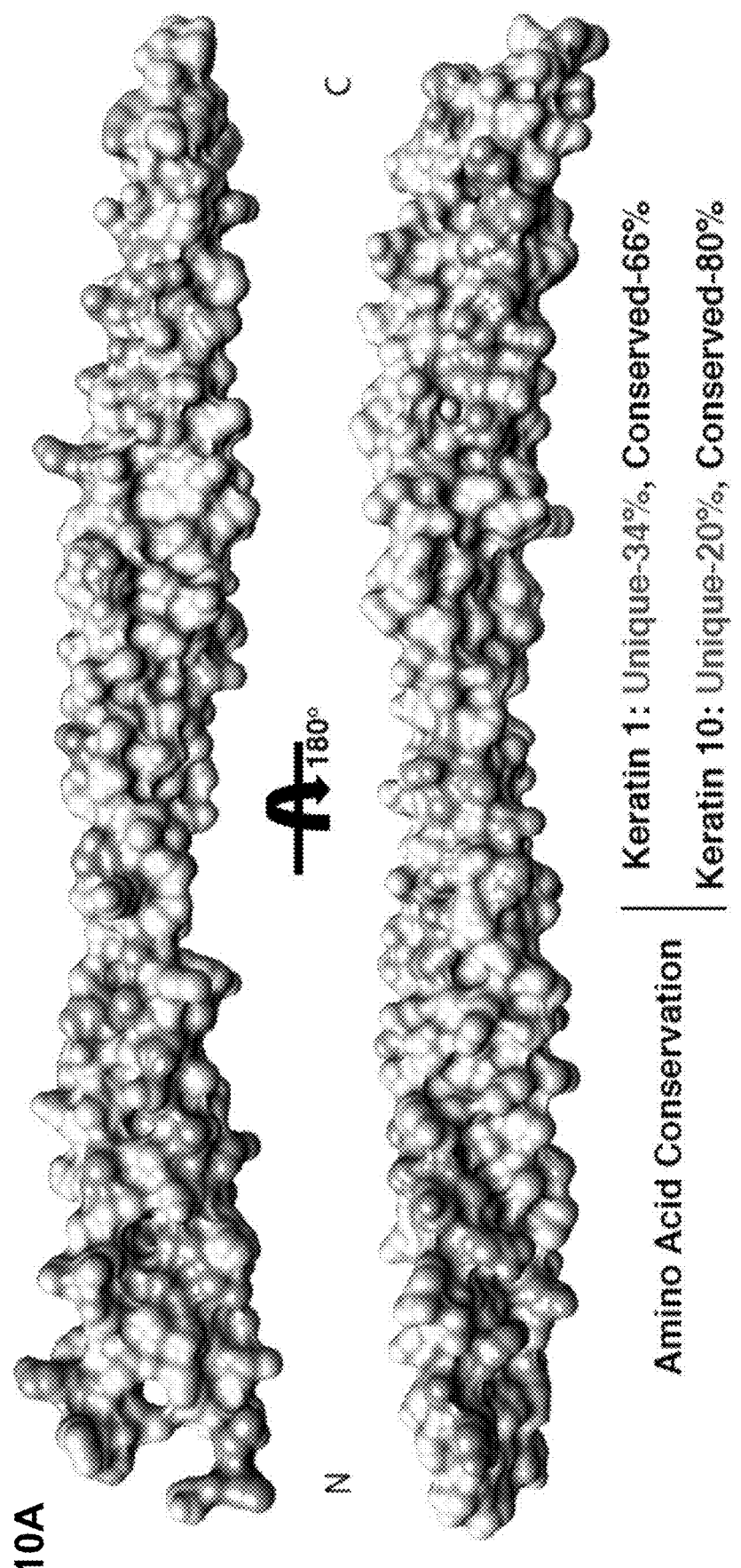
FIG. 10, comprising FIG. 10A
Figure 10:
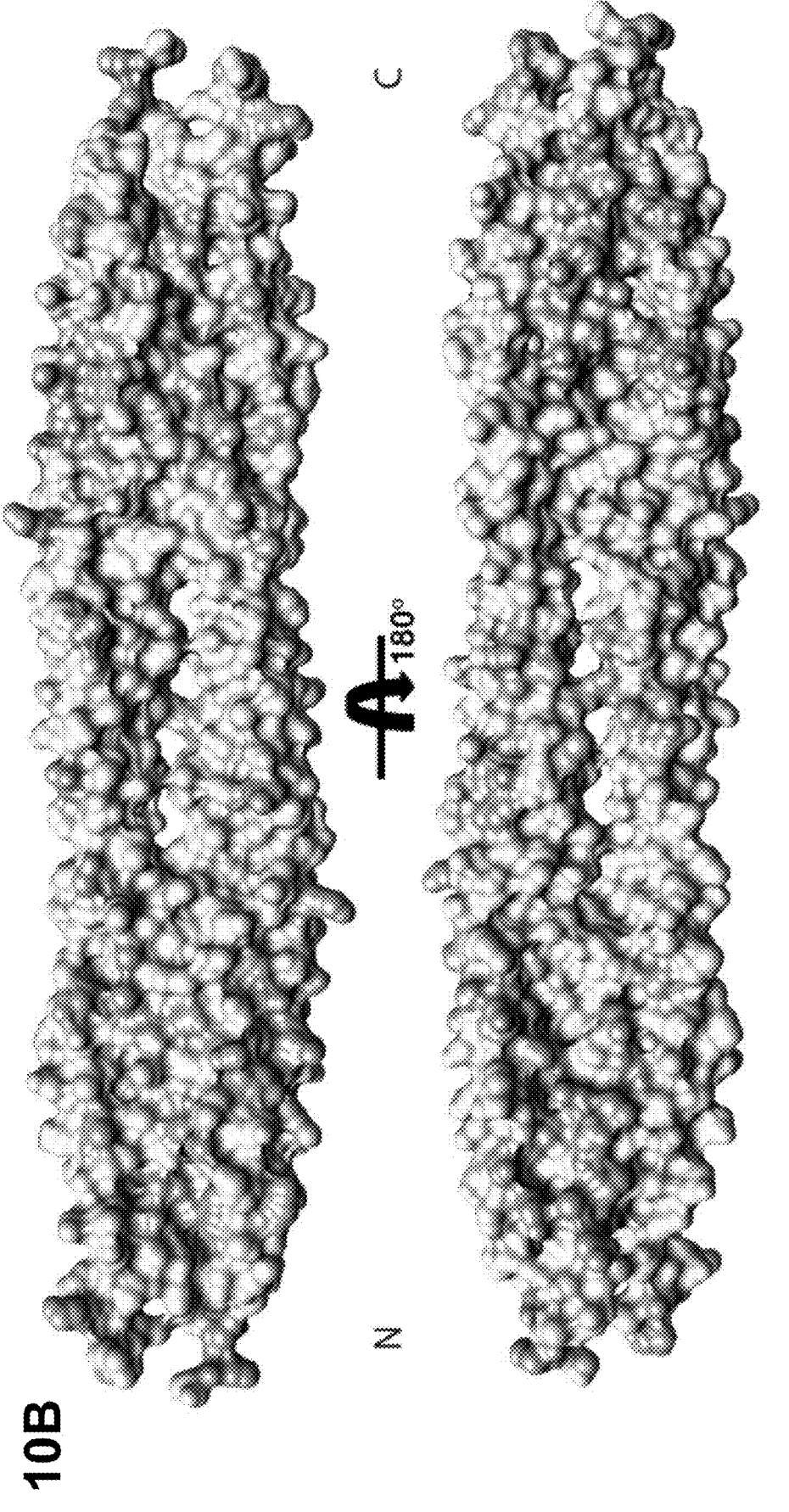
Figure 11:
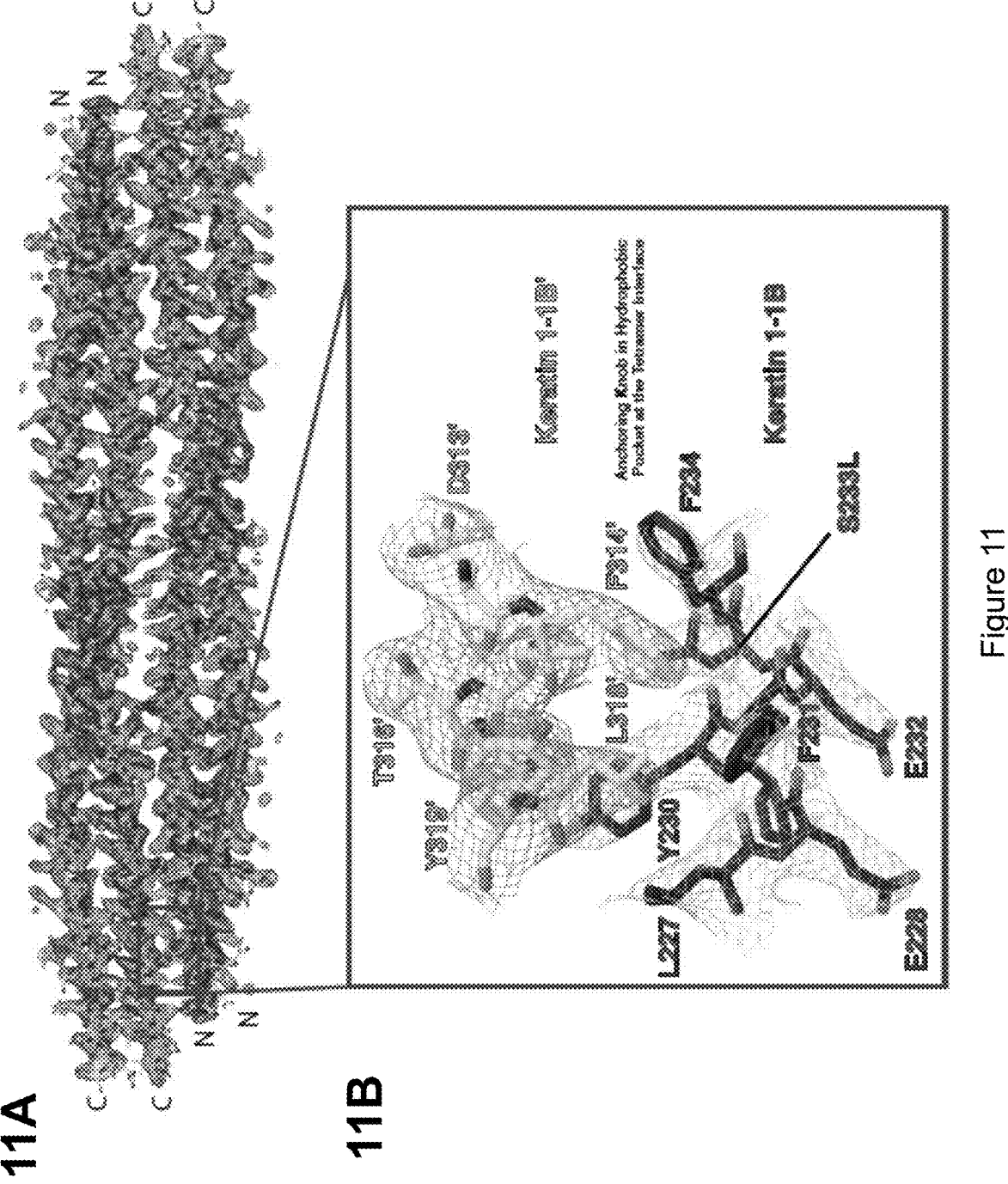
FIG. 11, comprising

The molecular surface features of IFs also contain significant differences. Perhaps the most important finding from the previous K1/K10-2B heterodimer structure was that only a small number of residue differences are needed to significantly alter the shape and chemistry of the keratin surface because most of the unique residues concentrate along the outer helical ridges of the coiled-coil. This holds true for K1/K10-1B as well (FIG. 10). An important question raised by the K1/K10-2B structure was whether the identified surface pockets had relevant biological function. The K1/K10-1B dimer and tetramer structures confirmed that a surface pocket (the N-terminal hydrophobic pocket) visualized in the heterodimer structure served as a receptacle for another part of the complex (the anchoring knob) to help align K1/K10 for higher order assembly (FIG. 11). This validates the concept that keratins contain molecular surface pockets that are biologically relevant, in this case for filament assembly, but in other cases possibly for association with non-keratin proteins.

The observation of a highly acidic groove across the molecular surface of the K1/K10-1B tetramer, but not the dimer, illustrates another important concept: higher order assemblies of keratins may contain new surface features that are not present at the heterodimer level. In other words, some keratin structural features that may be critical for filament assembly or interaction with non-keratin proteins cannot be discovered without structures of higher order keratin complexes. The acidic groove in the K1/K10-1B tetramer extends the full length of the 1B helix, raising questions to its biological purpose. While it could help protofibril formation, an alternative hypothesis is that it serves as the binding site for the non-keratin, positively-charged protein, filaggrin. The atomic resolution mechanism by which filaggrin, short for "filament aggregating protein," binds keratin is unknown; Steinert and colleagues proposed an "ionic zipper hypothesis." The tetramer face opposite the long acidic groove also contains two smaller grooves and a larger pocket; further studies to understand the purpose of each surface feature is critical to elucidating the keratin structure-function paradigm.

The biochemical and structural studies of $K1^{S233L}$/K10-1B demonstrate how a single missense mutation relevant to human skin disease can alter the behavior of KIFs. In this case, $K1^{S233L}$ caused erroneous hydrophobic interactions between the mutant L233 and key residues involved in the hydrophobic pocket/anchoring knob mechanism of tetramer assembly. Even though the $K1^{S233L}$/K10-1B structure did not fully recapitulate tonotubular keratin, it did recapitulate aberrant association of K1/K10 into higher order aggregates. The most likely reason complete tonotubular keratin was not observed is that only the 1B subdomain of K1/K10 was used (flexible full-length keratins are problematic for crystallization); the other portions of intact K1/K10 must play a role in transforming the aberrant tetramer aggregation into a tubular morphology.

The crystal structures of the wild-type keratin 1/10-1B tetramer and the mutant $K1^{S233L}$/K10-1B octamer described here establish a foundation for understanding the molecular determinants of KIF assembly at atomic resolution. The mechanism of $A_{11}$ axial alignment in the keratin 1B region utilizes precise molecular interactions, which raises questions as to how KIFs utilize other predicted modes of alignment, such as the $A_{22}$, $A_{12}$, or $A_{CN}$ modes. Answering this question requires further atomic resolution insight into KIF assembly, with a focus needed on the biochemical determinants of alignment within other keratin subdomains (e.g. 1A, 2A, 2B) and for the different predicted modes of axial alignment.

Figure 12:
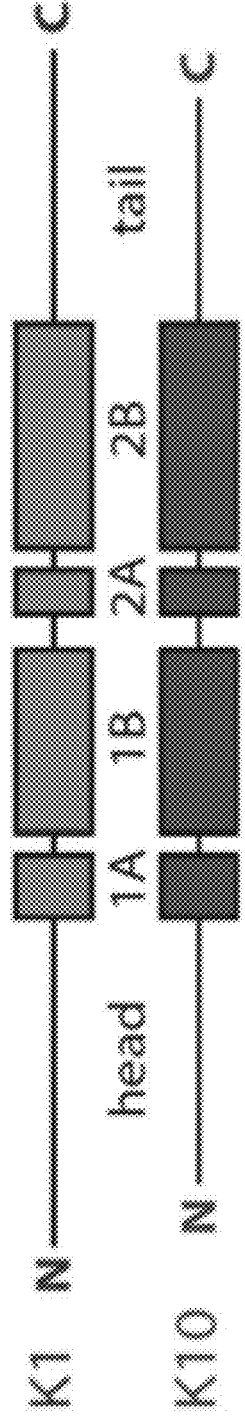
FIG. 12 is a schematic depicting the basic domain organization of keratins 1 and 10.

Example 2: Development of First-in-Class Anti-Cancer Therapeutics Targeting Keratin Intermediate Filaments The crystal structure of the keratin 1/keratin 10 helix 1B heterotetramer, described in Example 1, revealed a novel hydrophobic pocket-anchoring knob mechanism for KIF assembly that offers a novel potential target for anti-cancer therapy. The 1B subdomain is the critical region of keratin for initiating higher order KIF assembly (dimers to tetramers to protofibrils to 10-nm KIFs) (FIG. 12). Described herein are keratin-specific therapeutics that disrupt cancer cell function (e.g. invasion, migration, immune evasion) and viability by directly inhibiting tetramer formation during KIF assembly. Preventing the formation of the KIF cytoskeleton has profound anti-cancer effect, and is analogous to the anti-cancer effect from taxanes and vinca alkaloids which disrupt microtubule polymerization. Two different types of therapeutics that can bind into the hydrophobic pocket are: small-molecule compounds and peptides. This anti-cancer strategy is broadly applicable to multiple cancer types.

Figure 6:
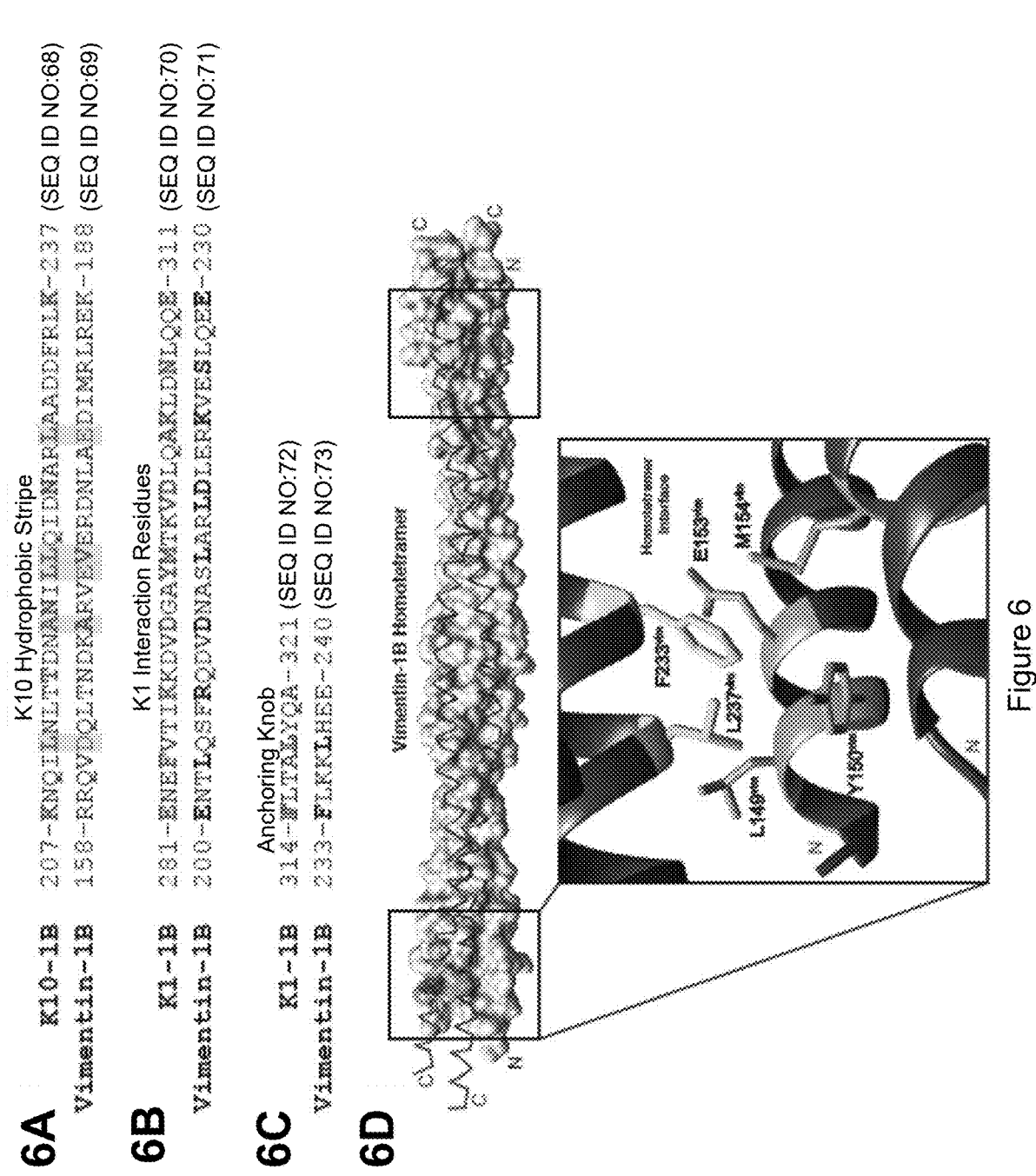
FIG. 6, comprising

Importantly, this knob-pocket mechanism is conserved among type II (keratins) and type III (e.g. vimentin) IFs (FIG. 6). It is demonstrated herein using negative-stain electron microscopy (EM) that mutation of the knob abolishes vimentin IF and severely harms keratin IF assembly in vitro. A new class of anti-cancer therapeutics is developed targeting this newly discovered knob-pocket mechanism to disrupt cancer cell function, especially migration and invasion, by directly inhibiting tetramer formation during IF assembly.

Peptide Inhibitors of Keratin 1/10 Tetramerization

The x-ray crystal structure of the keratin 1/10-1B tetramer shows that an "anchoring knob," consisting of keratin 1 residues F314 and L318, binds into a hydrophobic pocket to drive keratin tetramerization (see Example 1). Since F314 and L318 function as the critical anchor, a set of peptides of varying lengths and amino acid sequences are created around these residues and examined for their ability to disrupt keratin 1/10-1B tetramerization. The strength of binding to the hydrophobic pocket is evaluated for all promising peptides. Lead candidates are then analyzed by electron microscopy for their ability to prevent intact keratin filament formation.

Peptide Synthesis

The keratin 1 sequence ranging from V299 to 5331 contains the critical F314 and L318 residues that function as the anchoring knob:

(SEQ ID NO: 3)
299-VDLQAKLDNLQQEIDFLTALYQAELSQMQTQIS-331.

Multiple peptides from this K1 region are designed to span all possible length and size permutations around F314 and L318. For example, the smallest possible inhibitor is: 314-FLTAL-318 (SEQ ID NO:3). The shortest possible inhibitor is tested first, and then increasing in length to assess for efficacy in inhibiting K1/10-1B tetramerization. For example, other peptides to analyze include 314-FL-TALY-319 (SEQ ID NO:5), 313-DFLTAL-318 (SEQ ID NO:6), 313-DFLTALY-319 (SEQ ID NO:7) and so forth until generating the full V299-5331 sequence (SEQ ID NOs:8-34). The range of peptide length is 5 to 33 amino acids. Some peptides include N- or C-terminal modifications (such as acetylation or amidation). Since the peptides come from a K1 region that is helical in structure (FIGS. 1-3, 5 and 9), they are to be helical themselves; this is examined using circular dichroism.

Tetramer Inhibition Assay

Multi-angle light scattering (MALS) has been used to demonstrate K1/K10-1B forms a stable tetramer in solution. To assess for inhibition of tetramer formation, individual keratin 1-1B and keratin 10-1B proteins are combined in the presence or absence of K1 anchoring knob peptide. Heterodimer formation, but not tetramer formation, occurs when the peptide inhibitor is successful. Samples are passed over a Superdex gel filtration column in tandem with a DAWN HELEOS II light scattering instrument. The molecular weight of a tetramer (~50 kDa) is distinguished from a dimer (~25 kDa) by MALS providing precise data on whether the K1 anchoring knob peptide is effective in inhibiting keratin tetramerization.

Characterize Strength of Binding

All successful peptides in the tetramer inhibition assay are subjected to isothermal titration calorimetry analysis of the keratin-peptide interaction. This establishes the binding affinity and thermodynamics of peptide binding, further refining the lead candidates.

Inhibiting Intact Filaments

K1 anchoring knob peptides are tested for their ability to inhibit the formation of intact KIFs. Full-length, recombinantly produced and purified K1 and K10 proteins will be combined in the presence or absence of K1 anchoring knob peptide, and the solutions examined by electron microscopy. Both negative stain and cryo-EM are possible on this instrument.

Small Molecule Inhibitors of Keratin 1/10 Tetramerization

The hydrophobic pocket discovered the x-ray crystal structure of the keratin 1/10-1B tetramer is defined by four keratin 1 residues: L227, Y230, F231, and F234 (see Example 1). A distinct approach to inhibiting keratin filament formation is developing small molecules that bind strongly to the hydrophobic pocket and thereby prevent the anchoring knob from interacting with its receptor site. Small molecule chemical library screening is used to identify lead candidates for inhibiting keratin 1/10 tetramerization. Identified lead molecules are analyzed by electron microscopy for their ability to prevent intact keratin filament formation.

Screening Assay Development

A biochemical assay using AlphaScreen bead technology is produced and validated (FIG. 13). To properly address inhibition of tetramerization, it is important that the two K1 molecules binding each other via the pocket/knob mechanism are linked to different affinity tags. The same approach, but placing the tags on K10, can be examined if the tags interfere with K1 interaction High-Throughput Chemical Library Screening 50,000 small molecule compounds are screened for their ability to inhibit keratin tetramerization.

Inhibiting Intact Filaments

Small molecule inhibitors are tested for their ability to inhibit the formation of intact KIFs. Full-length, recombinantly produced and purified K1 and K10 proteins are combined in the presence or absence of small molecule inhibitors identified in the screening process. The solutions are examined by negative-stain electron microscopy (using a FEI Talos L120C electron microscope).

Lead Optimization

Identified leads are optimized for chemistry, structure-activity relationship, bioavailability and toxicity.

Validation of KIF Inhibitors on Cancer Cells and Other Intermediate Filament Systems Peptide and small-molecule inhibitor leads identified are investigated for their ability to affect or inhibit the function and viability of cancer cells in vitro. Multiple human cancer cell lines (e.g. skin, breast, colon, liver, lung, pancreatic, and prostate) are examined because the hydrophobic pocket-anchoring knob mechanism is highly conserved among all type II keratin intermediate filaments (e.g. K1-K8 and K71-K86) (see Example 1). Lead compounds developed for K1/K10 tetramer inhibition are examined for their ability to inhibit other IF systems commonly expressed in various human cancers, such as K8/K18. Modification to lead compounds or the development of new ones is also performed for other filament systems. The effects on cellular function (migration) and viability (inhibition of proliferation, induction of apoptosis) is screened in established, high-throughput micro-titer in vitro assays.

Applying Keratin Tetramerization Inhibitors to Cancer Cells

Multiple human cancer cell lines are used in cell-based assays to examine how peptide and/or small-molecule keratin tetramerization inhibitors affect three key behaviors of cancer cells: cell proliferation, apoptosis, and cell migration. These cell-based assays aid in the transition from hits to true lead compounds with demonstrated anti-cancer effects. The human cancer cell lines tested are known to have over-expression of type II keratins (which contain the pocket-knob mechanism): either keratin 1 (squamous cell of the skin) or keratins 5, 6, 7, 8 (biliary duct, transitional cell of the bladder, breast, cervix, colon, renal, liver, small cell lung, ovarian, pancreatic, mesothelioma, prostate, stomach, uterine). Cell proliferation is assessed using the CellTiter-Glo Luminescent Cell Viability Assay, apoptosis using the Promega Caspase-Glo 3/7 Assay, and cell migration using a Boyden Chamber assay.

Expand Keratin Tetramerization Inhibitors to Other IF Systems

For the human cancer cell lines noted above, keratins 7 and 8 are the most widely expressed across these different cancers. While not wishing to be bound to any particular theory, keratin tetramerization inhibitors may be broadly effective because type II keratins having highly homologous amino acid sequence at the hydrophobic pocket and anchoring knob. K1-specific leads are optimized or new leads are obtained that target K7 and K8 following the same procedures described elsewhere herein.

Structure-Based Drug Design

The crystallization of human keratins (see Example 1) allows for development of broadly effective anti-keratin cancer therapies and to determine x-ray crystal structures of K1/10 bound to drug candidates. Structures of other cancer-related keratins, such as K8/18, are also provided. In silico drug screening is also performed.

Example 3: Anchoring Knob Mutants Inhibit K1/K10 Tetramer Formation

Figure 14:
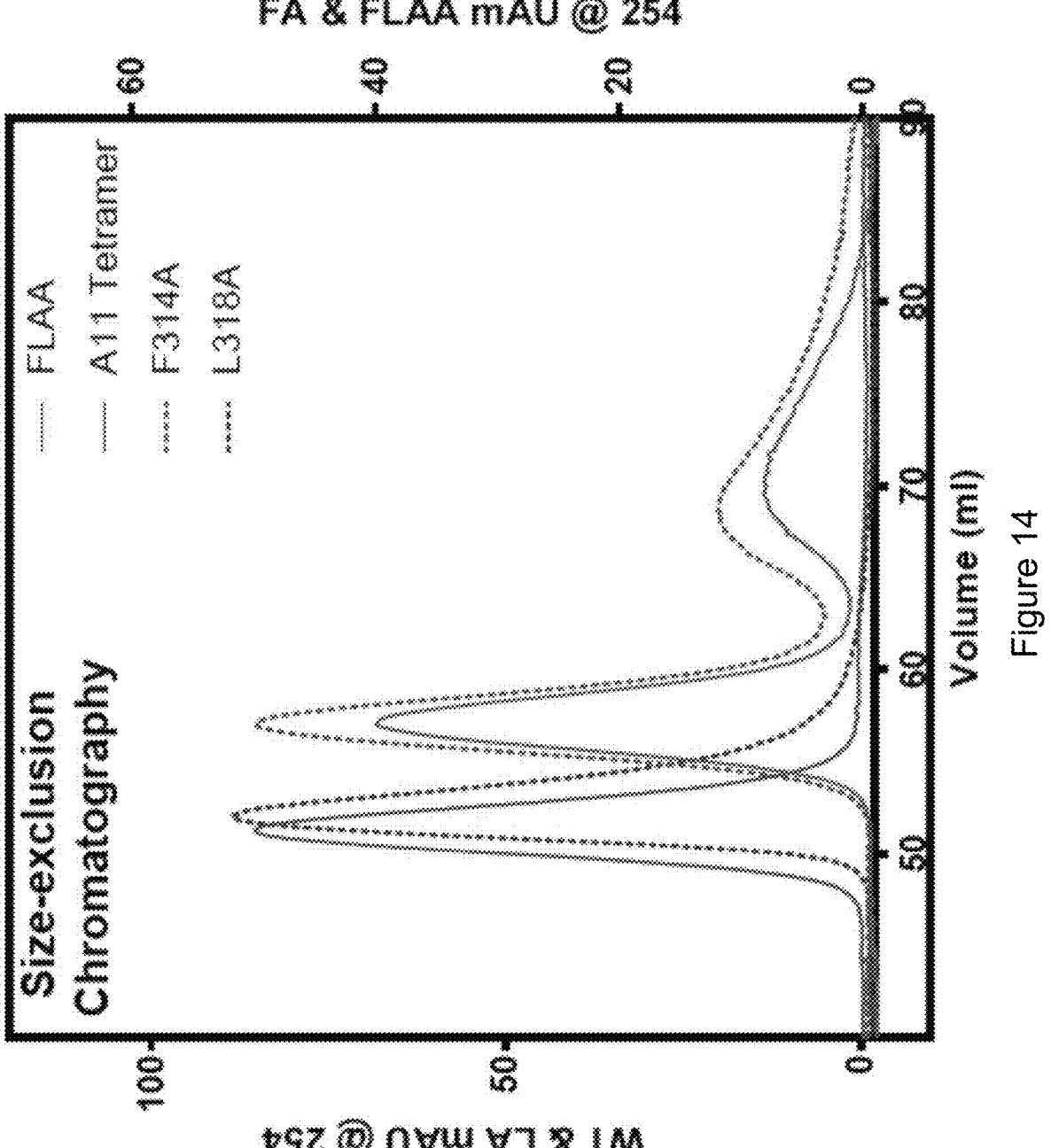
FIG. 14 depicts gel filtration data demonstrating that purified K1/10-1B tetramer (A11 Tetramer, solid blue line) separates as a higher molecular weight species than a K1-F314A/10-1B mutant (dotted red line), suggesting the mutation of the anchoring knob residue F314 to alanine abolishes the tetramer formation. A K1-L318A/10-1B mutant (dotted blue line) migrated at the same position as the wildtype A11 tetramer, suggesting that the mutation of the anchoring knob residue L318 to alanine did not abolish tetramer formation. The results suggest the F314 residue is critical for keratin 1B tetramer formation. A double mutant with both F314A+L318A (FLAA) (solid red line) also abolished tetramer formation.

Gel filtration data demonstrated that purified K1/10-1B tetramer (A11 Tetramer, solid blue line) separates as a higher molecular weight species than a K1-F314A/10-1B mutant (dotted red line) (FIG. 14). This suggests that the mutation of the anchoring knob residue F314 to alanine abolishes the tetramer formation. A K1-L318A/10-1B mutant (dotted blue line) migrated at the same position as the wildtype A11 tetramer, suggesting that the mutation of the anchoring knob residue L318 to alanine did not abolish tetramer formation. This suggests that the F314 residue is critical for keratin 1B tetramer formation. A double mutant with both F314A+ L318A (FLAA) (solid red line) also abolished tetramer formation (FIG. 14).

Figure 15:
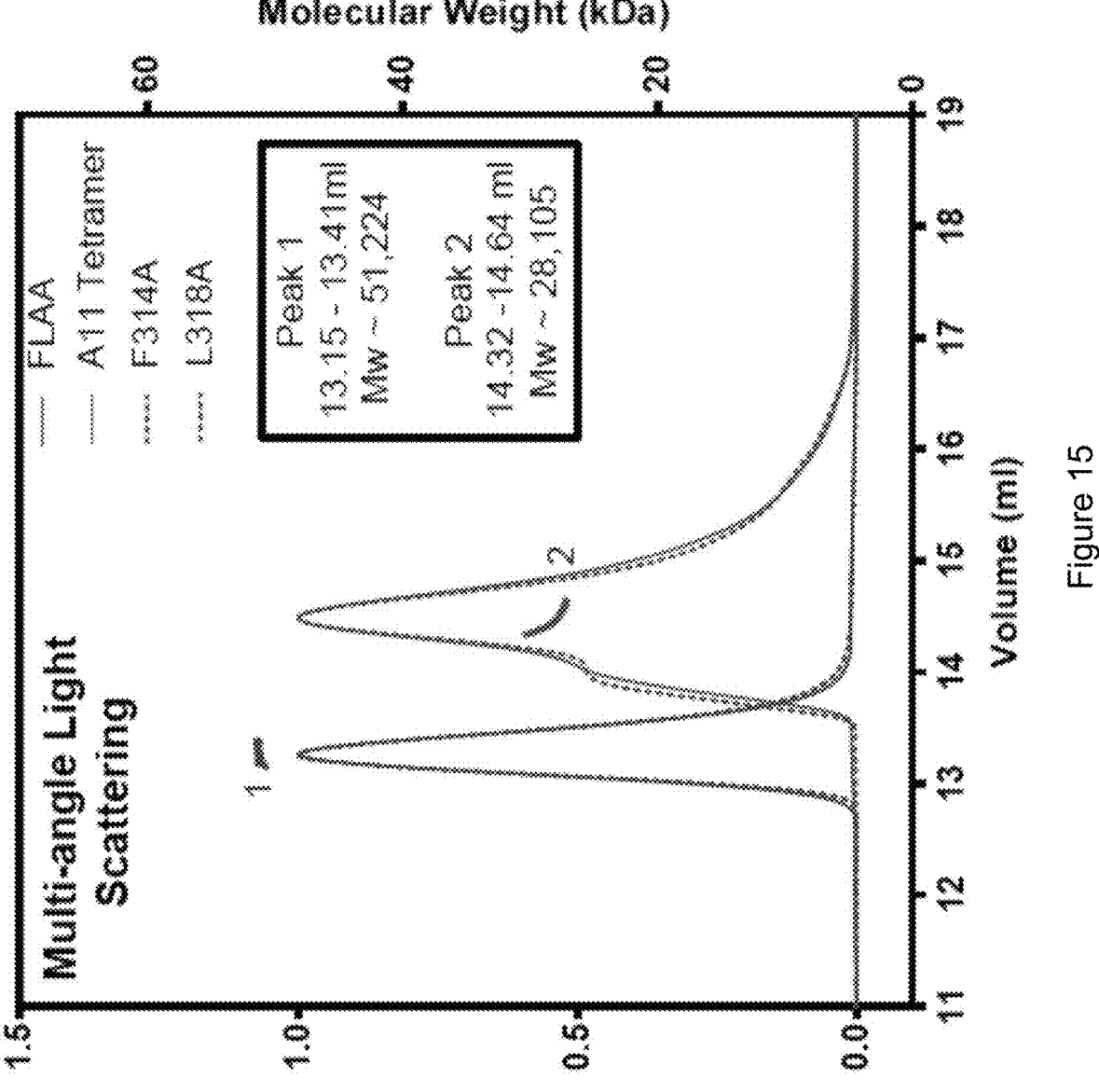
FIG. 15 depicts multi-angle light scattering data for the wild-type K1/K10-1B tetramer (A11 Tetramer, solid blue line) and 3 K1 anchoring knob mutants. The A11 Tetramer (Peak 1, solid blue line) had a molecular weight consistent with tetramer, approximately 51,000. A K1-L318A/10-1B mutant (Peak 1, dotted blue line) also migrated at the same molecular weight as the tetramer, suggesting L318A mutation alone does not abolish tetramer formation. A K1-F314A/10-1B mutant (Peak 2, dotted red line) had a molecular weight approximately 28,000, consistent with dimer formation only. This suggests that F314A mutation in K1 anchoring knob abolishes A11 tetramer formation. A double mutant with F314A+L318A in K1 anchoring knob (Peak 2, solid red line) also destroyed/prevented tetramer formation.

Multi-angle light scattering was performed for the wild-type K1/K10-1B tetramer (A11 Tetramer, solid blue line) and 3 K1 anchoring knob mutants (FIG. 15). The A11 Tetramer (Peak 1, solid blue line) had a molecular weight consistent with tetramer, approximately 51,000. A K1-L318A/10-1B mutant (Peak 1, dotted blue line) also migrated at the same molecular weight as the tetramer, suggesting L318A mutation alone does not abolish tetramer formation. A K1-F314A/10-1B mutant (Peak 2, dotted red line) had a molecular weight approximately 28,000, consistent with dimer formation only. This suggests that F314A mutation in K1 anchoring knob abolishes A11 tetramer formation. A double mutant with F314A+L318A in K1 anchoring knob (Peak 2, solid red line) also destroyed/prevented tetramer formation.

Figure 16:
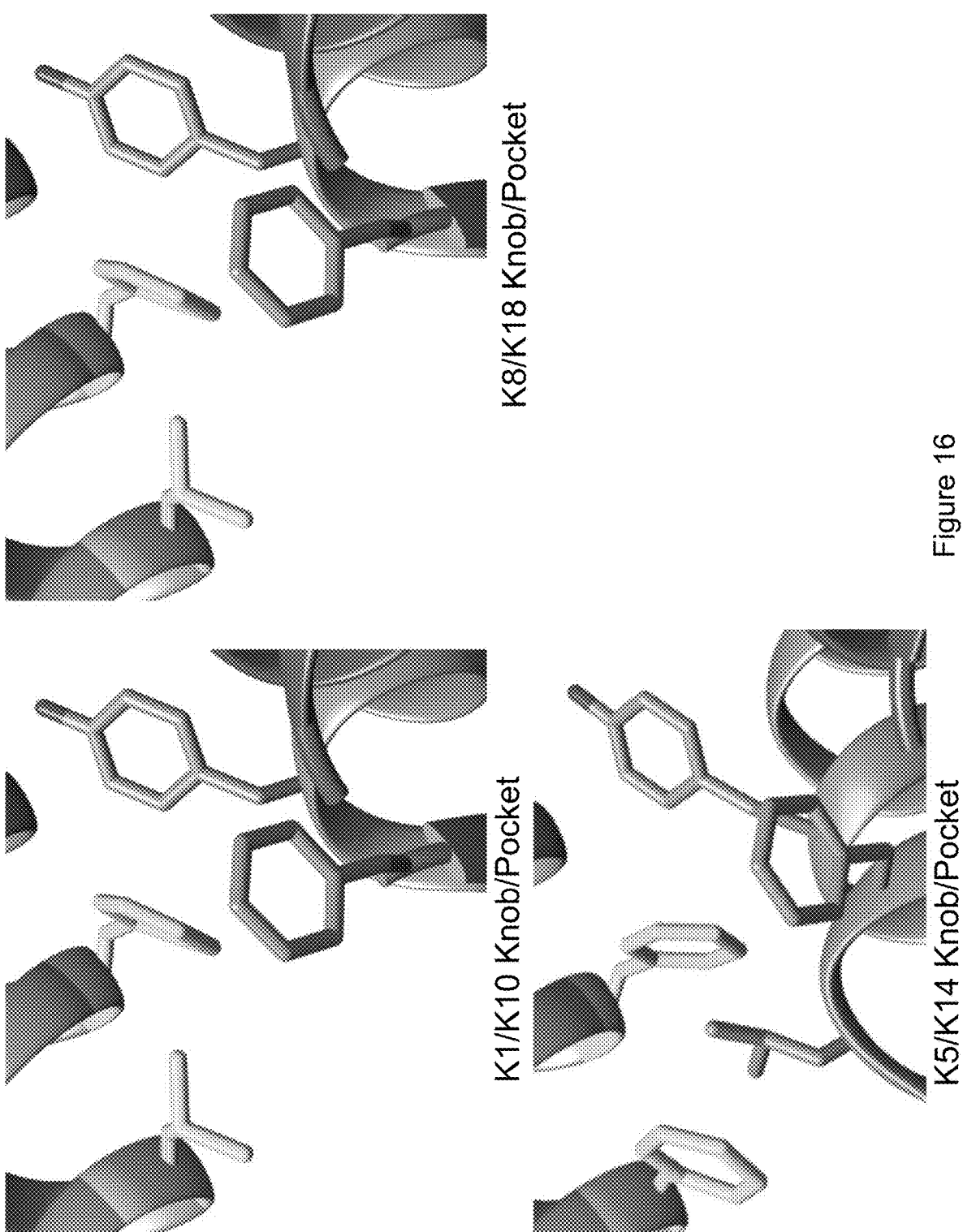
FIG. 16 depicts a model the knob-pocket for K5/K14 and K8/K18.

Multiple sequence alignment showed the anchoring knob/hydrophobic pocket mechanism is conserved for all type II keratins, as well as some non-keratin IFs, such as vimentin. A model of the knob-pocket for K5/K14 and K8/K18 is shown in FIG. 16. The mechanism discovered with K1/K10 is valid for K5/K14 and K8/K18 tetramer formation, in addition to other keratins.

Example 4: Characterizing Skin Cancer Cell Behavior after Disruption of Keratin Intermediate Filament Assembly To evaluate the impact of anchoring knob mutations on intermediate filament formation and the functions of cutaneous squamous and melanoma cancer cells experiments are performed.

First, keratin and vimentin anchoring knob mutations are examined in skin cancer cells. In skin cancer cell lines endogenous keratins (K1, K5, K6, K8) and/or vimentin are knocked-down with siRNA and subsequently the cells are transiently transfected with tagged-keratin or tagged-vimentin (both wild-type and mutants). The expression of the transfected gene is confirmed using Western-blotting; changes to cellular morphology, physiology, and the KIF network of the transfected cancer cell are reported and captured by confocal imaging after labeling with the direct/indirect immunofluorescence technique.

Skin cancer cell lines with keratin anchoring knob mutations are created. Metastatic and non-metastatic cancer cell models for both squamous cell carcinoma and melanoma with anchoring knob mutations in K1, K5, K6, K8 and/or vimentin are created using CRISPR/Cas9 technology. Cell-based assays are used to examine how keratin's anchoring knob mutation influences the three main behaviors of cancer cells: cell proliferation, apoptosis, and cell migration. Cell proliferation is assessed using the Cell Titer-Glo Luminescent Cell Viability Assay, apoptosis using the Promega Caspase-Glo 3/7 Assay, and cell migration using a Boyden Chamber Assay.

While not wishing to be bound to any particular theory, these studies demonstrate that anchoring knob mutations on type II keratins eliminate (or severely alter) KIF assembly leading to reduced proliferation, decreased metastasis, and increased apoptosis of squamous cell and melanoma skin cancer.

Example 5: Keratin 1/10-1B Tetramer Structures Reveal Knob-Pocket Mechanism in Intermediate Filament Assembly The data presented herein demonstrates the determination of the wild-type human keratin-1/keratin-10 helix 1B heterotetramer structure at 3.0 Å resolution. It revealed biochemical determinants for the $A_{11}$ mode of axial alignment in keratin filaments. Four regions on a hydrophobic face of the K1/K10-1B heterodimer dictated tetramer assembly: the N-terminal hydrophobic pocket (defined by $L227^{K1}$, $Y230^{K1}$, $F231^{K1}$, $F234^{K1}$), the K10 hydrophobic stripe, K1 interaction residues, and the C-terminal anchoring knob (formed by $F314^{K1}$, $L318^{K1}$). Mutation of both knob residues to alanine disrupted keratin 1B tetramer and full-length filament assembly. Individual knob residue mutant $F314A^{K1}$, but not $L318A^{K1}$, abolished 1B tetramer formation. The K1-1B knob/pocket mechanism is conserved across keratins and many non-keratin intermediate filaments. To demonstrate how pathogenic mutations cause skin disease by altering filament assembly, the 2.39 Å structure of K1/10-1B containing a $S233L^{K1}$ mutation linked to epidermolytic palmoplantar keratoderma was determined. Light scattering and circular dichroism measurements demonstrated enhanced aggregation of $K1^{S233L}/K10$-1B in solution without affecting secondary structure. The $K1^{S233L}/K10$-1B octamer structure revealed $S233L^{K1}$ causes aberrant hydrophobic interactions between 1B tetramers.

The materials and methods are now described.

Protein Production & Purification pET-based plasmids of K1-1B (res. 226-331), K10-1B (res. 195-296), K1-1B (res. 226-331), and the K1-1B mutants F314A, L318A and F314A+L318A were purchased from GenScript (Piscataway, NJ). Proteins were expressed in *Escherichia coli* strain BL21(DE3) (Agilent Technologies, Santa Clara, CA) at 37 C in Luria Broth Miller (EMD Millipore, Burlington, MA). Protein expression was induced with 1 mM isopropyl-D-thiogalactopyranoside (IPTG) and proceeded for 3-4 hrs. After pelleting cells by centrifugation at 2500×g, 10 min., at 4 C, they were suspended in 50 mM Tris-HCl buffer (pH 7.8) containing 0.5M NaCl, 20 mM imidazole, 1% Nonidet P-40, 6 mM MgCl, 1 mM CaCl and 1× EDTA-free protease inhibitor cocktail (Roche Diagnostics). For wild-type heterodimer, K1-1B cell suspension was mixed with K10-1B cell suspension. For K1 mutant, K1-1B cell suspension was mixed with K10-1B cell suspension.

Both wild-type and mutant heterodimers were purified using the same procedure. Cells were lysed by sonication on ice, followed by incubation of lysate with ~30 units/mL DNase I at 37 C for 15 min. The solution was centrifuged at 15000×g, 15 min, at 4 C. The supernatant underwent batch nickel affinity purification using previously described methods (Bunick, Presland et al., 2015). The clarified solution containing untagged heterocomplex was applied to a Superdex75 (26/60) gel filtration column in 100 mM Tris-HCl buffer (pH 7.4) containing 0.2M NaCl. Collected fractions were analyzed by sodium dodecyl sulfate polyacrylamide gel electrophoresis (SDS-PAGE), and selected pooled fractions were concentrated in a 10,000 Da molecular weight cutoff centrifugal filter unit (EMD Millipore).

Multi-Angle Light Scattering

K1/K10-1B (2.4 mg/ml) in 20 mM Tris-HCl buffer (pH 7.4) containing 100 mM NaCl was applied at 0.5 ml per minute to Superdex 75 gel filtration column in-line with DAWN HELEOS II light scattering instrument (Wyatt Technology, Santa Barbra, CA; laser wavelength 658 nm). Data collection and analysis used Astra software (Wyatt technology) version 5.3.4.20. This procedure was repeated using K1/K10-1B (2.3 mg/ml); it was also repeated with buffer containing 200 mM NaCl using a Superdex 200 gel filtration column. Analysis of K1/K10-1B, K1/K10-1B, and K1/K10-1B was performed similarly, using 100 mM Tris-HCl buffer (pH 7.4) containing 0.2M NaCl.

Circular Dichroism

Circular dichroism (CD) measurements were made on solutions containing wild-type K1/K10-1B or mutant K1/K10-1B at 0.5 mg/mL in 100 mM Tris-HCl buffer (pH 7.4) containing 200 mM NaCl. A Chirascan spectrometer (Applied Photophysics, Beverly, MA) was used to scan the samples in a 0.1 cm pathlength cuvette from wavelength 260 nm to 190 nm (2 nm/s) at 22 C.

Electron Microscopy Analysis of Intermediate Filaments pET-21a(+) based plasmids of human full-length wild-type K1, K1 containing F314A+L318A mutations, wild-type K8, K8 containing F223A+L227A mutations, wild-type vimentin, and vimentin containing F233A+L237A mutations were purchased from GenScript (Piscataway, NJ); wild-type K10 and K18 were similarly purchased in pET-24a(+) plasmid. K10 was expressed in *E. coli* BL21(DE3) pLysS cells (Invitrogen, Waltham, MA) at 20° C. for 72 hrs using an autoinduction method (Studier, 2005). Expression of all other keratins and vimentins occurred in *E. coli* BL21(DE3) cells using lysogeny broth at 37° C. for 3 hrs with 1 mM IPTG for induction. An inclusion body pellet was purified from the cells using a previous protocol (Nagai & Thogersen, 1987) modified to include sonication at each step of pellet resuspension. Inclusion bodies were resuspended in 6M urea solution and purified by anion exchange chromatography (Q/SP sepharose, GE Healthcare, Marlborough, MA) as described (Coulombe & Fuchs, 1990, Paladini, Takahashi et al., 1996) using a 200 mM guanidine-HCl gradient, followed by size exclusion chromatography (Superdex 75, GE) using 6M urea solution. Heterodimeric complexes of K1/K10 and K8/K18, and homodimeric complex of vimentin, were made by mixing individual protein in a 1:1 molar ratio; the complexes subsequently were purified with Q sepharose using a 200 mM guanidine-HCl gradient, and then dialyzed into 50 mM Tris-HCl buffer (pH 8.5) containing 6M urea and 2 mM DTT. Before initiating filament assembly, all IF complexes were concentrated to 0.49 µg/µL and dialyzed into 25 mM Tris-HCl buffer (pH 8.5) containing 9M urea and 2 mM DTT at room temperature for 4 hrs. K1/K10 filament formation followed established "Assembly method 4", whereas K8/18 and vimentin filaments were assembled from established "Assembly method 1" (Herrmann, Wedig et al., 2002). Filament assembly was terminated after 10 min by adding stop buffer (0.2% glutaraldehyde, 20 mM KCl, 0.7 mM NaHPO). Filament samples were immediately applied to a Carbon type B-400 mesh-Copper grid charged with Pelco easiGlow (Ted Pella, Redding, CA) at 25 mA for 30s, and negatively stained using 2% aqueous uranyl acetate. Images were captured with a Talos L120C Electron Microscope from FEI (Hillsboro, OR).

Crystallization and X-Ray Data Collection

Sitting-drop vapor diffusion crystallization was performed at 25° C. by mixing 3 µl of protein with 3 µl of reservoir solution. X-ray data was collected on crystals maintained at ~100K using the 24-ID-C beamline at the Advanced Photon Source at Argonne National Laboratory. Diffraction data was processed using HKL-2000 (Otwinowski & Minor, 1997).

Wild-type K1/K10-1B (23.7 mg/ml) in 100 mM Tris-HCl buffer (pH 7.4) containing 200 mM NaCl was crystallized using 100 mM HEPES buffer (pH 7.5) containing 5 mM cobalt(II) chloride, 5 mM cadmium dichloride, 5 mM magnesium chloride, 5 mM nickel(II) chloride, and 11% polyethylene glycol 3350. Crystals were soaked 1-3 min in a cryoprotectant solution containing 25% propylene glycol in mother liquor prior to flash-freezing in liquid nitrogen. A native data set on a single crystal was collected ($\lambda=0.9795$ Å). The crystal belonged to the trigonal space group P3 21 (cell dimensions: a=106.69 Å, b=106.69 Å, c=70.32 Å, $\alpha=\beta=90$, $\gamma=120$). A second data set was collected on a different crystal from the same growth condition at the cadmium edge ($\lambda=1.4586$ Å) and had strong anomalous signal.

Mutant K1/K10-1B (22.8 mg/ml) in 100 mM Tris-HCl buffer (pH 7.4) containing 200 mM NaCl was crystallized using 100 mM Tris buffer (pH 8.5) containing 1.5M ammonium sulfate and 12% glycerol. Crystals were soaked 1-3 min in a cryoprotectant solution containing 27% glycerol in mother liquor prior to flash-freezing in liquid nitrogen. One native data set on a single crystal was collected ($\lambda=0.9795$ Å). The native crystal belonged to the hexagonal space group P6 22 (cell dimensions: a=93.29 Å, b=93.29 Å, c=124.74 Å, $\alpha=\beta=90$, $\gamma=120$). A second data set was collected to ~2.2 Å resolution, using a different crystal from the same growth condition soaked in mercury solution, at the mercury edge ($\lambda=1.00841$ Å) and had strong anomalous signal. The heavy atom soak was performed as follows: a K1/K10-1B crystal was transferred to a 10 µL drop of mother liquor solution containing 1 mM potassium tetraiodomercurate(II) and soaked for 1 hour at room temperature. It was then transferred and soaked for 1 minute in a cryoprotectant solution containing 27% glycerol in mother liquor prior to flash-freezing in liquid nitrogen. The heavy atom crystal belonged to the hexagonal space group P6 22 (cell dimensions: a=93.62 Å, b=93.62 Å, c=122.74 Å, $\alpha=\beta=90$, $\gamma=120$).

Structure Determination, Refinement, and Analysis

Phaser-EP (PHENIX) (Adams, Afonine et al., 2010) was used to fit a poly-alanine coiled-coil model into the mercury heavy atom data for K1/K10-1B. The mercury sites were used to align the coiled-coil register, and the correct protein sequence manually built. The structure was refined using PHENIX, and subsequently used for molecular replacement into the wild-type K1/K10-1B data and the native K1/K10-1B data using MOLREP (Vagin & Teplyakov, 2010). Molecular replacement bias was reduced using a simulated annealing composite omit map generated in PHENIX for each structure. The structures underwent iterative rounds of model building (Coot) (Emsley & Cowtan, 2004) and refinement (PHENIX) (Adams et al., 2010) using standard geometric (bond length, bond angle) and secondary structure restraints (Table 1). The final model of the wild-type K1/K10-1B crystal asymmetric unit contained one K1-1B and one K10-1B molecule in a heterodimer complex. The biologically relevant structure in the unit cell was a tetramer composed of two K1/K10-1B heterodimers. The final Ramachandran statistics were: residues in favorable regions, 99%; in allowed regions, 0.49%; in outlier regions, 0.49%.

The final model of the K1/K10-1B mutant crystal asymmetric unit contained one K1-1B and one K10-1B molecule in a heterodimer complex. A biologically relevant structure in the unit cell was a tetramer composed of two K1/K10-1B heterodimers; these tetramers aggregated into an octamer via K1. The final Ramachandran statistics were: residues in favorable regions, 100%. Electrostatics were calculated using PDB2PQR (Dolinsky, Nielsen et al., 2004) and Adaptive Poisson-Boltzmann Software (APBS) (Baker, Sept et al., 2001). Structural analyses were performed using Coot, UCSF Chimera (Resource for Biocomputing, Visualization, and Informatics, University of California, San Francisco), WHAT IF (Vriend, 1990), ESBRI (Costantini, Colonna et al., 2008), and PDBePISA (The European Bioinformatics Institute, European Molecular Biology Laboratory, UK). Figures were prepared using UCSF Chimera and Adobe Illustrator.

Data Availability

Atomic coordinates and structure factors have been deposited in the Protein Data Bank under the accession codes 6EC0 (wild-type) and 6E2J (mutant).

The results are now described.

Wild-Type K1/K10-1B Structure

Using the divide-and-conquer approach (Strelkov, Herrmann et al., 2001), the x-ray crystal structure of the human K1/K10 helix 1B heterotetrameric complex was determined to 3.0 Å resolution (FIG. 1A and Table 1) (Eldirany, Hinbest et al., 2018). The tetramer is composed of two K1/K10-1B heterodimers arranged anti-parallel (one heterodimer is the crystal asymmetric unit). The K1 and K10 molecules within the heterodimer structure form a parallel coiled-coil, spanning K1 residues (226-331) and K10 residues (195-296). Key molecular interactions along the K1/K10-1B heterodimer interface are detailed (FIGS. 7A and 7B). The K1/K10-1B tetramer did not exhibit supercoiling of the coiled-coil heterodimers. Throughout this example, the protein-protein interactions occurring between the two antiparallel dimers of the tetramer are denoted by associating a prime symbol with the residue(s) from the second dimer (e.g. K1-K1').

The electrostatic surface potential of the K1/K10-1B heterodimer is similar to that observed in the K1/K10-2B heterodimer (Bunick & Milstone, 2017): there is polarization of charge with the distal three-fourths of the complex being acidic, whereas the proximal one-fourth is more basic (FIG. 1B). The basic patch at the N-terminus of K1/K10-1B contains residues from both K1 (R239, R240, R241) and K10 (K198, K201, K207) (FIG. 1C); this is in contrast to the 2B heterodimer, where a linear N-terminal basic patch was solely formed by nine K1 residues (Bunick & Milstone, 2017).

Acidic Groove on Molecular Surface of 1B Tetramer

Due to anti-parallel alignment of K1/K10-1B heterodimers in the tetramer, the basic electrostatic surface potential at the N-terminus of the heterodimer is diminished by the strength of the adjacent acidic C-terminus in the tetramer (FIG. 1D). The electrostatic surface potential of the K1/K10-1B tetramer is mainly acidic.

Figure 18:
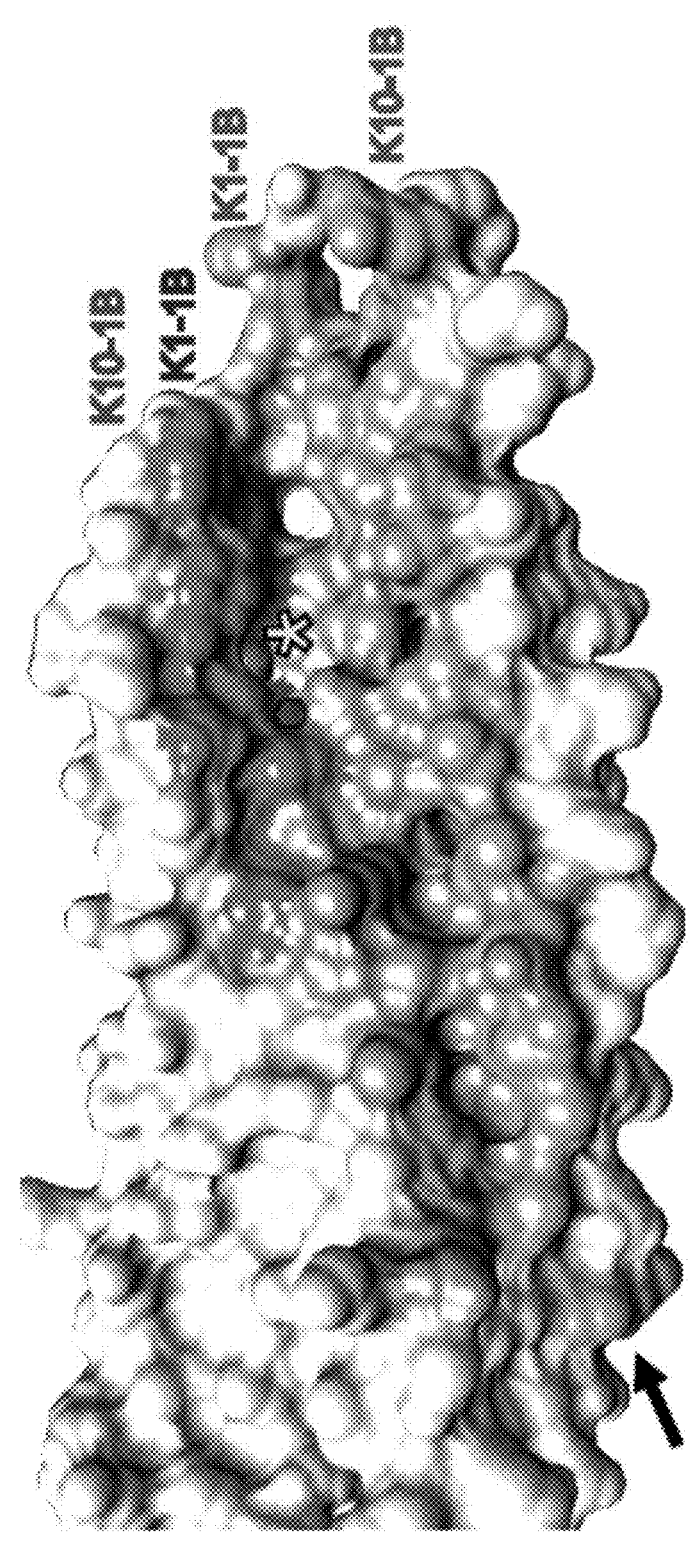
FIG. 18 depicts a close-up of one "angled groove" (arrow) in the K1/K10-1B tetramer colored to demonstrate a portion of all four tetramer helices contributes to groove formation. Some of the anchoring knob/hydrophobic pocket residues are accessible in the groove (yellow asterisk).

There are unique surface contours present in the K1/K10-1B tetramer that are not present in the heterodimer structure (FIGS. 1D and 1E). One face of the tetramer contains a linear groove that extends from one end all the way to the other; this groove has the highest acidic electrostatic surface potential in the K1/K10-1B tetramer structure (FIGS. 1D and 1E). In contrast, the tetramer face 180° opposite the acidic linear groove contains a central concave pocket ~66.7 Å long by 17.7 Å wide (FIG. 1F), flanked by two symmetric angled grooves ~54.9 Å long at either end of the molecule (FIG. 18).

Hydrophobic Interactions Drive 1B Tetramer Formation

Figure 19:
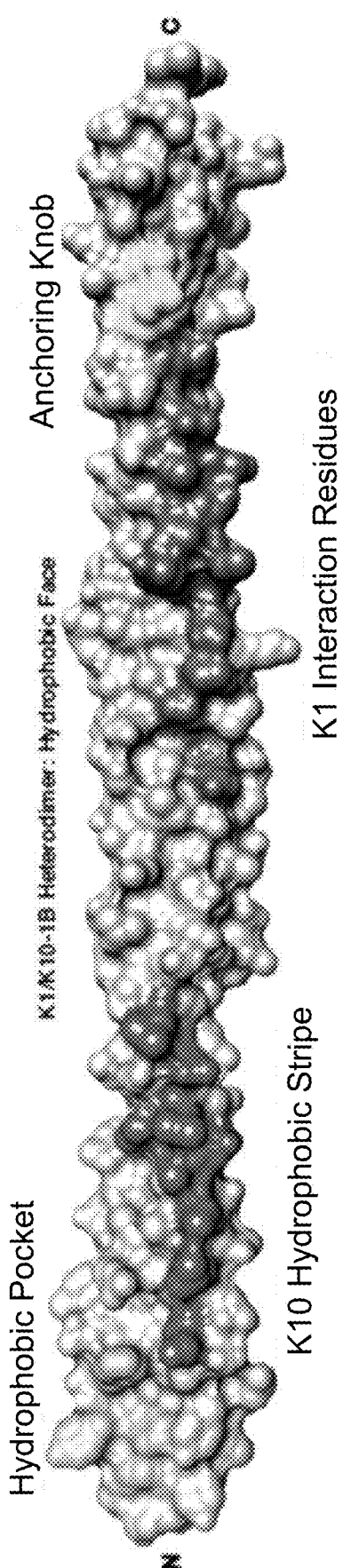
FIG. 19 depicts experimental results demonstrating the biochemical basis for K1/K10-1B heterotetramer formation. Four key regions along the hydrophobic face of the K1/K10-1B heterodimer drive tetramer formation: an N-terminal K1 hydrophobic pocket (gold), a K10 hydrophobic stripe (purple), K1 interaction residues (green), and a C-terminal K1 anchoring knob (yellow). All of the following panels show tetramer interactions FIG. 20, comprising FIG. 20A through FIG. 20C depicts experimental results demonstrating that the anchoring knob mutation disrupts IF assembly for three IF systems.

Mapping of hydrophobic surface potential onto the K1/K10-1B heterodimer structure demonstrates that one heterodimer face contains multiple surface-exposed hydrophobic residues, whereas the face 180° opposite is largely polar with only a few exposed hydrophobic residues (FIG. 2A). The hydrophobic face of the K1/K10-1B heterodimer contains the molecular determinants of tetramer assembly. They can be divided into four key segments from N- to C-terminus: a K1 hydrophobic pocket, a K10 hydrophobic stripe, K1 interaction residues, and a K1 anchoring knob (FIG. 19).

At the N-terminus of the K1/K10-1B heterodimer there is a hydrophobic pocket formed by four K1 residues (L227, Y230, F231, and F234). The concavity between the aromatic residues is the receptor site for the C-terminal anchoring knob on a neighboring K1/K10-1B heterodimer, facilitating tetramer formation (FIG. 2C). The C-terminal anchoring knob is composed of two K1 residues (F314 and L318). $F314^{K1'}$ binds by wedging between $F231^{K1}$ and $F234^{K1}$, creating a ring-stacking interaction with $F234^{K1}$ (FIG. 2D). $L318^{K1'}$ interacts with $F231^{K1}$ and $Y230^{K1}$ (~3.3 and 4.2 Å respectively), and knob-pocket docking brings $A321^{K1'}$ near $Y230^{K1}$ (~3.6 Å) and $L318^{K1'}$ near $L227^{K1}$ (~4.6 Å).

Adjacent to the hydrophobic pocket, and aligned along the outer aspect of the α-helical ridge, are several K10 residues constituting a predominantly hydrophobic stripe (FIGS. 2A and 2B). A type I keratin "hydrophobic stripe" was identified from modeling analyses of K6/K16/K17 dimers (Bernot, Lee et al., 2005); this work showed that most, but not all (e.g. K10), type I keratins contained a consensus hydrophobic sequence at alternating b- and f-positions of the heptad repeat (L-x-x-x-(I/V)-x-x-A-x-x-x-L) contributing to tetramer stability. However, K10 has threonine in the second position of this motif, and in the K1/K10-1B tetramer structure the function of this protein region proves complex—there exists an interacting stripe, but the interactions are not strictly hydrophobic. The K10 helical ridge on the N-terminal half of the K1/K10-1B heterodimer is defined by eleven K10 residues: K207, L211, T215, A218, N219, L221, L222, N226, L229, K237, and L236. Several of these residues are not hydrophobic (K207, T215, N219, N226, K237) but make meaningful interactions to stabilize tetramer assembly and thus are considered part of the stripe (FIG. 2E). $K207^{K10}$ forms a salt bridge with $E311^{K1'}$, while $T215^{K10}$ interacts with $M296^{K1'}$ and $D300^{K1'}$ (FIGS. 2D and 2E). K10 hydrophobic residues L211, A218, L221, L222 and L229 all have interactions with Kr residues less than 5 Å apart. L236, on the other hand, is involved in K10-K10' interactions only (FIG. 2F).

The hydrophobic face of the K1/10-1B heterodimer contains a segment consisting of "K1 interaction residues" between the K10 hydrophobic stripe and the C-terminal anchoring knob. K1 interaction residues exist on the K1 α-helix whose helical ridge forms most of the distal hydrophobic face. In the K1/10-1B tetramer twelve K1 residues from this segment have hydrophobic or electrostatic interactions with ten K10 hydrophobic stripe residues from the binding heterodimer (FIG. 2E).

S233LK1 Mutation Drives Aggregation of K1/K10-1B in Solution

Keratin 1 containing the missense mutation S233L, which is pathogenic for epidermolytic palmoplantar keratoderma, was produced and purified to investigate how the mutation affects K1/K10-1B heterodimer structure and function (FIG. 3A). After His-tag removal from K10, wildtype K1/K10-1B and mutant $K1^{S233L}$/K10-1B complexes were analyzed by gel filtration. Wildtype K1/K10-1B separated into two main peaks (FIG. 3B, solid line), whereas $K1^{S233L}$/K10-1B formed one major peak (FIG. 3B, dotted line) that eluted earlier than the wild-type complex. This suggested $K1^{S233L}$/K10-1B formed a higher molecular weight complex in solution than wild-type K1/K10-1B.

To characterize the oligomerization state of these complexes, K1/K10-1B and $K1^{S233L}$/K10-1B were analyzed by multi-angle light scattering in either 100 mM NaCl or 200 mM NaCl solutions (FIG. 3C). Wild-type K1/K10-1B (solid line) formed a tetramer species (peak 2, ~49 kDa) and a dimer species (peak 3, ~24-26 kDa) in both 100 mM and 200 mM NaCl conditions (wild-type heterodimer calculated MW is 24,840). In contrast, $K1^{S233L}$/K10-1B (dotted line) formed a single species of ~62 kDa in 100 mM NaCl solution and ~86 kDa in 200 mM NaCl solution. This demonstrated that $K1^{S233L}$/K10-1B formed higher molecular weight aggregates than wild-type K1/K10-1B in solution. The increased MW for the mutant complex under higher ionic strength is consistent with enhanced hydrophobic interaction.

Circular dichroism measurements demonstrated that $S233L^{K1}$ does not alter the secondary structure of K1/K10-1B (FIG. 3D). Both wild-type K1/K10-1B (solid line) and $K1^{S233L}$/K10-1B (dotted line) complexes had identical α-helical secondary structure in solution.

Pseudo-Tonotubular Keratin in Mutant K1S233L/K10-1B Octamer Structure

To further investigate how $S233L^{K1}$ mutation impacts K1/K10-1B structure, the $K1^{S233L}$/K10-1B crystal structure was determined to 2.39 Å resolution (Table 1). Both S233 from the wild-type K1/K10-1B structure and L233 from the mutant $K1^{S233L}$/K10-1B structure occupy solvent exposed positions at the N-terminus of the 1B heterodimer. The $S233L^{K1}$ mutation changes the surface potential at this site from polar (wild-type) to hydrophobic (mutant) (FIG. 4A). Near position 233, along the inter-molecular interface of the 1B heterodimer, are two critical K1 phenylalanines (F231 and F234) involved in heterodimer stabilization and in forming the hydrophobic pocket.

The increased hydrophobic surface potential created by $S233L^{K1}$ mutation did not alter heterodimer or tetramer formation, but rather altered how tetramers interacted with each other (FIG. 4B). This explains why the $K1^{S233L}$/K10-1B structure was determined as an octamer. Specifically, $L233^{K1}$ from one tetramer bound to five residues from a different tetramer (the aromatic portion of $Y230^{K1'}$, $L233^{K1'}$, $F234^{K1'}$, $F314^{K1'}$ and $Ala317^{K1'}$) to drive hydrophobic assembly of an octamer (FIG. 4C). Due to the anti-parallel symmetry of the tetramer, the same interactions by $L233^{K1}$ occur at both ends of the octamer. $L233^{K1}$ closely interacts with itself, $L233^{K1'}$ (~3.8 Å), and $Ala317^{K1'}$ (~3.9 Å). L233K1 additionally interacts with three aromatic residues over slightly longer distances: 4.3 Å ($F314^{K1'}$), 4.8 Å ($Y230^{K1'}$) and 5.5 Å ($F234^{K1'}$). All three of these aromatic residues are involved in the anchoring knob/hydrophobic pocket mechanism of tetramer assembly. As two tetramers bind in the $K1^{S233L}$/K10-1B octamer, Y230 from one hydrophobic pocket binds with Y230 from the adjacent pocket (FIG. 4C).

Examination of $K1^{S233L}$/K10-1B crystal lattice packing revealed a repetitive arrangement of a circular structure (the $K1^{S233L}$/K10-1B octamer) (FIG. 4D). At first glance it appears the octamer mimics the tonotubular keratin observed under electron microscopy from EPPK skin. The diameter of the octamer, however, is only ~45 Å (4.5 nm), which is about one-tenth the diameter of the observed in vitro tonotubular keratin (430 Å or 43 nm) (Wevers et al., 1991). Hence, the octamer is referred to as pseudo-tonotubular keratin.

Comparing wild-type K1/K10-1B and mutant $K1^{S233L}$/K10-1B tetramer structures, the major interactions between the hydrophobic pocket and anchoring knob, as described above for the wild-type structure, are preserved in the mutant. However, there are additional features in the higher resolution mutant structure that better characterize the anchoring knob/hydrophobic pocket mechanism for tetramer assembly. First, the $L227^{K1}$ sidechain occupies a position much closer to $L318^{K1'}$, forming the N-terminal wall of the hydrophobic pocket and stabilizing the anchoring knob via interactions with $L318^{K1'}$ (L318' Cd1 to L227 Cb distance decreases from 4.7 to 3.9 Å; L318' Cd1 to L227 Cd2 distance decreases from 6.0 to 4.8 Å; L318' Cd1 to L227 Cd1 distance decreases from 7.1 to 3.6 Å) (FIG. 4E). The conformation of $L227^{K1}$ appears to be altered by cadmium binding of the N-terminal methionine in the wild-type K1/K10-1B structure (FIG. 4F); this does not occur in the $K1^{S233L}$/K10-1B mutant structure because its crystallization condition did not contain cadmium. Second, there are two K10 residues, $Y200^{K10}$ and $I203^{K10}$, that in the mutant structure are less than 4.3 Å away from $F314^{K1'}$ and $L318^{K1'}$ (FIG. 4F); they are ~5 Å away in the wild-type structure. These conformational differences are not a direct consequence of the $K1^{S233L}$ mutation itself, but rather local structure perturbations from cadmium binding at the N-terminus of K1 (N-terminal methionine) and C-terminus of K1/K10 ($E322^{K1}$ and $H287^{K10}$) in the wild-type K1/K10-1B tetramer crystals (FIG. 4F).

One K10 helical ridge hydrophobic residue (L236) is not considered part of the hydrophobic stripe because it functions differently than the stripe residues. All ten K10 residues defined above as "hydrophobic stripe" contribute to tetramer formation by binding K1 residues from the partner heterodimer. $L236^{10}$ exists at the interface between K10 helices in the center of the 1B tetramer structure, and thus is involved in K10-K10' interactions. In the wild-type K1/K10-1B structure $L236^{K10}$ is ~4.9 Å away from its closest hydrophobic neighbor ($L244^{K10'}$); however, in the mutant $K1^{S233L}$/K10-1B structure $L236^{K10}$ and $L244^{K10'}$ are ~4.0 Å apart signifying this interaction could have a role in K10-K10' stabilization in the tetramer (FIG. 2F).

Structural Modeling of F231LK1 and R267YK1 Mutations

Literature on EPPK patients with tonotubular keratin references two additional mutations: a pathogenic $F231L^{K1}$ mutation causing EPPK and tonotubular keratin (Grimberg, Hausser et al., 2009), and a non-pathogenic R267YK1 mutation in a British control subject with no skin disease (Terron-Kwiatkowski et al., 2006). To explain the discrepancy in pathogenicity between these mutations at a structural level, the wild-type K1/K10-1B crystal structure was used to model F231L$^{K1}$ and R267Y$^{K1}$ mutations. The lack of pathogenicity for R267Y$^{K1}$ is the most straightforward of the two; R267 occupies a solvent-exposed position in the central aspect of the K1-1B coil that is not involved in heterodimer, tetramer, or octamer formation (FIG. 5A). R267Y$^{K1}$ can be accommodated without major structural consequence, thus it is more appropriate to consider it a normal variant.

F231L$^{K1}$ alters the structure of the hydrophobic pocket that binds the anchoring knob in K1/K10-1B tetramer assembly. F231L$^{K1}$ changes the parameters of interaction with the key anchoring knob residues, F314$^{K1'}$ and L318$^{K1'}$ (FIGS. 19 and 2D). Specifically, the interaction distance between L318$^{K1'}$ and mutant L231$^{K1}$ is ~1.6 Å longer (4.9 Å) compared to wild-type F231$^{K1}$ (3.3 Å) (FIG. 5B). The closest interaction distance between F314$^{K1'}$ and mutant L231$^{K1}$ (3.4 Å) is unchanged compared to wild-type F231$^{K1}$ (3.4 Å), but F314$^{K1'}$ loses its interactions with the F231 aromatic ring. Together, the modeling data suggests mutant L231$^{K1}$ has weakened interactions with F314$^{K1'}$ and L318$^{K1'}$, potentially leading to pathogenic disruption of the anchoring knob/hydrophobic pocket tetramer assembly mechanism.

Mutation of Both Anchoring Knob Residues to Alanine Abolishes 1B Tetramer Formation To validate the analysis of the K1/K10-1B wild-type structure, the K1$^{S233L}$/K10-1B mutant structure, and the K1$_{F231L}$/K10-1B structural model, K1 anchoring knob residues were mutated to alanine and assessed the effect on tetramer formation. The double mutation F314A$^{K1}$+ L318A$^{K1}$ (FLAA) led to complete loss of K1/K10-1B tetramer formation as assessed by gel filtration (FIG. 14) and multi-angle light scattering (FIG. 15). Similarly, the individual mutation F314A$^{K1}$ (FA) abolished tetramer complex formation compared to wild-type K1/K10-1B. In contrast, the individual mutation L318A$^{K1}$ (LA) did not abolish K1/K10-1B tetramer formation.

Figure 20:
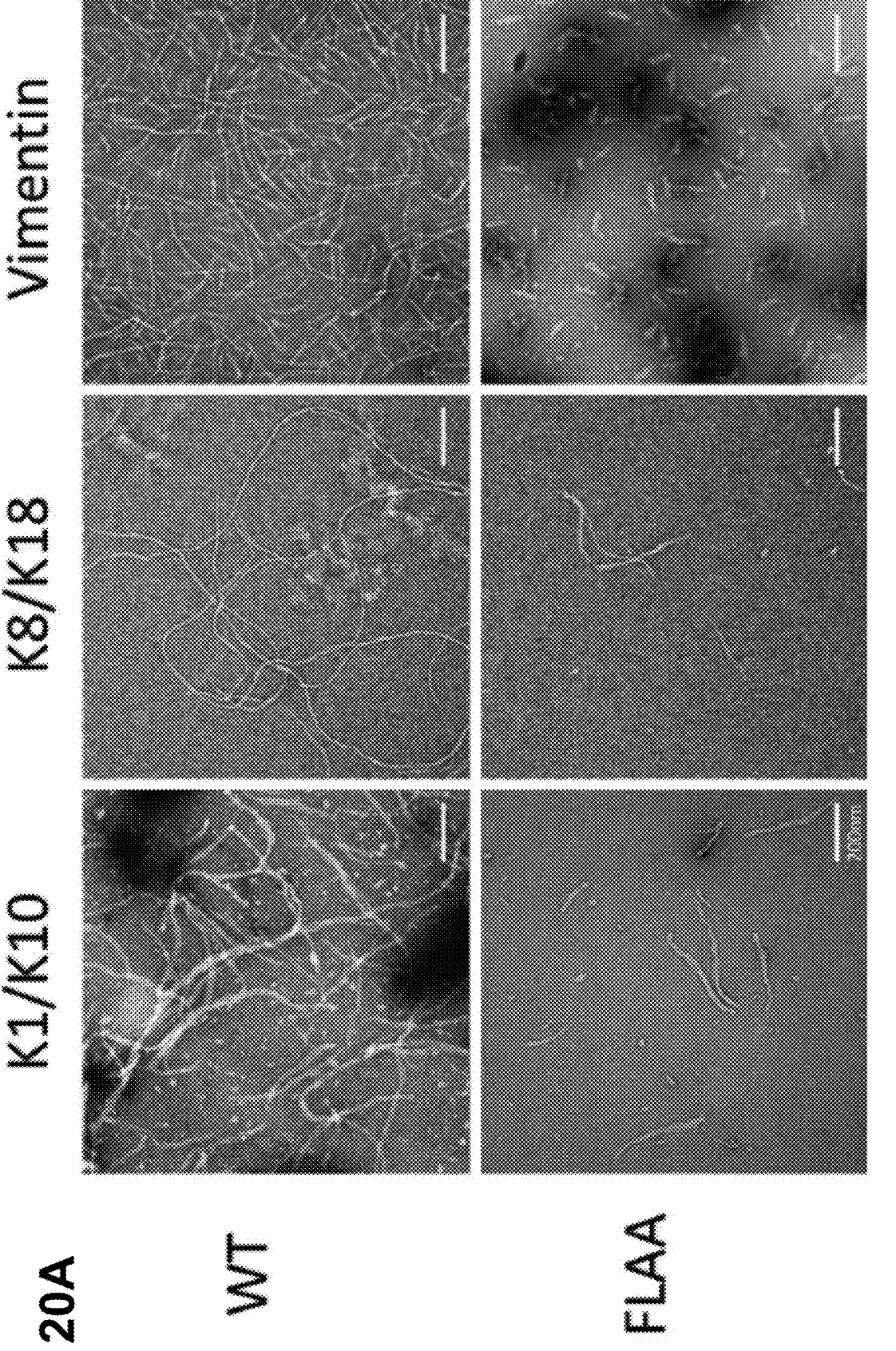
FIG. 20A depicts negative stain electron microscopy (EM) images comparing wild-type (WT) and anchoring knob mutant (FLAA) filament formation for full-length K1/K10, K8/K18, and vimentin. The duration of filament assembly was 10 minutes for all three IF systems. Double mutation (FLAA) of F314A+L318A in K1, F223A+L227A in K8, and F233A+L237A in vimentin causes detrimental effects on K1/K10, K8/K18, and vimentin IF assembly, respectively. The FLAA filaments are fewer in number and shorter in length despite IF assembly and EM protocols identical to the WT. These data strongly indicate the anchoring knob interaction with the hydrophobic pocket plays an important structural role in stabilizing the IF tetramer, unit-length-filament, and intact filament. The experiments were independently replicated twice.
FIG. 20B depicts coomassie-stained SDSPAGE demonstrating purified, recombinant wild-type (WT) and mutant (FLAA) full-length proteins for K1/K10 (left), K8/K18 (center), and vimentin (right) used in this EM analysis.
FIG. 20C depicts an illustration of the domain organization for the IF proteins in this EM experiment in order to highlight the differences in overall protein length, the length of the heads and tails, and the dimerization state (hetero- vs homo-). The location of the hydrophobic pocket and anchoring knob at the N- and C-termini of helix 1B for K1, K8, and vimentin is noted.

Electron Microscopy Demonstrates Knob Mutation is Detrimental to IF Assembly in Three IF Systems To take the mutation analysis further, it was determined whether the K1$^{FLAA}$ mutation could also affect intermediate filament assembly of full-length proteins (recombinantly produced and purified). To assess intermediate filament assembly, negative-stain electron microscopy was used (FIG. 20). Full-length wild-type K1 and K10 were assembled into K1/K10 filaments under identical parameters and conditions (e.g. 10 minutes assembly time) as full-length K1$^{FLAA}$ mutant with K10. The K1$^{FLAA}$ mutation caused a significant reduction in the number and length of filaments formed (FIG. 20A). The fewer, shorter filamentous structures visible for K1$^{FLAA}$ suggest that loss of the anchoring knob in K1 generates instability at the tetramer and unit-length-filament level that precludes formation of normal wild-type filaments.

Since multiple sequence alignment and homology modeling suggested the anchoring knob is conserved among type II and type III IFs (see FIGS. 9 and 21 and Discussion), it was additionally examined whether FLAA mutation altered filament assembly in two other IF systems (K8/K18 and vimentin) (FIG. 20B). Full-length recombinant wild-type K8 and K18 were assembled into K8/K18 filaments under identical parameters and conditions as full-length K8$^{FLAA}$ mutant (F223A+L227A) with K18. K8$^{FLAA}$ had similar effect as K1$^{FLAA}$ on filament formation, causing a reduction in number and length of filaments formed (FIG. 20A). Full-length recombinant vimentin (which forms homodimers) was assembled into vimentin filaments under identical parameters and conditions as full-length vimentin$^{FLAA}$ mutant (F233A+L237A). Vimentin$^{FLAA}$ was unable to form short or long filamentous structures, and appeared arrested at the unit-length filament stage of IF assembly. In summary, EM studies demonstrate that loss of knob structure has a damaging impact on IF assembly (the rate of and/or the length of) across IF types (type II vs type III), for keratins with long heads and tails (K1/K10), for keratins with short heads and tails (K8/18), and for heterodimeric and homodimeric (vimentin) IF proteins (FIG. 20C).

DISCUSSION

The wild-type K1/K10-1B tetramer and mutant K1$^{S233L}$/K10-1B octamer crystal structures provide key insights into human keratin tetramer assembly in the A$_{11}$ mode of axial alignment and illustrate how a pathogenic mutation associated with EPPK can disrupt normal tetramer interactions. This work addresses the lack of atomic resolution structural data for the keratin intermediate filament (KIF) assembly mechanism. KIFs are more than ever implicated in cellular processes and functions beyond structural and mechanical integrity (Loschke, Seltmann et al., 2015). Many human diseases caused by keratin mutation do not affect heterodimer structure, but rather alter or disrupt KIF assembly; this creates a need for experimentally determined high resolution structures focused on understanding KIF assembly.

The structural data presented herein, as well as gel filtration and light scattering studies demonstrating K1/K10-1B exists as a tetramer in solution prior to crystallization, give strong support to the previously proposed Au alignment of the K1/K10-1B tetramer (Steinert et al., 1993a, Steinert et al., 1993c). First, the K1/K10-1B tetramer is consistent with cross-linking studies predicting A$_{11}$ alignment. The cross-linking data by Steinert and colleagues provides an important means to correlate and validate IF domain packing in crystal lattices with the packing observed in filaments. They identified five cross-linked tryptic peptides from mouse K1/K10 filaments mapped to helix 1B (Steinert et al., 1993a); all five lysine pairings can be explained by structural proximity in the human K1/K10-1B tetramer structure (FIGS. 8A and 8B). Second, Coulombe and colleagues identified a hydrophobic stripe on type I keratins during K6/K16/K17 modeling (Bernot et al., 2005); the K10 hydrophobic stripe participates in K1/K10-1B tetramer formation. However, the stripe's role in A$_{11}$ tetramer formation proved more complex than anticipated: it was one of four key regions defining tetramer assembly, it did not self-associate, and its main interactions occurred with K1 residues. Importantly, prior mutation of hydrophobic stripe residues in mouse K16 and K17 did not significantly affect mature filament formation in vitro (Bernot et al., 2005); this is in contrast to anchoring knob mutants of human K1, K8, and vimentin which impaired in vitro filament formation for K1/K10, K8/K18, and vimentin (FIG. 20). Third, the A$_{11}$ alignment validates that the S233L$^{K1}$ mutation alters heterodimer and/or filament interactions through the creation of aberrant surface hydrophobicity, ultimately leading to tono-tubular keratin (Terron-Kwiatkowski et al., 2006). The K1$^{S233L}$/K10-1B structure validated this by showing S233L$^{K1}$ caused tetramer aggregation through specific hydrophobic interactions with residues involved in the tetramer assembly mechanism.

The structural analysis comparing the K1/K10-1B heterotetramer with the vimentin-1B A$_{11}$-homotetramer (a type III IF) (Aziz et al., 2012) revealed major differences between the determinants of keratin and vimentin tetramer formation while confirming that the anchoring knob/hydrophobic pocket mechanism of tetramer assembly is generally conserved. Besides the obvious difference that vimentin forms homodimers rather than heterodimers like the keratins, vimentin does not contain a hydrophobic stripe aiding tetramer formation. The K10 hydrophobic stripe contains five key hydrophobic residues with interactions (to K1') that stabilize the 1B tetramer; only one hydrophobic residue is conserved (A218$^{K10}$) and one similar (L222$^{K10}$ to valine) in vimentin (FIG. 21A). Vimentin conserves none of the four critical leucine residues in the K10 hydrophobic stripe. Of the twelve K1 interaction residues, five are completely conserved and another five are similar in vimentin (FIG. 21B). In contrast to the K10 hydrophobic stripe and K1 interaction residues, the C-terminal anchoring knob is entirely conserved in vimentin helix 1B (FIG. 21C). Vimentin's F233 and L237 form an anchoring knob homologous to F314 and L318 in K1. Like K1/K10, the vimentin anchoring knob binds into a hydrophobic pocket at the N terminus of a neighboring vimentin-1B homodimer. Vimentin's hydrophobic pocket, however, is formed differently than K1. There are four key vimentin residues that form the hydrophobic pocket: L149, Y150, E153 (the aliphatic portion), and M154. Unlike K1/K10-1B, where all of the hydrophobic pocket is formed by K1 residues (and not K10), vimentin's hydrophobic pocket is formed by residues from both homodimer helices. L149, Y150, and E153 are on one helix and M154 comes from the homodimer partner helix (FIG. 21D). The identification of the anchoring knob/hydrophobic pocket mechanism in vimentin-1B tetramer formation may explain why several prior vimentin crystal structures failed to show tetramerization: the vimentin construct either didn't contain the N-terminal sequence needed to form a complete hydrophobic pocket (PDB Codes 3SWK and 4YPC) or lacked the C-terminal sequence containing the anchoring knob (PDB Codes 3SSU and 3S4R) (Chernyatina, Hess et al., 2016, Chernyatina et al., 2012). Structural models of K5/K14-1B and K8/K18-1B illustrate anchoring knob/hydrophobic pocket conservation like K1/K10-1B and vimentin-1B (FIG. 21E).

The importance of the anchoring knob/hydrophobic pocket mechanism to higher order KIF formation is demonstrated by the mutational studies on the anchoring knob (FIGS. 5, 14, 15 and 20); this data is validated further by multiple sequence alignment. For all type II keratins, including the hair and nail keratins, the anchoring knob positions are highly conserved: position 314$^{K1}$ is conserved as phenylalanine in 25/26 type II keratins (K80 has leucine); position 318$^{K1}$ is conserved as leucine in 23/26 type II keratins (K5 has phenylalanine, K75 valine, and K80 isoleucine) (FIG. 9). Similarly, the hydrophobic pocket is highly conserved: positions 227$^{K1}$ and 230$^{K1}$ are conserved as large hydrophobic residues in 26/26 and 25/26 type II keratins, respectively (K76 has cysteine at 230); position 231$^{K1}$ is conserved as an aromatic residue in 22/26 type II keratins (K71, K73, K74, and K77 have leucine); position 234$^{K1}$ is conserved as an aromatic residue in 23/26 type II keratins (K3 has histidine, K7 glutamine, and K78 cysteine) (FIG. 9A).

The 28 type I keratins do not have a hydrophobic pocket or anchoring knob (FIG. 9B). There are no large hydrophobic residues at the analogous Y230$^{K1}$ position, 20/28 residues at the analogous F234$^{K1}$ position are threonine, and 25/28 residues at the analogous L318$^{K1}$ position are asparagine. Except for syncoilin (no similarity), the primary sequences of type III IFs indicate they contain a vimentin-like hydrophobic pocket and a K1- and vimentin-like anchoring knob (FIG. 9C). Type IV IFs appear to have a vimentin-like hydrophobic pocket and an aromatic or hydrophobic residue at the corresponding F314$^{K1}$ knob position (which was the essential site in these mutational studies), but they lack a bulky hydrophobic residue at the equivalent L318$^{K1}$ knob position (FIG. 9D). Type V IFs (lamins) and the type VI IFs (eye lens) do not have sequence resemblance to either the K1 pocket or knob (FIGS. 9E and 9F). Together, these findings suggest that this mechanism of higher order A$_{11}$ intermediate filament assembly is very similar for several IF types, but is not identical across all IF types.

The molecular surfaces of IFs contain features critical to their assembly and function. Perhaps the most important finding from the previous K1/K10-2B heterodimer structure was that only a small number of residue differences are needed to significantly alter the shape and chemistry of the keratin surface because most of the unique residues concentrate along the outer helical ridges of the coiled-coil (Bunick & Milstone, 2017). This holds true for K1/K10-1B as well (FIGS. 10A-10B and 23A-23D). An important question raised by the K1/K10-2B structure was whether the identified surface pockets had relevant biological function. The K1/K10-1B dimer and tetramer structures confirmed that a surface pocket (the N-terminal hydrophobic pocket) visualized in the heterodimer structure served as a receptacle for another part of the complex (the anchoring knob) to help align K1/K10 for higher order assembly (FIGS. 11A and 11B). This validates the concept that keratins contain molecular surface pockets that are biologically relevant, in this case for filament assembly, but in other cases possibly for association with non-keratin proteins.

The observation of a highly acidic groove across the molecular surface of the K1/K10-1B tetramer, but not the dimer, illustrates another important concept: higher order assemblies of keratins may contain new surface features that are not present at the heterodimer level. In other words, some keratin structural features that may be critical for filament assembly or interaction with non-keratin proteins cannot be discovered without structures of higher order keratin complexes. The acidic groove in the K1/K10-1B tetramer extends the full length of the 1B helix, raising questions about its biological purpose. Alternatively, it serves as the binding site for the non-keratin, positively-charged protein, filaggrin. The atomic resolution mechanism by which filaggrin, short for "filament aggregating protein," binds keratin is unknown; Steinert and colleagues proposed an "ionic zipper hypothesis" (Mack, Steven et al., 1993). The tetramer face opposite the long acidic groove also contains two smaller grooves and a larger pocket; further studies to understand the purpose of each surface feature is critical to elucidating the keratin structure function paradigm.

The biochemical and structural studies of K1$^{S233L}$/K10-1B demonstrate how a single missense mutation relevant to human skin disease can alter the behavior of KIFs. In this case, K1$^{S233L}$ caused erroneous hydrophobic interactions between the mutant L233 and key residues involved in the anchoring knob/hydrophobic pocket mechanism of tetramer assembly. Even though the K1$^{S233L}$/K10-1B structure did not fully recapitulate tonotubular keratin, it did recapitulate aberrant association of K1/K10 into higher order aggregates. The most likely reason complete tonotubular keratin was not observed is that only the 1B subdomain of K1/K10 was used (flexible full-length keratins are problematic for crystallization (Strelkov et al., 2001)); the other portions of intact K1/K10 must play a role in transforming the aberrant tetramer aggregation into a tubular morphology.

Figure 22:
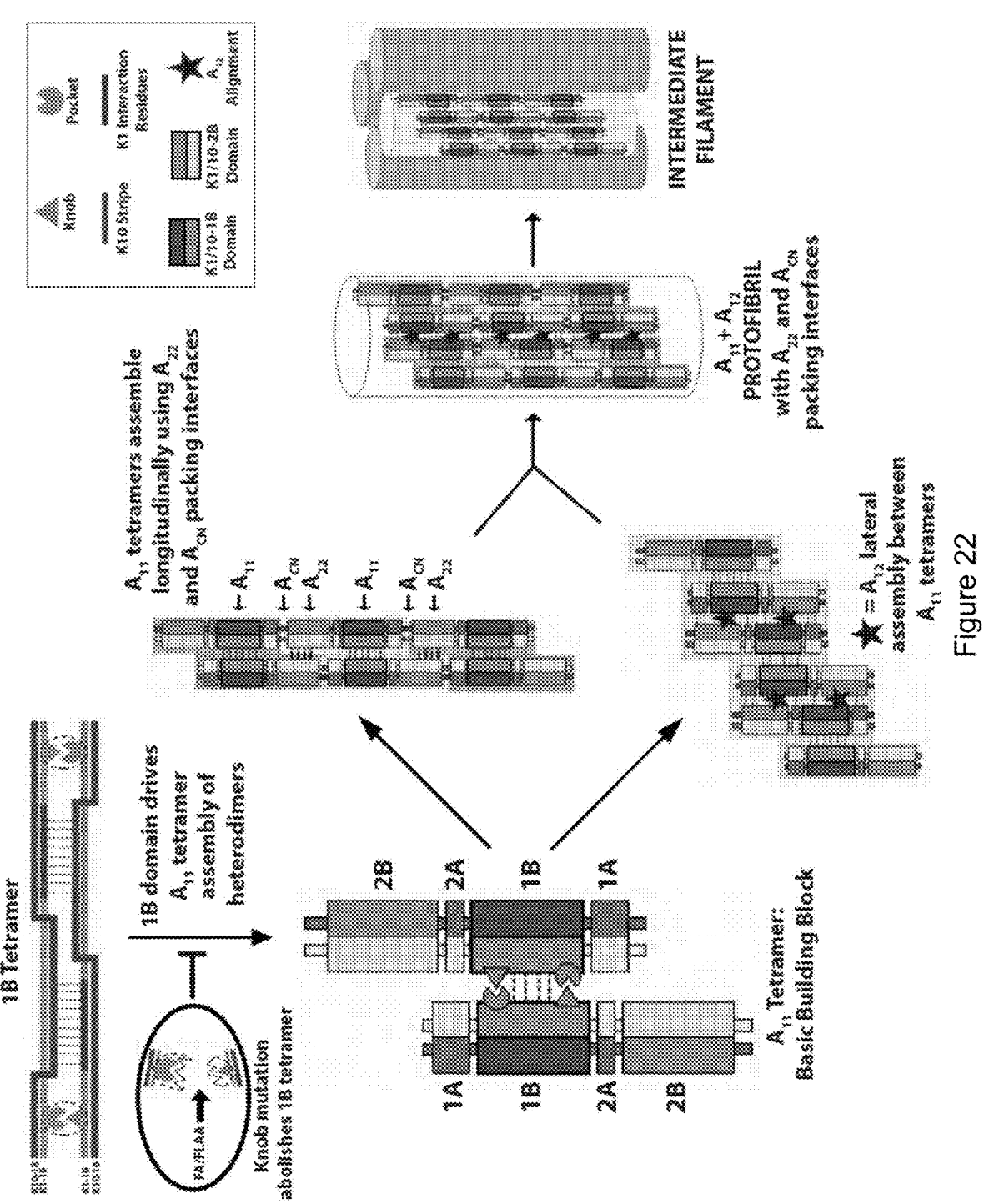
FIG. 22 depicts a model for keratin intermediate filament assembly based on K1/K10-1B tetramer structures. Analysis of the K1/K10-1B and K1$^{S233L}$/K10-1B tetramer structures identified a critical anchoring knob/hydrophobic pocket mechanism that orients, drives assembly of, and stabilizes the A$_{11}$ tetramer. The importance of this mechanism was demonstrated by studies showing anchoring knob mutants failed to form 1B-tetramers and formed aberrant full-length IFs on EM. The strength of the anchoring knob/hydrophobic pocket mechanism in the keratin 1B region suggests that the A$_{11}$ tetramer is the basic building block for filament formation, consistent with established literature. The helix 2B overhang in the A$_{11}$ tetramer enables multiple A11 tetramers to assemble longitudinally so that the 2B helices are in phase (the A$_{22}$ packing interface) and the head and tail regions overlap (the A$_{CN}$ packing interface). Lateral assembly of A$_{11}$ tetramers occurs by a distinct mode of alignment, the A$_{12}$ mode, where the 1A-1B region from one tetramer and the 2A-2B region from an adjacent tetramer pack anti-parallel (black star). Together, the A$_{11}$ and A$_{12}$ modes of alignment are used by A$_{11}$ tetramers to generate a protofibril; four protofibrils then assemble to form a 10-nm intermediate filament (Aebi et al., 1983, Herrmann & Aebi, 1999, Steven, Hainfeld et al., 1983, Steven, Wall et al., 1982).
Figure 23:
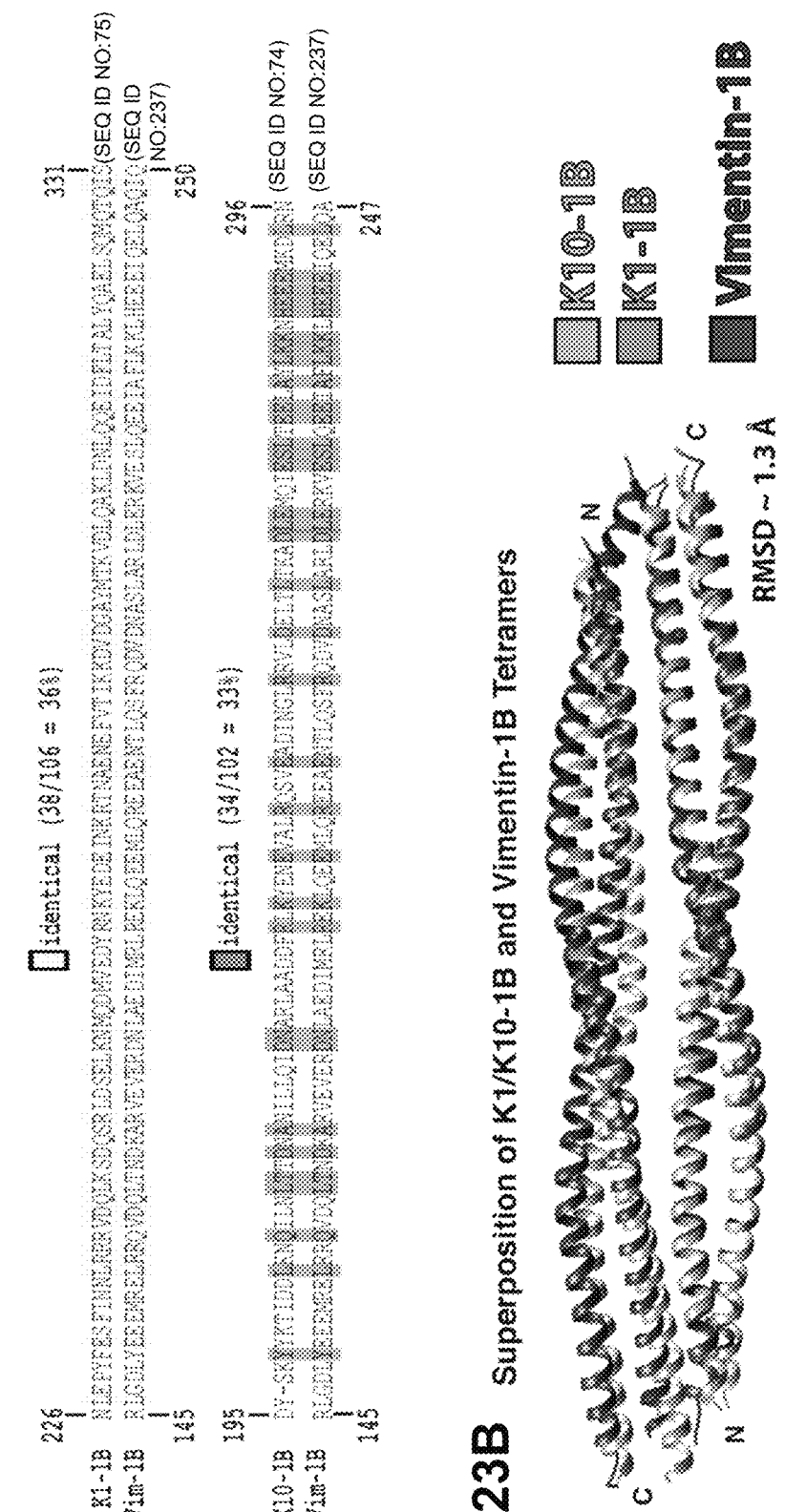
FIG. 23, comprising
Figure 23:
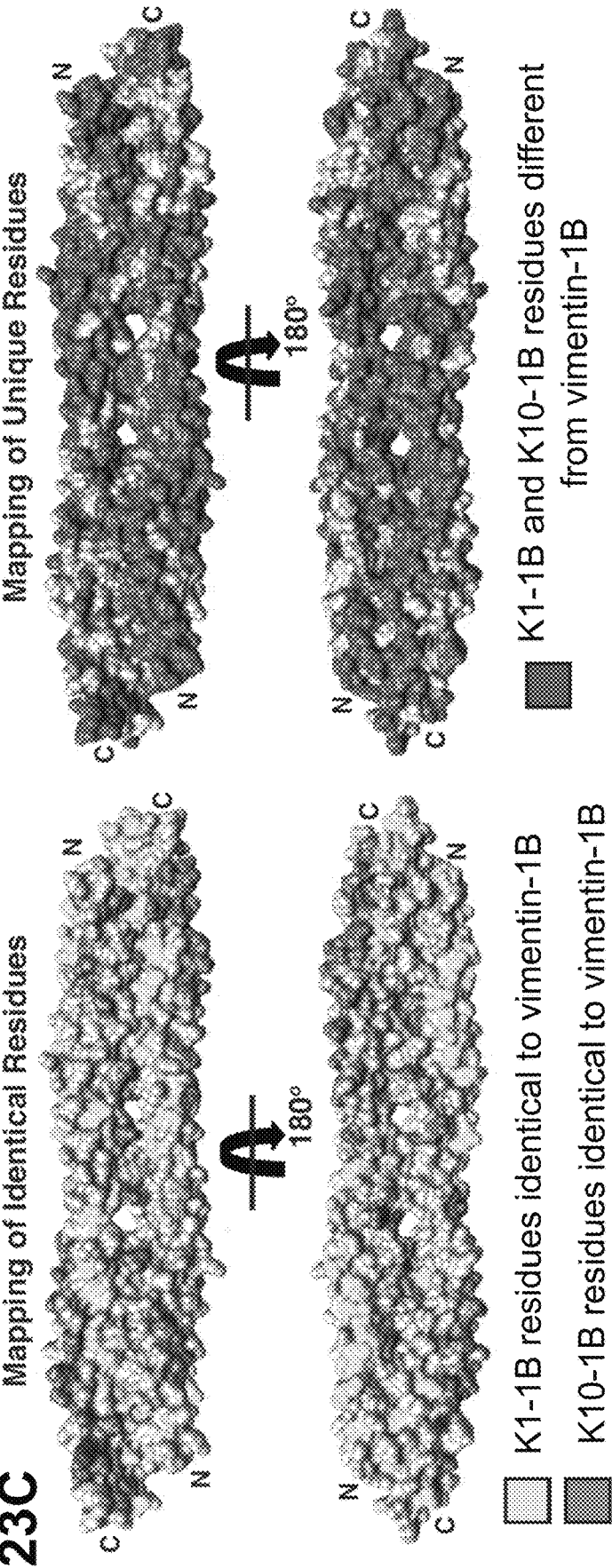
Figure 23:
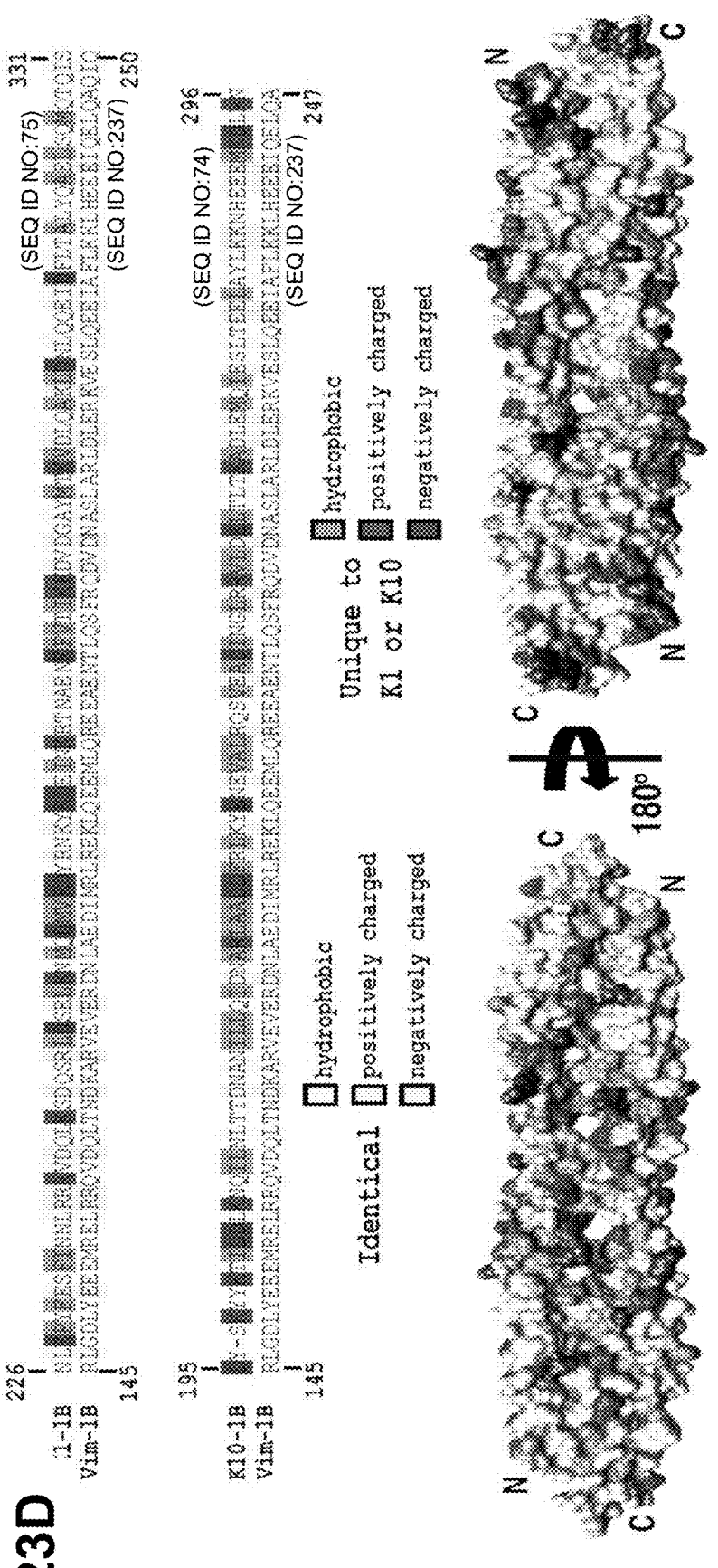

The crystal structures of the wild-type keratin 1/10-1B tetramer and the mutant $K1^{S233L}$/K10-1B octamer described here establish a foundation for understanding the molecular determinants of KIF assembly at atomic resolution. The mechanism of $A_{11}$ axial alignment in the keratin 1B region utilizes precise molecular interactions, which raises questions as to how KIFs utilize other predicted modes of alignment, such as the $A_{22}$, $A_{CN}$, or $A_{12}$ modes. The model discussed herein is a simplified model where the $A_{11}$ tetramer is the building block for KIF assembly based on its strength, stability, and molecular precision as observed in this data and as observed in previous studies (Aziz et al., 2012, Herrmann & Aebi, 2016, Kim, Kim et al., 2018, Mucke, Wedig et al., 2004, Premchandar, Mucke et al., 2016, Steinert et al., 1993a, Steinert et al., 1993c) (FIG. 22). Both the $A_{22}$ and $A_{CN}$ alignments essentially describe how an Au tetramer packs onto itself during the longitudinal elongation of tetramers into a protofilament (i.e. establishing length). Thus, $A_{22}$ and $A_{CN}$ describe packing interfaces of the $A_{11}$ building block more than they represent their own distinct mode of alignment. The EM data supports this concept: knob mutation causes misalignment and/or instability in the $A_{11}$-tetramer, which impairs its ability to pack properly using $A_{22}$ and $A_{CN}$ interactions, ultimately reflected in aberrant filaments. $A_{12}$ on the other hand is a unique alignment mode that describes the side-to-side packing of tetramers (i.e. establishing width) through largely the helix 1B-helix 2B interaction. The orthogonal relationship between the $A_{12}$ mode and the $A_{11}$/$A_{12}$ modes is supported by a recent vimentin-1B structure (Pang, Obiero et al., 2018). The model also illustrates how the $A_{12}$ interactions may cause the pitch or spiraling behavior observed in prior electron microscopy (Aebi et al., 1983) and cross-linking studies (Steinert et al., 1993a, Steinert, Marekov et al., 1993d). It is emphasized that the molecular surfaces of keratin occluded in $A_{11}$ tetramer formation and elongation are completely different than the surfaces needed for $A_{12}$ alignment.

It is evident from the model presented herein, as well as in cross-linking studies (Steinert et al., 1993a, Steinert, Marekov et al., 1993b, Steinert et al., 1993d), that coils 1A and 2A also play a role in Au tetramer stabilization and intermediate filament formation. This was confirmed by hydrogen-deuterium exchange experiments on vimentin filament assembly; the stability of coils 1A and 2A increased during filament formation (Premchandar et al., 2016). Importantly, hydrogen-deuterium exchange also identified the N and C termini of vimentin coil 1B as the most stable segments of the entire vimentin tetramer. The biochemical, structural, and electron microscopy data presented here provide a molecular basis for why this occurs in multiple IF systems: symmetrical knob-pocket interactions at the termini of coil 1B enhance tetramer formation and filament stability. In conclusion, to fully characterize intermediate filament formation, additional atomic resolution structures of KIF assemblies are needed. It will be important to focus on the biochemical determinants of alignment within other keratin subdomains (e.g. 1A, 2A, 2B and head/tail domains) and for the different packing interfaces ($A_{22}$, $A_{CN}$) and modes of axial alignment ($A_{11}$, $A_{12}$).

Example 6: Characterizing Cancer Cell Behavior after Disruption of Vimentin Intermediate Filament Assembly Intermediate filaments are involved in human cancers. For years keratin and vimentin intermediate filaments (IFs) have served as diagnostic and prognostic markers in tumor pathology. At least 17 types of cancer are associated with over-expressed IFs that serve as diagnostic tumor markers, including skin, breast, colon, liver, lung, pancreatic, and prostate cancers. Keratin expression patterns affect prognosis in at least 11 types of cancer. Furthermore, KIFs are increasingly being found to have a direct, active role in cancer, including cancer cell invasion and metastasis. For example, K1/K10 was found to be focally expressed in squamous cell carcinoma (SCC) and K6/K16 upregulated in poorly differentiated SCC; K8 recently was found to directly enhance growth of anaplastic thyroid cancer. K8/K18 has been linked to cancer proliferation, whereas another non-keratin IF protein, vimentin, causes increased invasion and metastasis of multiple cancer types. Despite these findings, IFs are not targeted with any current anti-cancer therapy, possibly because IF assembly mechanisms are poorly understood.

Figure 21:
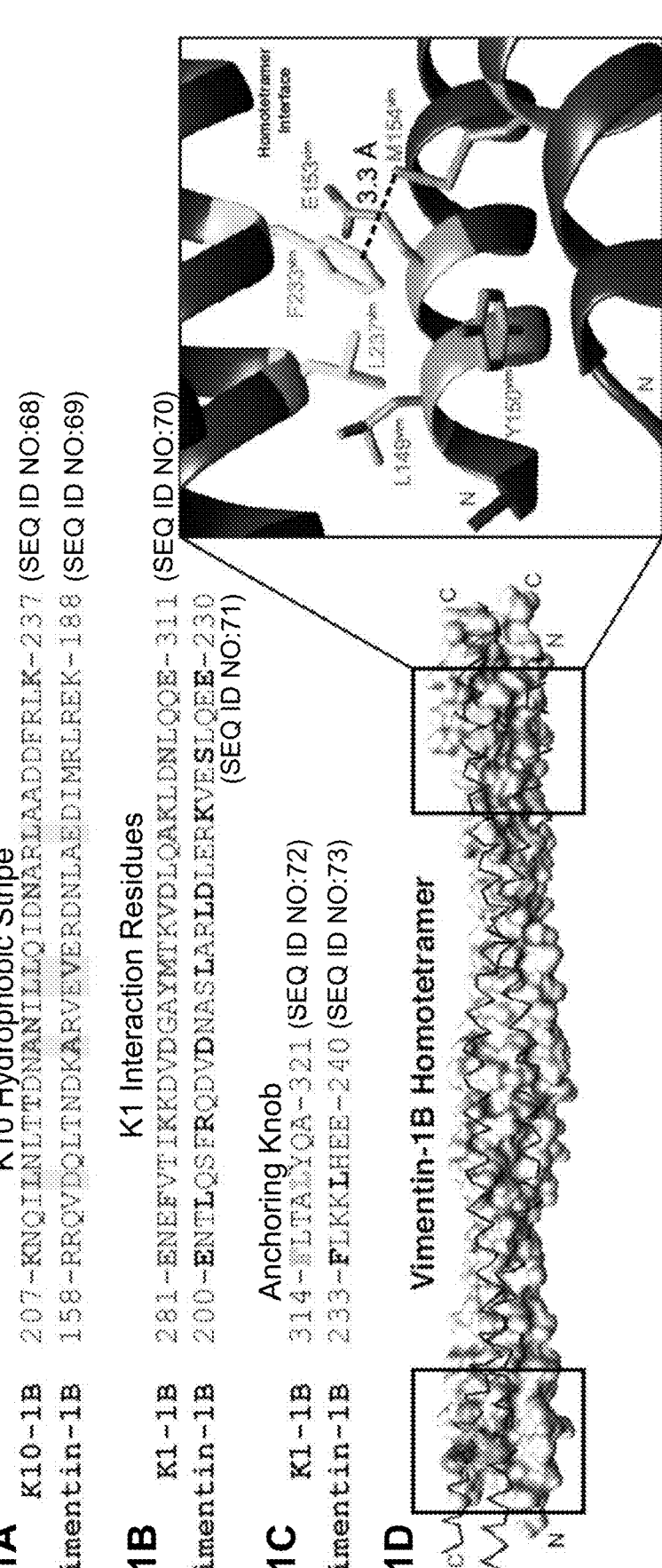
FIG. 21, comprising FIG. 21A through FIG. 21E depicts a comparison between the K1/K10-1B A11-heterotetramer and the vimentin-1B A11-homotetramer.

Examples 1 and 5 demonstrate the first higher-order human keratin x-ray crystal structure: the structure of the keratin 1/keratin 10 helix 1B heterotetramer. The 1B domain is the critical region of IFs for initiating higher order IF assembly (dimers to tetramers to protofibrils to 10-nm IFs) (FIG. 12). The crystal structure revealed a novel anchoring knob-hydrophobic pocket mechanism for keratin and vimentin IF assembly that offers a new target for anti-cancer therapy (see Example 1, Example 5, and FIGS. 1, 2, 4, and 9). Importantly, this knob-pocket mechanism is conserved among type II keratins (e.g. K8) and vimentin (a type III IF) (FIG. 21). Example 6 successfully demonstrated using electron microscopy that mutation of the knob abolishes vimentin IF assembly in vitro (FIGS. 15 and 20A). Vimentin's direct role in the metastasis of cancers, including its facilitation of invadopodia, makes it an attractive target to study how disruption of the knob-pocket mechanism (and hence vimentin IF assembly) affects cancer cells.

The vimentin knob mutation negatively disrupts cancer cell behavior. The disruption of a cytoskeleton component has precedent in *vinca* alkaloids and taxanes, which disrupt microtubule polymerization and de-polymerization, respectively. Recently, it was shown that a small molecule could target vimentin and disrupt the mitotic network in mesenchymal cancers.

Characterizing the Effects of Anchoring Knob Mutation on Vimentin Intermediate Filament Formation and Human Cancer Cell Migration and Viability (Proliferation, Induction of Apoptosis).

Examine changes to vimentin IF network in cancer cells due to anchoring knob mutations.

A few specific cell lines are selected for investigation. First, a breast cancer cell line (MCF7) is used that does not express vimentin. In this case, vimentin knock-down (such as with siRNA) is not necessary. The untransfected cell line is used as a negative control and is compared to cells transiently transfected with tagged vimentin (both wild-type and FLAA knob mutant as in FIG. 21A). In addition, a common HeLa cell line is tested. Endogenous vimentin is knocked down with siRNA and the cells are subsequently transiently transfected with tagged vimentin (both wild-type and FLAA knob mutant). The expression of the transfected gene is confirmed using Western-blotting; changes to cellular morphology, physiology, and the vimentin IF network of the transfected cancer cell is captured by confocal imaging after labeling with the direct/indirect immunofluorescence technique.

Second, using similar techniques how vimentin knob mutation affects the VIF network is evaluated in two other specific cancer cell lines: one from skin (melanoma) and one internal cancer (non-small cell lung cancer). Each of these cancers has shown increased metastatic potential due to elevated vimentin expression. Third, cell-based assays are used to examine how vimentin's anchoring knob mutation influences the three main behaviors of cancer cells: cell proliferation, apoptosis, and cell migration. Cell proliferation is assessed using the Cell Titer-Glo Luminescent Cell Viability Assay, apoptosis using the Promega Caspase-Glo 3/7 Assay, and cell migration using a Boyden Chamber Assay.

Evaluate Whether Vimentin Anchoring Knob Peptides can Harm Cancer Cell Functions Using the cancer cell lines developed in the above experiments, it is evaluated whether a set of vimentin knob peptides can negatively impact cancer cell proliferation and migration, or cause apoptosis. Several vimentin knob peptides are assessed for their ability to harm VIF assembly and cancer cell function. The vimentin sequence ranging from E221 to Q250 contains the critical F233 and L237 residues (underlined) that function as the anchoring knob: 221-ERKVESLQEEIAFLKKLHEEEIQELQAQIQ-250. Several peptides from this vimentin region are designed around F233 and L237. For example, the smallest possible inhibitor is: 233-FLKKL-237. N- or C-terminal modifications (such as acetylation or amidation) are used as necessary to stabilize a helical peptide structure.

First, vimentin anchoring knob peptides are tested for their ability to inhibit the formation of intact VIFs in vitro. Full-length, recombinantly produced and purified vimentin (as in FIG. 21A) are combined in the presence or absence of vimentin anchoring knob peptide(s), and the solutions are examined by negative-stain electron microscopy for VIF assembly. Second, peptides effective in vitro at preventing VIF assembly are incubated with human cancer cell lines and proliferation is assessed using the Cell Titer-Glo Luminescent Cell Viability Assay, apoptosis using the Promega Caspase-Glo 3/7 Assay, and cell migration using a Boyden Chamber Assay.

Example 7

IF proteins are divided into six types, the most abundant being types I and II which represent the 54 different keratins. Type III IFs include vimentin, desmin, and glial fibrillary acidic protein; type IV IFs are neurofilament proteins; type V IFs are nuclear lamins; and type VI IFs are eye lens proteins. There is a shared core structure among all of these IFs: a central coiled-coil (divided into four helical domains: 1A, 1B, 2A, 2B) that is flanked on either end by head and tail domains of varying lengths and composition (FIG. 12). As shown in Examples 1 and 5, using keratin IFs (KIFs) as an example, multiple biophysical studies have defined the stages of KIF assembly as: one type I keratin and one type II keratin pair to form a parallel heterodimer; heterodimers then bind to form an anti-parallel tetramer; eight tetramers then merge to form a protofibril/unit-length filament; and finally four protofibrils assemble into the complete KIF. A major knowledge gap exists in understanding the biochemical and structural determinants of IF assembly at atomic resolution.

As shown in Example 5, there are four modes of axial alignment of keratin heterodimers within a filament based on keratin 1/10 and 5/14 crosslinking studies (FIG. 17). Two modes contain heterodimers in an anti-parallel, staggered alignment such that either the 1B coiled-coil segments are in phase (A11 mode) or the 2B coiled-coil segments are in phase (A22 mode). One mode contains two anti-parallel heterodimers in almost exact register (A12 mode), but without any specific coiled-coil region being in-phase with itself. The fourth mode is a head-to-tail alignment of the helical rod domain (i.e., helices 1A, 1B, 2A, 2B) with ~10 residues overlapping between the 1A helix from one heterodimer and the 2B helix from another (CAN mode). My laboratory's K1/K10-1B tetramer structures captured the A11-tetrameric assembly stage and represent the first crystal structures of human keratins that elucidate the molecular mechanisms of any of these proposed axial alignments.

Analysis of the K1/K10-1B A11-tetramer structures led to the discovery of a novel "anchoring knob-hydrophobic pocket" mechanism in the 1B domain of IFs that drives the tetramerization step of IF assembly shown if Examples 1 and 5. Site-directed mutagenesis of the knob residues to demonstrated that loss of the knob structure abolishes K1/K10-1B tetramerization and prevents formation of mature, full-length filaments by EM.

A new class of anti-cancer therapeutics is developed targeting the knob-pocket mechanism to disrupt cancer cell function (e.g. invasion, migration, immune evasion) and viability by directly inhibiting tetramer formation during IF assembly. Studying IF assembly across multiple timepoints generates new insights into how and when knob mutation alters the rate and/or length of filament assembly. Examining multiple new IF systems (e.g. K6/K16, K5/14, desmin, GFAP), the conservation and importance of the knob-pocket mechanism is demonstrated herein; each of these IF systems is associated with different medical diseases. Examining the knob-pocket interaction from the perspective of the hydrophobic pocket significantly enhances the mechanistic understanding of IF assembly. Demonstrating that peptides of the K1 (or vimentin) knob can inhibit IF assembly in vitro establishes new technology and a foundation for exploring healthcare therapies targeting IF assembly mechanisms.

Crystal structure of the K1/K10-1B A11 tetramer reveals a knob-pocket mechanism

Analysis of the K1/K10-1B heterotetramer structure at 3.0 Å resolution revealed two symmetric (due to the anti-parallel arrangement of heterodimers in the tetramer) knob-pocket interactions at each end of the 1B tetramer (see Example 1, Example 5, and FIGS. 1, 2, 4, and 9). The hydrophobic pocket (K1 residues L227, Y230, F231, and F234) exists at the N-terminus of K1-1B and the anchoring knob (K1 residues F314 and L318) at the C-terminus of K1-1B. Multiple sequence alignment demonstrates conservation among all type II keratins. Studies on K1 knob mutants demonstrate the knob is critical for IF assembly Three K1 knob mutants were developed—F314A (FA), L318A (LA), and the double mutant F314A+L318A (FLAA). Knob mutation did not impact heterodimer formation. Evaluated by multi-angle light scattering, F314A and FLAA knob mutation abolished K1/K10-1B tetramer formation, whereas L318A did not (FIG. 15). This suggests F314A is the critical residue in knob-pocket binding. FLAA knob mutants were further evaluated using EM for their affect on full-length filament assembly for three IF systems (K1/K10, K8/K18, and vimentin). EM analysis of wild-type (WT) and knob mutant (FLAA) in vitro IF assembly demonstrated the FLAA mutations were detrimental to mature IF formation (FIG. 20A). This example further investigates how knob mutation affects the dynamics of full-length filament formation and examines the hydrophobic pocket residues to determine which are most critical to IF assembly.

A Model for Intermediate Filament Assembly

Shown herein is a model where the $A_{11}$ tetramer is the building block for IF assembly based on its strength, stability, and molecular precision as shown in Examples 1 and 5 (FIG. 22). Both the $A_{22}$ and $A_{CN}$ alignments essentially describe how an $A_{11}$ tetramer packs onto itself during the longitudinal elongation of tetramers into a protofilament (i.e. establishing length). Thus, $A_{22}$ and $A_{CN}$ describe packing interfaces of the $A_{11}$ building block more than they represent their own distinct mode of alignment. The EM data presented herein supports this concept: knob mutation causes misalignment and/or instability in the $A_{11}$-tetramer, which impairs its ability to pack properly using $A_{22}$ and $A_{CN}$ interactions, ultimately reflected in aberrant filaments. $A_{12}$ on the other hand is a unique alignment mode describes the side-to-side packing of tetramers (i.e. establishing width) through largely the helix 1B-helix 2B interaction. The model also illustrates how the $A_{12}$ interactions may cause the pitch or spiraling behavior observed in prior electron microscopy and cross-linking studies.

Characterize how Disruption of the Knob-Pocket IF Assembly Mechanism Affects the Dynamics (Rate and Length) of Filament Formation.

Examples 1 and 5 demonstrate the discovery of a novel knob-pocket mechanism critical for IF assembly. Initial EM studies examined one IF assembly timepoint (10 min). More EM experiments across multiple IF assembly timepoints are carried out to characterize how the knob-pocket mechanism affects the dynamics of IF assembly. The knob mutation disrupts IF assembly by decreasing both the rate of IF assembly and the overall filament length because of propagated misalignment/instability at the tetramer level.

To determine how knob mutation affects the rate and length of IF assembly three experimental tasks are performed.

Protein production and purification: Full-length wild-type K1, K10, K8, K18, and vimentin constructs in pET-21a(+) or pET-24a(+) based plasmids are used. K1, K8, and vimentin knob mutants (both individual [FA, LA] and double [FLAA] residue mutants) are also used. K10 is expressed in *E. coli* BL21(DE3)pLysS cells at 20° C. for 72 hours using an autoinduction method. Expression of all other keratins and vimentins occur in *E. coli* BL21(DE3) cells using LB at 37° C. for 3 hours with 1 mM IPTG for induction. Inclusion body pellets are purified from cells using a previous protocol modified to include sonication at each step of pellet resuspension. Inclusion bodies are resuspended in 6M urea solution and purified by anion exchange chromatography (Q/SP sepharose) using a 200 mM guanidine-HCl gradient, followed by size exclusion chromatography (Superdex 75) using 6M urea solution. Heterodimeric complexes of K1/K10 and K8/K18, and homodimeric complex of vimentin, are made by mixing individual protein in a 1:1 molar ratio; the complexes subsequently are purified with Q sepharose using a 200 mM guanidine-HCl gradient, and then dialyzed into 50 mM Tris-HCl buffer (pH 8.5) containing 6M urea and 2 mM DTT. If needed, IF assembly protocols are modified (e.g. vary pH, salinity, temperature) to achieve mature wild-type filament formation before analyzing mutants. Alternatively, ultracentrifugation is used to study size differences in IF assembly.

Filament assembly: Before initiating filament assembly, all IF complexes are concentrated to ~0.5 μg/μL and dialyzed into 25 mM Tris-HCl buffer (pH 8.5) containing 9M urea and 2 mM DTT at 20° C. for 4 hours. Filament formation follows established "Assembly methods". To capture various IF assembly timepoints, filament assembly is terminated after either 30 s, 1 min, 3 min, 5 min, 10 min, 1 hr, or 5 hrs by adding stop buffer (0.2% glutaraldehyde, 20 mM KCl, 0.7 mM NaHPO).]

Electron microscopy: Filament samples are immediately applied to a Carbon type B-400 mesh-Copper grid charged with Pelco easiGlow (Ted Pella, Redding, CA) at 25 mA for 30s, and negatively stained using 2% aqueous uranyl acetate. Images are captured with a Talos L120C Electron Microscope from FEI. Images are analyzed for the number, length, width, and shape of filamentous structures formed at each timepoint to evaluate the dynamics of IF assembly in vitro for both wild-type and knob mutant proteins.

To determine whether the knob-pocket mechanism governs assembly of other keratins and type III Ifs, other biologically relevant IF systems (K5/14, K6/16/17, desmin, GFAP) are examined to ascertain if the knob-pocket mechanism is critical for their assembly. Wild-type and knob mutants for each IF system are designed, produced, purified, assembled and evaluated by EM using the same methods outlined above.

Homodimeric IFs (type III) have a slower rate and shorter final length of assembly compared to heterodimeric IFs (type I/II). For these new IF systems tested, those affected by knob mutation are subjected to a full dynamics assessment as outlined above.

Determine which Hydrophobic Pocket Residues are Most Critical for IF Assembly and Whether the Pocket can be Targeted with Knob Peptide Mimics to Disrupt IF Assembly.

Examples 1 and 5 demonstrate that that F314A, but not L318A, abolishes K1/K10-1B tetramer formation.

To determine which residues of the pocket are most important to knob binding, the K1 hydrophobic pocket is examined using multi-angle light scattering (MALS) and EM. Four K1-1B and four full-length K1 pocket mutants are studied: L227A, Y230A, F231A, and F234A. Two phenylalanines provide the strongest knob binding. The 1B domain mutants are analyzed for their ability to form K1/K10-1B tetramers using MALS (as in FIG. 15). Full-length K1 pocket mutants are analyzed by EM for their ability to form mature K1/K10 IFs (as in FIG. 20A) using the IF assembly protocol. Data is validated by repeating the study on K5/K14, K8/K18, and vimentin pocket mutants.

Determine whether peptides that mimic the anchoring knob can inhibit IF assembly. The K1 knob peptides binds the K1 hydrophobic pocket causing disruption of IF formation.

Peptide synthesis: The keratin 1 sequence ranging from V299 to S331 contains the critical F314 and L318 residues (underlined) that function as the anchoring knob: 299DLQAKLDNLQQEIDFLTALYQAELSQMQTQIS-331. K1 peptides are designed to span multiple lengths (5 to 33 amino acids) around F314 and L318. N- or C-terminal modifications (such as acetylation or amidation) are used.

Tetramer and Filament Inhibition: The shortest possible peptide (314-FLTAL-318) is examined first and then in peptide length is incrementally increased to assess for efficacy in inhibiting K1/10-1B tetramerization (using MALS) and K1/K10 mature IF formation (using EM). Individual K1 and K10 proteins are combined in the presence or absence of K1 anchoring knob peptide. Heterodimer formation occurs, but not tetramer or filament formation when the peptide blocks native knob pocket interaction. The same approach is performed in parallel with vimentin. Isothermal titration calorimetry is used to analyze keratin-peptide binding strength for successful peptides.

Example 8: Developing Therapies that Prevent Cancer Cell Metastasis and Migration by Disrupting Intermediate Filament Assembly Examples 1-7 demonstrate the first higher-order human keratin crystal structure: the keratin 1/keratin 10 helix 1B heterotetramer. The 1B domain is the critical region of IFs for initiating higher-order IF assembly (dimers to tetramers to protofibrils to 10-nm IFs) (FIG. 12). This structure revealed a novel anchoring knob-hydrophobic pocket mechanism for keratin and vimentin IF assembly that offers a new target for anti-cancer therapy (Example 1, FIGS. 1A, 2C, 4E, and 9A). Importantly, this knob-pocket mechanism is conserved among type II (keratins) and type III (e.g. vimentin) IFs (FIG. 6). Using negative-stain electron microscopy (EM), it was demonstrated that mutation of the knob abolishes vimentin IF and severely harms keratin IF assembly in vitro (see Example 1). A new class of anti-cancer therapeutics is developed targeting the newly discovered knob-pocket mechanism to disrupt cancer cell function, especially migration and invasion, by directly inhibiting tetramer formation during IF assembly.

Development of First-in-Class Anti-Metastasis Peptide Therapeutics

Figure 24:
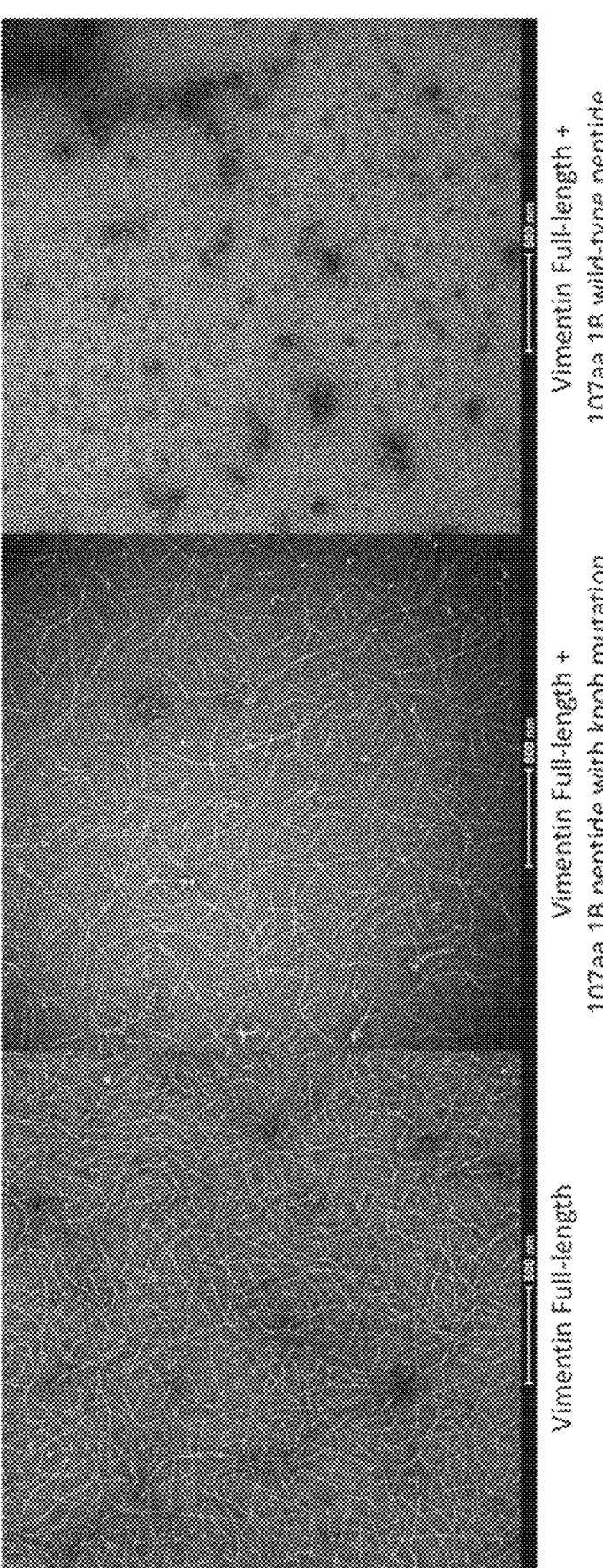
FIG. 24 depicts the negative-stain EM showing vimentin filament assembly is completely abolished in the presence of a wild-type 107 amino acid 1B peptide. Mutation of the anchoring knob in the peptide causes the peptide to lose its efficacy, highlighting the importance of the knob-pocket mechanism and validating it as a drug target.

Therapeutic peptides are an emerging approach to cancer treatment because they offer several advantages over larger proteins or antibodies: easy synthesis, high target specificity and selectivity, low toxicity, and low accumulation in tissues. Peptides that inhibit the natural knob-pocket interaction necessary for vimentin tetramerization. The result is the inability for vimentin to form mature filaments in vivo and hence vimentin is unable to drive cancer cell migration and metastasis. Both the anchoring knob and hydrophobic pocket exist on a-helices because IFs are naturally helical, thereby enabling a logical design of peptide inhibitors that either contain the knob (knob peptides) or pocket (pocket peptides). The knob and pocket peptides are helical as well and therefore retain the biological activity of the full knob-pocket interaction. Knob peptides bind in the native hydrophobic pocket to prevent filament assembly, whereas pocket peptides bind and cover all native knobs to prevent filament assembly. A 107 amino acid vimentin coil 1B peptide abolished vimentin filament assembly (FIG. 24). Furthermore, mutation of a key knob residue abated the effect of the peptide, demonstrating the knob-pocket mechanism is essential to targeting the filament assembly process.

The knob and pocket peptides are designed using a combination of primary sequence and crystal structure analysis. The secondary structure of the peptides is determined by circular dichroism using methods established for keratins (see Example 1). N- or C-terminal modifications (such as acetylation or amidation) are used as necessary to stabilize a helical peptide structure. Peptide stapling is used to improve peptide stability and enhance cell penetration. All synthesized knob and pocket peptides are tested for their ability to inhibit formation of intact vimentin IFs in vitro using the Filament Inhibition Assay (see Example 1). Full-length, recombinantly produced vimentin protein are combined in the presence or absence of vimentin knob or pocket peptides prior to initiating filament assembly, and the solutions are examined by negative-stain EM for mature vimentin filament formation.

Peptides that inhibit vimentin filament assembly are further analyzed using isothermal titration calorimetry (ITC) to determine the binding affinities of the peptides to vimentin. ITC provides data to rank the peptides from strongest to weakest binding. The two peptides with the strongest binding affinity to vimentin are crystallized bound to the vimentin coil 1B dimer so that the drug-target interaction is fully characterized structurally.

Design and Validation of a Screening Assay for Identification of Small-Molecule Inhibitors Small-molecule inhibitors of vimentin IF assembly are identified. To prepare for high-throughput chemical library screening, screening assays are developed and validated.

The first screening assay uses ANS (8-anilino-1-napthale-nesulfonic acid) fluorescence. The ANS probe binds hydrophobic regions of proteins and binds to the hydrophobic pocket in the N-terminus of vimentin coil 1B. Therefore, successful small-molecule inhibitors in these screening assay cause a reduction in ANS fluorescence signal by excluding the ANS probe from the vimentin hydrophobic pocket. The advantages of this screening assay are that it provides for an easy to monitor signal (fluorescence) and it can be scaled up for the high-throughput screening of tens of thousands of compounds. The design of the ANS fluorescence screening assay is innovative because it utilizes a unique vimentin coil 1B mutant that does not tetramerize; this is key for allowing the ANS probe access to the hydrophobic pocket.

A second, complementary biochemical assay is developed based on AlphaScreen bead technology. The concept is illustrated in FIG. 13, which shows measuring light emission from the "acceptor" bead when a knob-pocket interaction brings two distinctly tagged vimentin homodimers together into a tetramer. Successful small molecule inhibitors prevent light emission. The advantage of this technology is its ability to work for both vimentin coil 1B and full-length proteins To validate the ANS fluorescence and Alpha-Screen assays, the knob and pocket peptides described above to demonstrate that they diminish fluorescence or light emission, respectively, when bound to vimentin.

High-Throughput Screening for First-in-Class Small-Molecule Inhibitors of IF Assembly The ANS fluorescence and AlphaScreen biochemical assays developed above are used for chemical library screening of approximately 165,000 unique small molecule compounds. All the small molecule "hits" from these assays are tested in the Filament Inhibition Assay for their ability to prevent vimentin filament formation. Compounds that prove effective both in the screening assays and in preventing vimentin filament formation in vitro are analyzed by ITC for binding affinity to vimentin. Compounds then undergo optimization for chemistry, structure-activity relationship, bioavailability, and toxicity. The final optimized lead compound(s) are crystallized bound to the vimentin hydrophobic pocket in order to fully characterize the molecular mechanism of action.

In Vitro Testing of Inhibitors on Multiple Human Cancer Cell Lines

Peptides and small molecules are tested for their influence of three main behaviors of cancer cells: cell proliferation, apoptosis, and cell migration. While the peptides and small molecules target the inhibition of cancer cell metastasis, it is important to investigate the effect of these inhibitors on cell proliferation and apoptosis in order to fully comprehend the mechanisms of action of the drugs. Cell proliferation is assessed using the Promega Cell Titer-Glo Luminescent Cell Viability Assay, apoptosis using the Promega Caspase-Glo 3/7 Assay, and cell migration using a Boyden Chamber Assay (Cell Biolabs, Inc The cancer cell studies occur in two stages. First, two cancer cell lines are used which have displayed increased metastatic potential due to elevated vimentin expression:

one skin (melanoma) and one internal cancer (non-small cell lung cancer, NSCLC). For each peptide or small molecule tested, several concentrations of the drug are examined for its effect on proliferation, apoptosis, and cell migration. Cell behaviors in the presence of different drug concentrations are compared with cell behavior in the absence of drug. Second, cell-based assays are expanded to include cell lines from all types of cancer known to have up-regulated expression of either vimentin or keratins. This includes, but is not limited to, skin (melanoma, squamous cell, basal cell), lung, breast, prostate, bladder, colorectal, gastric, biliary, pancreatic, liver, ovarian, endometrial, uterine, lymphoma, thyroid, cervical, renal, and brain cancers.

Adapt to IFs Other than Vimentin (e.g. Keratins)

What makes this work around the knob-pocket mechanism powerful is that it translates to multiple IF systems. This means one mechanism can serve as the innovative platform for many new technologies. New technologies are developed targeting the knob-pocket mechanism across several IF types. It is demonstrated herein that the knob-pocket mechanism is conserved among type I and II IFs (keratins), type III IFs (e.g. vimentin, desmin, GFAP), type IV IFs (neurofilaments), and even type V IFs.

Characterize the Effects of the Most Potent Inhibitors on the Cytoskeleton

Vimentin and keratin tetramerization inhibitors are investigated for their ability to prevent mature filament formation within the cell. A complete loss of the vimentin or keratin filaments is seen (as demonstrated in FIG. 4), rather than filament aggregates. Confocal microscopy is used to visualize the changes in the IF cytoskeleton when human cancer cells are exposed to the most promising inhibitors. Inhibitors demonstrating the greatest efficacy are used along with the human cancer cell lines in which they demonstrate that efficacy. Cancer cells are transiently transfected with fluorescently tagged-keratin or tagged-vimentin and the fluorescent proteins are allowed to incorporate into the endogenous IF network. Then the cells are incubated with the IF assembly inhibitor(s), and examined for the obliteration, disruption, alteration, or aggregation of the IF cytoskeleton using confocal microscopy.

Example 9: Identification of Knob-Pocket Mechanism

Figure 25:
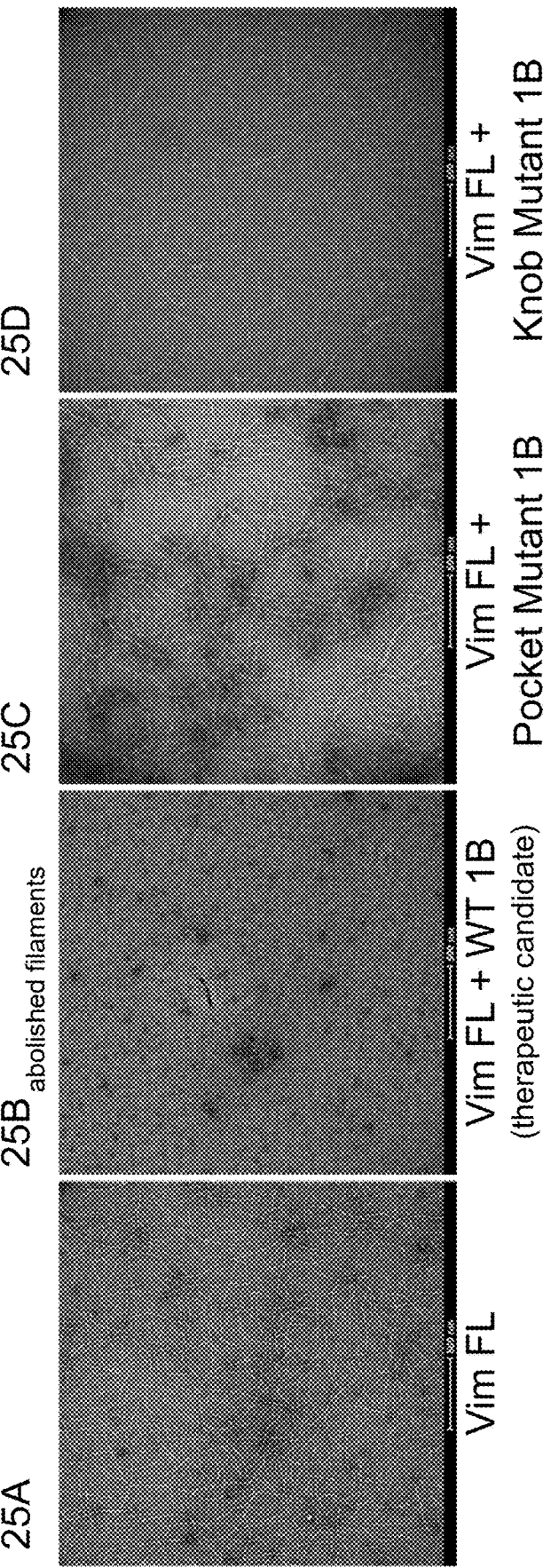
FIG. 25, comprising FIG. 25A through FIG. 25D depicts electron microscopy experimental results demonstrating that vimentin filament assembly can be blocked using a native peptide containing the knob and pocket. Mutation of either that knob or pocket mitigates the inhibitory effect.
Figure 26:
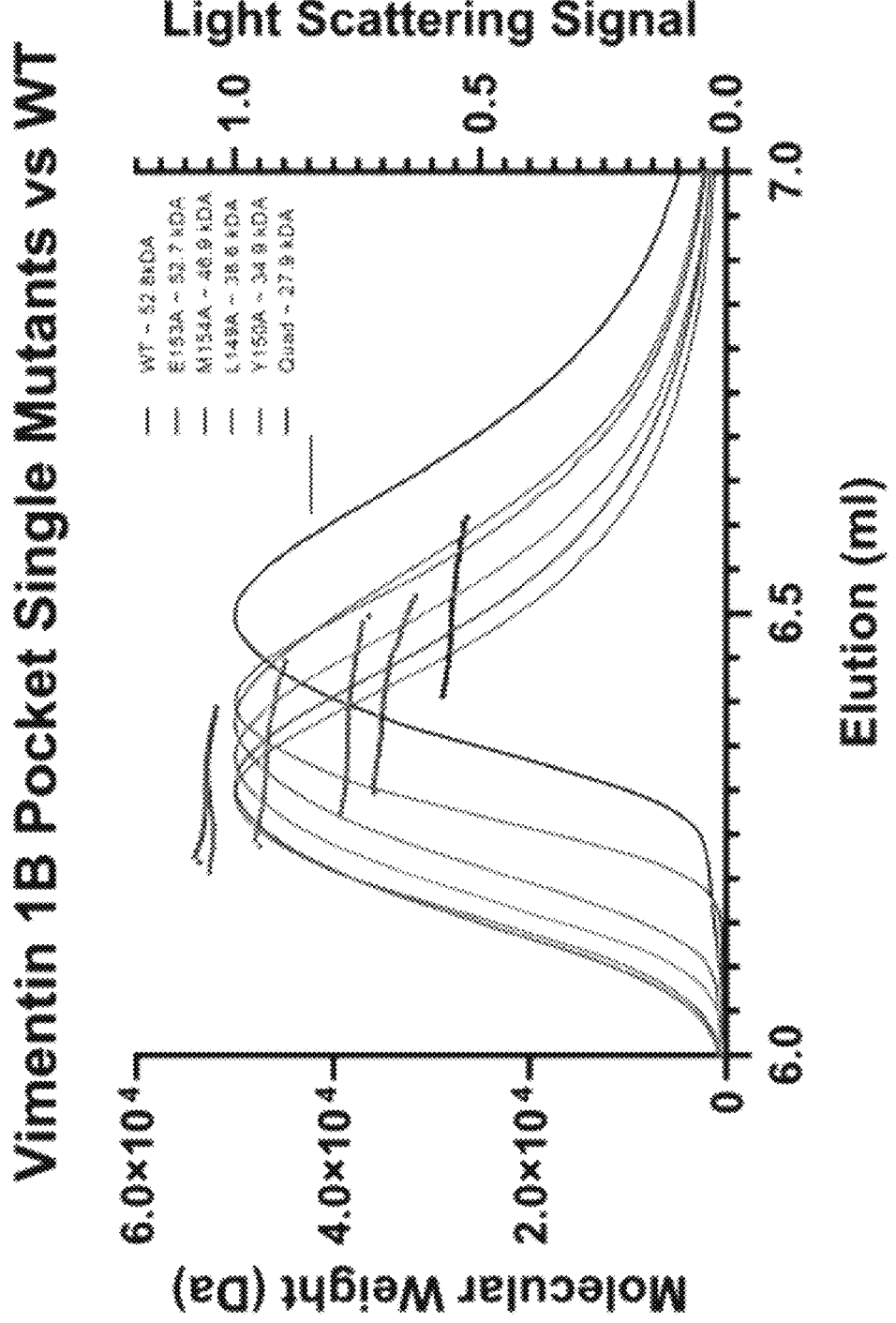
FIG. 26 depicts mutagenesis studies of Vimentin 1B pocket single mutants compared to WT.
Figure 27:
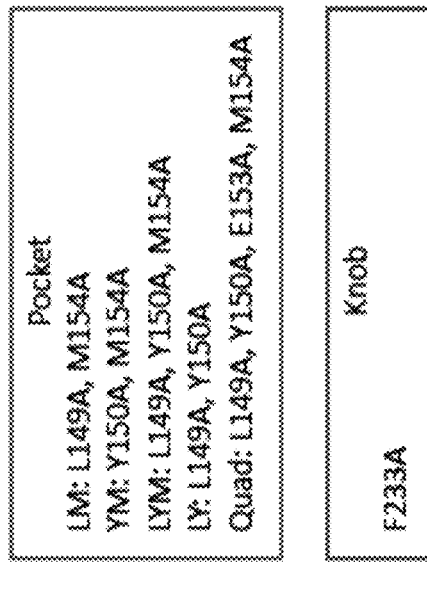
FIG. 27 depicts mutagenesis studies of Vimentin 1B pocket double and triple mutants compared to WT.
Figure 28:
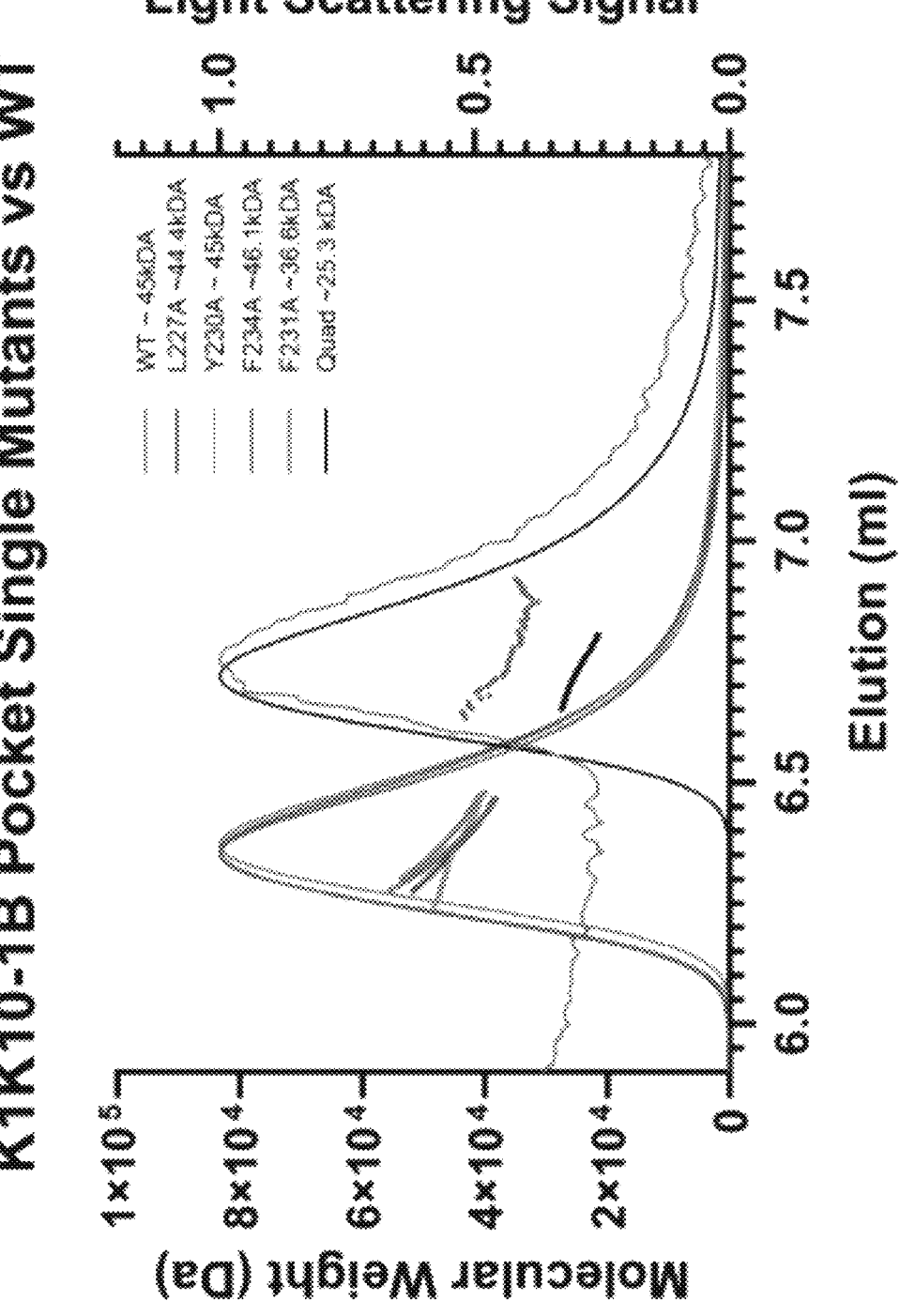
FIG. 28 depicts mutagenesis studies of K1/K10-1B pocket single mutants compared to WT.
Figure 30:
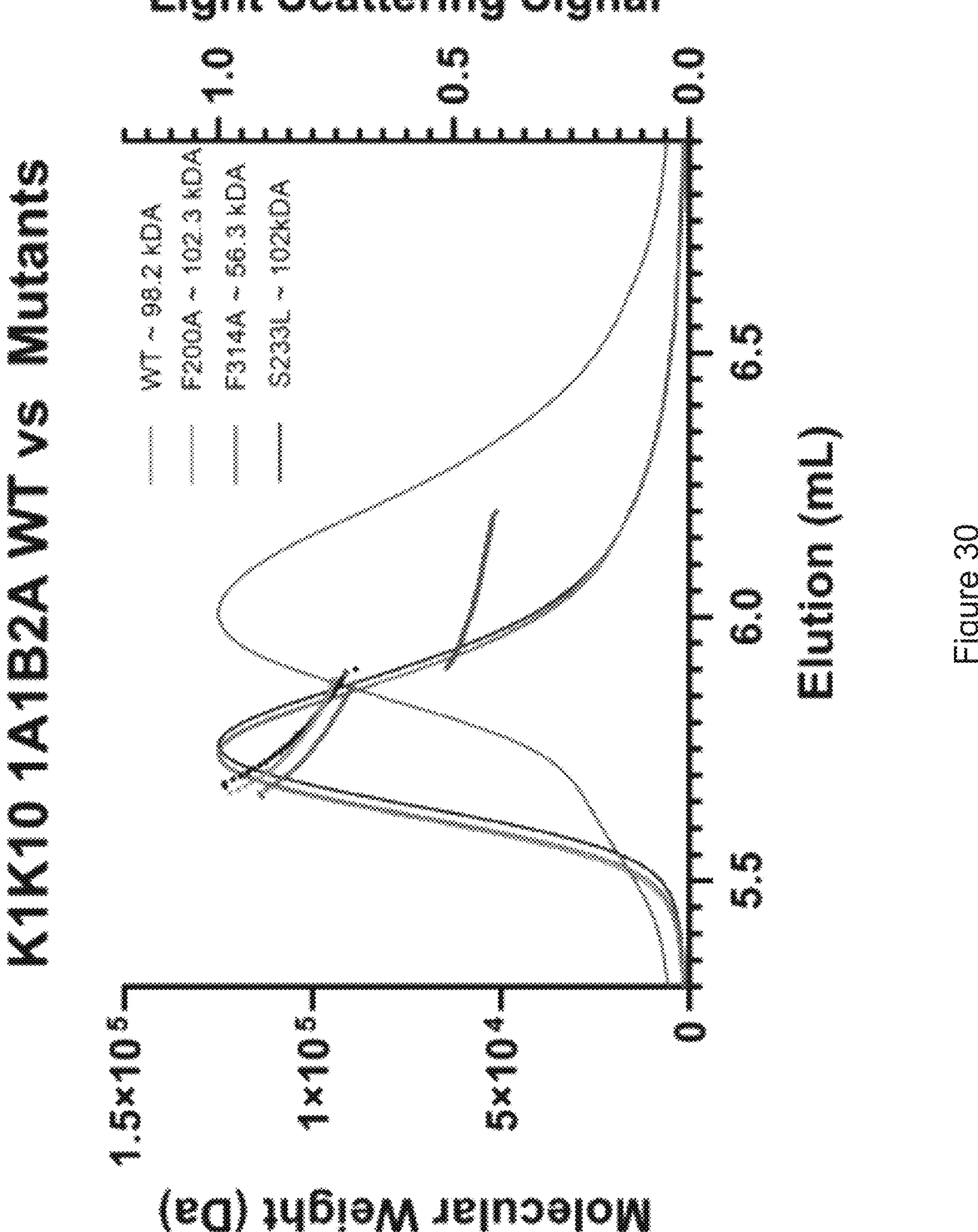
FIG. 30 depicts mutagenesis studies of K1K10 1A1B2A WT compared to WT.

The data presented herein demonstrates the molecular mechanism of the knob-pocket interaction. FIG. 25 depicts electron microscopy demonstrating that vimentin filament assembly can be blocked using a native peptide containing the knob and pocket. Mutation of either that knob or pocket mitigates the inhibitory effect. (FIG. 25). These mutagenesis studies identifying the most critical residues within the pocket for knob-pocket interaction for vimentin and keratin 1/10 complex (FIGS. 26-30). The pocket mutagenesis data confirms that the residues comprising the pocket function cooperatively to bind the knob. Double, triple, or quadruple pocket mutants are needed to completely disrupt tetramerization when a normal knob is present.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of screening a library of compounds to provide an inhibitor of intermediate filament formation, wherein the inhibitor inhibits the interaction between an anchoring knob domain in segment 1B of a first intermediate filament dimer and a hydrophobic pocket domain in segment 1B of a second intermediate filament dimer, the method comprising:

(a) contacting a hydrophobic pocket domain in segment 1B of an intermediate filament dimer with at least one compound in the library of compounds;

(b) measuring a binding of the at least one compound to the hydrophobic pocket domain in segment 1B;

(c) comparing the binding of the at least one compound to the hydrophobic pocket domain in segment 1B, with a binding of a comparator control to the hydrophobic pocket domain in segment 1B; and (d) selecting the at least one compound from the library when the binding of the at least one compound to the hydrophobic pocket domain in segment 1B, is increased at a statistically significant amount when compared with.

2. A method of screening a library of compounds to provide an inhibitor of intermediate filament tetramer formation, wherein the inhibitor inhibits the interaction between an anchoring knob domain in segment 1B of a first intermediate filament dimer and a hydrophobic pocket domain in segment 1B of a second intermediate filament dimer, the method comprising:

(a) mixing a first intermediate filament dimer with at least one compound from the library to form a mixture;

(b) adding a second intermediate filament dimer to the mixture;

(c) measuring intermediate filament formation;

(d) comparing the tetramer formation to a comparator control; and (e) selecting the at least one compound from the library when the tetramer formation is altered at a statistically significant amount when compared with the tetramer formation of the comparator control.

* * * * *

SEQUENCE LISTING

```
<160> NUMBER OF SEQ ID NOS: 237

<210> SEQ ID NO 1
<211> LENGTH: 644
<212> TYPE: PRT
<213> ORGANISM: Artificial Sequence
<220> FEATURE:
<223> OTHER INFORMATION: K1

<400> SEQUENCE: 1

Met Ser Arg Gln Phe Ser Ser Arg Ser Gly Tyr Arg Ser Gly Gly Gly
1               5                   10                  15

Phe Ser Ser Gly Ser Ala Gly Ile Ile Asn Tyr Gln Arg Arg Thr Thr
            20                  25                  30

Ser Ser Ser Thr Arg Arg Ser Gly Gly Gly Gly Gly Arg Phe Ser Ser
        35                  40                  45

Cys Gly Gly Gly Gly Ser Phe Gly Ala Gly Gly Gly Phe Gly Ser
    50                  55                  60

Arg Ser Leu Val Asn Leu Gly Gly Ser Lys Ser Ile Ser Ile Ser Val
65                  70                  75                  80

Ala Arg Gly Gly Gly Arg Gly Ser Gly Phe Gly Gly Gly Tyr Gly Gly
                85                  90                  95

Gly Gly Phe Gly Gly Gly Gly Phe Gly Gly Gly Gly Phe Gly Gly Gly
            100                 105                 110

Gly Ile Gly Gly Gly Gly Phe Gly Gly Phe Gly Ser Gly Gly Gly Gly
            115                 120                 125
```

-continued

```
Phe Gly Gly Gly Gly Phe Gly Gly Gly Tyr Gly Gly Gly Tyr Gly
    130                 135                 140

Pro Val Cys Pro Pro Gly Gly Ile Gln Glu Val Thr Ile Asn Gln Ser
145                 150                 155                 160

Leu Leu Gln Pro Leu Asn Val Glu Ile Asp Pro Glu Ile Gln Lys Val
                165                 170                 175

Lys Ser Arg Glu Arg Glu Gln Ile Lys Ser Leu Asn Asn Gln Phe Ala
            180                 185                 190

Ser Phe Ile Asp Lys Val Arg Phe Leu Glu Gln Gln Asn Gln Val Leu
            195                 200                 205

Gln Thr Lys Trp Glu Leu Leu Gln Gln Val Asp Thr Ser Thr Arg Thr
    210                 215                 220

His Asn Leu Glu Pro Tyr Phe Glu Ser Phe Ile Asn Asn Leu Arg Arg
225                 230                 235                 240

Arg Val Asp Gln Leu Lys Ser Asp Gln Ser Arg Leu Asp Ser Glu Leu
                245                 250                 255

Lys Asn Met Gln Asp Met Val Glu Asp Tyr Arg Asn Lys Tyr Glu Asp
            260                 265                 270

Glu Ile Asn Lys Arg Thr Asn Ala Glu Asn Glu Phe Val Thr Ile Lys
        275                 280                 285

Lys Asp Val Asp Gly Ala Tyr Met Thr Lys Val Asp Leu Gln Ala Lys
    290                 295                 300

Leu Asp Asn Leu Gln Gln Glu Ile Asp Phe Leu Thr Ala Leu Tyr Gln
305                 310                 315                 320

Ala Glu Leu Ser Gln Met Gln Thr Gln Ile Ser Glu Thr Asn Val Ile
                325                 330                 335

Leu Ser Met Asp Asn Asn Arg Ser Leu Asp Leu Asp Ser Ile Ile Ala
            340                 345                 350

Glu Val Lys Ala Gln Asn Glu Asp Ile Ala Gln Lys Ser Lys Ala Glu
        355                 360                 365

Ala Glu Ser Leu Tyr Gln Ser Lys Tyr Glu Glu Leu Gln Ile Thr Ala
    370                 375                 380

Gly Arg His Gly Asp Ser Val Arg Asn Ser Lys Ile Glu Ile Ser Glu
385                 390                 395                 400

Leu Asn Arg Val Ile Gln Arg Leu Arg Ser Glu Ile Asp Asn Val Lys
                405                 410                 415

Lys Gln Ile Ser Asn Leu Gln Gln Ser Ile Ser Asp Ala Glu Gln Arg
            420                 425                 430

Gly Glu Asn Ala Leu Lys Asp Ala Lys Asn Lys Leu Asn Asp Leu Glu
            435                 440                 445

Asp Ala Leu Gln Gln Ala Lys Glu Asp Leu Ala Arg Leu Leu Arg Asp
    450                 455                 460

Tyr Gln Glu Leu Met Asn Thr Lys Leu Ala Leu Asp Leu Glu Ile Ala
465                 470                 475                 480

Thr Tyr Arg Thr Leu Leu Glu Gly Glu Glu Ser Arg Met Ser Gly Glu
                485                 490                 495

Cys Ala Pro Asn Val Ser Val Ser Val Ser Thr Ser His Thr Thr Ile
            500                 505                 510

Ser Gly Gly Gly Ser Arg Gly Gly Gly Gly Gly Tyr Gly Ser Gly
            515                 520                 525

Gly Ser Ser Tyr Gly Ser Gly Gly Gly Ser Tyr Gly Ser Gly Gly Gly
    530                 535                 540

Gly Gly Gly Gly Arg Gly Ser Tyr Gly Ser Gly Gly Ser Ser Tyr Gly
```

```
545              550              555              560

Ser Gly Gly Gly Ser Tyr Gly Ser Gly Gly Gly Gly Gly His Gly
                565              570              575

Ser Tyr Gly Ser Gly Ser Ser Ser Gly Gly Tyr Arg Gly Gly Ser Gly
        580              585              590

Gly Gly Gly Gly Gly Ser Ser Gly Gly Arg Gly Ser Gly Gly Gly Ser
        595              600              605

Ser Gly Gly Ser Ile Gly Gly Arg Gly Ser Ser Ser Gly Gly Val Lys
    610              615              620

Ser Ser Gly Gly Ser Ser Ser Val Arg Phe Val Ser Thr Thr Tyr Ser
625              630              635              640

Gly Val Thr Arg

<210> SEQ ID NO 2
<211> LENGTH: 584
<212> TYPE: PRT
<213> ORGANISM: Artificial Sequence
<220> FEATURE:
<223> OTHER INFORMATION: K10

<400> SEQUENCE: 2

Met Ser Val Arg Tyr Ser Ser Ser Lys His Tyr Ser Ser Ser Arg Ser
1               5               10              15

Gly Gly Gly Gly Gly Gly Gly Gly Cys Gly Gly Gly Gly Gly Val Ser
                20              25              30

Ser Leu Arg Ile Ser Ser Ser Lys Gly Ser Leu Gly Gly Gly Phe Ser
        35              40              45

Ser Gly Gly Phe Ser Gly Gly Ser Phe Ser Arg Gly Ser Ser Gly Gly
    50              55              60

Gly Cys Phe Gly Gly Ser Gly Gly Tyr Gly Gly Leu Gly Gly Phe
65              70              75              80

Gly Gly Gly Ser Phe Arg Gly Ser Tyr Gly Ser Ser Ser Phe Gly Gly
                85              90              95

Ser Tyr Gly Gly Ile Phe Gly Gly Gly Ser Phe Gly Gly Gly Ser Phe
        100             105             110

Gly Gly Gly Ser Phe Gly Gly Gly Gly Phe Gly Gly Gly Gly Phe Gly
        115             120             125

Gly Gly Phe Gly Gly Gly Phe Gly Gly Asp Gly Gly Leu Leu Ser Gly
        130             135             140

Asn Glu Lys Val Thr Met Gln Asn Leu Asn Asp Arg Leu Ala Ser Tyr
145             150             155             160

Leu Asp Lys Val Arg Ala Leu Glu Glu Ser Asn Tyr Glu Leu Glu Gly
                165             170             175

Lys Ile Lys Glu Trp Tyr Glu Lys His Gly Asn Ser His Gln Gly Glu
                180             185             190

Pro Arg Asp Tyr Ser Lys Tyr Tyr Lys Thr Ile Asp Asp Leu Lys Asn
        195             200             205

Gln Ile Leu Asn Leu Thr Thr Asp Asn Ala Asn Ile Leu Leu Gln Ile
        210             215             220

Asp Asn Ala Arg Leu Ala Ala Asp Asp Phe Arg Leu Lys Tyr Glu Asn
225             230             235             240

Glu Val Ala Leu Arg Gln Ser Val Glu Ala Asp Ile Asn Gly Leu Arg
                245             250             255

Arg Val Leu Asp Glu Leu Thr Leu Thr Lys Ala Asp Leu Glu Met Gln
        260             265             270
```

-continued

```
Ile Glu Ser Leu Thr Glu Glu Leu Ala Tyr Leu Lys Lys Asn His Glu
        275                 280                 285

Glu Glu Met Lys Asp Leu Arg Asn Val Ser Thr Gly Asp Val Asn Val
        290                 295                 300

Glu Met Asn Ala Ala Pro Gly Val Asp Leu Thr Gln Leu Leu Asn Asn
305                 310                 315                 320

Met Arg Ser Gln Tyr Glu Gln Leu Ala Glu Gln Asn Arg Lys Asp Ala
                325                 330                 335

Glu Ala Trp Phe Asn Glu Lys Ser Lys Glu Leu Thr Thr Glu Ile Asp
                340                 345                 350

Asn Asn Ile Glu Gln Ile Ser Ser Tyr Lys Ser Glu Ile Thr Glu Leu
        355                 360                 365

Arg Arg Asn Val Gln Ala Leu Glu Ile Glu Leu Gln Ser Gln Leu Ala
        370                 375                 380

Leu Lys Gln Ser Leu Glu Ala Ser Leu Ala Glu Thr Glu Gly Arg Tyr
385                 390                 395                 400

Cys Val Gln Leu Ser Gln Ile Gln Ala Gln Ile Ser Ala Leu Glu Glu
                405                 410                 415

Gln Leu Gln Gln Ile Arg Ala Glu Thr Glu Cys Gln Asn Thr Glu Tyr
        420                 425                 430

Gln Gln Leu Leu Asp Ile Lys Ile Arg Leu Glu Asn Glu Ile Gln Thr
        435                 440                 445

Tyr Arg Ser Leu Leu Glu Gly Glu Gly Ser Ser Gly Gly Gly Gly Arg
        450                 455                 460

Gly Gly Gly Ser Phe Gly Gly Tyr Gly Gly Ser Ser Gly Gly
465                 470                 475                 480

Gly Ser Ser Gly Gly Gly His Gly Gly Gly His Gly Gly Ser Ser Gly
                485                 490                 495

Gly Gly Tyr Gly Gly Gly Ser Ser Gly Gly Gly Ser Ser Gly Gly Gly
                500                 505                 510

Tyr Gly Gly Gly Ser Ser Ser Gly Gly His Gly Gly Ser Ser Ser Gly
        515                 520                 525

Gly Tyr Gly Gly Gly Ser Ser Gly Gly Gly Gly Gly Tyr Gly Gly
        530                 535                 540

Gly Ser Ser Gly Gly Gly Ser Ser Ser Gly Gly Gly Tyr Gly Gly Gly
545                 550                 555                 560

Ser Ser Ser Gly Gly His Lys Ser Ser Ser Ser Gly Ser Val Gly Glu
                565                 570                 575

Ser Ser Ser Lys Gly Pro Arg Tyr
            580
```

```
<210> SEQ ID NO 3
<211> LENGTH: 33
<212> TYPE: PRT
<213> ORGANISM: Artificial Sequence
<220> FEATURE:
<223> OTHER INFORMATION: chemically synthesized

<400> SEQUENCE: 3

Val Asp Leu Gln Ala Lys Leu Asp Asn Leu Gln Gln Glu Ile Asp Phe
1               5                   10                  15

Leu Thr Ala Leu Tyr Gln Ala Glu Leu Ser Gln Met Gln Thr Gln Ile
                20                  25                  30

Ser
```

<210> SEQ ID NO 4
<211> LENGTH: 5
<212> TYPE: PRT
<213> ORGANISM: Artificial Sequence
<220> FEATURE:
<223> OTHER INFORMATION: chemically synthesized

<400> SEQUENCE: 4

Phe Leu Thr Ala Leu
1               5

<210> SEQ ID NO 5
<211> LENGTH: 6
<212> TYPE: PRT
<213> ORGANISM: Artificial Sequence
<220> FEATURE:
<223> OTHER INFORMATION: chemically synthesized

<400> SEQUENCE: 5

Phe Leu Thr Ala Leu Tyr
1               5

<210> SEQ ID NO 6
<211> LENGTH: 6
<212> TYPE: PRT
<213> ORGANISM: Artificial Sequence
<220> FEATURE:
<223> OTHER INFORMATION: chemically synthesized

<400> SEQUENCE: 6

Asp Phe Leu Thr Ala Leu
1               5

<210> SEQ ID NO 7
<211> LENGTH: 7
<212> TYPE: PRT
<213> ORGANISM: Artificial Sequence
<220> FEATURE:
<223> OTHER INFORMATION: chemically synthesized

<400> SEQUENCE: 7

Asp Phe Leu Thr Ala Leu Tyr
1               5

<210> SEQ ID NO 8
<211> LENGTH: 7
<212> TYPE: PRT
<213> ORGANISM: Artificial Sequence
<220> FEATURE:
<223> OTHER INFORMATION: chemically synthesized

<400> SEQUENCE: 8

Ile Asp Phe Leu Thr Ala Leu
1               5

<210> SEQ ID NO 9
<211> LENGTH: 8
<212> TYPE: PRT
<213> ORGANISM: Artificial Sequence
<220> FEATURE:
<223> OTHER INFORMATION: chemically synthesized

<400> SEQUENCE: 9

Ile Asp Phe Leu Thr Ala Leu Tyr
1               5

-continued

```
<210> SEQ ID NO 10
<211> LENGTH: 8
<212> TYPE: PRT
<213> ORGANISM: Artificial Sequence
<220> FEATURE:
<223> OTHER INFORMATION: chemically synthesized

<400> SEQUENCE: 10

Glu Ile Asp Phe Leu Thr Ala Leu
1               5

<210> SEQ ID NO 11
<211> LENGTH: 9
<212> TYPE: PRT
<213> ORGANISM: Artificial Sequence
<220> FEATURE:
<223> OTHER INFORMATION: chemically synthesized

<400> SEQUENCE: 11

Glu Ile Asp Phe Leu Thr Ala Leu Tyr
1               5

<210> SEQ ID NO 12
<211> LENGTH: 10
<212> TYPE: PRT
<213> ORGANISM: Artificial Sequence
<220> FEATURE:
<223> OTHER INFORMATION: chemically synthesized

<400> SEQUENCE: 12

Glu Ile Asp Phe Leu Thr Ala Leu Tyr Gln
1               5                   10

<210> SEQ ID NO 13
<211> LENGTH: 11
<212> TYPE: PRT
<213> ORGANISM: Artificial Sequence
<220> FEATURE:
<223> OTHER INFORMATION: chemically synthesized

<400> SEQUENCE: 13

Glu Ile Asp Phe Leu Thr Ala Leu Tyr Gln Ala
1               5                   10

<210> SEQ ID NO 14
<211> LENGTH: 12
<212> TYPE: PRT
<213> ORGANISM: Artificial Sequence
<220> FEATURE:
<223> OTHER INFORMATION: chemically synthesized

<400> SEQUENCE: 14

Glu Ile Asp Phe Leu Thr Ala Leu Tyr Gln Ala Glu
1               5                   10

<210> SEQ ID NO 15
<211> LENGTH: 13
<212> TYPE: PRT
<213> ORGANISM: Artificial Sequence
<220> FEATURE:
<223> OTHER INFORMATION: chemically synthesized

<400> SEQUENCE: 15

Glu Ile Asp Phe Leu Thr Ala Leu Tyr Gln Ala Glu Leu
1               5                   10

<210> SEQ ID NO 16
```

```
<211> LENGTH: 14
<212> TYPE: PRT
<213> ORGANISM: Artificial Sequence
<220> FEATURE:
<223> OTHER INFORMATION: chemically synthesized

<400> SEQUENCE: 16

Glu Ile Asp Phe Leu Thr Ala Leu Tyr Gln Ala Glu Leu Ser
1               5                   10

<210> SEQ ID NO 17
<211> LENGTH: 15
<212> TYPE: PRT
<213> ORGANISM: Artificial Sequence
<220> FEATURE:
<223> OTHER INFORMATION: chemically synthesized

<400> SEQUENCE: 17

Glu Ile Asp Phe Leu Thr Ala Leu Tyr Gln Ala Glu Leu Ser Gln
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: chemically synthesized

<400> SEQUENCE: 18

Glu Ile Asp Phe Leu Thr Ala Leu Tyr Gln Ala Glu Leu Ser Gln Met
1               5                   10                  15

<210> SEQ ID NO 19
<211> LENGTH: 17
<212> TYPE: PRT
<213> ORGANISM: Artificial Sequence
<220> FEATURE:
<223> OTHER INFORMATION: chemically synthesized

<400> SEQUENCE: 19

Glu Ile Asp Phe Leu Thr Ala Leu Tyr Gln Ala Glu Leu Ser Gln Met
1               5                   10                  15

Gln

<210> SEQ ID NO 20
<211> LENGTH: 18
<212> TYPE: PRT
<213> ORGANISM: Artificial Sequence
<220> FEATURE:
<223> OTHER INFORMATION: chemically synthesized

<400> SEQUENCE: 20

Glu Ile Asp Phe Leu Thr Ala Leu Tyr Gln Ala Glu Leu Ser Gln Met
1               5                   10                  15

Gln Thr

<210> SEQ ID NO 21
<211> LENGTH: 19
<212> TYPE: PRT
<213> ORGANISM: Artificial Sequence
<220> FEATURE:
<223> OTHER INFORMATION: chemically synthesized

<400> SEQUENCE: 21

Glu Ile Asp Phe Leu Thr Ala Leu Tyr Gln Ala Glu Leu Ser Gln Met
1               5                   10                  15
```

Gln Thr Gln

<210> SEQ ID NO 22
<211> LENGTH: 20
<212> TYPE: PRT
<213> ORGANISM: Artificial Sequence
<220> FEATURE:
<223> OTHER INFORMATION: chemically synthesized

<400> SEQUENCE: 22

Glu Ile Asp Phe Leu Thr Ala Leu Tyr Gln Ala Glu Leu Ser Gln Met
1               5                   10                  15

Gln Thr Gln Ile
            20

<210> SEQ ID NO 23
<211> LENGTH: 21
<212> TYPE: PRT
<213> ORGANISM: Artificial Sequence
<220> FEATURE:
<223> OTHER INFORMATION: chemically synthesized

<400> SEQUENCE: 23

Glu Ile Asp Phe Leu Thr Ala Leu Tyr Gln Ala Glu Leu Ser Gln Met
1               5                   10                  15

Gln Thr Gln Ile Ser
            20

<210> SEQ ID NO 24
<211> LENGTH: 22
<212> TYPE: PRT
<213> ORGANISM: Artificial Sequence
<220> FEATURE:
<223> OTHER INFORMATION: chemically synthesized

<400> SEQUENCE: 24

Gln Glu Ile Asp Phe Leu Thr Ala Leu Tyr Gln Ala Glu Leu Ser Gln
1               5                   10                  15

Met Gln Thr Gln Ile Ser
            20

<210> SEQ ID NO 25
<211> LENGTH: 23
<212> TYPE: PRT
<213> ORGANISM: Artificial Sequence
<220> FEATURE:
<223> OTHER INFORMATION: chemically synthesized

<400> SEQUENCE: 25

Gln Gln Glu Ile Asp Phe Leu Thr Ala Leu Tyr Gln Ala Glu Leu Ser
1               5                   10                  15

Gln Met Gln Thr Gln Ile Ser
            20

<210> SEQ ID NO 26
<211> LENGTH: 24
<212> TYPE: PRT
<213> ORGANISM: Artificial Sequence
<220> FEATURE:
<223> OTHER INFORMATION: chemically synthesized

<400> SEQUENCE: 26

Leu Gln Gln Glu Ile Asp Phe Leu Thr Ala Leu Tyr Gln Ala Glu Leu
1               5                   10                  15

```
Ser Gln Met Gln Thr Gln Ile Ser
        20

<210> SEQ ID NO 27
<211> LENGTH: 25
<212> TYPE: PRT
<213> ORGANISM: Artificial Sequence
<220> FEATURE:
<223> OTHER INFORMATION: chemically synthesized

<400> SEQUENCE: 27

Asn Leu Gln Gln Glu Ile Asp Phe Leu Thr Ala Leu Tyr Gln Ala Glu
1               5                   10                  15

Leu Ser Gln Met Gln Thr Gln Ile Ser
            20                  25

<210> SEQ ID NO 28
<211> LENGTH: 26
<212> TYPE: PRT
<213> ORGANISM: Artificial Sequence
<220> FEATURE:
<223> OTHER INFORMATION: chemically synthesized

<400> SEQUENCE: 28

Asp Asn Leu Gln Gln Glu Ile Asp Phe Leu Thr Ala Leu Tyr Gln Ala
1               5                   10                  15

Glu Leu Ser Gln Met Gln Thr Gln Ile Ser
            20                  25

<210> SEQ ID NO 29
<211> LENGTH: 27
<212> TYPE: PRT
<213> ORGANISM: Artificial Sequence
<220> FEATURE:
<223> OTHER INFORMATION: chemically synthesized

<400> SEQUENCE: 29

Leu Asp Asn Leu Gln Gln Glu Ile Asp Phe Leu Thr Ala Leu Tyr Gln
1               5                   10                  15

Ala Glu Leu Ser Gln Met Gln Thr Gln Ile Ser
            20                  25

<210> SEQ ID NO 30
<211> LENGTH: 28
<212> TYPE: PRT
<213> ORGANISM: Artificial Sequence
<220> FEATURE:
<223> OTHER INFORMATION: chemically synthesized

<400> SEQUENCE: 30

Lys Leu Asp Asn Leu Gln Gln Glu Ile Asp Phe Leu Thr Ala Leu Tyr
1               5                   10                  15

Gln Ala Glu Leu Ser Gln Met Gln Thr Gln Ile Ser
            20                  25

<210> SEQ ID NO 31
<211> LENGTH: 29
<212> TYPE: PRT
<213> ORGANISM: Artificial Sequence
<220> FEATURE:
<223> OTHER INFORMATION: chemically synthesized

<400> SEQUENCE: 31

Ala Lys Leu Asp Asn Leu Gln Gln Glu Ile Asp Phe Leu Thr Ala Leu
```

-continued

```
1               5               10              15

Tyr Gln Ala Glu Leu Ser Gln Met Gln Thr Gln Ile Ser
            20              25
```

<210> SEQ ID NO 32
<211> LENGTH: 30
<212> TYPE: PRT
<213> ORGANISM: Artificial Sequence
<220> FEATURE:
<223> OTHER INFORMATION: chemically synthesized

<400> SEQUENCE: 32

```
Gln Ala Lys Leu Asp Asn Leu Gln Gln Glu Ile Asp Phe Leu Thr Ala
1               5               10              15

Leu Tyr Gln Ala Glu Leu Ser Gln Met Gln Thr Gln Ile Ser
            20              25              30
```

<210> SEQ ID NO 33
<211> LENGTH: 31
<212> TYPE: PRT
<213> ORGANISM: Artificial Sequence
<220> FEATURE:
<223> OTHER INFORMATION: chemically synthesized

<400> SEQUENCE: 33

```
Leu Gln Ala Lys Leu Asp Asn Leu Gln Gln Glu Ile Asp Phe Leu Thr
1               5               10              15

Ala Leu Tyr Gln Ala Glu Leu Ser Gln Met Gln Thr Gln Ile Ser
            20              25              30
```

<210> SEQ ID NO 34
<211> LENGTH: 32
<212> TYPE: PRT
<213> ORGANISM: Artificial Sequence
<220> FEATURE:
<223> OTHER INFORMATION: chemically synthesized

<400> SEQUENCE: 34

```
Asp Leu Gln Ala Lys Leu Asp Asn Leu Gln Gln Glu Ile Asp Phe Leu
1               5               10              15

Thr Ala Leu Tyr Gln Ala Glu Leu Ser Gln Met Gln Thr Gln Ile Ser
            20              25              30
```

<210> SEQ ID NO 35
<211> LENGTH: 466
<212> TYPE: PRT
<213> ORGANISM: Artificial Sequence
<220> FEATURE:
<223> OTHER INFORMATION: vimentin

<400> SEQUENCE: 35

```
Met Ser Thr Arg Ser Val Ser Ser Ser Tyr Arg Arg Met Phe Gly
1               5               10              15

Gly Pro Gly Thr Ala Ser Arg Pro Ser Ser Ser Arg Ser Tyr Val Thr
            20              25              30

Thr Ser Thr Arg Thr Tyr Ser Leu Gly Ser Ala Leu Arg Pro Ser Thr
        35              40              45

Ser Arg Ser Leu Tyr Ala Ser Ser Pro Gly Gly Val Tyr Ala Thr Arg
    50              55              60

Ser Ser Ala Val Arg Leu Arg Ser Ser Val Pro Gly Val Arg Leu Leu
65              70              75              80

Gln Asp Ser Val Asp Phe Ser Leu Ala Asp Ala Ile Asn Thr Glu Phe
```

-continued

```
                    85              90              95

Lys Asn Thr Arg Thr Asn Glu Lys Val Glu Leu Gln Glu Leu Asn Asp
            100             105             110

Arg Phe Ala Asn Tyr Ile Asp Lys Val Arg Phe Leu Glu Gln Gln Asn
            115             120             125

Lys Ile Leu Leu Ala Glu Leu Glu Gln Leu Lys Gly Gln Gly Lys Ser
            130             135             140

Arg Leu Gly Asp Leu Tyr Glu Glu Glu Met Arg Glu Leu Arg Arg Gln
145             150             155             160

Val Asp Gln Leu Thr Asn Asp Lys Ala Arg Val Glu Val Glu Arg Asp
                165             170             175

Asn Leu Ala Glu Asp Ile Met Arg Leu Arg Glu Lys Leu Gln Glu Glu
            180             185             190

Met Leu Gln Arg Glu Glu Ala Glu Asn Thr Leu Gln Ser Phe Arg Gln
            195             200             205

Asp Val Asp Asn Ala Ser Leu Ala Arg Leu Asp Leu Glu Arg Lys Val
    210             215             220

Glu Ser Leu Gln Glu Glu Ile Ala Phe Leu Lys Lys Leu His Glu Glu
225             230             235             240

Glu Ile Gln Glu Leu Gln Ala Gln Ile Gln Glu Gln His Val Gln Ile
            245             250             255

Asp Val Asp Val Ser Lys Pro Asp Leu Thr Ala Ala Leu Arg Asp Val
            260             265             270

Arg Gln Gln Tyr Glu Ser Val Ala Ala Lys Asn Leu Gln Glu Ala Glu
            275             280             285

Glu Trp Tyr Lys Ser Lys Phe Ala Asp Leu Ser Glu Ala Ala Asn Arg
    290             295             300

Asn Asn Asp Ala Leu Arg Gln Ala Lys Gln Glu Ser Thr Glu Tyr Arg
305             310             315             320

Arg Gln Val Gln Ser Leu Thr Cys Glu Val Asp Ala Leu Lys Gly Thr
            325             330             335

Asn Glu Ser Leu Glu Arg Gln Met Arg Glu Met Glu Glu Asn Phe Ala
            340             345             350

Val Glu Ala Ala Asn Tyr Gln Asp Thr Ile Gly Arg Leu Gln Asp Glu
            355             360             365

Ile Gln Asn Met Lys Glu Glu Met Ala Arg His Leu Arg Glu Tyr Gln
    370             375             380

Asp Leu Leu Asn Val Lys Met Ala Leu Asp Ile Glu Ile Ala Thr Tyr
385             390             395             400

Arg Lys Leu Leu Glu Gly Glu Glu Ser Arg Ile Ser Leu Pro Leu Pro
            405             410             415

Asn Phe Ser Ser Leu Asn Leu Arg Glu Thr Asn Leu Asp Ser Leu Pro
            420             425             430

Leu Val Asp Thr His Ser Lys Arg Thr Leu Leu Ile Lys Thr Val Glu
            435             440             445

Thr Arg Asp Gly Gln Val Ile Asn Glu Thr Ser Gln His His Asp Asp
    450             455             460

Leu Glu
465

<210> SEQ ID NO 36
<211> LENGTH: 33
<212> TYPE: PRT
<213> ORGANISM: Artificial Sequence
```

-continued

```
<220> FEATURE:
<223> OTHER INFORMATION: chemically synthesized

<400> SEQUENCE: 36

Leu Asp Leu Glu Arg Lys Val Glu Ser Leu Gln Glu Glu Ile Ala Phe
1               5                   10                  15

Leu Lys Lys Leu His Glu Glu Glu Ile Gln Glu Leu Gln Ala Gln Ile
            20                  25                  30

Gln

<210> SEQ ID NO 37
<211> LENGTH: 5
<212> TYPE: PRT
<213> ORGANISM: Artificial Sequence
<220> FEATURE:
<223> OTHER INFORMATION: chemically synthesized

<400> SEQUENCE: 37

Phe Leu Lys Lys Leu
1               5

<210> SEQ ID NO 38
<211> LENGTH: 6
<212> TYPE: PRT
<213> ORGANISM: Artificial Sequence
<220> FEATURE:
<223> OTHER INFORMATION: chemically synthesized

<400> SEQUENCE: 38

Phe Leu Lys Lys Leu His
1               5

<210> SEQ ID NO 39
<211> LENGTH: 6
<212> TYPE: PRT
<213> ORGANISM: Artificial Sequence
<220> FEATURE:
<223> OTHER INFORMATION: chemically synthesized

<400> SEQUENCE: 39

Ala Phe Leu Lys Lys Leu
1               5

<210> SEQ ID NO 40
<211> LENGTH: 7
<212> TYPE: PRT
<213> ORGANISM: Artificial Sequence
<220> FEATURE:
<223> OTHER INFORMATION: chemically synthesized

<400> SEQUENCE: 40

Ala Phe Leu Lys Lys Leu His
1               5

<210> SEQ ID NO 41
<211> LENGTH: 7
<212> TYPE: PRT
<213> ORGANISM: Artificial Sequence
<220> FEATURE:
<223> OTHER INFORMATION: chemically synthesized

<400> SEQUENCE: 41

Ile Ala Phe Leu Lys Lys Leu
1               5
```

-continued

```
<210> SEQ ID NO 42
<211> LENGTH: 8
<212> TYPE: PRT
<213> ORGANISM: Artificial Sequence
<220> FEATURE:
<223> OTHER INFORMATION: chemically synthesized

<400> SEQUENCE: 42

Ile Ala Phe Leu Lys Lys Leu His
1               5

<210> SEQ ID NO 43
<211> LENGTH: 8
<212> TYPE: PRT
<213> ORGANISM: Artificial Sequence
<220> FEATURE:
<223> OTHER INFORMATION: chemically synthesized

<400> SEQUENCE: 43

Glu Ile Ala Phe Leu Lys Lys Leu
1               5

<210> SEQ ID NO 44
<211> LENGTH: 9
<212> TYPE: PRT
<213> ORGANISM: Artificial Sequence
<220> FEATURE:
<223> OTHER INFORMATION: chemically synthesized

<400> SEQUENCE: 44

Glu Ile Ala Phe Leu Lys Lys Leu His
1               5

<210> SEQ ID NO 45
<211> LENGTH: 10
<212> TYPE: PRT
<213> ORGANISM: Artificial Sequence
<220> FEATURE:
<223> OTHER INFORMATION: chemically synthesized

<400> SEQUENCE: 45

Glu Ile Ala Phe Leu Lys Lys Leu His Glu
1               5                   10

<210> SEQ ID NO 46
<211> LENGTH: 11
<212> TYPE: PRT
<213> ORGANISM: Artificial Sequence
<220> FEATURE:
<223> OTHER INFORMATION: chemically synthesized

<400> SEQUENCE: 46

Glu Ile Ala Phe Leu Lys Lys Leu His Glu Glu
1               5                   10

<210> SEQ ID NO 47
<211> LENGTH: 12
<212> TYPE: PRT
<213> ORGANISM: Artificial Sequence
<220> FEATURE:
<223> OTHER INFORMATION: chemically synthesized

<400> SEQUENCE: 47

Glu Ile Ala Phe Leu Lys Lys Leu His Glu Glu Glu
1               5                   10

<210> SEQ ID NO 48
```

```
<211> LENGTH: 13
<212> TYPE: PRT
<213> ORGANISM: Artificial Sequence
<220> FEATURE:
<223> OTHER INFORMATION: chemically synthesized

<400> SEQUENCE: 48

Glu Ile Ala Phe Leu Lys Lys Leu His Glu Glu Glu Ile
1               5                   10

<210> SEQ ID NO 49
<211> LENGTH: 14
<212> TYPE: PRT
<213> ORGANISM: Artificial Sequence
<220> FEATURE:
<223> OTHER INFORMATION: chemically synthesized

<400> SEQUENCE: 49

Glu Ile Ala Phe Leu Lys Lys Leu His Glu Glu Glu Ile Gln
1               5                   10

<210> SEQ ID NO 50
<211> LENGTH: 15
<212> TYPE: PRT
<213> ORGANISM: Artificial Sequence
<220> FEATURE:
<223> OTHER INFORMATION: chemically synthesized

<400> SEQUENCE: 50

Glu Ile Ala Phe Leu Lys Lys Leu His Glu Glu Glu Ile Gln Glu
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: chemically synthesized

<400> SEQUENCE: 51

Glu Ile Ala Phe Leu Lys Lys Leu His Glu Glu Glu Ile Gln Glu Leu
1               5                   10                  15

<210> SEQ ID NO 52
<211> LENGTH: 17
<212> TYPE: PRT
<213> ORGANISM: Artificial Sequence
<220> FEATURE:
<223> OTHER INFORMATION: chemically synthesized

<400> SEQUENCE: 52

Glu Ile Ala Phe Leu Lys Lys Leu His Glu Glu Glu Ile Gln Glu Leu
1               5                   10                  15

Gln

<210> SEQ ID NO 53
<211> LENGTH: 18
<212> TYPE: PRT
<213> ORGANISM: Artificial Sequence
<220> FEATURE:
<223> OTHER INFORMATION: chemically synthesized

<400> SEQUENCE: 53

Glu Ile Ala Phe Leu Lys Lys Leu His Glu Glu Glu Ile Gln Glu Leu
1               5                   10                  15

Gln Ala
```

-continued

```
<210> SEQ ID NO 54
<211> LENGTH: 19
<212> TYPE: PRT
<213> ORGANISM: Artificial Sequence
<220> FEATURE:
<223> OTHER INFORMATION: chemically synthesized

<400> SEQUENCE: 54

Glu Ile Ala Phe Leu Lys Lys Leu His Glu Glu Glu Ile Gln Glu Leu
1               5                   10                  15

Gln Ala Gln

<210> SEQ ID NO 55
<211> LENGTH: 20
<212> TYPE: PRT
<213> ORGANISM: Artificial Sequence
<220> FEATURE:
<223> OTHER INFORMATION: chemically synthesized

<400> SEQUENCE: 55

Glu Ile Ala Phe Leu Lys Lys Leu His Glu Glu Glu Ile Gln Glu Leu
1               5                   10                  15

Gln Ala Gln Ile
            20

<210> SEQ ID NO 56
<211> LENGTH: 21
<212> TYPE: PRT
<213> ORGANISM: Artificial Sequence
<220> FEATURE:
<223> OTHER INFORMATION: chemically synthesized

<400> SEQUENCE: 56

Glu Ile Ala Phe Leu Lys Lys Leu His Glu Glu Glu Ile Gln Glu Leu
1               5                   10                  15

Gln Ala Gln Ile Gln
            20

<210> SEQ ID NO 57
<211> LENGTH: 22
<212> TYPE: PRT
<213> ORGANISM: Artificial Sequence
<220> FEATURE:
<223> OTHER INFORMATION: chemically synthesized

<400> SEQUENCE: 57

Glu Glu Ile Ala Phe Leu Lys Lys Leu His Glu Glu Glu Ile Gln Glu
1               5                   10                  15

Leu Gln Ala Gln Ile Gln
            20

<210> SEQ ID NO 58
<211> LENGTH: 23
<212> TYPE: PRT
<213> ORGANISM: Artificial Sequence
<220> FEATURE:
<223> OTHER INFORMATION: chemically synthesized

<400> SEQUENCE: 58

Gln Glu Glu Ile Ala Phe Leu Lys Lys Leu His Glu Glu Glu Ile Gln
1               5                   10                  15

Glu Leu Gln Ala Gln Ile Gln
            20
```

<210> SEQ ID NO 59
<211> LENGTH: 24
<212> TYPE: PRT
<213> ORGANISM: Artificial Sequence
<220> FEATURE:
<223> OTHER INFORMATION: chemically synthesized

<400> SEQUENCE: 59

Leu Gln Glu Glu Ile Ala Phe Leu Lys Lys Leu His Glu Glu Glu Ile
1               5                   10                  15

Gln Glu Leu Gln Ala Gln Ile Gln
            20

<210> SEQ ID NO 60
<211> LENGTH: 25
<212> TYPE: PRT
<213> ORGANISM: Artificial Sequence
<220> FEATURE:
<223> OTHER INFORMATION: chemically synthesized

<400> SEQUENCE: 60

Ser Leu Gln Glu Glu Ile Ala Phe Leu Lys Lys Leu His Glu Glu Glu
1               5                   10                  15

Ile Gln Glu Leu Gln Ala Gln Ile Gln
            20                  25

<210> SEQ ID NO 61
<211> LENGTH: 26
<212> TYPE: PRT
<213> ORGANISM: Artificial Sequence
<220> FEATURE:
<223> OTHER INFORMATION: chemically synthesized

<400> SEQUENCE: 61

Glu Ser Leu Gln Glu Glu Ile Ala Phe Leu Lys Lys Leu His Glu Glu
1               5                   10                  15

Glu Ile Gln Glu Leu Gln Ala Gln Ile Gln
            20                  25

<210> SEQ ID NO 62
<211> LENGTH: 27
<212> TYPE: PRT
<213> ORGANISM: Artificial Sequence
<220> FEATURE:
<223> OTHER INFORMATION: chemically synthesized

<400> SEQUENCE: 62

Val Glu Ser Leu Gln Glu Glu Ile Ala Phe Leu Lys Lys Leu His Glu
1               5                   10                  15

Glu Glu Ile Gln Glu Leu Gln Ala Gln Ile Gln
            20                  25

<210> SEQ ID NO 63
<211> LENGTH: 28
<212> TYPE: PRT
<213> ORGANISM: Artificial Sequence
<220> FEATURE:
<223> OTHER INFORMATION: chemically synthesized

<400> SEQUENCE: 63

Lys Val Glu Ser Leu Gln Glu Glu Ile Ala Phe Leu Lys Lys Leu His
1               5                   10                  15

Glu Glu Glu Ile Gln Glu Leu Gln Ala Gln Ile Gln

```
                20              25

<210> SEQ ID NO 64
<211> LENGTH: 29
<212> TYPE: PRT
<213> ORGANISM: Artificial Sequence
<220> FEATURE:
<223> OTHER INFORMATION: chemically synthesized

<400> SEQUENCE: 64

Arg Lys Val Glu Ser Leu Gln Glu Glu Ile Ala Phe Leu Lys Lys Leu
1               5                   10                  15

His Glu Glu Glu Ile Gln Glu Leu Gln Ala Gln Ile Gln
                20                  25

<210> SEQ ID NO 65
<211> LENGTH: 30
<212> TYPE: PRT
<213> ORGANISM: Artificial Sequence
<220> FEATURE:
<223> OTHER INFORMATION: chemically synthesized

<400> SEQUENCE: 65

Glu Arg Lys Val Glu Ser Leu Gln Glu Glu Ile Ala Phe Leu Lys Lys
1               5                   10                  15

Leu His Glu Glu Glu Ile Gln Glu Leu Gln Ala Gln Ile Gln
                20                  25                  30

<210> SEQ ID NO 66
<211> LENGTH: 31
<212> TYPE: PRT
<213> ORGANISM: Artificial Sequence
<220> FEATURE:
<223> OTHER INFORMATION: chemically synthesized

<400> SEQUENCE: 66

Leu Glu Arg Lys Val Glu Ser Leu Gln Glu Glu Ile Ala Phe Leu Lys
1               5                   10                  15

Lys Leu His Glu Glu Glu Ile Gln Glu Leu Gln Ala Gln Ile Gln
                20                  25                  30

<210> SEQ ID NO 67
<211> LENGTH: 32
<212> TYPE: PRT
<213> ORGANISM: Artificial Sequence
<220> FEATURE:
<223> OTHER INFORMATION: chemically synthesized

<400> SEQUENCE: 67

Asp Leu Glu Arg Lys Val Glu Ser Leu Gln Glu Glu Ile Ala Phe Leu
1               5                   10                  15

Lys Lys Leu His Glu Glu Glu Ile Gln Glu Leu Gln Ala Gln Ile Gln
                20                  25                  30

<210> SEQ ID NO 68
<211> LENGTH: 31
<212> TYPE: PRT
<213> ORGANISM: Artificial Sequence
<220> FEATURE:
<223> OTHER INFORMATION: chemically synthesized

<400> SEQUENCE: 68

Lys Asn Gln Ile Leu Asn Leu Thr Thr Asp Asn Ala Asn Ile Leu Leu
1               5                   10                  15
```

```
Gln Ile Asp Asn Ala Arg Leu Ala Ala Asp Asp Phe Arg Leu Lys
            20                  25                  30

<210> SEQ ID NO 69
<211> LENGTH: 31
<212> TYPE: PRT
<213> ORGANISM: Artificial Sequence
<220> FEATURE:
<223> OTHER INFORMATION: chemically synthesized

<400> SEQUENCE: 69

Arg Arg Gln Val Asp Gln Leu Thr Asn Asp Lys Ala Arg Val Glu Val
1               5                   10                  15

Glu Arg Asp Asn Leu Ala Glu Asp Ile Met Arg Leu Arg Glu Lys
            20                  25                  30

<210> SEQ ID NO 70
<211> LENGTH: 31
<212> TYPE: PRT
<213> ORGANISM: Artificial Sequence
<220> FEATURE:
<223> OTHER INFORMATION: chemically synthesized

<400> SEQUENCE: 70

Glu Asn Glu Phe Val Thr Ile Lys Lys Asp Val Asp Gly Ala Tyr Met
1               5                   10                  15

Thr Lys Val Asp Leu Gln Ala Lys Leu Asp Asn Leu Gln Gln Glu
            20                  25                  30

<210> SEQ ID NO 71
<211> LENGTH: 31
<212> TYPE: PRT
<213> ORGANISM: Artificial Sequence
<220> FEATURE:
<223> OTHER INFORMATION: Chemically synthesized

<400> SEQUENCE: 71

Glu Asn Thr Leu Gln Ser Phe Arg Gln Asp Val Asp Asn Ala Ser Leu
1               5                   10                  15

Ala Arg Leu Asp Leu Glu Arg Lys Val Glu Ser Leu Gln Glu Glu
            20                  25                  30

<210> SEQ ID NO 72
<211> LENGTH: 8
<212> TYPE: PRT
<213> ORGANISM: Artificial Sequence
<220> FEATURE:
<223> OTHER INFORMATION: chemically synthesized

<400> SEQUENCE: 72

Phe Leu Thr Ala Leu Tyr Gln Ala
1               5

<210> SEQ ID NO 73
<211> LENGTH: 8
<212> TYPE: PRT
<213> ORGANISM: Artificial Sequence
<220> FEATURE:
<223> OTHER INFORMATION: chemically synthesized

<400> SEQUENCE: 73

Phe Leu Lys Lys Leu His Glu Glu
1               5

<210> SEQ ID NO 74
```

```
<211> LENGTH: 102
<212> TYPE: PRT
<213> ORGANISM: Artificial Sequence
<220> FEATURE:
<223> OTHER INFORMATION: chemically synthesized

<400> SEQUENCE: 74

Asp Tyr Ser Lys Tyr Tyr Lys Thr Ile Asp Asp Leu Asn Lys Gln Ile
1               5                   10                  15

Leu Asn Leu Thr Thr Asp Asn Ala Asn Ile Leu Leu Gln Ile Asp Asn
            20                  25                  30

Ala Arg Leu Ala Ala Asp Asp Phe Arg Leu Lys Tyr Glu Asn Glu Val
        35                  40                  45

Ala Leu Arg Gln Ser Val Glu Ala Asp Ile Asn Gly Leu Arg Arg Val
    50                  55                  60

Leu Asp Glu Leu Thr Leu Thr Lys Ala Asp Leu Glu Met Gln Ile Glu
65                  70                  75                  80

Ser Leu Thr Glu Glu Leu Ala Tyr Leu Lys Lys Asn His Glu Glu Glu
                85                  90                  95

Met Lys Asp Leu Arg Asn
            100

<210> SEQ ID NO 75
<211> LENGTH: 105
<212> TYPE: PRT
<213> ORGANISM: Artificial Sequence
<220> FEATURE:
<223> OTHER INFORMATION: chemically synthesized

<400> SEQUENCE: 75

Asn Leu Glu Pro Tyr Phe Glu Ser Phe Ile Asn Asn Leu Arg Arg Arg
1               5                   10                  15

Val Asp Gln Leu Lys Ser Asp Gln Ser Arg Leu Asp Ser Glu Leu Lys
            20                  25                  30

Asn Met Gln Asp Met Val Glu Asp Tyr Arg Asn Lys Tyr Glu Asp Glu
        35                  40                  45

Ile Asn Lys Arg Thr Asn Ala Glu Asn Glu Phe Val Thr Ile Lys Lys
    50                  55                  60

Asp Val Asp Gly Ala Tyr Met Thr Lys Val Asp Leu Gln Ala Lys Leu
65                  70                  75                  80

Asp Asn Leu Gln Gln Glu Ile Asp Phe Leu Thr Ala Leu Tyr Gln Ala
                85                  90                  95

Glu Leu Ser Gln Met Gln Thr Ile Ser
            100                 105

<210> SEQ ID NO 76
<211> LENGTH: 10
<212> TYPE: PRT
<213> ORGANISM: Artificial Sequence
<220> FEATURE:
<223> OTHER INFORMATION: chemically synthesized

<400> SEQUENCE: 76

Val Asp Ser Leu Lys Ser Asp Gln Ser Arg
1               5                   10

<210> SEQ ID NO 77
<211> LENGTH: 7
<212> TYPE: PRT
<213> ORGANISM: Artificial Sequence
<220> FEATURE:
```

-continued

<223> OTHER INFORMATION: chemically synthesized

<400> SEQUENCE: 77

Val Glu Leu Gln Ala Lys Arg
1               5

<210> SEQ ID NO 78
<211> LENGTH: 12
<212> TYPE: PRT
<213> ORGANISM: Artificial Sequence
<220> FEATURE:
<223> OTHER INFORMATION: chemically sythensized

<400> SEQUENCE: 78

Thr Asn Ala Glu Asn Glu Phe Val Thr Ile Lys Lys
1               5                   10

<210> SEQ ID NO 79
<211> LENGTH: 10
<212> TYPE: PRT
<213> ORGANISM: Artificial Sequence
<220> FEATURE:
<223> OTHER INFORMATION: chemically synthesized

<400> SEQUENCE: 79

Leu Lys Tyr Glu Asn Glu Val Thr Leu Arg
1               5                   10

<210> SEQ ID NO 80
<211> LENGTH: 10
<212> TYPE: PRT
<213> ORGANISM: Artificial Sequence
<220> FEATURE:
<223> OTHER INFORMATION: chemically synthesized

<400> SEQUENCE: 80

Thr Lys Tyr Glu Asp Glu Met Asn Lys Arg
1               5                   10

<210> SEQ ID NO 81
<211> LENGTH: 10
<212> TYPE: PRT
<213> ORGANISM: Artificial Sequence
<220> FEATURE:
<223> OTHER INFORMATION: chemically synthesized

<400> SEQUENCE: 81

Leu Lys Tyr Glu Asn Glu Val Thr Leu Arg
1               5                   10

<210> SEQ ID NO 82
<211> LENGTH: 9
<212> TYPE: PRT
<213> ORGANISM: Artificial Sequence
<220> FEATURE:
<223> OTHER INFORMATION: chemically synthesized

<400> SEQUENCE: 82

Tyr Tyr Lys Thr Ile Asp Asp Leu Lys
1               5

<210> SEQ ID NO 83
<211> LENGTH: 16
<212> TYPE: PRT
<213> ORGANISM: Artificial Sequence
<220> FEATURE:
<223> OTHER INFORMATION: chemically synthesized

<400> SEQUENCE: 83

Glu Met Gln Ile Glu Ser Leu Asn Glu Glu Leu Ala Tyr Leu Lys Lys
1               5                   10                  15

<210> SEQ ID NO 84
<211> LENGTH: 10
<212> TYPE: PRT
<213> ORGANISM: Artificial Sequence
<220> FEATURE:
<223> OTHER INFORMATION: chemically synthesized

<400> SEQUENCE: 84

Val Asp Gln Leu Lys Ser Asp Gln Ser Arg
1               5                   10

<210> SEQ ID NO 85
<211> LENGTH: 7
<212> TYPE: PRT
<213> ORGANISM: Artificial Sequence
<220> FEATURE:
<223> OTHER INFORMATION: chemically synthesized

<400> SEQUENCE: 85

Val Asp Leu Gln Ala Lys Leu
1               5

<210> SEQ ID NO 86
<211> LENGTH: 8
<212> TYPE: PRT
<213> ORGANISM: Artificial Sequence
<220> FEATURE:
<223> OTHER INFORMATION: chemically synthesized

<400> SEQUENCE: 86

Tyr Glu Asp Glu Ile Asn Lys Arg
1               5

<210> SEQ ID NO 87
<211> LENGTH: 9
<212> TYPE: PRT
<213> ORGANISM: Artificial Sequence
<220> FEATURE:
<223> OTHER INFORMATION: chemically synthesized

<400> SEQUENCE: 87

Leu Lys Glu Asn Glu Val Ala Leu Arg
1               5

<210> SEQ ID NO 88
<211> LENGTH: 10
<212> TYPE: PRT
<213> ORGANISM: Artificial Sequence
<220> FEATURE:
<223> OTHER INFORMATION: chemically synthesized

<400> SEQUENCE: 88

Asn Lys Tyr Glu Asp Glu Ile Asn Lys Arg
1               5                   10

<210> SEQ ID NO 89
<211> LENGTH: 10
<212> TYPE: PRT
<213> ORGANISM: Artificial Sequence
<220> FEATURE:
<223> OTHER INFORMATION: chemically synthesized

<400> SEQUENCE: 89

Leu Lys Tyr Glu Asn Glu Val Ala Leu Arg
1               5                   10

<210> SEQ ID NO 90
<211> LENGTH: 9
<212> TYPE: PRT
<213> ORGANISM: Artificial Sequence
<220> FEATURE:
<223> OTHER INFORMATION: chemically synthesized

<400> SEQUENCE: 90

Tyr Tyr Lys Thr Ile Glu Asp Leu Lys
1               5

<210> SEQ ID NO 91
<211> LENGTH: 9
<212> TYPE: PRT
<213> ORGANISM: Artificial Sequence
<220> FEATURE:
<223> OTHER INFORMATION: chemically synthesized

<400> SEQUENCE: 91

Leu Glu Pro Tyr Phe Glu Ser Phe Ile
1               5

<210> SEQ ID NO 92
<211> LENGTH: 9
<212> TYPE: PRT
<213> ORGANISM: Artificial Sequence
<220> FEATURE:
<223> OTHER INFORMATION: chemically synthesized

<400> SEQUENCE: 92

Leu Glu Pro Ile Phe Gln Gly Tyr Ile
1               5

<210> SEQ ID NO 93
<211> LENGTH: 9
<212> TYPE: PRT
<213> ORGANISM: Artificial Sequence
<220> FEATURE:
<223> OTHER INFORMATION: chemically synthesized

<400> SEQUENCE: 93

Leu Glu Pro Leu Phe Glu Asn His Ile
1               5

<210> SEQ ID NO 94
<211> LENGTH: 9
<212> TYPE: PRT
<213> ORGANISM: Artificial Sequence
<220> FEATURE:
<223> OTHER INFORMATION: chemically synthesized

<400> SEQUENCE: 94

Leu Glu Pro Leu Phe Glu Thr Tyr Leu
1               5

<210> SEQ ID NO 95
<211> LENGTH: 9
<212> TYPE: PRT
<213> ORGANISM: Artificial Sequence
<220> FEATURE:
<223> OTHER INFORMATION: chemically synthesized

<400> SEQUENCE: 95

-continued

```
Leu Glu Pro Leu Phe Glu Gln Tyr Ile
1               5

<210> SEQ ID NO 96
<211> LENGTH: 9
<212> TYPE: PRT
<213> ORGANISM: Artificial Sequence
<220> FEATURE:
<223> OTHER INFORMATION: chemically synthesized

<400> SEQUENCE: 96

Leu Glu Pro Leu Phe Glu Gln Tyr Ile
1               5

<210> SEQ ID NO 97
<211> LENGTH: 9
<212> TYPE: PRT
<213> ORGANISM: Artificial Sequence
<220> FEATURE:
<223> OTHER INFORMATION: chemically synthesized

<400> SEQUENCE: 97

Leu Glu Pro Leu Phe Glu Gln Tyr Ile
1               5

<210> SEQ ID NO 98
<211> LENGTH: 9
<212> TYPE: PRT
<213> ORGANISM: Artificial Sequence
<220> FEATURE:
<223> OTHER INFORMATION: chemically synthesized

<400> SEQUENCE: 98

Leu Pro Asp Ile Phe Glu Ala Gln Ile
1               5

<210> SEQ ID NO 99
<211> LENGTH: 9
<212> TYPE: PRT
<213> ORGANISM: Artificial Sequence
<220> FEATURE:
<223> OTHER INFORMATION: chemically synthesized

<400> SEQUENCE: 99

Met Asp Asn Met Phe Glu Ser Tyr Ile
1               5

<210> SEQ ID NO 100
<211> LENGTH: 9
<212> TYPE: PRT
<213> ORGANISM: Artificial Sequence
<220> FEATURE:
<223> OTHER INFORMATION: chemically synthesized

<400> SEQUENCE: 100

Leu Glu Pro Ile Leu Glu Gly Tyr Ile
1               5

<210> SEQ ID NO 101
<211> LENGTH: 9
<212> TYPE: PRT
<213> ORGANISM: Artificial Sequence
<220> FEATURE:
<223> OTHER INFORMATION: chemically synthesized

<400> SEQUENCE: 101
```

-continued

```
Leu Glu Pro Ile Leu Glu Gly Tyr Ile
1               5

<210> SEQ ID NO 102
<211> LENGTH: 9
<212> TYPE: PRT
<213> ORGANISM: Artificial Sequence
<220> FEATURE:
<223> OTHER INFORMATION: chemically synthesized

<400> SEQUENCE: 102

Leu Glu Pro Ile Leu Glu Gly Tyr Ile
1               5

<210> SEQ ID NO 103
<211> LENGTH: 9
<212> TYPE: PRT
<213> ORGANISM: Artificial Sequence
<220> FEATURE:
<223> OTHER INFORMATION: chemically synthesized

<400> SEQUENCE: 103

Leu Glu Pro Ile Leu Glu Gly Tyr Ile
1               5

<210> SEQ ID NO 104
<211> LENGTH: 9
<212> TYPE: PRT
<213> ORGANISM: Artificial Sequence
<220> FEATURE:
<223> OTHER INFORMATION: chemically synthesized

<400> SEQUENCE: 104

Leu Glu Pro Ile Leu Glu Gly Tyr Ile
1               5

<210> SEQ ID NO 105
<211> LENGTH: 9
<212> TYPE: PRT
<213> ORGANISM: Artificial Sequence
<220> FEATURE:
<223> OTHER INFORMATION: chemically synthesized

<400> SEQUENCE: 105

Leu Glu Pro Leu Phe Asp Ser Tyr Asp
1               5

<210> SEQ ID NO 106
<211> LENGTH: 9
<212> TYPE: PRT
<213> ORGANISM: Artificial Sequence
<220> FEATURE:
<223> OTHER INFORMATION: chemically synthesized

<400> SEQUENCE: 106

Leu Glu Pro Cys Phe Glu Ser Tyr Ile
1               5

<210> SEQ ID NO 107
<211> LENGTH: 9
<212> TYPE: PRT
<213> ORGANISM: Artificial Sequence
<220> FEATURE:
<223> OTHER INFORMATION: chemically synthesized

<400> SEQUENCE: 107

Leu Glu Pro Leu Leu Glu Asn Tyr Ile
```

```
1               5
```

```
<210> SEQ ID NO 108
<211> LENGTH: 9
<212> TYPE: PRT
<213> ORGANISM: Artificial Sequence
<220> FEATURE:
<223> OTHER INFORMATION: chemically synthesized

<400> SEQUENCE: 108

Leu Glu Pro Val Phe Glu Ala Cys Leu
1               5

<210> SEQ ID NO 109
<211> LENGTH: 9
<212> TYPE: PRT
<213> ORGANISM: Artificial Sequence
<220> FEATURE:
<223> OTHER INFORMATION: chemically synthesized

<400> SEQUENCE: 109

Leu Glu Pro Leu Phe Glu Ala Tyr Leu
1               5

<210> SEQ ID NO 110
<211> LENGTH: 9
<212> TYPE: PRT
<213> ORGANISM: Artificial Sequence
<220> FEATURE:
<223> OTHER INFORMATION: chemically synthesized

<400> SEQUENCE: 110

Leu Gly His Leu Tyr Glu Glu Tyr Gln
1               5

<210> SEQ ID NO 111
<211> LENGTH: 9
<212> TYPE: PRT
<213> ORGANISM: Artificial Sequence
<220> FEATURE:
<223> OTHER INFORMATION: chemically synthesized

<400> SEQUENCE: 111

Leu Glu Pro Leu Phe Glu Gly Tyr Ile
1               5

<210> SEQ ID NO 112
<211> LENGTH: 9
<212> TYPE: PRT
<213> ORGANISM: Artificial Sequence
<220> FEATURE:
<223> OTHER INFORMATION: chemically synthesized

<400> SEQUENCE: 112

Ile Glu Pro Ile Phe Glu Gly Tyr Ile
1               5

<210> SEQ ID NO 113
<211> LENGTH: 9
<212> TYPE: PRT
<213> ORGANISM: Artificial Sequence
<220> FEATURE:
<223> OTHER INFORMATION: chemically synthesized

<400> SEQUENCE: 113

Leu Glu Pro Leu Phe Ala Gly Tyr Ile
1               5
```

```
<210> SEQ ID NO 114
<211> LENGTH: 9
<212> TYPE: PRT
<213> ORGANISM: Artificial Sequence
<220> FEATURE:
<223> OTHER INFORMATION: chemically synthesized

<400> SEQUENCE: 114

Leu Glu Pro Leu Phe Glu Ser Tyr Ile
1               5

<210> SEQ ID NO 115
<211> LENGTH: 9
<212> TYPE: PRT
<213> ORGANISM: Artificial Sequence
<220> FEATURE:
<223> OTHER INFORMATION: chemically synthesized

<400> SEQUENCE: 115

Leu Glu Pro Leu Phe Ser Gly Tyr Ile
1               5

<210> SEQ ID NO 116
<211> LENGTH: 9
<212> TYPE: PRT
<213> ORGANISM: Artificial Sequence
<220> FEATURE:
<223> OTHER INFORMATION: chemically synthesized

<400> SEQUENCE: 116

Leu Glu Pro Leu Phe Ser Gly Tyr Ile
1               5

<210> SEQ ID NO 117
<211> LENGTH: 7
<212> TYPE: PRT
<213> ORGANISM: Artificial Sequence
<220> FEATURE:
<223> OTHER INFORMATION: chemically synthesized

<400> SEQUENCE: 117

Phe Leu Thr Ala Leu Tyr Gln
1               5

<210> SEQ ID NO 118
<211> LENGTH: 8
<212> TYPE: PRT
<213> ORGANISM: Artificial Sequence
<220> FEATURE:
<223> OTHER INFORMATION: chemically synthesized

<400> SEQUENCE: 118

Phe Leu Lys Val Leu Tyr Asp Ala
1               5

<210> SEQ ID NO 119
<211> LENGTH: 8
<212> TYPE: PRT
<213> ORGANISM: Artificial Sequence
<220> FEATURE:
<223> OTHER INFORMATION: chemically synthesized

<400> SEQUENCE: 119

Phe Leu Arg Thr Leu Tyr Asp Ala
1               5
```

<210> SEQ ID NO 120
<211> LENGTH: 8
<212> TYPE: PRT
<213> ORGANISM: Artificial Sequence
<220> FEATURE:
<223> OTHER INFORMATION: chemically synthesized

<400> SEQUENCE: 120

Phe Leu Lys Val Leu Tyr Asp Ala
1               5

<210> SEQ ID NO 121
<211> LENGTH: 8
<212> TYPE: PRT
<213> ORGANISM: Artificial Sequence
<220> FEATURE:
<223> OTHER INFORMATION: chemically synthesized

<400> SEQUENCE: 121

Phe Met Lys Met Phe Phe Asp Ala
1               5

<210> SEQ ID NO 122
<211> LENGTH: 8
<212> TYPE: PRT
<213> ORGANISM: Artificial Sequence
<220> FEATURE:
<223> OTHER INFORMATION: chemically synthesized

<400> SEQUENCE: 122

Phe Leu Arg Ala Leu Tyr Asp Ala
1               5

<210> SEQ ID NO 123
<211> LENGTH: 8
<212> TYPE: PRT
<213> ORGANISM: Artificial Sequence
<220> FEATURE:
<223> OTHER INFORMATION: chemically synthesized

<400> SEQUENCE: 123

Phe Leu Arg Ala Leu Tyr Asp Ala
1               5

<210> SEQ ID NO 124
<211> LENGTH: 8
<212> TYPE: PRT
<213> ORGANISM: Artificial Sequence
<220> FEATURE:
<223> OTHER INFORMATION: chemically synthesized

<400> SEQUENCE: 124

Phe Leu Arg Ala Leu Tyr Asp Ala
1               5

<210> SEQ ID NO 125
<211> LENGTH: 8
<212> TYPE: PRT
<213> ORGANISM: Artificial Sequence
<220> FEATURE:
<223> OTHER INFORMATION: chemically synthesized

<400> SEQUENCE: 125

Phe Leu Arg Thr Leu Asn Glu Thr
1               5

```
<210> SEQ ID NO 126
<211> LENGTH: 8
<212> TYPE: PRT
<213> ORGANISM: Artificial Sequence
<220> FEATURE:
<223> OTHER INFORMATION: chemically synthesized

<400> SEQUENCE: 126

Leu Phe Arg Gln Leu Tyr Glu Glu
1               5

<210> SEQ ID NO 127
<211> LENGTH: 8
<212> TYPE: PRT
<213> ORGANISM: Artificial Sequence
<220> FEATURE:
<223> OTHER INFORMATION: chemically synthesized

<400> SEQUENCE: 127

Phe Phe Arg Cys Leu Phe Glu Ala
1               5

<210> SEQ ID NO 128
<211> LENGTH: 8
<212> TYPE: PRT
<213> ORGANISM: Artificial Sequence
<220> FEATURE:
<223> OTHER INFORMATION: chemically synthesized

<400> SEQUENCE: 128

Phe Phe Lys Cys Leu Tyr Glu Gly
1               5

<210> SEQ ID NO 129
<211> LENGTH: 8
<212> TYPE: PRT
<213> ORGANISM: Artificial Sequence
<220> FEATURE:
<223> OTHER INFORMATION: chemically synthesized

<400> SEQUENCE: 129

Phe Phe Lys Cys Leu Tyr Glu Gly
1               5

<210> SEQ ID NO 130
<211> LENGTH: 8
<212> TYPE: PRT
<213> ORGANISM: Artificial Sequence
<220> FEATURE:
<223> OTHER INFORMATION: chemically synthesized

<400> SEQUENCE: 130

Phe Leu Lys Cys Leu Tyr Asp Ala
1               5

<210> SEQ ID NO 131
<211> LENGTH: 8
<212> TYPE: PRT
<213> ORGANISM: Artificial Sequence
<220> FEATURE:
<223> OTHER INFORMATION: chemically synthesized

<400> SEQUENCE: 131

Phe Ile His Ser Val Phe Asp Ala
1               5

<210> SEQ ID NO 132
```

```
<211> LENGTH: 8
<212> TYPE: PRT
<213> ORGANISM: Artificial Sequence
<220> FEATURE:
<223> OTHER INFORMATION: chemically synthesized

<400> SEQUENCE: 132

Phe Leu Arg Thr Leu Tyr Glu Met
1               5

<210> SEQ ID NO 133
<211> LENGTH: 8
<212> TYPE: PRT
<213> ORGANISM: Artificial Sequence
<220> FEATURE:
<223> OTHER INFORMATION: chemically synthesized

<400> SEQUENCE: 133

Phe Leu Lys Tyr Leu Phe Leu Thr
1               5

<210> SEQ ID NO 134
<211> LENGTH: 8
<212> TYPE: PRT
<213> ORGANISM: Artificial Sequence
<220> FEATURE:
<223> OTHER INFORMATION: chemically synthesized

<400> SEQUENCE: 134

Phe Leu Lys His Leu Asn Glu Glu
1               5

<210> SEQ ID NO 135
<211> LENGTH: 8
<212> TYPE: PRT
<213> ORGANISM: Artificial Sequence
<220> FEATURE:
<223> OTHER INFORMATION: chemically synthesized

<400> SEQUENCE: 135

Phe Leu Gln Gln Leu Tyr Glu Met
1               5

<210> SEQ ID NO 136
<211> LENGTH: 8
<212> TYPE: PRT
<213> ORGANISM: Artificial Sequence
<220> FEATURE:
<223> OTHER INFORMATION: chemically synthesized

<400> SEQUENCE: 136

Leu Met Lys Thr Ile Tyr Glu Gln
1               5

<210> SEQ ID NO 137
<211> LENGTH: 8
<212> TYPE: PRT
<213> ORGANISM: Artificial Sequence
<220> FEATURE:
<223> OTHER INFORMATION: chemically synthesized

<400> SEQUENCE: 137

Phe Leu Arg Arg Leu Tyr Glu Glu
1               5

<210> SEQ ID NO 138
<211> LENGTH: 8
```

<212> TYPE: PRT
<213> ORGANISM: Artificial Sequence
<220> FEATURE:
<223> OTHER INFORMATION: chemically synthesized

<400> SEQUENCE: 138

Phe Leu Lys Ser Leu Tyr Glu Glu
1               5

<210> SEQ ID NO 139
<211> LENGTH: 8
<212> TYPE: PRT
<213> ORGANISM: Artificial Sequence
<220> FEATURE:
<223> OTHER INFORMATION: chemically synthesized

<400> SEQUENCE: 139

Phe Leu Arg Arg Leu Tyr Glu Glu
1               5

<210> SEQ ID NO 140
<211> LENGTH: 8
<212> TYPE: PRT
<213> ORGANISM: Artificial Sequence
<220> FEATURE:
<223> OTHER INFORMATION: chemically synthesized

<400> SEQUENCE: 140

Phe Leu Lys Thr Leu Tyr Met Glu
1               5

<210> SEQ ID NO 141
<211> LENGTH: 8
<212> TYPE: PRT
<213> ORGANISM: Artificial Sequence
<220> FEATURE:
<223> OTHER INFORMATION: chemically synthesized

<400> SEQUENCE: 141

Phe Leu Arg Arg Leu Tyr Glu Glu
1               5

<210> SEQ ID NO 142
<211> LENGTH: 8
<212> TYPE: PRT
<213> ORGANISM: Artificial Sequence
<220> FEATURE:
<223> OTHER INFORMATION: chemically synthesized

<400> SEQUENCE: 142

Phe Leu Arg Arg Leu Tyr Glu Glu
1               5

<210> SEQ ID NO 143
<211> LENGTH: 9
<212> TYPE: PRT
<213> ORGANISM: Artificial Sequence
<220> FEATURE:
<223> OTHER INFORMATION: chemically synthesized

<400> SEQUENCE: 143

Asp Tyr Ser Lys Tyr Tyr Lys Thr Ile
1               5

<210> SEQ ID NO 144
<211> LENGTH: 9
<212> TYPE: PRT

-continued

```
<213> ORGANISM: Artificial Sequence
<220> FEATURE:
<223> OTHER INFORMATION: chemically synthesized

<400> SEQUENCE: 144

Asn Tyr Ser Pro Tyr Tyr Asn Thr Ile
1               5

<210> SEQ ID NO 145
<211> LENGTH: 9
<212> TYPE: PRT
<213> ORGANISM: Artificial Sequence
<220> FEATURE:
<223> OTHER INFORMATION: chemically synthesized

<400> SEQUENCE: 145

Asp Tyr Ser Lys Tyr Tyr Pro Leu Ile
1               5

<210> SEQ ID NO 146
<211> LENGTH: 9
<212> TYPE: PRT
<213> ORGANISM: Artificial Sequence
<220> FEATURE:
<223> OTHER INFORMATION: chemically synthesized

<400> SEQUENCE: 146

Asp Tyr Ser Pro Tyr Tyr Lys Thr Ile
1               5

<210> SEQ ID NO 147
<211> LENGTH: 9
<212> TYPE: PRT
<213> ORGANISM: Artificial Sequence
<220> FEATURE:
<223> OTHER INFORMATION: chemically synthesized

<400> SEQUENCE: 147

Asp Tyr Ser Pro Tyr Phe Lys Thr Ile
1               5

<210> SEQ ID NO 148
<211> LENGTH: 9
<212> TYPE: PRT
<213> ORGANISM: Artificial Sequence
<220> FEATURE:
<223> OTHER INFORMATION: chemically synthesized

<400> SEQUENCE: 148

Asp Tyr Ser Pro Tyr Phe Lys Thr Ile
1               5

<210> SEQ ID NO 149
<211> LENGTH: 9
<212> TYPE: PRT
<213> ORGANISM: Artificial Sequence
<220> FEATURE:
<223> OTHER INFORMATION: chemically synthesized

<400> SEQUENCE: 149

Asp Tyr Ser Pro Tyr Phe Lys Thr Ile
1               5

<210> SEQ ID NO 150
<211> LENGTH: 9
<212> TYPE: PRT
<213> ORGANISM: Artificial Sequence
```

-continued

```
<220> FEATURE:
<223> OTHER INFORMATION: chemically synthesized

<400> SEQUENCE: 150

Asp Tyr Ser Gln Tyr Tyr Arg Thr Ile
1               5

<210> SEQ ID NO 151
<211> LENGTH: 9
<212> TYPE: PRT
<213> ORGANISM: Artificial Sequence
<220> FEATURE:
<223> OTHER INFORMATION: chemically synthesized

<400> SEQUENCE: 151

Asp Trp Ser His Tyr Phe Lys Ile Ile
1               5

<210> SEQ ID NO 152
<211> LENGTH: 9
<212> TYPE: PRT
<213> ORGANISM: Artificial Sequence
<220> FEATURE:
<223> OTHER INFORMATION: chemically synthesized

<400> SEQUENCE: 152

Asp Tyr Ser His Tyr Tyr Thr Thr Ile
1               5

<210> SEQ ID NO 153
<211> LENGTH: 9
<212> TYPE: PRT
<213> ORGANISM: Artificial Sequence
<220> FEATURE:
<223> OTHER INFORMATION: chemically synthesized

<400> SEQUENCE: 153

Asp Tyr Ser Ala Tyr Tyr Arg Gln Ile
1               5

<210> SEQ ID NO 154
<211> LENGTH: 9
<212> TYPE: PRT
<213> ORGANISM: Artificial Sequence
<220> FEATURE:
<223> OTHER INFORMATION: chemically synthesized

<400> SEQUENCE: 154

Asp Tyr Ser Gln Tyr Glu Glu Asn Ile
1               5

<210> SEQ ID NO 155
<211> LENGTH: 9
<212> TYPE: PRT
<213> ORGANISM: Artificial Sequence
<220> FEATURE:
<223> OTHER INFORMATION: chemically synthesized

<400> SEQUENCE: 155

Asp Tyr Ser Lys Tyr Tyr Ser Ile Ile
1               5

<210> SEQ ID NO 156
<211> LENGTH: 9
<212> TYPE: PRT
<213> ORGANISM: Artificial Sequence
<220> FEATURE:
```

<223> OTHER INFORMATION: chemically synthesized

<400> SEQUENCE: 156

Asp Tyr Ser Arg Tyr Phe Pro Ile Ile
1               5

<210> SEQ ID NO 157
<211> LENGTH: 9
<212> TYPE: PRT
<213> ORGANISM: Artificial Sequence
<220> FEATURE:
<223> OTHER INFORMATION: chemically synthesized

<400> SEQUENCE: 157

Asp Tyr Ser Arg Tyr Phe Ser Val Ile
1               5

<210> SEQ ID NO 158
<211> LENGTH: 9
<212> TYPE: PRT
<213> ORGANISM: Artificial Sequence
<220> FEATURE:
<223> OTHER INFORMATION: chemically synthesized

<400> SEQUENCE: 158

Asp Tyr Ser Arg Tyr Phe Pro Ile Ile
1               5

<210> SEQ ID NO 159
<211> LENGTH: 9
<212> TYPE: PRT
<213> ORGANISM: Artificial Sequence
<220> FEATURE:
<223> OTHER INFORMATION: chemically synthesized

<400> SEQUENCE: 159

Asp Tyr Ser Arg Tyr His Leu Thr Ile
1               5

<210> SEQ ID NO 160
<211> LENGTH: 9
<212> TYPE: PRT
<213> ORGANISM: Artificial Sequence
<220> FEATURE:
<223> OTHER INFORMATION: chemically synthesized

<400> SEQUENCE: 160

Ser Tyr Gln Ser Tyr Phe Lys Thr Ile
1               5

<210> SEQ ID NO 161
<211> LENGTH: 9
<212> TYPE: PRT
<213> ORGANISM: Artificial Sequence
<220> FEATURE:
<223> OTHER INFORMATION: chemically synthesized

<400> SEQUENCE: 161

Asp Tyr Gln Ser His Phe Arg Thr Ile
1               5

<210> SEQ ID NO 162
<211> LENGTH: 9
<212> TYPE: PRT
<213> ORGANISM: Artificial Sequence
<220> FEATURE:
<223> OTHER INFORMATION: chemically synthesized -continued

<400> SEQUENCE: 162

Ser Tyr Gln Ser Tyr Phe Lys Thr Ile
1               5

<210> SEQ ID NO 163
<211> LENGTH: 9
<212> TYPE: PRT
<213> ORGANISM: Artificial Sequence
<220> FEATURE:
<223> OTHER INFORMATION: chemically synthesized

<400> SEQUENCE: 163

Ser Tyr Gln Ser Tyr Phe Lys Thr Ile
1               5

<210> SEQ ID NO 164
<211> LENGTH: 9
<212> TYPE: PRT
<213> ORGANISM: Artificial Sequence
<220> FEATURE:
<223> OTHER INFORMATION: chemically synthesized

<400> SEQUENCE: 164

Ser Tyr Gln Ser Tyr Phe Lys Thr Ile
1               5

<210> SEQ ID NO 165
<211> LENGTH: 9
<212> TYPE: PRT
<213> ORGANISM: Artificial Sequence
<220> FEATURE:
<223> OTHER INFORMATION: chemically synthesized

<400> SEQUENCE: 165

Asp Tyr Gln Ser Tyr Phe Arg Thr Ile
1               5

<210> SEQ ID NO 166
<211> LENGTH: 9
<212> TYPE: PRT
<213> ORGANISM: Artificial Sequence
<220> FEATURE:
<223> OTHER INFORMATION: chemically synthesized

<400> SEQUENCE: 166

Asp Tyr Gln Ser Tyr Phe Lys Thr Ile
1               5

<210> SEQ ID NO 167
<211> LENGTH: 9
<212> TYPE: PRT
<213> ORGANISM: Artificial Sequence
<220> FEATURE:
<223> OTHER INFORMATION: chemically synthesized

<400> SEQUENCE: 167

Lys Tyr Gln Ser Tyr Phe Arg Thr Ile
1               5

<210> SEQ ID NO 168
<211> LENGTH: 9
<212> TYPE: PRT
<213> ORGANISM: Artificial Sequence
<220> FEATURE:
<223> OTHER INFORMATION: chemically synthesized

```
<400> SEQUENCE: 168

Ser Tyr Gln Ser Tyr Phe His Thr Ile
1               5

<210> SEQ ID NO 169
<211> LENGTH: 9
<212> TYPE: PRT
<213> ORGANISM: Artificial Sequence
<220> FEATURE:
<223> OTHER INFORMATION: chemically synthesized

<400> SEQUENCE: 169

Asp Tyr Leu Ser Tyr Tyr Thr Thr Ile
1               5

<210> SEQ ID NO 170
<211> LENGTH: 9
<212> TYPE: PRT
<213> ORGANISM: Artificial Sequence
<220> FEATURE:
<223> OTHER INFORMATION: chemically synthesized

<400> SEQUENCE: 170

Asp Tyr Gln Arg Tyr Phe Asn Thr Ile
1               5

<210> SEQ ID NO 171
<211> LENGTH: 8
<212> TYPE: PRT
<213> ORGANISM: Artificial Sequence
<220> FEATURE:
<223> OTHER INFORMATION: chemically synthesized

<400> SEQUENCE: 171

Tyr Leu Lys Lys Asn His Glu Glu
1               5

<210> SEQ ID NO 172
<211> LENGTH: 9
<212> TYPE: PRT
<213> ORGANISM: Artificial Sequence
<220> FEATURE:
<223> OTHER INFORMATION: chemically synthesized

<400> SEQUENCE: 172

Ala Leu Lys Lys Asn His Glu Lys Glu
1               5

<210> SEQ ID NO 173
<211> LENGTH: 8
<212> TYPE: PRT
<213> ORGANISM: Artificial Sequence
<220> FEATURE:
<223> OTHER INFORMATION: chemically synthesized

<400> SEQUENCE: 173

Tyr Met Lys Lys Asn His Glu Asp
1               5

<210> SEQ ID NO 174
<211> LENGTH: 8
<212> TYPE: PRT
<213> ORGANISM: Artificial Sequence
<220> FEATURE:
<223> OTHER INFORMATION: chemically synthesized

<400> SEQUENCE: 174
```

```
Tyr Met Lys Lys Asn His Glu Glu
1               5

<210> SEQ ID NO 175
<211> LENGTH: 8
<212> TYPE: PRT
<213> ORGANISM: Artificial Sequence
<220> FEATURE:
<223> OTHER INFORMATION: chemically synthesized

<400> SEQUENCE: 175

Tyr Leu Lys Lys Asn His Glu Glu
1               5

<210> SEQ ID NO 176
<211> LENGTH: 8
<212> TYPE: PRT
<213> ORGANISM: Artificial Sequence
<220> FEATURE:
<223> OTHER INFORMATION: chemically synthesized

<400> SEQUENCE: 176

Tyr Leu Lys Lys Asn His Glu Glu
1               5

<210> SEQ ID NO 177
<211> LENGTH: 8
<212> TYPE: PRT
<213> ORGANISM: Artificial Sequence
<220> FEATURE:
<223> OTHER INFORMATION: chemically synthesized

<400> SEQUENCE: 177

Tyr Leu Arg Lys Asn His Glu Glu
1               5

<210> SEQ ID NO 178
<211> LENGTH: 8
<212> TYPE: PRT
<213> ORGANISM: Artificial Sequence
<220> FEATURE:
<223> OTHER INFORMATION: chemically synthesized

<400> SEQUENCE: 178

Tyr Leu Lys Lys Asn His Glu Glu
1               5

<210> SEQ ID NO 179
<211> LENGTH: 8
<212> TYPE: PRT
<213> ORGANISM: Artificial Sequence
<220> FEATURE:
<223> OTHER INFORMATION: chemically synthesized

<400> SEQUENCE: 179

Phe Met Lys Lys Asn His Glu Glu
1               5

<210> SEQ ID NO 180
<211> LENGTH: 8
<212> TYPE: PRT
<213> ORGANISM: Artificial Sequence
<220> FEATURE:
<223> OTHER INFORMATION: chemically synthesized

<400> SEQUENCE: 180
```

Tyr Leu Lys Lys Asn His Glu Glu
1               5

<210> SEQ ID NO 181
<211> LENGTH: 8
<212> TYPE: PRT
<213> ORGANISM: Artificial Sequence
<220> FEATURE:
<223> OTHER INFORMATION: chemically synthesized

<400> SEQUENCE: 181

Leu Leu Lys Lys Glu His Gln Glu
1               5

<210> SEQ ID NO 182
<211> LENGTH: 8
<212> TYPE: PRT
<213> ORGANISM: Artificial Sequence
<220> FEATURE:
<223> OTHER INFORMATION: chemically synthesized

<400> SEQUENCE: 182

Leu Met Lys Lys His His Glu Gln
1               5

<210> SEQ ID NO 183
<211> LENGTH: 8
<212> TYPE: PRT
<213> ORGANISM: Artificial Sequence
<220> FEATURE:
<223> OTHER INFORMATION: chemically synthesized

<400> SEQUENCE: 183

Tyr Leu Arg Lys Asn His Glu Glu
1               5

<210> SEQ ID NO 184
<211> LENGTH: 8
<212> TYPE: PRT
<213> ORGANISM: Artificial Sequence
<220> FEATURE:
<223> OTHER INFORMATION: chemically synthesized

<400> SEQUENCE: 184

Tyr Leu Lys Lys Asn His Lys Glu
1               5

<210> SEQ ID NO 185
<211> LENGTH: 8
<212> TYPE: PRT
<213> ORGANISM: Artificial Sequence
<220> FEATURE:
<223> OTHER INFORMATION: chemically synthesized

<400> SEQUENCE: 185

Tyr Leu Lys Lys Ser His Glu Glu
1               5

<210> SEQ ID NO 186
<211> LENGTH: 8
<212> TYPE: PRT
<213> ORGANISM: Artificial Sequence
<220> FEATURE:
<223> OTHER INFORMATION: chemically synthesized

<400> SEQUENCE: 186

Tyr Leu Lys Lys Asn His Glu Glu

-continued

```
1               5

<210> SEQ ID NO 187
<211> LENGTH: 8
<212> TYPE: PRT
<213> ORGANISM: Artificial Sequence
<220> FEATURE:
<223> OTHER INFORMATION: chemically synthesized

<400> SEQUENCE: 187

Tyr Leu Lys Lys Asn His Glu Glu
1               5

<210> SEQ ID NO 188
<211> LENGTH: 8
<212> TYPE: PRT
<213> ORGANISM: Artificial Sequence
<220> FEATURE:
<223> OTHER INFORMATION: chemically synthesized

<400> SEQUENCE: 188

Cys Leu Lys Ser Asn His Glu Gln
1               5

<210> SEQ ID NO 189
<211> LENGTH: 8
<212> TYPE: PRT
<213> ORGANISM: Artificial Sequence
<220> FEATURE:
<223> OTHER INFORMATION: chemically synthesized

<400> SEQUENCE: 189

Cys Leu Lys Lys Asn His Glu Glu
1               5

<210> SEQ ID NO 190
<211> LENGTH: 8
<212> TYPE: PRT
<213> ORGANISM: Artificial Sequence
<220> FEATURE:
<223> OTHER INFORMATION: chemically synthesized

<400> SEQUENCE: 190

Cys Leu Lys Gln Asn His Glu Gln
1               5

<210> SEQ ID NO 191
<211> LENGTH: 8
<212> TYPE: PRT
<213> ORGANISM: Artificial Sequence
<220> FEATURE:
<223> OTHER INFORMATION: chemically synthesized

<400> SEQUENCE: 191

Ser Leu Lys Gln Asn His Glu Gln
1               5

<210> SEQ ID NO 192
<211> LENGTH: 8
<212> TYPE: PRT
<213> ORGANISM: Artificial Sequence
<220> FEATURE:
<223> OTHER INFORMATION: chemically synthesized

<400> SEQUENCE: 192

Cys Leu Lys Lys Asn His Glu Glu
1               5
```

<210> SEQ ID NO 193
<211> LENGTH: 7
<212> TYPE: PRT
<213> ORGANISM: Artificial Sequence
<220> FEATURE:
<223> OTHER INFORMATION: chemically synthesized

<400> SEQUENCE: 193

Cys Leu Lys Asn His Glu Glu
1               5

<210> SEQ ID NO 194
<211> LENGTH: 8
<212> TYPE: PRT
<213> ORGANISM: Artificial Sequence
<220> FEATURE:
<223> OTHER INFORMATION: chemically synthesized

<400> SEQUENCE: 194

Cys Leu Lys Lys Asn His Glu Glu
1               5

<210> SEQ ID NO 195
<211> LENGTH: 8
<212> TYPE: PRT
<213> ORGANISM: Artificial Sequence
<220> FEATURE:
<223> OTHER INFORMATION: chemically synthesized

<400> SEQUENCE: 195

Ser Leu Lys Ser His Asn Glu Gln
1               5

<210> SEQ ID NO 196
<211> LENGTH: 8
<212> TYPE: PRT
<213> ORGANISM: Artificial Sequence
<220> FEATURE:
<223> OTHER INFORMATION: chemically synthesized

<400> SEQUENCE: 196

Ser Leu Lys Ser Asn His Glu Gln
1               5

<210> SEQ ID NO 197
<211> LENGTH: 8
<212> TYPE: PRT
<213> ORGANISM: Artificial Sequence
<220> FEATURE:
<223> OTHER INFORMATION: chemically synthesized

<400> SEQUENCE: 197

Cys Leu Lys Asn Asn His Lys Glu
1               5

<210> SEQ ID NO 198
<211> LENGTH: 8
<212> TYPE: PRT
<213> ORGANISM: Artificial Sequence
<220> FEATURE:
<223> OTHER INFORMATION: chemically synthesized

<400> SEQUENCE: 198

Cys Leu Lys Lys Asn His Glu Glu
1               5

<210> SEQ ID NO 199
<211> LENGTH: 9
<212> TYPE: PRT
<213> ORGANISM: Artificial Sequence
<220> FEATURE:
<223> OTHER INFORMATION: chemically synthesized

<400> SEQUENCE: 199

Leu Gly Asp Leu Tyr Glu Glu Glu Met
1               5

<210> SEQ ID NO 200
<211> LENGTH: 9
<212> TYPE: PRT
<213> ORGANISM: Artificial Sequence
<220> FEATURE:
<223> OTHER INFORMATION: chemically synthesized

<400> SEQUENCE: 200

Val Ala Glu Leu Tyr Glu Glu Glu Leu
1               5

<210> SEQ ID NO 201
<211> LENGTH: 9
<212> TYPE: PRT
<213> ORGANISM: Artificial Sequence
<220> FEATURE:
<223> OTHER INFORMATION: chemically synthesized

<400> SEQUENCE: 201

Leu Ala Asp Val Tyr Gln Ala Glu Leu
1               5

<210> SEQ ID NO 202
<211> LENGTH: 9
<212> TYPE: PRT
<213> ORGANISM: Artificial Sequence
<220> FEATURE:
<223> OTHER INFORMATION: chemically synthesized

<400> SEQUENCE: 202

Ala Asp Gln Leu Cys Gln Gln Glu Leu
1               5

<210> SEQ ID NO 203
<211> LENGTH: 9
<212> TYPE: PRT
<213> ORGANISM: Artificial Sequence
<220> FEATURE:
<223> OTHER INFORMATION: chemically synthesized

<400> SEQUENCE: 203

Ser Leu Arg Ala Glu Gln Ser Pro Ser
1               5

<210> SEQ ID NO 204
<211> LENGTH: 8
<212> TYPE: PRT
<213> ORGANISM: Artificial Sequence
<220> FEATURE:
<223> OTHER INFORMATION: chemically synthesized

<400> SEQUENCE: 204

Phe Leu Lys Lys Leu His Glu Glu
1               5

-continued

```
<210> SEQ ID NO 205
<211> LENGTH: 8
<212> TYPE: PRT
<213> ORGANISM: Artificial Sequence
<220> FEATURE:
<223> OTHER INFORMATION: chemically synthesized

<400> SEQUENCE: 205

Phe Leu Lys Lys Val His Glu Glu
1               5

<210> SEQ ID NO 206
<211> LENGTH: 8
<212> TYPE: PRT
<213> ORGANISM: Artificial Sequence
<220> FEATURE:
<223> OTHER INFORMATION: chemically synthesized

<400> SEQUENCE: 206

Phe Leu Arg Lys Ile His Glu Glu
1               5

<210> SEQ ID NO 207
<211> LENGTH: 8
<212> TYPE: PRT
<213> ORGANISM: Artificial Sequence
<220> FEATURE:
<223> OTHER INFORMATION: chemically synthesized

<400> SEQUENCE: 207

Phe Leu Lys Lys Leu His Glu Glu
1               5

<210> SEQ ID NO 208
<211> LENGTH: 8
<212> TYPE: PRT
<213> ORGANISM: Artificial Sequence
<220> FEATURE:
<223> OTHER INFORMATION: chemically synthesized

<400> SEQUENCE: 208

Leu Val Lys Gln Lys Leu Phe Lys
1               5

<210> SEQ ID NO 209
<211> LENGTH: 9
<212> TYPE: PRT
<213> ORGANISM: Artificial Sequence
<220> FEATURE:
<223> OTHER INFORMATION: chemically synthesized

<400> SEQUENCE: 209

Phe Arg Ala Leu Tyr Glu Gln Glu Ile
1               5

<210> SEQ ID NO 210
<211> LENGTH: 9
<212> TYPE: PRT
<213> ORGANISM: Artificial Sequence
<220> FEATURE:
<223> OTHER INFORMATION: chemically synthesized

<400> SEQUENCE: 210

Leu Gly Asp Ala Tyr Asp Gln Glu Ile
1               5

<210> SEQ ID NO 211
```

```
<211> LENGTH: 9
<212> TYPE: PRT
<213> ORGANISM: Artificial Sequence
<220> FEATURE:
<223> OTHER INFORMATION: chemically synthesized

<400> SEQUENCE: 211

Met Gly Glu Leu Tyr Glu Arg Glu Val
1               5

<210> SEQ ID NO 212
<211> LENGTH: 9
<212> TYPE: PRT
<213> ORGANISM: Artificial Sequence
<220> FEATURE:
<223> OTHER INFORMATION: chemically synthesized

<400> SEQUENCE: 212

Val Gly Glu Leu Phe Gln Arg Glu Leu
1               5

<210> SEQ ID NO 213
<211> LENGTH: 9
<212> TYPE: PRT
<213> ORGANISM: Artificial Sequence
<220> FEATURE:
<223> OTHER INFORMATION: chemically synthesized

<400> SEQUENCE: 213

Thr Val Gln Leu Tyr Glu Asp Glu Val
1               5

<210> SEQ ID NO 214
<211> LENGTH: 9
<212> TYPE: PRT
<213> ORGANISM: Artificial Sequence
<220> FEATURE:
<223> OTHER INFORMATION: chemically synthesized

<400> SEQUENCE: 214

Thr Val Gln Leu Tyr Glu Asp Glu Val
1               5

<210> SEQ ID NO 215
<211> LENGTH: 9
<212> TYPE: PRT
<213> ORGANISM: Artificial Sequence
<220> FEATURE:
<223> OTHER INFORMATION: chemically synthesized

<400> SEQUENCE: 215

Ala Val Glu Ala Leu Glu Gln Glu Lys
1               5

<210> SEQ ID NO 216
<211> LENGTH: 8
<212> TYPE: PRT
<213> ORGANISM: Artificial Sequence
<220> FEATURE:
<223> OTHER INFORMATION: chemically synthesized

<400> SEQUENCE: 216

Phe Leu Lys Lys Val His Glu Glu
1               5

<210> SEQ ID NO 217
<211> LENGTH: 8
```

```
<212> TYPE: PRT
<213> ORGANISM: Artificial Sequence
<220> FEATURE:
<223> OTHER INFORMATION: chemically synthesized

<400> SEQUENCE: 217

Phe Leu Arg Ser Asn His Glu Glu
1               5

<210> SEQ ID NO 218
<211> LENGTH: 8
<212> TYPE: PRT
<213> ORGANISM: Artificial Sequence
<220> FEATURE:
<223> OTHER INFORMATION: chemically synthesized

<400> SEQUENCE: 218

Tyr Leu Arg Arg His His Gln Glu
1               5

<210> SEQ ID NO 219
<211> LENGTH: 8
<212> TYPE: PRT
<213> ORGANISM: Artificial Sequence
<220> FEATURE:
<223> OTHER INFORMATION: chemically synthesized

<400> SEQUENCE: 219

Phe Val Arg Gln Val His Asp Glu
1               5

<210> SEQ ID NO 220
<211> LENGTH: 8
<212> TYPE: PRT
<213> ORGANISM: Artificial Sequence
<220> FEATURE:
<223> OTHER INFORMATION: chemically synthesized

<400> SEQUENCE: 220

Leu Ala Met Ala Asp Trp Leu Arg
1               5

<210> SEQ ID NO 221
<211> LENGTH: 8
<212> TYPE: PRT
<213> ORGANISM: Artificial Sequence
<220> FEATURE:
<223> OTHER INFORMATION: chemically synthesized

<400> SEQUENCE: 221

Leu Ala Met Ala Asp Trp Leu Arg
1               5

<210> SEQ ID NO 222
<211> LENGTH: 8
<212> TYPE: PRT
<213> ORGANISM: Artificial Sequence
<220> FEATURE:
<223> OTHER INFORMATION: chemically synthesized

<400> SEQUENCE: 222

Phe Leu Gln Ala Arg Thr Pro Thr
1               5

<210> SEQ ID NO 223
<211> LENGTH: 9
<212> TYPE: PRT
```

<213> ORGANISM: Artificial Sequence
<220> FEATURE:
<223> OTHER INFORMATION: chemically synthesized

<400> SEQUENCE: 223

Asn Trp Gly Ala Leu Arg Ala Ser Trp
1               5

<210> SEQ ID NO 224
<211> LENGTH: 9
<212> TYPE: PRT
<213> ORGANISM: Artificial Sequence
<220> FEATURE:
<223> OTHER INFORMATION: chemically synthesized

<400> SEQUENCE: 224

Leu Arg Ser Gln Leu Glu Glu Gly Arg
1               5

<210> SEQ ID NO 225
<211> LENGTH: 8
<212> TYPE: PRT
<213> ORGANISM: Artificial Sequence
<220> FEATURE:
<223> OTHER INFORMATION: chemically synthesized

<400> SEQUENCE: 225

Ser Leu Ser Arg Asn Tyr Glu Glu
1               5

<210> SEQ ID NO 226
<211> LENGTH: 8
<212> TYPE: PRT
<213> ORGANISM: Artificial Sequence
<220> FEATURE:
<223> OTHER INFORMATION: chemically synthesized

<400> SEQUENCE: 226

Arg Tyr His Arg Ile Ile Glu Ile
1               5

<210> SEQ ID NO 227
<211> LENGTH: 9
<212> TYPE: PRT
<213> ORGANISM: Artificial Sequence
<220> FEATURE:
<223> OTHER INFORMATION: chemically synthesized

<400> SEQUENCE: 227

Glu Thr Arg Leu Val Glu Val Asp Ser
1               5

<210> SEQ ID NO 228
<211> LENGTH: 9
<212> TYPE: PRT
<213> ORGANISM: Artificial Sequence
<220> FEATURE:
<223> OTHER INFORMATION: chemically synthesized

<400> SEQUENCE: 228

Glu Arg Arg Leu Val Glu Val Asp Ser
1               5

<210> SEQ ID NO 229
<211> LENGTH: 9
<212> TYPE: PRT
<213> ORGANISM: Artificial Sequence

```
<220> FEATURE:
<223> OTHER INFORMATION: chemically synthesized

<400> SEQUENCE: 229

Glu Thr Arg Leu Val Glu Ile Asp Asn
1               5

<210> SEQ ID NO 230
<211> LENGTH: 9
<212> TYPE: PRT
<213> ORGANISM: Artificial Sequence
<220> FEATURE:
<223> OTHER INFORMATION: chemically synthesized

<400> SEQUENCE: 230

Glu Thr Arg Leu Val Glu Ile Asp Asn
1               5

<210> SEQ ID NO 231
<211> LENGTH: 9
<212> TYPE: PRT
<213> ORGANISM: Artificial Sequence
<220> FEATURE:
<223> OTHER INFORMATION: chemically synthesized

<400> SEQUENCE: 231

Glu Thr Arg Leu Val Glu Ile Asp Asn
1               5

<210> SEQ ID NO 232
<211> LENGTH: 8
<212> TYPE: PRT
<213> ORGANISM: Artificial Sequence
<220> FEATURE:
<223> OTHER INFORMATION: chemically synthesized

<400> SEQUENCE: 232

Ala Cys Leu Glu Arg Ile Gln Glu
1               5

<210> SEQ ID NO 233
<211> LENGTH: 8
<212> TYPE: PRT
<213> ORGANISM: Artificial Sequence
<220> FEATURE:
<223> OTHER INFORMATION: chemically synthesized

<400> SEQUENCE: 233

Ala Ala Glu Asp Arg Ile Arg Glu
1               5

<210> SEQ ID NO 234
<211> LENGTH: 8
<212> TYPE: PRT
<213> ORGANISM: Artificial Sequence
<220> FEATURE:
<223> OTHER INFORMATION: chemically synthesized

<400> SEQUENCE: 234

Ala Lys Glu Ala Lys Leu Arg Asp
1               5

<210> SEQ ID NO 235
<211> LENGTH: 8
<212> TYPE: PRT
<213> ORGANISM: Artificial Sequence
<220> FEATURE:
```

```
<223> OTHER INFORMATION: chemically synthesized

<400> SEQUENCE: 235

Ala Lys Glu Ala Lys Leu Arg Asp
1               5

<210> SEQ ID NO 236
<211> LENGTH: 8
<212> TYPE: PRT
<213> ORGANISM: Artificial Sequence
<220> FEATURE:
<223> OTHER INFORMATION: chemically synthesized

<400> SEQUENCE: 236

Ala Lys Glu Ala Lys Leu Arg Asp
1               5

<210> SEQ ID NO 237
<211> LENGTH: 103
<212> TYPE: PRT
<213> ORGANISM: Artificial Sequence
<220> FEATURE:
<223> OTHER INFORMATION: chemically synthesized

<400> SEQUENCE: 237

Arg Leu Gly Asp Leu Tyr Glu Glu Glu Met Arg Glu Leu Arg Arg Gln
1               5                   10                  15

Val Asp Gln Leu Thr Asn Asp Lys Ala Arg Val Glu Val Glu Arg Asp
                20                  25                  30

Asn Leu Ala Glu Asp Ile Met Arg Leu Arg Glu Lys Leu Gln Glu Glu
        35                  40                  45

Met Leu Gln Arg Glu Glu Ala Glu Asn Thr Leu Gln Ser Phe Arg Gln
    50                  55                  60

Asp Val Asp Asn Ala Ser Leu Ala Arg Leu Asp Leu Glu Arg Lys Val
65                  70                  75                  80

Glu Ser Leu Gln Glu Glu Ile Ala Phe Leu Lys Lys Leu His Glu Glu
                85                  90                  95

Glu Ile Gln Glu Leu Gln Ala
            100
```